US012600709B2

(12) United States Patent
Zhao et al.

(10) Patent No.: US 12,600,709 B2
(45) Date of Patent: *Apr. 14, 2026

(54) NONPEPTIDE SOMATOSTATIN TYPE 5 RECEPTOR AGONISTS AND USES THEREOF

(71) Applicant: Crinetics Pharmaceuticals, Inc., San Diego, CA (US)

(72) Inventors: Jian Zhao, San Diego, CA (US); Yunfei Zhu, San Diego, CA (US); Shimiao Wang, San Diego, CA (US); Mi Chen, San Diego, CA (US); Joseph Pontillo, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/822,733

(22) Filed: Sep. 3, 2024

(65) Prior Publication Data

US 2025/0136573 A1 May 1, 2025

Related U.S. Application Data

(63) Continuation of application No. 18/612,585, filed on Mar. 21, 2024, which is a continuation of application No. 18/484,065, filed on Oct. 10, 2023, now abandoned, which is a continuation of application No. 18/190,681, filed on Mar. 27, 2023, now abandoned, which is a continuation of application No. 17/930,587, filed on Sep. 8, 2022, now abandoned, which is a continuation of application No. 16/989,193, filed on Aug. 10, 2020, now Pat. No. 11,479,540.

(60) Provisional application No. 62/886,764, filed on Aug. 14, 2019.

(51) Int. Cl.

| | |
|---|---|
| ***A61P 3/10*** | (2006.01) |
| ***C07D 401/04*** | (2006.01) |
| ***C07D 401/14*** | (2006.01) |

(52) U.S. Cl.

CPC .............. *C07D 401/04* (2013.01); *A61P 3/10* (2018.01); *C07D 401/14* (2013.01)

(58) Field of Classification Search

CPC ........ C07D 401/04; C07D 401/14; A61P 3/10

See application file for complete search history.

(56) References Cited

U.S. PATENT DOCUMENTS

| | | | |
|---|---|---|---|
| 6,025,372 | A | 2/2000 | Yang et al. |
| 6,127,343 | A | 10/2000 | Ankersen et al. |
| 7,754,744 | B2 | 7/2010 | Binggeli et al. |
| 8,110,574 | B2 | 2/2012 | Thurieau et al. |
| 8,778,925 | B2 | 7/2014 | McDonald et al. |
| 9,630,976 | B2 | 4/2017 | Ishida et al. |
| 9,643,951 | B2 | 5/2017 | Ishida et al. |
| 10,214,540 | B2 | 2/2019 | Ishida et al. |
| 10,696,689 | B2 | 6/2020 | Han et al. |
| 11,072,598 | B2 | 7/2021 | Han et al. |
| 11,186,590 | B2 | 11/2021 | Han et al. |
| 11,427,567 | B2 | 8/2022 | Ye et al. |
| 11,479,540 | B2 | 10/2022 | Zhao et al. |
| 11,608,335 | B2 | 3/2023 | Zhao et al. |
| 11,773,076 | B2 | 10/2023 | Zhao et al. |
| 11,834,462 | B2 | 12/2023 | Han et al. |
| 2006/0281764 | A1 | 12/2006 | Gaul et al. |
| 2011/0059971 | A1 | 3/2011 | Thurieau et al. |
| 2013/0040978 | A1 | 2/2013 | Duffy et al. |
| 2015/0232478 | A1 | 8/2015 | Ishida et al. |
| 2016/0311794 | A1 | 10/2016 | Ishida et al. |
| 2020/0000816 | A1 | 1/2020 | Ishida et al. |
| 2022/0048924 | A1 | 2/2022 | Han et al. |
| 2022/0144802 | A1 | 5/2022 | Zhao et al. |
| 2022/0323427 | A1 | 10/2022 | Ferrara-Cook et al. |
| 2023/0143091 | A1 | 5/2023 | Crowe et al. |

FOREIGN PATENT DOCUMENTS

| | | | |
|---|---|---|---|
| CA | 2925651 | A1 | 4/2015 |
| EP | 2871179 | A1 | 5/2015 |
| EP | 3053916 | A1 | 8/2016 |
| EP | 3053961 | A1 | 8/2016 |
| EP | 3053916 | B1 | 1/2019 |
| EP | 3581569 | A1 | 12/2019 |
| JP | 2008543760 | A | 12/2008 |
| WO | WO-9845285 | A1 | 10/1998 |
| WO | WO-2005047253 | A1 | 5/2005 |
| WO | WO-2008051272 | A2 | 5/2008 |
| WO | WO-2009051705 | A1 | 4/2009 |
| WO | WO-2009158467 | A2 | 12/2009 |
| WO | WO-2010041054 | A1 | 4/2010 |
| WO | WO-2011027249 | A2 | 3/2011 |
| WO | WO-2011144891 | A1 | 11/2011 |

(Continued)

OTHER PUBLICATIONS

Abbott et al. MiRP1 forms IKr potassium channels with HERG and is associated with cardiac arrhythmia. Cell 97:175-187 (1999).

(Continued)

*Primary Examiner* — Alicia L Otton

(74) *Attorney, Agent, or Firm* — WILSON SONSINI GOODRICH & ROSATI

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

4 Claims, No Drawings

(56) References Cited

FOREIGN PATENT DOCUMENTS

| | | | |
|---|---|---|---|
| WO | WO-2011146324 | A1 | 11/2011 |
| WO | WO-2014007228 | A1 | 1/2014 |
| WO | WO-2015046482 | A1 | 4/2015 |
| WO | WO-2018013676 | A1 | 1/2018 |
| WO | WO-2018147300 | A1 | 8/2018 |
| WO | WO-2018170284 | A1 | 9/2018 |
| WO | WO-2019023278 | A1 | 1/2019 |
| WO | WO-2019157458 | A1 | 8/2019 |
| WO | WO-2020061046 | A1 | 3/2020 |
| WO | WO-2020120697 | A1 | 6/2020 |
| WO | WO-2021030262 | A1 | 2/2021 |
| WO | WO-2022177974 | A1 | 8/2022 |
| WO | WO-2022177988 | A1 | 8/2022 |

OTHER PUBLICATIONS

Berge, Stephen M. et al. Pharmaceutical Salts. Journal of Pharmaceutical Sciences 66(1):1-19 (1977).
Brazeau, Paul et al. Hypothalamic Polypeptide That Inhibits the Secretion of Immunoreactive Pituitary Growth Hormone. Science 179(4068):77-79 (1973).
Bundgaard, Hans. Chapter 5: Design and Application of Prodrugs. In: Textbook of Drug Design and Development :113-191 (1991).
Bundgaard, Hans. Means to Enhance Penetration: Prodrugs as a Means to Improve the Delivery of Peptide Drugs. Advanced Drug Delivery Review 8(1):1-38 (1992).
Corda et al. Treatment with long-acting lanreotide autogel in early infancy in patients with severe neonatal hyperinsulinism. Orphanet J Rare Dis. 12(1):108 (2017).
Crider. Somatostatin receptor agonists and antagonists. Expert Opinion on Therapeutic Patents 13(9):1427-1441 (2003).
De Cosio et al. Current and emerging agents for the treatment of hypoglycemia in patients with congenital hyperinsulinism. Paediatr Drugs 21(3):123-136 (2019).
De Leon et al. Congenital hypoglycemia disorders: new aspects of etiology, diagnosis, treatment and outcomes: highlights of the proceedings of the Congenital Hypoglycemia Disorders Symposium, Philadelphia Apr. 2016. Pediatr Diabetes 18(1):3-9 (2017).
Esch, Fred et al. Primary Structure of Ovine Hypothalamic Somatostatin-28 and Somatostatin-25. Proceedings of the National Academy of Sciences of the United States of America 77(11):6827-6831 (1980).
Ferrara et al. Biomarkers of insulin for the diagnosis of hyperinsulinemic hypoglycemia in infants and children. J Pediatr 168:212-219 (2016).
Fowler et al. Discovery and Identification of Late Stage, Selective, Nonpeptide, Somatostatin Subtype 5 (Sst5) Agonists for the Treatment of Hyperinsulinemic Hypoglycemia. Poster #MON-089. Endo Online 2020. Jun. 8-22, 2020.
Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).
Khlebnikov et al. A Novel Strategy for the Synthesis of 3-(N-Heteryl)pyrrole Derivatives. Org Lett 14(14):3768-71 (2012).
Liu et al. Nonpeptide somatostatin agonists with sst4 selectivity: synthesis and structure-activity relationships of thioureas. J Med Chem 41(24):4693-705 (1998).
Lord et al. Hyperinsulinism in the neonate. Clin Perinatol. 45(1):61-74 (2018).
Mallinger et al. Discovery of Potent, Orally Bioavailable, Small-Molecule Inhibitors of WNT Signaling from a Cell-Based Pathway Screen. J Med Chem 58(4):1717-35 (2015).
Ortiz-Marciales et al. Catalytic enantioselective borane reduction of benzyl oximes: preparation of (S)-1-Pyridin-3-YL-Ethylamine BIS Hydrochloride. Organic Synth. 87:36-52 (2010).
Patel, Yogesh C, and Coimbatore B Srikant. Somatostatin Receptors. Trends in Endocrinology and Metabolism 8(10):398-405 (1997).
PCT/US2020/045610 International Search Report and Written Opinion dated Nov. 23, 2020.
Pradayrol, Lucien et al. N-Terminally Extended Somatostatin: The Primary Structure of Somatostatin-28. FEBS Letters 109(1):55-58 (1980).
Reisine, Terry, and Graeme I Bell. Molecular Biology of Somatostatin Receptors. Endocrine Reviews 16(4):427-442 (1995).
Rico-Bautista et al. Selective somatostatin 5 (SST5) and somatostatin 2 (SST2) nonpeptide agonists potently suppress glucose- and tolbutamide-stimulated dynamic insulin secretion from isolated human islets. Poster #8684 (2021).
Salomon-Estebanez et al. Conservatively treated congenital hyperinsulinism (CHI) due to K-ATP channel gene mutations: reducing severity over time. Orphanet J Rare Dis. 11(1):163 (2016).
Sanguinetti et al. hERG potassium channels and cardiac arrhythmia. Nature 440(7083):463-469 (2006).
Science IP Report. Chemical Structure Search (May 24, 2016) (311 pgs.).
Stanley. Perspective on the genetics and diagnosis of congenital hyperinsulinism disorders. J Clin Endocrinol Metab. 101(3):815-826 (2016).
Stella. Prodrugs: Some Thoughts and Current Issues. J Pharm Sci 99(12):4755-4765 (2010).
Sturchler et al. Selective Nonpeptide Somatostatin Receptor Subtype 5 (sst5) Agonists Suppress Glucose- and Sulfonylurea-induced Insulin Secretion in Rats. Poster. Endo 2019. Mar. 23-26, 2019; New Orleans.
Thornton et al. Recommendations from the Pediatric Endocrine Society for Evaluation and Management of Persistent Hypoglycemia in Neonates, Infants, and Children. J Pediatr. 167(2):238-245 (2015).
Van Der Steen et al. A Multicenter experience with long-acting somatostatin analogues in patients with congenital hyperinsulinism. Horm Res Paediatr. 89(2):82-89 (2018).
Wang et al. The effect of global SSTR5 gene ablation on the endocrine pancreas and glucose regulation in aging mice. J Surg Res. 129(1):64-72 (2005).
Weckbecker et al. Opportunities in somatostatin research: biological, chemical and therapeutic aspects. Nat Rev Drug Discov 2(12):999-1017 (2003).
Widder, Kenneth J. et al. Method in Enzymology. Academic Press 112:309-396 (1985).
Wolf et al. Cytochrome P450 CYP2D6. IARC Sci Publ 148:209-229 (1999).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).
Zhao et al. Discovery of nonpeptide 3,4-dihydroquinazoline-4-carboxamides as potent and selective sst2 agonists. Bioorg Med Chem Lett 30(17):127391 (2020).
Zhao et al. Discovery of substituted 3H-pyrido[2,3-d]pyrimidin-4-ones as potent, biased, and orally bioavailable sst2 agonist. Bioorg Med Chem Lett 30(21):127496 (2020).

NONPEPTIDE SOMATOSTATIN TYPE 5 RECEPTOR AGONISTS AND USES THEREOF

CROSS-REFERENCE

This application is a continuation of U.S. patent application Ser. No. 18/612,585, filed on Mar. 21, 2024, which is a continuation of U.S. patent application Ser. No. 18/484,065, filed on Oct. 10, 2023, which is a continuation of Ser. No. 18/190,681, filed on Mar. 27, 2023, which is a continuation of U.S. patent application Ser. No. 17/930,587, filed on Sep. 8, 2022, which is a continuation of U.S. patent application Ser. No. 16/989,193, filed on Aug. 10, 2020, now U.S. Pat. No. 11,479,540, issued on Oct. 25, 2022, which claims benefit of U.S. Provisional Patent Application No. 62/886,764, filed on Aug. 14, 2019, each of which is incorporated herein by reference in its entirety.

STATEMENT AS TO FEDERALLY SPONSORED RESEARCH

This invention was made with government support under grant number DK115290 awarded by the National Institutes of Health. The government has certain rights in the invention.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate one subtype somatostatin receptor. In some embodiments, compounds described herein modulate SST5 receptor. Somatostatin peptide analogs, such as octreotide, lanreotide and pasireotide, formulated as depot injections, are routinely used to normalize hormone levels for the treatment of Growth Hormone (GH) secreting adenomas, pancreatic neuroendocrine tumors, and carcinoid tumors. Octreotide is also reported to be used as a treatment for congenital hyperinsulinism (CHI, sometimes referred to as congenital hyperinsulinism of infancy, or persistent hyperinsulinemic hypoglycemia of infancy), a condition that causes individuals to have abnormally high levels of insulin, which in turn to lead to frequent episodes of low blood sugar (hypoglycemia). The depot preparations of these peptide drugs are extremely expensive and require frequent doctor's office visits for painful injections that can lead to injection site reactions. Compounds described herein are molecules that are structurally different from peptide analogs. The compounds described herein are somatostatin modulators that selectively activate somatostatin receptor subtype 5 (SSTR5) that in turn inhibits insulin secretion and promotes glucose release and also inhibits GH secretion.

In one aspect, described herein is a compound of Formula (I), or a pharmaceutically acceptable salt, or pharmaceutically acceptable solvate thereof:

Formula (I)

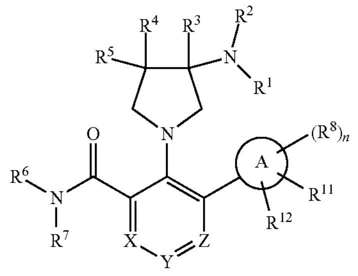

wherein:

Ring A is carbocycle or heterocycle;

X is N or C—$R^a$; Y is N or C—$R^b$; Z is N or C—$R^c$;

$R^a$, $R^b$, and $R^c$ are each independently hydrogen, halogen, —CN, —$N(R^9)_2$, —$OR^f$, —$CO_2R^9$, —C(═O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, or substituted or unsubstituted monocyclic heterocycle;

$R^f$ is -$L^1$-$R^g$;

$L^1$ is absent, $C_1$-$C_6$alkylene, $C_1$-$C_6$fluoroalkylene, or $C_1$-$C_6$heteroalkylene;

$R^g$ is hydrogen, substituted or unsubstituted $C_3$-$C_6$cycloalkyl, substituted or unsubstituted phenyl, —$CO_2R^9$, —C(═O)$N(R^9)_2$, or substituted or unsubstituted monocyclic heterocycle;

$R^1$ and $R^2$ are independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, or substituted or unsubstituted $C_3$-$C_5$heterocycloalkyl;

$R^3$ is hydrogen, —CN, —$CO_2R^9$, —C(═O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^4$ and $R^5$ are each independently hydrogen, halogen, —$OR^9$, —$N(R^9)_2$, —CN, —$CO_2R^9$, —C(═O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or -$L^2$-$R^{6a}$.

$L^2$ is absent, substituted or unsubstituted $C_1$-$C_8$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

$R^7$ is hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$ cycloalkyl, substituted or unsubstituted $C_6$-$C_{10}$ aryl, substituted or unsubstituted $C_2$-$C_{10}$ heterocycloalkyl, or substituted or unsubstituted $C_1$-$C_9$ heteroaryl;

or $R^6$ and $R^7$ are taken together with the nitrogen to which they are attached to form a substituted or unsubstituted N-containing heterocycle;

each $R^8$, $R^{11}$, and $R^{12}$ is independently hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —C(═O)$R^{10}$, —$CO_2R^9$, —C(═O)N($R^9$)$_2$, —N($R^9$)$_2$, —$NR^9$C(═O)$R^{10}$, —$NR^9$C(═O)O$R^{10}$, —$NR^9$C(═O)N($R^9$)$_2$, —C($R^9$)═N—O$R^9$, —S$R^9$, —S(═O)$R^9$, —$SO_2R^9$, or —$SO_2$N($R^9$)$_2$;

or $R^{11}$ is taken together with an adjacent $R^8$ and the atoms connecting the $R^{11}$ and the adjacent $R^8$ to form a fused substituted or unsubstituted carbocycle, or a fused substituted or unsubstituted heterocycle;

each $R^9$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl;

or two $R^9$ on the same N atom are taken together with the N atom to which they are attached to form a substituted or unsubstituted N-containing heterocycle;

each $R^{10}$ is independently substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl; and n is 0-3.

Any combination of the groups described above for the various variables is contemplated herein. Throughout the specification, groups and substituents thereof are chosen by one skilled in the field to provide stable moieties and compounds.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a compound described herein, or pharmaceutically acceptable salt, or solvate thereof, to the mammal in need thereof. In some embodiments, the compound described herein, or pharmaceutically acceptable salt, or solvate thereof, is orally administered. In some embodiments, the disease or condition is persistent or recurring hyperinsulinemia, hypoglycemia, acromegaly, a neuroendocrine tumor, an insulinoma, Cushing's disease, an ophthalmic disease or condition, cancer, pain, a neurodegenerative disease or condition, an inflammatory disease or condition, a psychiatric disease or condition, or combinations thereof. In some embodiments, the disease or condition is hyperinsulinemic hypoglycemia. In some embodiments, the disease or condition is hypoglycemia due to endogenous insulin, drug induced hyperinsulinism, or hypoglycemia due to exogenous insulin.

In any of the aforementioned aspects are further embodiments in which the effective amount of the compound of Formula (I), or a pharmaceutically acceptable salt, or solvate thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalami (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous system (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily.

It is possible to selectively modulate any one of the somatostatin receptor subtypes, or combination thereof. In some embodiments, selectively modulating any one of the somatostatin receptor subtypes relative to the other somatostatin receptor subtypes reduces unwanted side effects in a variety of clinical applications.

In one aspect, compounds described herein are modulators of SSTR5. In some embodiments, compounds described herein selectively modulate the activity of SSTR5 relative to the other somatostatin receptors. In some embodiments, compounds described herein selectively modulate the activity of SSTR5 relative to SSTR2.

In some embodiments, compounds described here are amenable to oral administration to a mammal in need of treatment with a somatostatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to, acromegaly, neuroendocrine tumors and hyperinsulinism. In some embodiments, somatostatin receptor modulators described herein are used in the treatment of hyperinsulinism in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, IGF-1 and insulin. The suppression of certain endocrine secretions is useful in the treatment of disorders such as acromegaly, hyperinsulinism, endocrine tumors such as carcinoids, VIPomas, insulinomas and glucagonomas. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, insulinomas, colon and pancreatic adenocarcinomas (ductal type), chondrosarcomas, and melanomas, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

In some embodiments, somatostatin receptor modulators described herein are used to treat hyperinsulinemia in a mammal. Hyperinsulinemia leads to several conditions, such as but not limited to, hypoglycemia or low blood sugar, diabetes or uncontrolled blood sugar that fluctuates between a low and high level, increased risk of Polycystic Ovarian Syndrome (PCOS), increased production of very low-density lipoproteins (VLDLs) (referred to as hypertriglyceridemia), increased risk of cardiovascular or heart disease, coronary artery disease (the high insulin level damages the endothelial cells that line the coronary arteries), hypertension or high blood pressure, underactive thyroid gland, weight gain and lethargy.

Hyperinsulinism refers to an above normal level of insulin in the blood of a person or animal. Normal insulin secretion and blood levels are closely related to the level of glucose in the blood, so that a given level of insulin can be normal for one blood glucose level but low or high for another. Hyperinsulinism can be associated with several types of medical problems, which can be roughly divided into two broad and largely non-overlapping categories: those tending toward reduced sensitivity to insulin and high blood glucose levels (hyperglycemia), and those tending toward excessive insulin secretion and low glucose levels (hypoglycemia).

Hyperinsulinemic hypoglycemia (HH) is one of the most frequent causes of persistent hypoglycemia in infants. It is a heterogeneous condition caused by increased insulin secretion from pancreatic β-cells. HH can result in apneas, seizures, developmental delays, learning disabilities, epilepsy, and even death. The most severe form of HH is inherited and referred to as congenital hyperinsulinism (CHI). As with many rare diseases, there are no current drugs specifically tailored for patients with CHI, though some drugs have been adapted for use, including but not limited to diazoxide and octreotide.

The pancreas is a principal site of somatostatin action, and there it inhibits the synthesis and secretion of the two major hormones that control glucose homeostasis: glucagon and insulin. Different somatostatin receptor subtypes control these vital processes: sst2 receptors suppress glucagon, while both sst2 and sst5 are responsible for the suppression of insulin.

Hypoglycemia due to excessive endogenous insulin can be congenital or acquired, apparent in the newborn period, or many years later. The hypoglycemia can be severe and life-threatening or a minor, occasional nuisance. By far the most common type of severe but transient hyperinsulinemic hypoglycemia occurs accidentally in persons with type 1 diabetes who take insulin.

Hypoglycemia due to endogenous insulin includes, but is not limited to, congenital hyperinsulinism, transient neonatal hyperinsulinism, focal hyperinsulinism (KATP channel disorders), diffuse hyperinsulinism, acquired forms of hyperinsulinism, insulinomas (insulin-secreting tumors), adult nesidioblastosis, autoimmune insulin syndrome, non-insulinoma pancreatogenous hypoglycemia, reactive hypoglycemia, a side effect of gastric bypass surgery or gastric dumping syndrome.

Drug induced hyperinsulinism results from exposure to certain drugs such as, but not limited to, sulfonylureas, aspirin, pentamidine, quinine, disopyramide, *Bordetella pertussis* vaccine or infection, D-chiro-inositol and myo-inositol.

Hypoglycemia due to exogenous (injected) insulin includes but is not limited to, insulin self-injected for treatment of diabetes (i.e., diabetic hypoglycemia), insulin self-injected surreptitiously (e.g., Munchausen syndrome), insulin self-injected in a suicide attempt or successful suicide, insulin potentiation therapy, and insulin-induced coma for depression treatment.

Compounds

Compounds of Formula (I), including pharmaceutically acceptable salts, prodrugs, active metabolites, and pharmaceutically acceptable solvates thereof, are somatostatin receptor modulators. In some embodiments, the compounds of Formula (I), including pharmaceutically acceptable salts, prodrugs, active metabolites, and pharmaceutically acceptable solvates thereof, are SST5 receptor modulators.

In some embodiments, compounds described herein are SST5 selective modulators. In some embodiments, compounds described herein are at least 10 times, at least 15 times, at least 20 times, at least 30 times, at least 40 times, at least 50 times, at least 100 times, at least 200 times, at least 300 times, at least 400 times, or greater than 500 times more selective at modulating SST5 receptor activity than SST1, SST2, SST3, and/or SST4 receptor activity. In some embodiments, compounds described herein are at least 10 times, at least 15 times, at least 20 times, at least 30 times, at least 40 times, at least 50 times, at least 100 times, at least 200 times, at least 300 times, at least 400 times, or greater than 500 times more selective at modulating SST5 receptor activity than SST2 receptor activity.

In one aspect, provided herein is a compound of Formula (I), or a pharmaceutically acceptable salt, or pharmaceutically acceptable solvate thereof:

Formula (I)

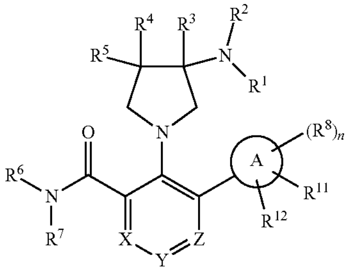

wherein:

Ring A is carbocycle or heterocycle;

X is N or C—$R^a$; Y is N or C—$R^b$; Z is N or C—$R^c$;

$R^a$, $R^b$, and $R^c$ are each independently hydrogen, halogen, —CN, —$N(R^9)_2$, —OR, —$CO_2R^9$, —C(=O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, or substituted or unsubstituted monocyclic heterocycle;

$R^f$ is -$L^1$-$R^g$;

$L^1$ is absent, $C_1$-$C_6$alkylene, $C_1$-$C_6$fluoroalkylene, or $C_1$-$C_6$heteroalkylene;

$R^g$ is hydrogen, substituted or unsubstituted $C_3$-$C_6$cycloalkyl, substituted or unsubstituted phenyl, —$CO_2R^9$, —C(=O)$N(R^9)_2$, or substituted or unsubstituted monocyclic heterocycle;

$R^1$ and $R^2$ are independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, or substituted or unsubstituted $C_3$-$C_5$heterocycloalkyl;

$R^3$ is hydrogen, —CN, —$CO_2R^9$, —C(=O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^4$ and $R^5$ are each independently hydrogen, halogen, —$OR^9$, —$N(R^9)_2$, —CN, —$CO_2R^9$, —C(=O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or -$L^2$-$R^{6a}$.

$L^2$ is absent, substituted or unsubstituted $C_1$-$C_8$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

$R^7$ is hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$ cycloalkyl, substituted or unsubstituted $C_6$-$C_{10}$ aryl, substituted or unsubstituted $C_2$-$C_{10}$ heterocycloalkyl, or substituted or unsubstituted $C_1$-$C_9$ heteroaryl;

or $R^6$ and $R^7$ are taken together with the nitrogen to which they are attached to form a substituted or unsubstituted N-containing heterocycle;

each $R^8$, $R^{11}$, and $R^{12}$ is independently hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —C(=O)$R^{10}$, —$CO_2R^9$, —C(=O)N$(R^9)_2$, —N$(R^9)_2$, —$NR^9$C(=O)$R^{10}$, —$NR^9$C(=O)O$R^{10}$, —$NR^9$C(=O)N$(R^9)_2$, —C$(R^9)$=N—O$R^9$, —S$R^9$, —S(=O)$R^9$, —$SO_2R^9$, or —$SO_2N(R^9)_2$;

or $R^{11}$ is taken together with an adjacent $R^8$ and the atoms connecting the $R^{11}$ and the adjacent $R^8$ to form a fused substituted or unsubstituted carbocycle, or a fused substituted or unsubstituted heterocycle;

each $R^9$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl;

or two $R^9$ on the same N atom are taken together with the N atom to which they are attached to form a substituted or unsubstituted N-containing heterocycle;

each $R^{10}$ is independently substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl; and n is 0-3.

For any and all of the embodiments, substituents are selected from among a subset of the listed alternatives. For example, in some embodiments, $R^1$ and $R^2$ are independently hydrogen, substituted or unsubstituted $C_1$-$C_6$alkyl, substituted or unsubstituted $C_1$-$C_6$fluoroalkyl, or substituted or unsubstituted $C_3$-$C_6$cycloalkyl. In some embodiments, $R^1$ and $R^2$ are independently hydrogen or substituted or unsubstituted $C_1$-$C_6$alkyl. In some embodiments, $R^1$ and $R^2$ are independently hydrogen or $C_1$-$C_6$alkyl. In some embodiments, $R^1$ is hydrogen and $R^2$ is hydrogen, substituted or unsubstituted $C_1$-$C_6$alkyl, substituted or unsubstituted $C_1$-$C_6$fluoroalkyl, or substituted or unsubstituted $C_3$-$C_6$cycloalkyl. In some embodiments, $R^1$ is hydrogen and $R^2$ is hydrogen or substituted or unsubstituted $C_1$-$C_6$alkyl. $R^1$ is hydrogen and $R^2$ is hydrogen or $C_1$-$C_6$alkyl. In some embodiments, $R^1$ and $R^2$ are each hydrogen.

In some embodiments, $R^3$ is hydrogen, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl. In some embodiments, $R^3$ is hydrogen, —CN, —$CO_2R^9$, —C(=O)N$(R^9)_2$, substituted or unsubstituted $C_1$-$C_4$alkyl, substituted or unsubstituted $C_1$-$C_4$fluoroalkyl or substituted or unsubstituted $C_1$-$C_4$heteroalkyl. In some embodiments, $R^3$ is hydrogen, substituted or unsubstituted $C_1$-$C_4$alkyl, substituted or unsubstituted $C_1$-$C_4$fluoroalkyl or substituted or unsubstituted $C_1$-$C_4$heteroalkyl. In some embodiments, $R^3$ is hydrogen, —CN, —$CO_2R^9$, —C(=O)N$(R^9)_2$, substituted or unsubstituted $C_1$-$C_6$alkyl, or substituted or unsubstituted $C_1$-$C_6$fluoroalkyl. In some embodiments, $R^3$ is hydrogen, substituted or unsubstituted $C_1$-$C_6$alkyl, or substituted or unsubstituted $C_1$-$C_6$fluoroalkyl. In some embodiments, $R^3$ is hydrogen, —CN, —$CO_2R^9$, —C(=O)N$(R^9)_2$, or substituted or unsubstituted $C_1$-$C_6$alkyl. In some embodiments, $R^3$ is hydrogen or substituted or unsubstituted $C_1$-$C_6$alkyl. In some embodiments, $R^3$ is hydrogen, $C_1$-$C_6$alkyl, $C_1$-$C_6$fluoroalkyl, $C_1$-$C_6$alkoxy, $C_1$-$C_6$fluoroalkoxy, or $C_1$-$C_6$heteroalkyl. In some embodiments, $R^3$ is hydrogen, —CN, —$CO_2R^9$, —C(=O)N$(R^9)_2$, $C_1$-$C_4$alkyl, $C_1$-$C_4$fluoroalkyl or $C_1$-$C_4$heteroalkyl. In some embodiments, $R^3$ is hydrogen, $C_1$-$C_4$alkyl, $C_1$-$C_4$fluoroalkyl or $C_1$-$C_4$heteroalkyl. In some embodiments, $R^3$ is hydrogen, —CN, —$CO_2R^9$, —C(=O)N$(R^9)_2$, $C_1$-$C_6$alkyl, or $C_1$-$C_6$fluoroalkyl. In some embodiments, $R^3$ is hydrogen, $C_1$-$C_6$alkyl, or $C_1$-$C_6$fluoroalkyl. In some embodiments, $R^3$ is hydrogen or $C_1$-$C_6$alkyl. In some embodiments, $R^3$ is hydrogen, —CN, —$CO_2R^9$, —C(=O)N$(R^9)_2$, or $C_1$-$C_6$alkyl. In some embodiments, $R^3$ is hydrogen, —CN, —$CO_2CH_3$, —$CO_2CH_2CH_3$, —C(=O)$NH_2$, —C(=O)$NHCH_3$, —C(=O)N$(CH_3)_2$, —$CH_3$, —$CH_2OH$, —$CH_2OCH_3$, —$CH_2CH_2F$, —$CH_2CHF_2$, or —$CH_2CF_3$. In some embodiments, $R^3$ is hydrogen, —CN, —$CO_2CH_3$, —$CO_2CH_2CH_3$, —C(=O)$NH_2$, —C(=O)$NHCH_3$, —C(=O)N$(CH_3)_2$, —$CH_3$, —$CH_2OH$, —$CH_2OCH_3$, or —$CH_2CHF_2$. In some embodiments, $R^3$ is hydrogen, —$CH_3$, —$CH_2OH$, —$CH_2OCH_3$, —$CH_2CH_2F$, —$CH_2CHF_2$, or —$CH_2CF_3$. In some embodiments, $R^3$ is hydrogen, —$CH_3$, —$CH_2OH$, —$CH_2OCH_3$, or —$CH_2CHF_2$. In some embodiments, $R^3$ is hydrogen or —$CH_3$. In some embodiments, $R^3$ is hydrogen. In some embodiments, $R^3$ is —$CH_3$.

In some embodiments, $R^4$ and $R^5$ are each independently hydrogen, halogen, —$OR^9$, —N$(R^9)_2$, —CN, —$CO_2R^9$, —C(=O)N$(R^9)_2$, substituted or unsubstituted $C_1$-$C_6$alkyl, or substituted or unsubstituted $C_1$-$C_6$fluoroalkyl. In some embodiments, $R^4$ and $R^5$ are each independently hydrogen, halogen, substituted or unsubstituted $C_1$-$C_6$alkyl, or substituted or unsubstituted $C_1$-$C_6$fluoroalkyl. In some embodiments, $R^4$ and $R^5$ are each independently hydrogen, halogen, $C_1$-$C_6$alkyl, or $C_1$-$C_6$fluoroalkyl. In some embodiments, $R^4$ and $R^5$ are each independently hydrogen or halogen. In some embodiments, $R^4$ and $R^5$ are each independently hydrogen or —F.

In some embodiments, $R^1$ is hydrogen; $R^2$ is hydrogen or $C_1$-$C_6$alkyl; $R^3$ is hydrogen, $C_1$-$C_6$alkyl, or $C_1$-$C_6$fluoroalkyl; and $R^4$ and $R^5$ are each independently hydrogen, halogen, $C_1$-$C_6$alkyl, or $C_1$-$C_6$fluoroalkyl. In some embodiments, $R^1$ and $R^2$ are each hydrogen; $R^3$ is hydrogen or —$CH_3$; and $R^4$ and $R^5$ are each hydrogen. In some embodiments, $R^1$ is hydrogen; $R^2$ is hydrogen or $C_1$-$C_6$alkyl; $R^3$ is hydrogen, $C_1$-$C_6$alkyl, or $C_1$-$C_6$fluoroalkyl; $R^4$ is hydrogen, halogen, $C_1$-$C_6$alkyl, or $C_1$-$C_6$fluoroalkyl; and $R^5$ is hydrogen, halogen, $C_1$-$C_6$alkyl, or $C_1$-$C_6$fluoroalkyl. In some embodiments, $R^1$ is hydrogen; $R^2$ is hydrogen; $R^3$ is hydrogen, —$CH_3$, —$CH_2OH$, —$CH_2OCH_3$, —$CH_2CH_2F$, —$CH_2CHF_2$, or —$CH_2CF_3$; $R^4$ is hydrogen or F; and $R^5$ is hydrogen or F. In some embodiments, $R^1$ is hydrogen; $R^2$ is hydrogen or $C_1$-$C_6$alkyl; $R^3$ is hydrogen, $C_1$-$C_4$alkyl, $C_1$-$C_4$fluoroalkyl or $C_1$-$C_4$heteroalkyl; $R^4$ is hydrogen, halogen, $C_1$-$C_4$alkyl, or $C_1$-$C_4$fluoroalkyl; and $R^5$ is hydrogen, halogen, $C_1$-$C_4$alkyl, or $C_1$-$C_4$fluoroalkyl.

In some embodiments, the compound has the structure of Formula (Ia) or (Ib), or a pharmaceutically acceptable salt, or solvate thereof:

Formula (Ia)

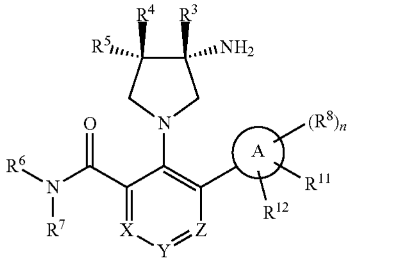

Formula (Ib)

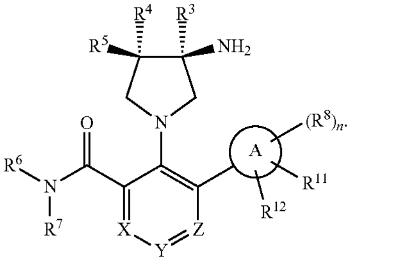

In some embodiments, the compound has the structure of Formula (Ia), or a pharmaceutically acceptable salt, or solvate thereof:

Formula (Ia)

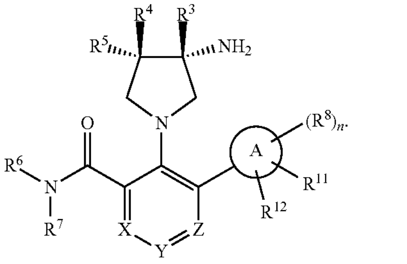

In some embodiments, the compound has the structure of Formula (Ib), or a pharmaceutically acceptable salt, or solvate thereof:

Formula (Ib)

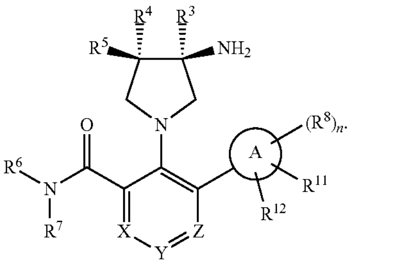

In some embodiments, X is C—$R^a$; Y is N; and Z is C—$R^c$; or X is CH; Y is N; and Z is C—$R^c$; or X is C—$R^a$; Y is N; and Z is CH; or X is N; Y is C—$R^b$; and Z is C—$R^c$; or X is C—$R^a$; Y is C—R; and Z is N; or X is N; Y is N; and Z is C—$R^c$; or X is C—$R^a$; Y is N; and Z is N. In some embodiments, X is C—$R^a$; Y is N; and Z is C—$R^c$. In some embodiments, X is CH; Y is N; and Z is C—$R^c$. In some embodiments, X is C—$R^a$; Y is N; and Z is CH. In some embodiments, X is N; Y is C—$R^b$; and Z is C—$R^c$. In some embodiments, X is C—$R^a$; Y is C—$R^b$; and Z is N. In some embodiments, X is N; Y is N; and Z is C—$R^c$. In some embodiments, X is C—$R^a$; Y is N; and Z is N.

In some embodiments, X is N or CH; Y is N or CH; and Z is N or C—$R^c$.

In some embodiments, $R^a$, $R^b$, and $R^c$ are each independently hydrogen, halogen, —CN, —$N(R^9)_2$, —$OR^e$, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$heteroalkyl, substituted or unsubstituted monocyclic carbocycle, or substituted or unsubstituted monocyclic heterocycle. In some embodiments, $R^a$, $R^b$, and $R^c$ are each independently hydrogen, halogen, —CN, —$OR^e$, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted monocyclic carbocycle. In some embodiments, $R^a$, $R^b$, and $R^c$ are each independently hydrogen, halogen, —CN, —$OR^e$, $C_1$-$C_6$alkyl, $C_1$-$C_6$fluoroalkyl, $C_1$-$C_6$fluoroalkoxy, or monocyclic carbocycle. In some embodiments, $R^a$, $R^b$, and $R^c$ are each independently hydrogen, halogen, —CN, —$N(R^9)_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl. In some embodiments, $R^a$, $R^b$, and $R^c$ are each independently hydrogen, halogen, —CN, —$N(R^9)_2$, —$OR^f$, —$CO_2R^9$, —C(═O)$N(R^9)_2$, $C_1$-$C_6$alkyl, $C_1$-$C_6$fluoroalkyl, $C_1$-$C_6$fluoroalkoxy, substituted or unsubstituted monocyclic $C_3$-$C_6$cycloalkyl, or substituted or unsubstituted monocyclic $C_2$-$C_5$heterocycloalkyl.

In some embodiments, $R^a$, $R^b$, and $R^c$ are each independently hydrogen, halogen, —CN, —$N(R^9)_2$, —$OR^e$, —$CO_2R^9$, —C(═O)$N(R^9)_2$, $C_1$-$C_6$alkyl, $C_1$-$C_6$fluoroalkyl, $C_1$-$C_6$fluoroalkoxy, or substituted or unsubstituted $C_1$-$C_6$heteroalkyl, substituted or unsubstituted monocyclic $C_3$-$C_6$cycloalkyl, substituted or unsubstituted monocyclic $C_2$-$C_5$heterocycloalkyl; $R^f$ is -$L^1$-$R^g$; $L^1$ is absent, or $C_1$-$C_6$alkylene; and $R^9$ is hydrogen, substituted or unsubstituted $C_3$-$C_6$cycloalkyl, substituted or unsubstituted phenyl, —$CO_2R^9$, —C(═O)$N(R^9)_2$, substituted or unsubstituted monocyclic $C_2$-$C_5$heterocycloalkyl. In some embodiments, $R^a$, $R^b$, and $R^c$ are each independently hydrogen, halogen, —CN, —$N(R^9)_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl; $R^f$ is -$L^1$-$R^g$; $L^1$ is absent or $C_1$-$C_6$alkylene; and $R^g$ is hydrogen, substituted or unsubstituted $C_3$-$C_6$cycloalkyl, substituted or unsubstituted phenyl, or —$CO_2R^9$.

In some embodiments, $R^a$, $R^b$, and $R^c$ are each independently hydrogen, —F, —Cl, —CN, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, —$CF_3$, —$CH_2CF_3$, —$OCH_3$, —$OCH_2CH_3$, —$OCF_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, —$OCH_2CH_2CH_2CO_2CH_2CH_3$, —$CO_2CH_3$, —$CO_2CH_2CH_3$, —C(═O)$NH_2$, —$CONHCH_3$, —C(═O)$N(CH_3)_2$, cyclopropyl cyclobutyl, cyclopentyl, cyclohexyl, azetidinyl, pyrrolidinyl, piperidinyl, or morpholinyl. In some embodiments, $R^a$, $R^b$, and $R^c$ are each independently hydrogen, —F, —Cl, —CN, $-CH_3$, $-CF_3$, $-OCH_3$, $-OCH_2CH_3$, $-OCH_2CHF_2$, $-OCH_2CF_3$, $-OCH_2CH_2OCH_3$, —O-(cyclopropyl), $-O-CH_2$-(cyclopropyl), $-O-CH_2$-(phenyl), $-OCH_2CO_2H$, $-OCH_2CH_2CO_2H$, $-OCH_2CH_2CH_2CO_2H$, $-OCH_2CO_2CH_3$, $-OCH_2CH_2CO_2CH_3$, $-OCH_2CH_2CH_2CO_2CH_3$, $-OCH_2CO_2CH_2CH_3$, $-OCH_2CH_2CO_2CH_2CH_3$, or $-OCH_2CH_2CH_2CO_2CH_2CH_3$. In some embodiments, $R^a$, $R^b$, and $R^c$ are each independently hydrogen, —CN, $-CH_3$, $-CF_3$, $-OCH_3$, $-OCF_3$, $-CO_2CH_3$, $-C(=O)NH_2$, $-CONHCH_3$, or $-C(=O)N(CH_3)_2$. In some embodiments, $R^a$, $R^b$, and $R^c$ are each independently hydrogen, —CN, $-CH_3$, $-CF_3$, $-OCH_3$, $-OCF_3$, $-CO_2CH_3$, $-C(=O)NH_2$, $-CONHCH_3$, or $-C(=O)N(CH_3)_2$, or cyclopropyl. In some embodiments, $R^a$, $R^b$, and $R^c$ are each independently hydrogen or —CN.

In some embodiments, the compound has the structure of Formula (II), or a pharmaceutically acceptable salt, or solvate thereof:

Formula (II)

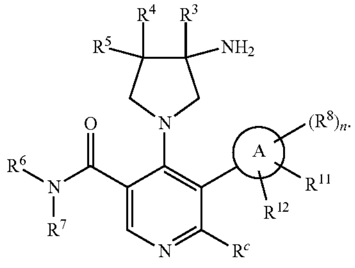

In some embodiments, the compound has the structure of Formula (IIa) or (IIb), or a pharmaceutically acceptable salt, or solvate thereof:

Formula (IIa)

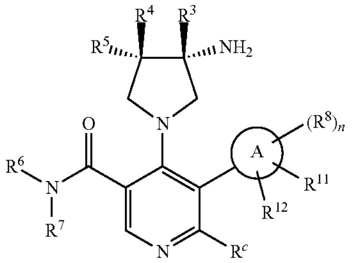

Formula (IIb)

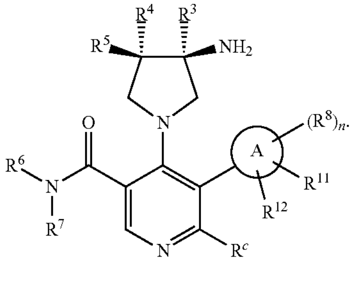

In some embodiments, the compound has the structure of Formula (IIa), or a pharmaceutically acceptable salt, or solvate thereof:

Formula (IIa)

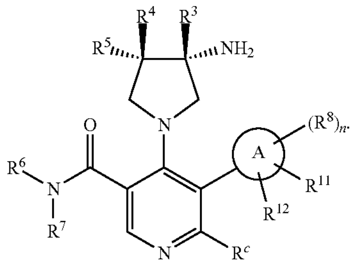

In some embodiments, the compound has the structure of Formula (IIb), or a pharmaceutically acceptable salt, or solvate thereof:

Formula (IIb)

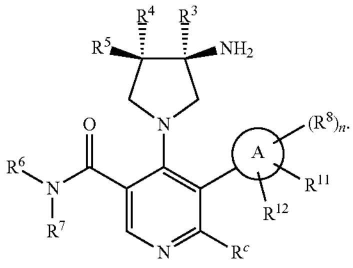

In some embodiments, the compound has the structure of Formula (IX), or a pharmaceutically acceptable salt, or solvate thereof:

Formula (IX)

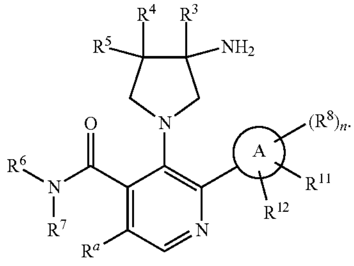

In some embodiments, the compound has the structure of Formula (IIa) or (IIb), or a pharmaceutically acceptable salt, or solvate thereof:

Formula (IXa)

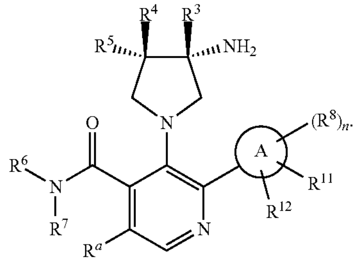

-continued

Formula (IXb)

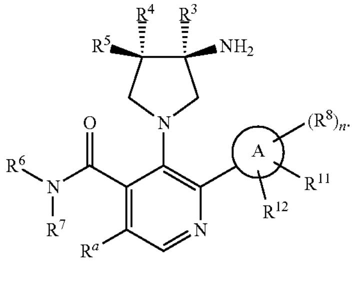

In some embodiments, the compound has the structure of Formula (X), or a pharmaceutically acceptable salt, or solvate thereof:

Formula (X)

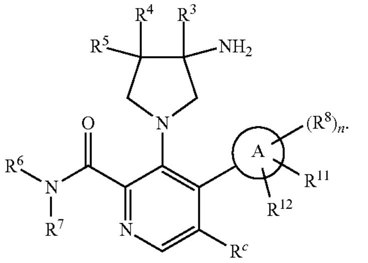

In some embodiments, the compound has the structure of Formula (Xa) or (Xb), or a pharmaceutically acceptable salt, or solvate thereof:

Formula (Xa)

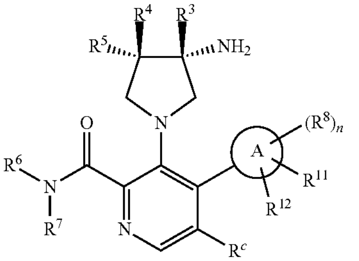

Formula (Xb)

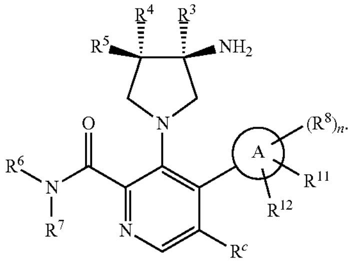

In some embodiments, Ring A is phenyl, monocyclic heteroaryl or bicyclic heteroaryl.

In some embodiments, Ring A is phenyl.

In some embodiments, Ring A is monocyclic heteroaryl; and n is 0, 1, or 2. In some embodiments, Ring A is pyrrolyl, furanyl, thiophenyl, imidazolyl, pyrazolyl, oxazolyl, thiazolyl, isoxazolyl, isothiazolyl, triazolyl, oxadiazolyl, thiadiazolyl, pyridinyl, pyrimidinyl, pyridazinyl, pyrazinyl, or triazinyl. In some embodiments, Ring A is pyrazolyl, thiazolyl, isoxazolyl, pyridinyl, or pyrimidinyl. In some embodiments, Ring A is pyridinyl.

In some embodiments, Ring A is phenyl or monocyclic heteroaryl. In some embodiments, Ring A is phenyl; or Ring A is pyridinyl; or Ring A is Ring A is pyrazolyl, thiazolyl, isoxazolyl, or pyrimidinyl. In some embodiments, Ring A is phenyl or pyridinyl.

In some embodiments, the compound has the structure of Formula (III), or a pharmaceutically acceptable salt, or solvate thereof:

Formula (III)

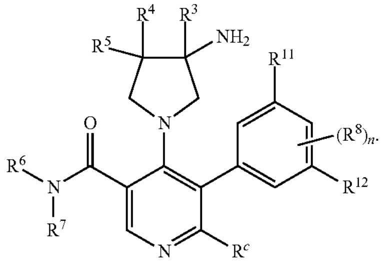

In some embodiments, the compound has the structure of Formula (IIIa) or (IIIb), or a pharmaceutically acceptable salt, or solvate thereof:

Formula (IIIa)

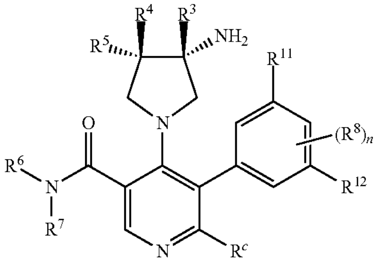

Formmula (IIIb)

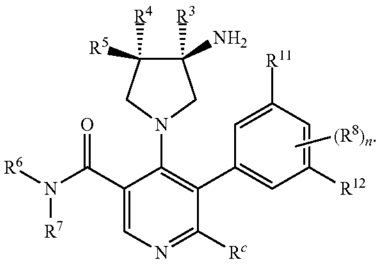

In some embodiments, the compound has the structure of Formula (IV), or a pharmaceutically acceptable salt, or solvate thereof:

Formula (IV)

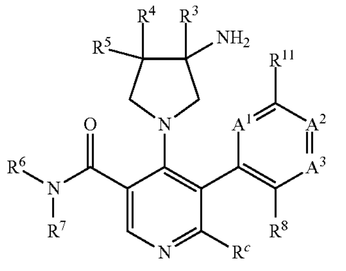

wherein:

$A^1$ and $A^2$ are each independently C—$R^8$ or N; and $A^3$ is C—$R^{12}$ or N.

In some embodiments, the compound has the structure of Formula (IVa) or (IVb), or a pharmaceutically acceptable salt, or solvate thereof:

Formula (IVa)

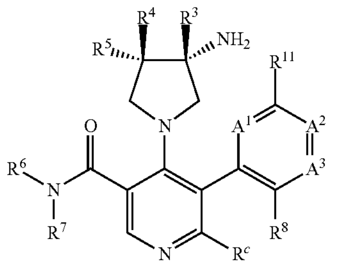

Formula (IVb)

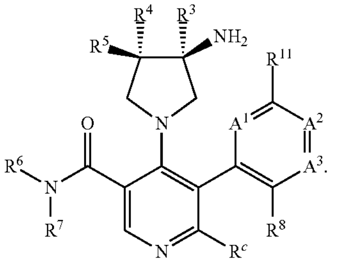

In some embodiments, $A^1$ is C—$R^8$; $A^2$ is C—$R^8$, and $A^3$ is C—$R^{12}$; or $A^1$ is N; $A^2$ is C—$R^8$, and $A^3$ is C—$R^{12}$; or $A^1$ is C—$R^8$; $A^2$ is N, and $A^3$ is C—$R^{12}$; or $A^1$ is C—$R^8$; $A^2$ is C—$R^8$, and $A^3$ is N. In some embodiments, $A^1$ is C—$R^8$; $A^2$ is C—$R^8$, and $A^3$ is C—$R^{12}$. In some embodiments, $A^1$ is N; $A^2$ is C—$R^8$, and $A^3$ is C—$R^{12}$. In some embodiments, $A^1$ is C—$R^8$; $A^2$ is N, and $A^3$ is C—$R^{12}$. In some embodiments, $A^1$ is C—$R^8$; $A^2$ is C—$R^8$, and $A^3$ is N.

In some embodiments, the compound has the structure of Formula (IVa-1) or (IVb-1), or a pharmaceutically acceptable salt, or solvate thereof:

Formula (IVa-1)

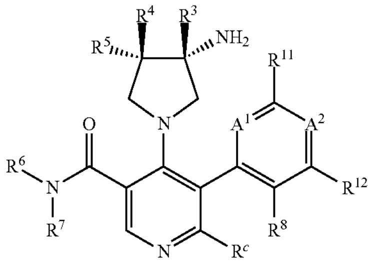

Formula (IVb-1)

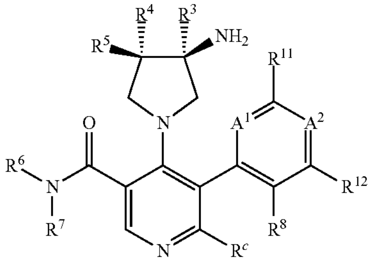

wherein:

$A^1$ is C—$R^8$; and $A^2$ is C—$R^8$; or $A^1$ is N; and $A^2$ is C—$R^8$; or $A^1$ is C—$R^8$; and $A^2$ is N.

In some embodiments, the compound has the structure of Formula (IVa-2), (IVb-2), (IVa-3), (IVb-3), (IVa-4), (IVb-4), (IVa-5), or (IVb-5), or a pharmaceutically acceptable salt, or solvate thereof:

Formula (IVa-2)

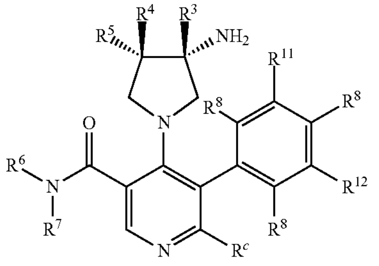

Formula (IVb-2)

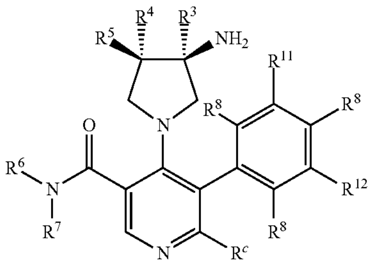

Formula (IVa-3)

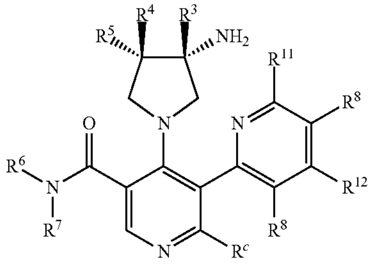

-continued

Formula (IVb-3)

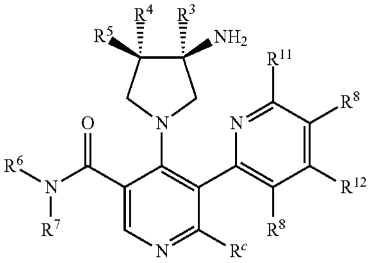

Formula (IVa-4)

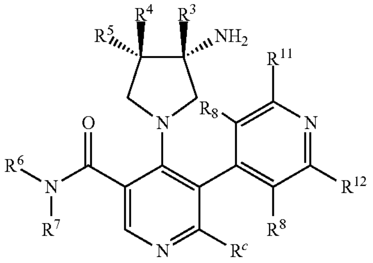

Formula (IVb-4)

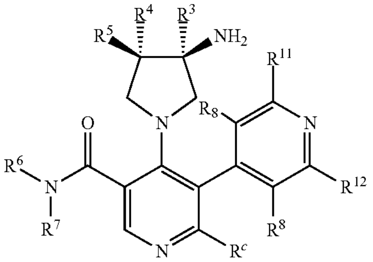

Formula (IVa-5)

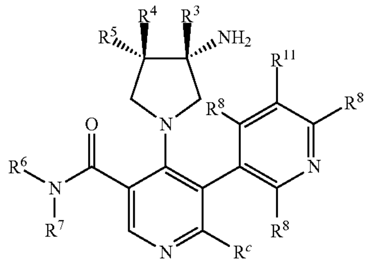

Formula (IVb-5)

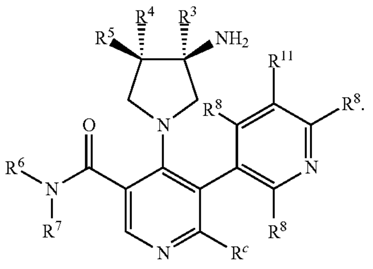

In some embodiments, the compound has the structure of Formula (V), or a pharmaceutically acceptable salt, or solvate thereof:

Formula (V)

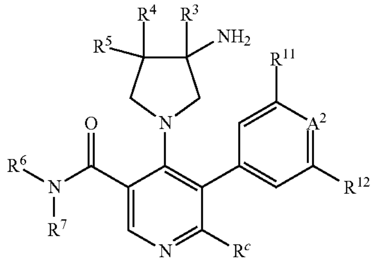

wherein:

$A^2$ is C—$R^8$ or N.

In some embodiments, the compound has the structure of Formula (Va) or (Vb), or a pharmaceutically acceptable salt, or solvate thereof:

Formula (Va)

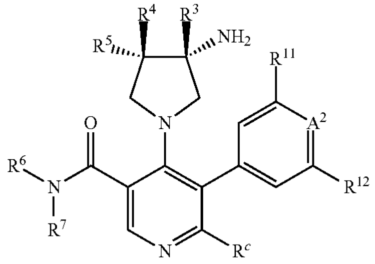

Formula (Vb)

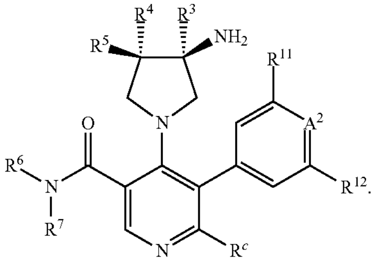

In some embodiments, the compound has the structure of Formula (Va-1), (Vb-1), (Va-2), or (Vb-2), or a pharmaceutically acceptable salt, or solvate thereof:

(Formula (Va-1)

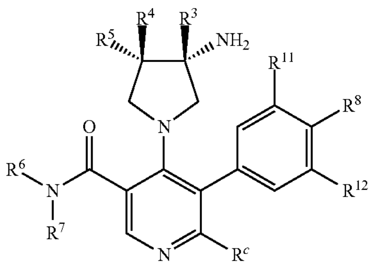

-continued

Formula (Vb-1)

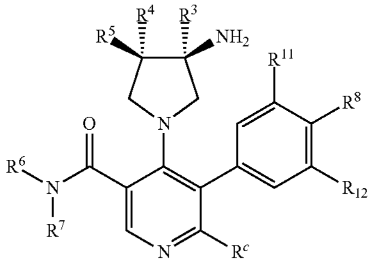

Formula (Va-2)

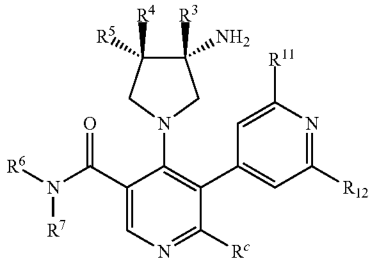

Formula (Vb-2)

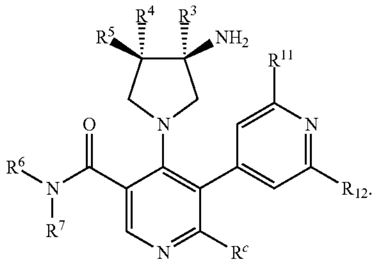

In some embodiments, each $R^8$ is independently hydrogen, halogen, substituted or unsubstituted $C_1$-$C_6$alkyl, substituted or unsubstituted $C_1$-$C_6$fluoroalkyl, substituted or unsubstituted monocyclic carbocycle, —CN, —$OR^9$, —$CO_2R^9$, —C(=O)N$(R^9)_2$, —N$(R^9)_2$, —$NR^9$C(=O)$R^{10}$, —$SO_2R^9$, or —$SO_2$N$(R^9)_2$. In some embodiments, each $R^8$ is independently hydrogen, halogen, substituted or unsubstituted $C_1$-$C_6$alkyl, substituted or unsubstituted $C_1$-$C_6$fluoroalkyl, —CN, —$OR^9$, —$CO_2R^9$, —C(=O)N$(R^9)_2$, —N$(R^9)_2$, or —$NR^9$C(=O)$R^{10}$. In some embodiments, each $R^8$ is independently hydrogen, halogen, substituted or unsubstituted $C_1$-$C_6$alkyl, or substituted or unsubstituted $C_1$-$C_6$fluoroalkyl. In some embodiments, each $R^8$ is independently hydrogen, halogen, $C_1$-$C_6$alkyl, or $C_1$-$C_6$fluoroalkyl. In some embodiments, each $R^8$ is independently hydrogen or halogen. In some embodiments, each $R^8$ is independently hydrogen, —F, or —Cl.

In some embodiments, the compound has the structure of Formula (Va-3) or (Vb-3), or a pharmaceutically acceptable salt, or solvate thereof:

Formula (Va-3)

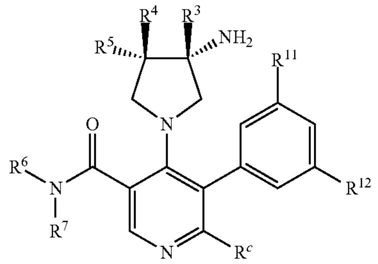

Formula (Vb-3)

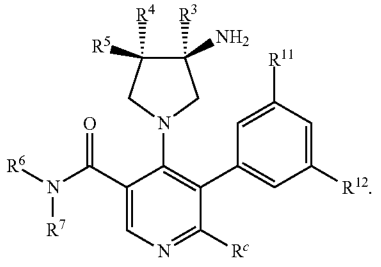

In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —$CO_2R^9$, —C(=O)N$(R^9)_2$, —N$(R^9)_2$, —$NR^9$C(=O)$R^{10}$, —$NR^9$C(=O)$OR^{10}$, —$NR^9$C(=O)N$(R^9)_2$, —C$(R^9)$=N—$OR^9$, —$SR^9$, —S(=O)$R^9$, —$SO_2R^9$, or —$SO_2$N$(R^9)_2$. In some embodiments, $R^{11}$ and $R^{12}$ are each independently hydrogen, halogen, $C_1$-$C_6$alkyl, $C_1$-$C_6$fluoroalkyl, —CN, —$OR^9$, —$CO_2R^9$, —C(=O)N$(R^9)_2$, —N$(R^9)_2$, or —$NR^9$C(=O)$R^{10}$, substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl. In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, —$CO_2R^9$, —C(=O)N$(R^9)_2$, —N$(R^9)_2$, or —$NR^9$C(=O)$R^{10}$, or substituted or unsubstituted monocyclic carbocycle. In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, —$CO_2R^9$, —C(=O)N$(R^9)_2$, —N$(R^9)_2$, or —$NR^9$C(=O)$R^{10}$, or substituted or unsubstituted monocyclic $C_3$-$C_8$cycloalkyl. In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, or substituted or unsubstituted monocyclic cycloalkyl. In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, or substituted or unsubstituted monocyclic $C_3$-$C_8$cycloalkyl. In some embodiments, $R^{11}$ and $R^{12}$ are each independently hydrogen, halogen, $C_1$-$C_6$alkyl, $C_1$-$C_6$fluoroalkyl, —CN, —$OR^9$, or substituted or unsubstituted monocyclic $C_3$-$C_8$cycloalkyl. In some embodiments, $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$. In some embodiments, $R^{11}$ and $R^{12}$ are each independently hydrogen, halogen, $C_1$-$C_6$alkyl, $C_1$-$C_6$fluoroalkyl, —CN, or —$OR^9$. In some embodiments, $R^{11}$ and $R^{12}$ are each independently hydrogen, —F, —Cl, —CN, —$CH_3$, —$CF_3$, —$OCH_3$, —$OCF_3$, or —$OCHF_2$. In some embodiments, $R^{11}$ and $R^{12}$ are each independently halogen. In some embodiments, $R^{11}$ and $R^{12}$ are each independently —F or —Cl. In some embodiments, $R^{11}$ and $R^{12}$ are each —F.

In some embodiments, $R^{11}$ is taken together with an adjacent $R^8$ and the atoms connecting the $R^{11}$ and the adjacent $R^8$ to form a fused substituted or unsubstituted carbocycle, or a fused substituted or unsubstituted heterocycle. In some embodiments, $R^{11}$ is taken together with an adjacent $R^8$ and the atoms connecting the $R^{11}$ and the adjacent $R^8$ to form a fused substituted or unsubstituted $C_3$-$C_8$cycloalkyl, or a fused substituted or unsubstituted $C_2$-$C_5$heterocycloalkyl. In some embodiments, $R^{11}$ is taken together with an adjacent $R^8$ and the atoms connecting the $R^{11}$ and the adjacent $R^8$ to form a fused substituted or unsubstituted $C_2$-$C_5$heterocycloalkyl. In some embodiments, $R^{11}$ is taken together with an adjacent $R^8$ and the atoms connecting the $R^{11}$ and the adjacent $R^8$ to form a fused substituted or unsubstituted dioxolane or a fused substituted or unsubstituted dioxane.

In some embodiments, each $R^8$ is independently hydrogen, halogen, substituted or unsubstituted $C_1$-$C_6$alkyl, substituted or unsubstituted $C_1$-$C_6$fluoroalkyl, —CN, —$OR^9$, —$CO_2R^9$, —C(=O)N($R^9$)$_2$, —N($R^9$)$_2$, or —$NR^9$C(=O)$R^{10}$; and $R^{11}$ and $R^{12}$ are each independently hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —$CO_2R^9$, —C(=O)N($R^9$)$_2$, —N($R^9$)$_2$, —$NR^9$C(=O)$R^{10}$, —$NR^9$C(=O)O$R^{10}$, —$NR^9$C(=O)N($R^9$)$_2$, —C($R^9$)=N—$OR^9$, —$SR^9$, —S(=O)$R^9$, —$SO_2R^9$, or —$SO_2$N($R^9$)$_2$. In some embodiments, each $R^8$ is independently hydrogen, halogen, substituted or unsubstituted $C_1$-$C_6$alkyl, or substituted or unsubstituted $C_1$-$C_6$fluoroalkyl; and $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, —$CO_2R^9$, —C(=O)N($R^9$)$_2$, —N($R^9$)$_2$, or —$NR^9$C(=O)$R^{10}$, or substituted or unsubstituted monocyclic carbocycle. In some embodiments, each $R^8$ is independently hydrogen or halogen; and $R^{11}$ and $R^2$ are each independently hydrogen, halogen, substituted or unsubstituted $C_1$-$C_6$alkyl, substituted or unsubstituted $C_1$-$C_6$fluoroalkyl, —CN, —$OR^9$, or substituted or unsubstituted monocyclic cycloalkyl. In some embodiments, each $R^8$ is independently hydrogen or halogen; and $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$, or substituted or unsubstituted monocyclic cycloalkyl. In some embodiments, each $R^8$ is independently hydrogen, —F, or —Cl; and $R^{11}$ and $R^{12}$ are each independently hydrogen, —F, —Cl, —CN, —$CH_3$, —$CF_3$, —$OCH_3$, —$OCF_3$, or —$OCHF_2$.

In some embodiments, the compound has the structure of Formula (VI), or a pharmaceutically acceptable salt, or solvate thereof.

Formula (VI)

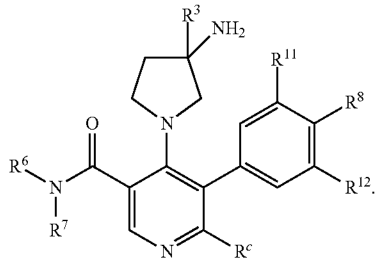

In some embodiments, $R^3$ is hydrogen or —$CH_3$; $R^8$ is hydrogen or halogen; $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$; $R^c$ is hydrogen, halogen, —CN, —N($R^9$)$_2$, —$OR^f$, —$CO_2R^9$, —C(=O)N($R^9$)$_2$, $C_1$-$C_6$alkyl, $C_1$-$C_6$fluoroalkyl, $C_1$-$C_6$fluoroalkoxy, substituted or unsubstituted $C_1$-$C_6$heteroalkyl, substituted or unsubstituted monocyclic $C_3$-$C_6$cycloalkyl, or substituted or unsubstituted monocyclic $C_2$-$C_5$heterocycloalkyl; $R^f$ is -$L^1$-$R^g$; $L^1$ is absent or $C_1$-$C_6$alkylene; and $R^9$ is hydrogen, substituted or unsubstituted $C_3$-$C_6$cycloalkyl, substituted or unsubstituted phenyl, —$CO_2R^9$, —C(=O)N($R^9$)$_2$, substituted or unsubstituted monocyclic $C_2$-$C_5$heterocycloalkyl.

In some embodiments, the compound has the structure of Formula (VIa) or (VIb), or a pharmaceutically acceptable salt, or solvate thereof.

Formula (VIa)

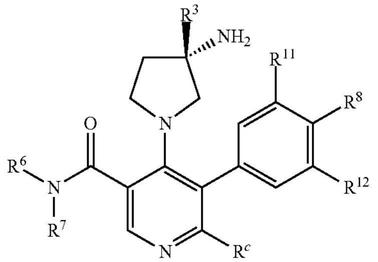

Formula (VIb)

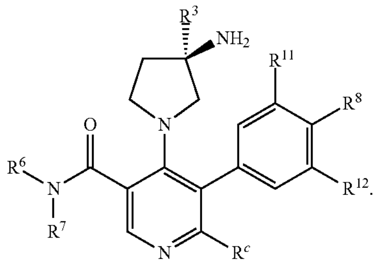

In some embodiments, $R^3$ is hydrogen or —$CH_3$; $R^8$ is hydrogen or halogen; $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$; $R^c$ is hydrogen, halogen, —CN, —N($R^9$)$_2$, —$OR^e$, —$CO_2R^9$, —C(=O)N($R^9$)$_2$, $C_1$-$C_6$alkyl, $C_1$-$C_6$fluoroalkyl, $C_1$-$C_6$fluoroalkoxy, substituted or unsubstituted $C_1$-$C_6$heteroalkyl, substituted or unsubstituted monocyclic $C_3$-$C_6$cycloalkyl, or substituted or unsubstituted monocyclic $C_2$-$C_5$heterocycloalkyl; $R^f$ is -$L^1$-$R^g$; $L^1$ is absent or $C_1$-$C_6$alkylene; and $R^9$ is hydrogen, substituted or unsubstituted $C_3$-$C_6$cycloalkyl, substituted or unsubstituted phenyl, —$CO_2R^9$, —C(=O)N$(R^9)_2$, substituted or unsubstituted monocyclic $C_2$-$C_5$heterocycloalkyl. In some embodiments, $R^c$ is hydrogen, halogen, —CN, —N$(R^9)_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl; $R^f$ is -$L^1$-$R^g$; $L^1$ is absent or $C_1$-$C_6$alkylene; and $R^9$ is hydrogen, substituted or unsubstituted $C_3$-$C_6$cycloalkyl, substituted or unsubstituted phenyl, or —$CO_2R^9$.

In some embodiments, $R^8$ is hydrogen, —F, or —Cl; $R^{11}$ and $R^{12}$ are each independently hydrogen, —F, —Cl, —CN, —$CH_3$, —$CF_3$, —$OCH_3$, —$OCF_3$, or —$OCHF_2$; and $R^c$ is hydrogen, —F, —Cl, —CN, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, —$CF_3$, —$CH_2CF_3$, —$OCH_3$, —$OCH_2CH_3$, —$OCF_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, —$OCH_2CH_2CH_2CO_2CH_2CH_3$, —$CO_2CH_3$, —$CO_2CH_2CH_3$, —C(=O)$NH_2$, —$CONHCH_3$, —C(=O)$N(CH_3)_2$, cyclopropyl, cyclobutyl, cyclopentyl, cyclohexyl, azetidinyl, pyrrolidinyl, piperidinyl, or morpholinyl. In some embodiments, $R^c$ is hydrogen, —F, —Cl, —CN, —$CH_3$, —$CF_3$, —$OCH_3$, —$OCH_2CH_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, or —$OCH_2CH_2CH_2CO_2CH_2CH_3$. In some embodiments, $R^c$ is hydrogen, —CN, —$CH_3$, —$CF_3$, —$OCH_3$, —$OCF_3$, —$CO_2CH_3$, —C(=O)$NH_2$, —$CONHCH_3$, or —C(=O)N$(CH_3)_2$, or cyclopropyl. In some embodiments, $R^c$ is hydrogen, —CN, —$CH_3$, —$CF_3$, —$OCH_3$, —$OCF_3$, —$CO_2CH_3$, —C(=O)$NH_2$, —$CONHCH_3$, or —C(=O)$N(CH_3)_2$.

In some embodiments, the compound has the structure of Formula (VIa-1) or (VIb-1), or a pharmaceutically acceptable salt, or solvate thereof:

Formula (VIa-1)

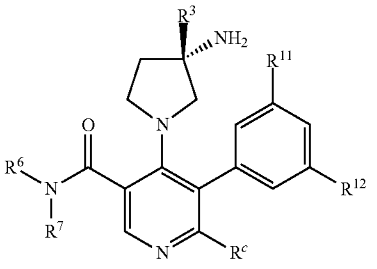

Formula (VIb-1)

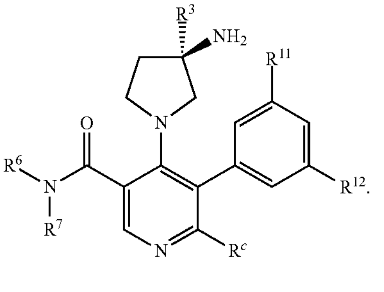

In some embodiments, $R^3$ is hydrogen or —$CH_3$; and $R^c$ is hydrogen, —CN, —$CH_3$, —$CF_3$, —$OCH_3$, —$OCF_3$, —$CO_2CH_3$, —C(=O)$NH_2$, —$CONHCH_3$, or —C(=O)N$(CH_3)_2$. In some embodiments, $R^{11}$ and $R^{12}$ are each independently hydrogen, halogen, $C_1$-$C_6$alkyl, $C_1$-$C_6$fluoroalkyl, —CN, or —$OR^9$. In some embodiments, $R^{11}$ and $R^{12}$ are each independently hydrogen, —F, —Cl, —CN, —$CH_3$, —$CF_3$, —$OCH_3$, —$OCF_3$, or —$OCHF_2$. In some embodiments, $R^{11}$ and $R^{12}$ are each independently halogen. In some embodiments, $R^{11}$ and $R^{12}$ are each independently —F or —Cl. In some embodiments, $R^{11}$ and $R^{12}$ are each —F.

In some embodiments, Ring A is bicyclic heteroaryl. In some embodiments, Ring A is 9- or 10-membered bicyclic heteroaryl. In some embodiments, Ring A is indolyl, isoindolyl, indazolyl, benzimidazolyl, azaindolyl, benzisoxazolyl, benzoxazolyl, benzoisoxazolyl, benzothiazolyl, benzoxadiazolyl, benzothiadiazolyl, quinolinyl, isoquinolinyl, quinoxalinyl, or quinazolinyl. In some embodiments, Ring A is benzimidazolyl, indazolyl, or benzoxadiazolyl. In some embodiments, Ring A is benzimidazolyl.

In some embodiments, the compound has the structure of Formula (VII), or a pharmaceutically acceptable salt, or solvate thereof:

Formula (VII)

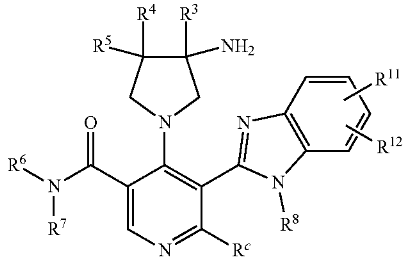

wherein:

$R^8$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl.

In some embodiments, the compound has the structure of Formula (VIIa) or (VIIb), or a pharmaceutically acceptable salt, or solvate thereof:

Formula (VIIa)

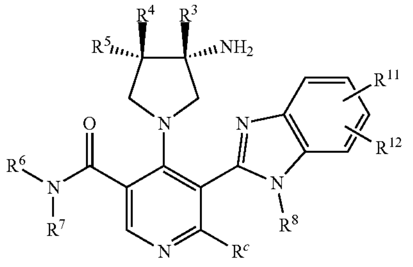

-continued

Formula (VIIb)

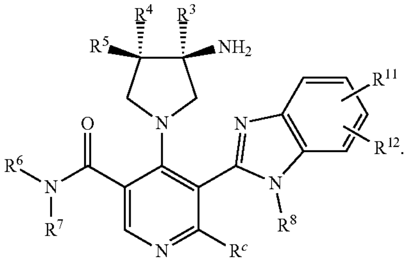

In some embodiments, $R^c$ is hydrogen, halogen, —CN, —$N(R^9)_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl; $R^f$ is -$L^1$-$R^g$; $L^1$ is absent or $C_1$-$C_6$alkylene; and $R^9$ is hydrogen, substituted or unsubstituted $C_3$-$C_6$cycloalkyl, substituted or unsubstituted phenyl, or —$CO_2R^9$. In some embodiments, $R^8$ is hydrogen, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, or —$C(CH_3)_3$; and $R^c$ is hydrogen, —F, —Cl, —CN, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)(CH_2CH_3)$, —$C(CH_3)_3$, —$CH_2F$, —$CHF_2$, —$CF_3$, —$CH_2CF_3$, —$OCH_3$, —$OCH_2CH_3$, —$OCF_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, —$OCH_2CH_2CH_2CO_2CH_2CH_3$, —$CO_2CH_3$, —$CO_2CH_2CH_3$, —C(═O)$NH_2$, —$CONHCH_3$, —C(═O)$N(CH_3)_2$, cyclopropyl, cyclobutyl, cyclopentyl, cyclohexyl, azetidinyl, pyrrolidinyl, piperidinyl, or morpholinyl. In some embodiments, $R^8$ is hydrogen, —$CH_3$, —$CH_2CH_3$; and $R^c$ is hydrogen, —F, —Cl, —CN, —$CH_3$, —$CF_3$, —$OCH_3$, —$OCH_2CH_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, or —$OCH_2CH_2CH_2CO_2CH_2CH_3$. In some embodiments, $R^c$ is hydrogen, —CN, —$CH_3$, —$CF_3$, —$OCH_3$, —$OCF_3$, —$CO_2CH_3$, —C(═O)$NH_2$, —$CONHCH_3$, or —C(═O)$N(CH_3)_2$, or cyclopropyl. In some embodiments, $R^c$ is hydrogen, —CN, —$CH_3$, —$CF_3$, —$OCH_3$, —$OCF_3$, —$CO_2CH_3$, —C(═O)$NH_2$, —$CONHCH_3$, or —C(═O)$N(CH_3)_2$.

In some embodiments, n is 0, 1, 2, or 3. In some embodiments, n is 0, 1, or 2. In some embodiments, n is 1, 2, or 3. In some embodiments, n is 2 or 3. In some embodiments, n is 0. In some embodiments, n is 1. In some embodiments, n is 2. In some embodiments, n is 3.

In some embodiments,

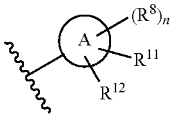

is

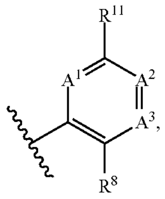

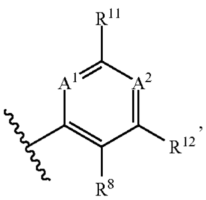

or

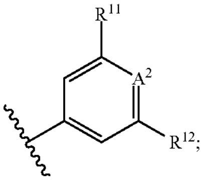

wherein $A^1$ and $A^2$ are each independently C—$R^8$ or N; and $A^3$ is C—$R^{12}$ or N. In some embodiments,

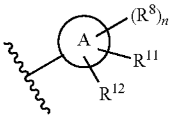

is

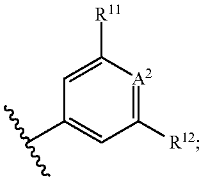

wherein $A^2$ is C—$R^8$ or N. In some embodiments,

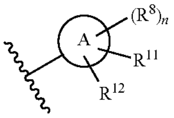

is

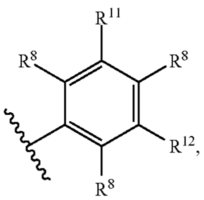

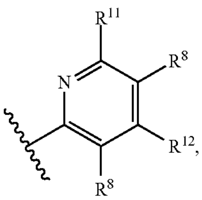

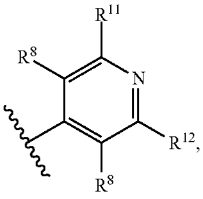

or

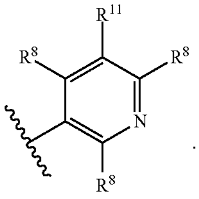

.

In some embodiments,

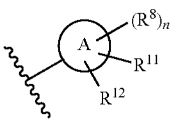

is

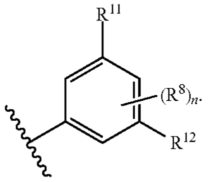

In some embodiments,

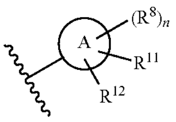

is

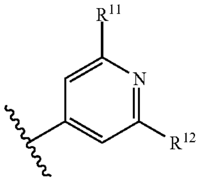

or

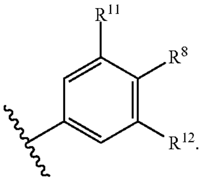

In some embodiments,

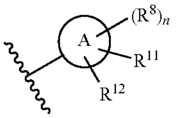

is

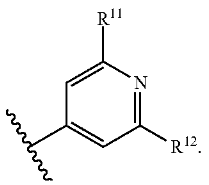

In some embodiments,

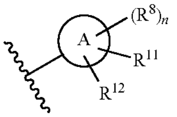

is

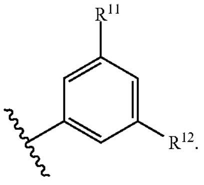

In some embodiments,

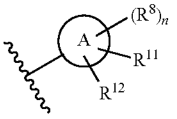

is

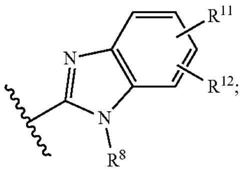

wherein $R^8$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl.

In some embodiments, $R^7$ is hydrogen, substituted or unsubstituted $C_1$-$C_6$alkyl, substituted or unsubstituted $C_1$-$C_6$fluoroalkyl, substituted or unsubstituted $C_3$-$C_4$ cycloalkyl, or substituted or unsubstituted $C_2$-$C_3$ heterocycloalkyl. In some embodiments, $R^7$ is hydrogen, substituted or unsubstituted $C_1$-$C_6$alkyl, substituted or unsubstituted $C_1$-$C_6$fluoroalkyl, substituted or unsubstituted $C_3$-$C_4$ cycloalkyl, or substituted or unsubstituted 3- or 4-membered heterocycloalkyl. In some embodiments, $R^7$ is hydrogen, substituted or unsubstituted $C_1$-$C_6$alkyl, or substituted or unsubstituted $C_1$-$C_6$fluoroalkyl. In some embodiments, $R^7$ is hydrogen or $C_1$-$C_6$alkyl. In some embodiments, $R^7$ is hydrogen or —$CH_3$. In some embodiments, $R^7$ is hydrogen. In some embodiments, $R^7$ is —$CH_3$.

In some embodiments, $R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or -$L^2$-$R^{6a}$; $L^2$ is absent, substituted or unsubstituted $C_1$-$C_8$alkylene, or —$CHR^{6b}$—; $R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl; $R^{6b}$ is hydrogen, $C_1$-$C_6$alkyl, $C_1$-$C_6$fluoroalkyl, or substituted or unsubstituted $C_3$-$C_6$cycloalkyl.

In some embodiments, $R^6$ is substituted or unsubstituted $C_1$-$C_8$alkyl, substituted or unsubstituted $C_1$-$C_8$fluoroalkyl, or substituted or unsubstituted $C_1$-$C_8$heteroalkyl. In some embodiments, $R^6$ is $C_1$-$C_8$alkyl, $C_1$-$C_8$fluoroalkyl, or substituted or unsubstituted $C_1$-$C_8$heteroalkyl. In some embodiments, $R^6$ is $C_1$-$C_6$alkyl, $C_1$-$C_6$fluoroalkyl, or substituted or unsubstituted $C_1$-$C_6$heteroalkyl. In some embodiments, $R^6$ is $C_1$-$C_6$alkyl, $C_1$-$C_6$fluoroalkyl, or $C_1$-$C_6$heteroalkyl. In some embodiments, $R^6$ is substituted or unsubstituted $C_1$-$C_8$alkyl, or substituted or unsubstituted $C_1$-$C_8$fluoroalkyl. In some embodiments, $R^6$ is substituted or unsubstituted $C_1$-$C_6$alkyl, or substituted or unsubstituted $C_1$-$C_6$fluoroalkyl. In some embodiments, $R^6$ is $C_1$-$C_6$alkyl or $C_1$-$C_6$fluoroalkyl. In some embodiments, $R^6$ is $C_1$-$C_6$alkyl. In some embodiments, $R^6$ is $C_1$-$C_6$fluoroalkyl. In some embodiments, $R^6$ is $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)(CH_2CH_3)$, $—CH(CH_2CH_3)(CH_2CH_3)$, $—CH(CH_2CH_2CH_3)(CH_2CH_3)$, $—C(CH_3)(CHCH_3)_2$, $—C(CH_3)_3$, $—CH_2F$, $—CHF_2$, $—CF_3$, $—CH_2CF_3$, $—CH(CF_3)(CH_3)$, $—CH(CF_3)(CH_2CH_3)$, $—CH_2CF_2CH_3$, or $—CH(CH_3)(CH_2CF_3)$. In some embodiments, $R^6$ is $—CH_3$, $—CH_2CH_3$, $—CH_2CH_2CH_3$, $—CH(CH_3)_2$, $—CH_2CH(CH_3)_2$, $—CH(CH_3)(CH_2CH_3)$, $—CH(CH_2CH_3)(CH_2CH_3)$, $—CH_2CF_3$, $—CH(CF_3)(CH_3)$, or $—CH(CF_3)(CH_2CH_3)$.

In some embodiments, $R^6$ is $-L^2-R^{6a}$.

In some embodiments, $L^2$ is absent, substituted or unsubstituted $C_1$-$C_8$alkylene, or $—CHR^{6b}—$. In some embodiments, $L^2$ is absent, substituted or unsubstituted $C_1$-$C_6$alkylene, or $—CHR^{6b}—$. In some embodiments, $L^2$ is absent, $C_1$-$C_6$alkylene, or $—CHR^{6b}—$. In some embodiments, $L^2$ is absent, $C_1$-$C_4$alkylene, or $—CHR^{6b}—$. In some embodiments, $L^2$ is absent, $—CH_2—$, $—CH_2CH_2—$, $—CH_2CH_2CH_2—$, or $—CHR^{6b}—$. In some embodiments, $L^2$ is $—CH_2—$, $—CH_2CH_2—$, $—CH_2CH_2CH_2—$, or $—CHR^{6b}—$. In some embodiments, $L^2$ is $—CH_2—$ or $—CHR^{6b}—$. In some embodiments, $L^2$ is $—CH_2—$, $—CH(CH_3)—$ or $—CH(CF_3)—$.

In some embodiments, $R^{6b}$ is hydrogen, $C_1$-$C_6$alkyl, $C_1$-$C_6$fluoroalkyl, or substituted or unsubstituted $C_3$-$C_6$cycloalkyl. In some embodiments, $R^{6b}$ is hydrogen, $C_1$-$C_6$alkyl, $C_1$-$C_6$fluoroalkyl, or substituted or unsubstituted $C_3$-$C_4$cycloalkyl. In some embodiments, $R^{6b}$ is hydrogen, $C_1$-$C_6$alkyl, $C_1$-$C_6$fluoroalkyl, or $C_3$-$C_4$cycloalkyl. In some embodiments, $R^{6b}$ is hydrogen, $C_1$-$C_4$alkyl, $C_1$-$C_4$fluoroalkyl, or $C_3$-$C_4$cycloalkyl. In some embodiments, $R^{6b}$ is hydrogen, $—CH_3$, $—CH_2CH_3$, $—CH_2CH_2CH_3$, $—CH(CH_3)_2$, $—CHF_2$, $—CH_2F$, $—CF_3$, cyclopropyl, or cyclobutyl. In some embodiments, $R^{6b}$ is hydrogen, $—CH_3$, $—CHF_2$, $—CF_3$, cyclopropyl, or cyclobutyl. In some embodiments, $R^{6b}$ is hydrogen, $—CH_3$, $—CF_3$, or cyclopropyl. In some embodiments, $R^{6b}$ is hydrogen, $—CH_3$, or $—CF_3$.

In some embodiments, $R^{6a}$ is substituted or unsubstituted monocyclic $C_3$-$C_8$cycloalkyl, substituted or unsubstituted polycyclic $C_5$-$C_{10}$cycloalkyl, substituted or unsubstituted phenyl, substituted or unsubstituted indanyl, substituted or unsubstituted tetrahydronaphthyl, substituted or unsubstituted naphthyl, substituted or unsubstituted monocyclic $C_2$-$C_5$heterocycloalkyl, substituted or unsubstituted polycyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl. In some embodiments, $R^{6a}$ is substituted or unsubstituted monocyclic $C_3$-$C_6$cycloalkyl, substituted or unsubstituted bridged $C_5$-$C_{10}$cycloalkyl, substituted or unsubstituted spirocyclic $C_5$-$C_{10}$cycloalkyl, substituted or unsubstituted adamantyl, substituted or unsubstituted phenyl, substituted or unsubstituted indanyl, substituted or unsubstituted tetrahydronaphthyl, or substituted or unsubstituted naphthyl. In some embodiments, $R^{6a}$ is substituted or unsubstituted monocyclic $C_2$-$C_5$heterocycloalkyl, substituted or unsubstituted bridged $C_5$-$C_{10}$heterocycloalkyl, substituted or unsubstituted spirocyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl.

In some embodiments, $R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl. In some embodiments, $R^{6a}$ is substituted or unsubstituted monocyclic 3- or 4-membered monocyclic cycloalkyl, 3- or 4-membered monocyclic heterocycloalkyl, substituted or unsubstituted monocyclic or bicyclic $C_5$-$C_{10}$cycloalkyl, or substituted or unsubstituted 5- to 10-membered heteroaryl.

In some embodiments, $R^{6a}$ is substituted or unsubstituted $C_3$-$C_4$cycloalkyl, or substituted or unsubstituted 3- or 4-membered $C_2$-$C_3$heterocycloalkyl. In some embodiments, $R^{6a}$ is substituted or unsubstituted cyclopropyl, substituted or unsubstituted cyclobutyl, substituted or unsubstituted azetidinyl, or substituted or unsubstituted oxetanyl. In some embodiments, $R^{6a}$ is substituted or unsubstituted $C_3$-$C_4$cycloalkyl. In some embodiments, $R^{6a}$ is substituted or unsubstituted cyclopropyl or substituted or unsubstituted cyclobutyl. In some embodiments, $R^{6a}$ is substituted or unsubstituted cyclopropyl. In some embodiments, $R^{6a}$ is substituted or unsubstituted cyclobutyl.

In some embodiments, $L^2$ is absent, substituted or unsubstituted $C_1$-$C_8$alkylene, or $—CHR^{6b}—$; $R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl; and $R^{6b}$ is hydrogen, $C_1$-$C_6$alkyl, $C_1$-$C_6$fluoroalkyl, or substituted or unsubstituted $C_3$-$C_6$cycloalkyl. In some embodiments, $L^2$ is absent, $C_1$-$C_6$alkylene, or $—CHR^{6b}—$; $R^{6a}$ is substituted or unsubstituted monocyclic $C_3$-$C_8$cycloalkyl, substituted or unsubstituted polycyclic $C_5$-$C_{10}$cycloalkyl, substituted or unsubstituted phenyl, substituted or unsubstituted indanyl, substituted or unsubstituted tetrahydronaphthyl, substituted or unsubstituted naphthyl, substituted or unsubstituted monocyclic $C_2$-$C_5$heterocycloalkyl, substituted or unsubstituted polycyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl; and $R^{6b}$ is hydrogen, $C_1$-$C_6$alkyl, $C_1$-$C_6$fluoroalkyl, or substituted or unsubstituted $C_3$-$C_6$cycloalkyl.

In some embodiments, $L^2$ is absent, $C_1$-$C_4$alkylene, or $—CHR^{6b}—$; and $R^{6b}$ is hydrogen, $C_1$-$C_4$alkyl, $C_1$-$C_4$fluoroalkyl, or substituted or unsubstituted $C_3$-$C_6$cycloalkyl. In some embodiments, $R^{6a}$ is substituted or unsubstituted monocyclic $C_3$-$C_6$cycloalkyl, substituted or unsubstituted bridged $C_5$-$C_{10}$cycloalkyl, substituted or unsubstituted spirocyclic $C_5$-$C_{10}$cycloalkyl, substituted or unsubstituted adamantyl, substituted or unsubstituted phenyl, substituted or unsubstituted indanyl, substituted or unsubstituted tetrahydronaphthyl, or substituted or unsubstituted naphthyl. In some embodiments, $R^{6a}$ is substituted or unsubstituted monocyclic $C_2$-$C_5$heterocycloalkyl, substituted or unsubstituted bridged $C_5$-$C_{10}$heterocycloalkyl, substituted or unsubstituted spirocyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl.

In some embodiments, $R^{6a}$ is substituted or unsubstituted $C_3$-$C_4$cycloalkyl, or substituted or unsubstituted 3- or 4-membered $C_2$-$C_3$heterocycloalkyl; and $R^{6b}$ is hydrogen, $C_1$-$C_6$alkyl, $C_1$-$C_6$fluoroalkyl, or substituted or unsubstituted $C_3$-$C_4$cycloalkyl. In some embodiments, $L^2$ is absent, —$CH_2$—, —$CH_2CH_2$—, —$CH_2CH_2CH_2$—, or —$CHR^{6b}$—; $R^{6a}$ is substituted or unsubstituted cyclopropyl, substituted or unsubstituted cyclobutyl, substituted or unsubstituted azetidinyl, or substituted or unsubstituted oxetanyl; and $R^{6b}$ is hydrogen, —$CH_3$, —$CH_2CH_3$, —$CH_2CH_2CH_3$, —$CH(CH_3)_2$, —$CHF_2$, —$CH_2F$, —$CF_3$, cyclopropyl, or cyclobutyl.

In some embodiments, $R^6$ and $R^7$ are taken together with the nitrogen to which they are attached to form a substituted or unsubstituted N-containing heterocycle. In some embodiments, $R^6$ and $R^7$ are taken together with the nitrogen to which they are attached to form a substituted or unsubstituted N-containing heterocycle that is monocyclic, bicyclic, or polycyclic. In some embodiments, $R^6$ and $R^7$ are taken together with the nitrogen to which they are attached to form a substituted or unsubstituted N-containing heterocycloalkyl. In some embodiments, $R^6$ and $R^7$ are taken together with the nitrogen to which they are attached to form a substituted or unsubstituted monocyclic N-containing heterocycloalkyl or a substituted or unsubstituted polycyclic N-containing heterocycloalkyl. In some embodiments, $R^6$ and $R^7$ are taken together with the nitrogen to which they are attached to form a substituted or unsubstituted monocyclic N-containing heterocycloalkyl containing 1-2 N atoms, 0-2 O atoms and 0-1 S. In some embodiments, $R^6$ and $R^7$ are taken together with the nitrogen to which they are attached to form a substituted or unsubstituted bicyclic N-containing $C_5$-$C_{10}$heterocycloalkyl, wherein bicyclic N-containing $C_5$-$C_{10}$heterocycloalkyl is a fused bicyclic $C_5$-$C_{10}$heterocycloalkyl, bridged bicyclic $C_5$-$C_{10}$heterocycloalkyl, or spiro bicyclic $C_5$-$C_{10}$heterocycloalkyl.

In some embodiments, $R^7$ is hydrogen, substituted or unsubstituted $C_1$-$C_6$alkyl, or substituted or unsubstituted $C_1$-$C_6$fluoroalkyl; and $R^6$ is substituted or unsubstituted $C_1$-$C_6$alkyl, substituted or unsubstituted $C_1$-$C_8$fluoroalkyl, substituted or unsubstituted $C_1$-$C_8$heteroalkyl, or -$L^2$-$R^{6a}$.

$L^2$ is absent, substituted or unsubstituted $C_1$-$C_8$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

or $R^6$ and $R^7$ are taken together with the nitrogen to which they are attached to form a substituted or unsubstituted N-containing heterocycloalkyl.

In some embodiments,

X is N or CH;

Y is N or CH;

Z is N or C—$R^c$.

$R^c$ is hydrogen, halogen, —CN, —$N(R^9)_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl;

$R^f$ is -$L^1$-$R^g$;

$L^1$ is absent, $C_1$-$C_6$alkylene, or $C_1$-$C_6$fluoroalkylene;

$R^g$ is hydrogen, substituted or unsubstituted $C_3$-$C_6$cycloalkyl, substituted or unsubstituted phenyl, —$CO_2R^9$, or —C(═O)$N(R^9)_2$;

$R^1$ is hydrogen;

$R^2$ is hydrogen or $C_1$-$C_6$alkyl;

$R^3$ is hydrogen, $C_1$-$C_6$alkyl, or $C_1$-$C_6$fluoroalkyl;

$R^4$ is hydrogen, halogen, $C_1$-$C_6$alkyl, or $C_1$-$C_6$fluoroalkyl;

$R^5$ is hydrogen, halogen, $C_1$-$C_6$alkyl, or $C_1$-$C_6$fluoroalkyl;

$R^6$ is $C_1$-$C_8$alkyl, $C_1$-$C_8$fluoroalkyl, or -$L^2$-$R^{6a}$.

$L^2$ is absent, $C_1$-$C_6$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

$R^7$ is hydrogen or $C_1$-$C_6$alkyl;

or $R^6$ and $R^7$ are taken together with the nitrogen to which they are attached to form a substituted or unsubstituted heterocycle.

In some embodiments, X is N or CH;

Y is N or CH;

Z is N or C—$R^c$.

$R^c$ is hydrogen, —CN, —$CH_3$, —$CF_3$, —$OCH_3$, —$OCF_3$, —$CO_2CH_3$, —C(═O)$NH_2$, —$CONHCH_3$, or —C(═O)$N(CH_3)_2$;

$R^1$ is hydrogen;

$R^2$ is hydrogen;

$R^3$ is hydrogen, —$CH_3$, —$CH_2OH$, —$CH_2OCH_3$, —$CH_2CH_2F$, —$CH_2CHF_2$, or —$CH_2CF_3$;

$R^4$ is hydrogen or F;

$R^5$ is hydrogen or F;

$R^6$ is $C_1$-$C_6$alkyl, $C_1$-$C_6$fluoroalkyl, or -$L^2$-$R^{6a}$.

$L^2$ is absent, $C_1$-$C_6$alkylene or —$CHR^{6b}$—;

$R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl;

$R^{6b}$ is hydrogen, $C_1$-$C_4$alkyl, $C_1$-$C_4$fluoroalkyl, or substituted or unsubstituted monocyclic $C_3$-$C_4$cycloalkyl;

$R^7$ is hydrogen or $C_1$-$C_6$alkyl;

or $R^6$ and $R^7$ are taken together with the nitrogen to which they are attached to form a substituted or unsubstituted heterocycle.

In some embodiments, the compound has the structure of Formula (VIII), or a pharmaceutically acceptable salt, or solvate thereof:

Formula (VIII)

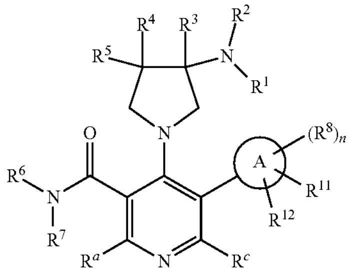

wherein:

Ring A is phenyl or pyridinyl;

$R^a$ and $R^c$ are each independently hydrogen, halogen, —CN, —$N(R^9)_2$, —$OR^e$, —$CO_2R^9$, —C(=O)$N(R^9)_2$, $C_1$-$C_6$alkyl, $C_1$-$C_6$fluoroalkyl, $C_1$-$C_6$fluoroalkoxy, substituted or unsubstituted monocyclic $C_3$-$C_6$cycloalkyl, or substituted or unsubstituted monocyclic $C_2$-$C_5$heterocycloalkyl;

$R^f$ is -$L^1$-$R^g$;

$L^1$ is absent, or $C_1$-$C_6$alkylene;

$R^g$ is hydrogen, substituted or unsubstituted $C_3$-$C_6$cycloalkyl, substituted or unsubstituted phenyl, —$CO_2R^9$, or —C(=O)$N(R^9)_2$, or substituted or unsubstituted monocyclic $C_2$-$C_5$heterocycloalkyl;

$R^1$ is hydrogen;

$R^2$ is hydrogen or $C_1$-$C_6$alkyl;

$R^3$ is hydrogen, $C_1$-$C_4$alkyl, $C_1$-$C_4$fluoroalkyl or $C_1$-$C_4$heteroalkyl;

$R^4$ is hydrogen, halogen, $C_1$-$C_4$alkyl, or $C_1$-$C_4$fluoroalkyl;

$R^5$ is hydrogen, halogen, $C_1$-$C_4$alkyl, or $C_1$-$C_4$fluoroalkyl;

$R^6$ is $C_1$-$C_6$alkyl, $C_1$-$C_6$fluoroalkyl, or -$L^2$-$R^{6a}$.

$L^2$ is absent, $C_1$-$C_6$alkylene or —$CHR^{6b}$—;

$R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl;

$R^{6b}$ is hydrogen, $C_1$-$C_4$alkyl, $C_1$-$C_4$fluoroalkyl, or substituted or unsubstituted monocyclic $C_3$-$C_4$cycloalkyl;

$R^7$ is hydrogen or $C_1$-$C_6$alkyl;

each $R^8$ is independently hydrogen, halogen, $C_1$-$C_6$alkyl, or $C_1$-$C_6$fluoroalkyl;

$R^{11}$ and $R^{12}$ are each independently hydrogen, halogen, $C_1$-$C_6$alkyl, $C_1$-$C_6$fluoroalkyl, —CN, —$OR^9$, —$CO_2R^9$, —C(=O)$N(R^9)_2$, —$N(R^9)_2$, or —$NR^9C$(=O)$R^{10}$, or substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl;

each $R^9$ is independently hydrogen, substituted or unsubstituted $C_1$-$C_6$alkyl, or substituted or unsubstituted $C_1$-$C_6$fluoroalkyl;

or two $R^9$ on the same N atom are taken together with the N atom to which they are attached to form a substituted or unsubstituted N-containing heterocycle;

each $R^{10}$ is independently substituted or unsubstituted $C_1$-$C_6$alkyl, or substituted or unsubstituted $C_1$-$C_6$fluoroalkyl; and n is 0-3.

In some embodiments, the compound has the structure of Formula (VIIIa) or (VIIIb), or a pharmaceutically acceptable salt, or solvate thereof.

Formula (VIIIa)

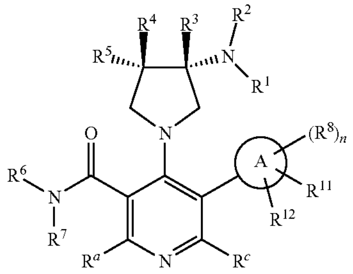

Formula (VIIIb)

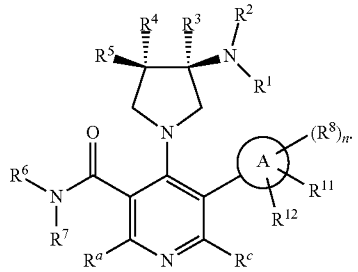

In some embodiments, the compound has the structure of Formula (VIIIa-1) or (VIIIb-1), or a pharmaceutically acceptable salt, or solvate thereof:

Formula (VIIIa-1)

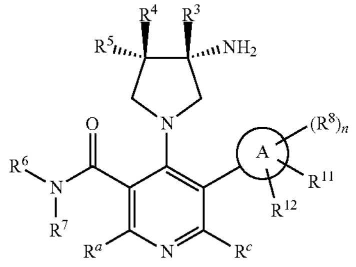

Formula (VIIIb-1)

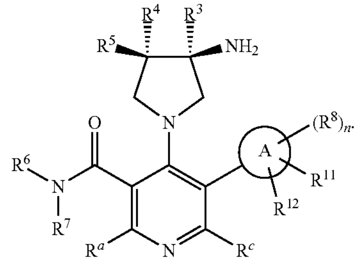

In some embodiments, $R^3$ is hydrogen or —$CH_3$; $R^4$ and $R^5$ are each hydrogen; each $R^8$ is independently hydrogen or halogen; and $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$.

In some embodiments, $R^6$ is $C_1$-$C_6$alkyl, $C_1$-$C_6$fluoroalkyl, or -$L^2$-$R^{6a}$; $L^2$ is absent, $C_1$-$C_6$alkylene or —$CHR^{6b}$—; $R^{6a}$ is substituted or unsubstituted monocyclic 3-4 membered $C_3$-$C_4$cycloalkyl, substituted or unsubstituted monocyclic or bicyclic 5-10 membered $C_5$-$C_{10}$cycloalkyl, substituted or unsubstituted 6-10 membered $C_6$-$C_{10}$aryl, substituted or unsubstituted monocyclic 3-4 membered $C_2$-$C_3$heterocycloalkyl, substituted or unsubstituted monocyclic or bicyclic 5-10 membered $C_4$-$C_{10}$heterocycloalkyl, or substituted or unsubstituted 5-10 membered $C_1$-$C_9$heteroaryl; $R^{6b}$ is hydrogen, $C_1$-$C_4$alkyl, $C_1$-$C_4$fluoroalkyl, or substituted or unsubstituted monocyclic $C_3$-$C_4$cycloalkyl; $R^7$ is hydrogen or $C_1$-$C_6$alkyl.

In some embodiments, $R^6$ is $C_1$-$C_6$alkyl, $C_1$-$C_6$fluoroalkyl, or -$L^2$-$R^{6a}$; $L^2$ is absent, $C_1$-$C_4$alkylene or —$CHR^{6b}$—; $R^{6a}$ is substituted or unsubstituted cyclopropyl, substituted or unsubstituted cyclobutyl, substituted or unsubstituted azetidinyl, substituted or unsubstituted aziridinyl, substituted or unsubstituted oxetanyl, or substituted or unsubstituted theitanyl; $R^{6b}$ is hydrogen, $C_1$-$C_4$alkyl, $C_1$-$C_4$fluoroalkyl, or substituted or unsubstituted monocyclic $C_3$-$C_4$cycloalkyl; $R^7$ is hydrogen or $C_1$-$C_6$alkyl.

In some embodiments, the compound has the structure of Formula (IX), or a pharmaceutically acceptable salt, or solvate thereof:

Formula (IX)

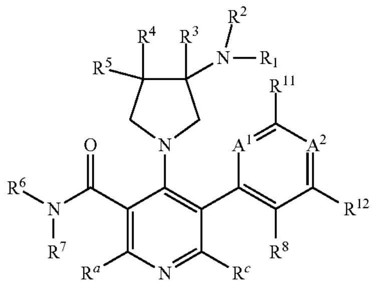

wherein:

$A^1$ is C—$R^8$; and $A^2$ is C—$R^8$; or $A^1$ is N; and $A^2$ is C—$R^8$; or $A^1$ is C—$R^8$; and $A^2$ is N;

$R^a$ and $R^c$ are each independently hydrogen, halogen, —CN, —$N(R^9)_2$, —OR, —$CO_2R^9$, —C(═O)$N(R^9)_2$, $C_1$-$C_6$alkyl, $C_1$-$C_6$fluoroalkyl, $C_1$-$C_6$fluoroalkoxy, substituted or unsubstituted monocyclic $C_3$-$C_6$cycloalkyl, or substituted or unsubstituted monocyclic $C_2$-$C_5$heterocycloalkyl;

$R^f$ is -$L^1$-$R^g$;

$L^1$ is absent, or $C_1$-$C_6$alkylene;

$R^9$ is hydrogen, substituted or unsubstituted $C_3$-$C_6$cycloalkyl, substituted or unsubstituted phenyl, —$CO_2R^9$, or —C(═O)$N(R^9)_2$, or substituted or unsubstituted monocyclic $C_2$-$C_5$heterocycloalkyl;

$R^3$ is hydrogen, $C_1$-$C_4$alkyl, $C_1$-$C_4$fluoroalkyl or $C_1$-$C_4$heteroalkyl;

$R^4$ is hydrogen, halogen, $C_1$-$C_4$alkyl, or $C_1$-$C_4$fluoroalkyl;

$R^5$ is hydrogen, halogen, $C_1$-$C_4$alkyl, or $C_1$-$C_4$fluoroalkyl;

$R^6$ is $C_1$-$C_6$alkyl, $C_1$-$C_6$fluoroalkyl, or -$L^2$-$R^{6a}$.

$L^2$ is absent, $C_1$-$C_6$alkylene or —$CHR^{6b}$—;

$R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl;

$R^{6b}$ is hydrogen, $C_1$-$C_4$alkyl, $C_1$-$C_4$fluoroalkyl, or substituted or unsubstituted monocyclic $C_3$-$C_4$cycloalkyl;

$R^7$ is hydrogen or $C_1$-$C_6$alkyl;

each $R^8$ is independently hydrogen, halogen, $C_1$-$C_6$alkyl, or $C_1$-$C_6$fluoroalkyl;

$R^{11}$ and $R^{12}$ are each independently hydrogen, halogen, $C_1$-$C_6$alkyl, $C_1$-$C_6$fluoroalkyl, —CN, —$OR^9$, —$CO_2R^9$, —C(═O)$N(R^9)_2$, —$N(R^9)_2$, or —$NR^9C$(═O)$R^{10}$, or substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl;

each $R^9$ is independently hydrogen, substituted or unsubstituted $C_1$-$C_6$alkyl, or substituted or unsubstituted $C_1$-$C_6$fluoroalkyl;

or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl, or substituted or unsubstituted $C_1$-$C_6$fluoroalkyl.

In some embodiments, the compound has the structure of Formula (IXa) or (IXb), or a pharmaceutically acceptable salt, or solvate thereof:

Formula (IXa)

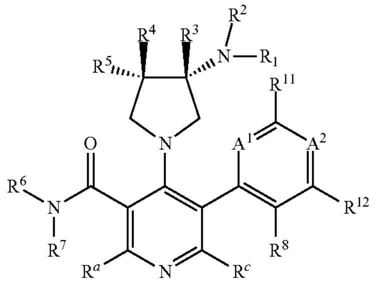

Formula (IXb)

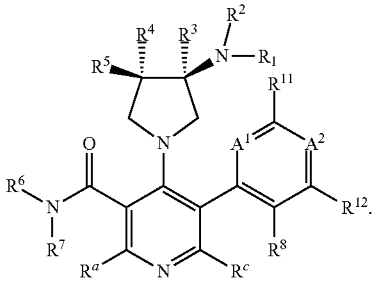

In some embodiments, the compound has the structure of Formula (VIIIa-1) or (VIIIb-1), or a pharmaceutically acceptable salt, or solvate thereof:

Formula (IXa-1)

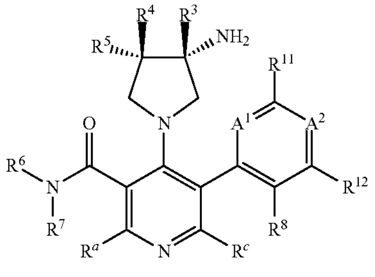

-continued

Formula (IXb-1)

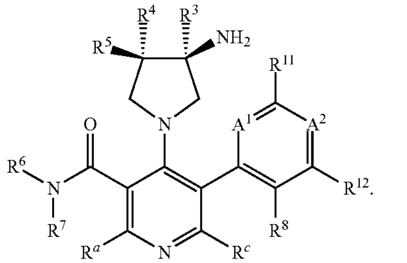

In some embodiments, $R^3$ is hydrogen or —$CH_3$; $R^4$ and $R^5$ are each hydrogen; each $R^8$ is independently hydrogen or halogen; and $R^{11}$ and $R^{12}$ are each independently hydrogen, halogen, substituted or unsubstituted $C_1$-$C_6$alkyl, substituted or unsubstituted $C_1$-$C_6$fluoroalkyl, —CN, —$OR^9$.

In some embodiments, $R^6$ is $C_1$-$C_6$alkyl, $C_1$-$C_6$fluoroalkyl, or -$L^2$-$R^{6a}$; $L^2$ is absent, $C_1$-$C_6$alkylene or —$CHR^{6b}$—; $R^{6a}$ is substituted or unsubstituted monocyclic 3-4 membered $C_3$-$C_4$cycloalkyl, substituted or unsubstituted monocyclic or bicyclic 5-10 membered $C_5$-$C_{10}$cycloalkyl, substituted or unsubstituted 6-10 membered $C_6$-$C_{10}$aryl, substituted or unsubstituted monocyclic 3-4 membered $C_2$-$C_3$heterocycloalkyl, substituted or unsubstituted monocyclic or bicyclic 5-10 membered $C_4$-$C_{10}$heterocycloalkyl, or substituted or unsubstituted 5-10 membered $C_1$-$C_9$heteroaryl; $R^{6b}$ is hydrogen, $C_1$-$C_4$alkyl, $C_1$-$C_4$fluoroalkyl, or substituted or unsubstituted monocyclic $C_3$-$C_4$cycloalkyl; $R^7$ is hydrogen or $C_1$-$C_6$alkyl.

In some embodiments, $R^6$ is $C_1$-$C_6$alkyl, $C_1$-$C_6$fluoroalkyl, or -$L^2$-$R^{6a}$; $L^2$ is absent, $C_1$-$C_4$alkylene or —$CHR^{6b}$—; $R^{6a}$ is substituted or unsubstituted cyclopropyl, substituted or unsubstituted cyclobutyl, substituted or unsubstituted azetidinyl, substituted or unsubstituted aziridinyl, substituted or unsubstituted oxetanyl, or substituted or unsubstituted theitanyl; $R^{6b}$ is hydrogen, $C_1$-$C_4$alkyl, $C_1$-$C_4$fluoroalkyl, or substituted or unsubstituted monocyclic $C_3$-$C_4$cycloalkyl; $R^7$ is hydrogen or $C_1$-$C_6$alkyl.

In some embodiments, each $R^9$ is independently hydrogen, substituted or unsubstituted $C_1$-$C_6$alkyl, substituted or unsubstituted $C_1$-$C_6$fluoroalkyl, substituted or unsubstituted $C_3$-$C_7$cycloalkyl, or substituted or unsubstituted monocyclic 3- to 8-membered heterocycloalkyl; or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl, substituted or unsubstituted $C_1$-$C_6$fluoroalkyl, substituted or unsubstituted $C_3$-$C_7$cycloalkyl, or substituted or unsubstituted monocyclic 3- to 8-membered heterocycloalkyl. In some embodiments, each $R^9$ is independently hydrogen, substituted or unsubstituted $C_1$-$C_6$alkyl, or substituted or unsubstituted $C_1$-$C_6$fluoroalkyl; or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl or substituted or unsubstituted $C_1$-$C_6$fluoroalkyl. In some embodiments, each $R^9$ is independently hydrogen, $C_1$-$C_6$alkyl, or $C_1$-$C_6$fluoroalkyl; or two $R^9$ on the same N atom are taken together with the N atom to which they are attached to form a substituted or unsubstituted N-containing heterocycle; and each $R^{10}$ is independently $C_1$-$C_6$alkyl or $C_1$-$C_6$fluoroalkyl.

In one aspect, provided herein is a compound of Formula (A1), or a pharmaceutically acceptable salt, or pharmaceutically acceptable solvate thereof.

Formula (A1)

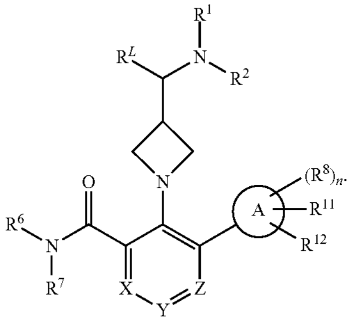

wherein:

Ring A is carbocycle or heterocycle;

X is N or C—$R^a$; Y is N or C—$R^b$; Z is N or C—$R^c$;

$R^L$ is hydrogen, substituted or unsubstituted $C_1$-$C_6$alkyl, or substituted or unsubstituted $C_1$-$C_6$fluoroalkyl;

$R^a$, $R^b$, and $R^c$ are each independently hydrogen, halogen, —CN, —$N(R^9)_2$, —$OR^e$, —$CO_2R^9$, —C(═O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$heteroalkyl, substituted or unsubstituted monocyclic carbocycle, or substituted or unsubstituted monocyclic heterocycle;

$R^f$ is -$L^1$-$R^g$;

$L^1$ is absent, $C_1$-$C_6$alkylene, $C_1$-$C_6$fluoroalkylene, or $C_1$-$C_6$heteroalkylene;

$R^9$ is hydrogen, substituted or unsubstituted $C_3$-$C_6$cycloalkyl, substituted or unsubstituted phenyl, —$CO_2R^9$, —C(═O)$N(R^9)_2$, or substituted or unsubstituted monocyclic heterocycle;

$R^1$ and $R^2$ are independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, or substituted or unsubstituted $C_3$-$C_5$heterocycloalkyl;

$R^3$ is hydrogen, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^4$ and $R^5$ are each independently hydrogen, halogen, —$OR^9$, —$N(R^9)_2$, —CN, —$CO_2R^9$, —C(═O)$N(R^9)_2$, substituted or unsubstituted $C_1$-$C_6$alkyl, substituted or unsubstituted $C_1$-$C_6$fluoroalkyl, substituted or unsubstituted $C_1$-$C_6$alkoxy, substituted or unsubstituted $C_1$-$C_6$fluoroalkoxy, or substituted or unsubstituted $C_1$-$C_6$heteroalkyl;

$R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or -$L^2$-$R^{6a}$.

$L^2$ is absent, substituted or unsubstituted $C_1$-$C_8$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

$R^7$ is hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_1$O cycloalkyl, substituted or unsubstituted $C_6$-$C_{10}$ aryl, substituted or unsubstituted $C_2$-$C_{10}$ heterocycloalkyl, or substituted or unsubstituted $C_1$-$C_9$ heteroaryl;

or $R^6$ and $R^7$ are taken together with the nitrogen to which they are attached to form a substituted or unsubstituted N-containing heterocycle;

each $R^8$, $R^{11}$, and $R^{12}$ is independently hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —C(═O)$R^{10}$, —$CO_2R^9$, —C(═O)N($R^9$)$_2$, —N($R^9$)$_2$, —$NR^9$C(═O)$R^{10}$, —$NR^9$C(═O)O$R^{10}$, —$NR^9$C(═O)N($R^9$)$_2$, —C($R^9$)═N—O$R^9$, —S$R^9$, —S(═O)$R^9$, —$SO_2R^9$, or —$SO_2$N($R^9$)$_2$;

or $R^{11}$ is taken together with an adjacent $R^8$ and the atoms connecting the $R^{11}$ and the adjacent $R^8$ to form a fused substituted or unsubstituted carbocycle, or a fused substituted or unsubstituted heterocycle;

each $R^9$ is independently hydrogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl;

or two $R^9$ on the same N atom are taken together with the N atom to which they are attached to form a substituted or unsubstituted N-containing heterocycle;

each $R^{10}$ is independently substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_7$cycloalkyl, substituted or unsubstituted monocyclic 3- to 8-membered heterocycloalkyl, substituted or unsubstituted phenyl, and substituted or unsubstituted monocyclic heteroaryl; and n is 0-3.

In some embodiments, $R^L$ is substituted or unsubstituted $C_1$-$C_6$alkyl, or substituted or unsubstituted $C_1$-$C_6$fluoroalkyl. In some embodiments, $R^L$ is $C_1$-$C_6$alkyl or $C_1$-$C_6$fluoroalkyl. In some embodiments, $R^L$ is $C_1$-$C_6$alkyl. In some embodiments, $R^L$ is —$CH_3$.

In some embodiments, $R^1$ and $R^2$ are independently hydrogen, substituted or unsubstituted $C_1$-$C_6$alkyl, substituted or unsubstituted $C_1$-$C_6$fluoroalkyl, or substituted or unsubstituted $C_3$-$C_6$cycloalkyl. In some embodiments, $R^1$ and $R^2$ are independently hydrogen or substituted or unsubstituted $C_1$-$C_6$alkyl. In some embodiments, $R^1$ and $R^2$ are independently hydrogen or $C_1$-$C_6$alkyl. In some embodiments, $R^1$ is hydrogen and $R^2$ is hydrogen, substituted or unsubstituted $C_1$-$C_6$alkyl, substituted or unsubstituted $C_1$-$C_6$fluoroalkyl, or substituted or unsubstituted $C_3$-$C_6$cycloalkyl. In some embodiments, $R^1$ is hydrogen and $R^2$ is hydrogen or substituted or unsubstituted $C_1$-$C_6$alkyl. $R^1$ is hydrogen and $R^2$ is hydrogen or $C_1$-$C_6$alkyl. In some embodiments, $R^1$ and $R^2$ are each hydrogen.

In some embodiments, $R^1$ is hydrogen; $R^2$ is hydrogen or substituted or unsubstituted $C_1$-$C_6$alkyl; and $R^L$ is substituted or unsubstituted $C_1$-$C_6$alkyl. In some embodiments, $R^1$ is hydrogen; $R^2$ is hydrogen; and $R^L$ is —$CH_3$.

In some embodiments, X, Y, Z, $R^a$, $R^b$, $R^c$ are as described for Formula (I).

In some embodiments, X is C—$R^a$; Y is N; and Z is C—$R^c$; or X is CH; Y is N; and Z is C—$R^c$; or X is C—$R^a$; Y is N; and Z is CH; or X is N; Y is C—$R^b$; and Z is C—$R^c$; or X is C—$R^a$; Y is C—R; and Z is N; or X is N; Y is N; and Z is C—$R^c$; or X is C—$R^a$; Y is N; and Z is N. In some embodiments, X is N or CH; Y is N or CH; and Z is N or C—$R^c$.

In some embodiments, $R^a$, $R^b$, and $R^c$ are each independently hydrogen, halogen, —CN, —N($R^9$)$_2$, —$OR^e$, $C_1$-$C_6$alkyl, $C_1$-$C_6$fluoroalkyl, $C_1$-$C_6$fluoroalkoxy, or substituted or unsubstituted $C_1$-$C_6$heteroalkyl; $R^f$ is -$L^1$-$R^g$; $L^1$ is absent or $C_1$-$C_6$alkylene; and $R^9$ is hydrogen, substituted or unsubstituted $C_3$-$C_6$cycloalkyl, substituted or unsubstituted phenyl, or —$CO_2R^9$. In some embodiments, $R^a$, $R^b$, and $R^c$ are each independently hydrogen, —CN, —$CH_3$, —$CF_3$, —$OCH_3$, —$OCF_3$, —$CO_2CH_3$, —C(═O)$NH_2$, —$CONHCH_3$, or —C(═O)N($CH_3$)$_2$, or cyclopropyl.

In some embodiments, Ring A, each $R^8$, $R^{11}$, $R^{12}$, and n are as described for Formula (I).

In some embodiments, Ring A is phenyl, monocyclic heteroaryl or bicyclic heteroaryl. In some embodiments, Ring A is phenyl or monocyclic heteroaryl. In some embodiments, Ring A is phenyl; or Ring A is pyridinyl; or Ring A is Ring A is pyrazolyl, thiazolyl, isoxazolyl, or pyrimidinyl. In some embodiments, Ring A is phenyl or pyridinyl. In some embodiments, Ring A is bicyclic heteroaryl. In some embodiments, Ring A is benzimidazolyl, indazolyl, or benzoxadiazolyl.

In some embodiments, each $R^8$ is independently hydrogen, halogen, substituted or unsubstituted $C_1$-$C_6$alkyl, substituted or unsubstituted $C_1$-$C_6$fluoroalkyl, substituted or unsubstituted monocyclic carbocycle, —CN, —$OR^9$, —$CO_2R^9$, —C(═O)N($R^9$)$_2$, —N($R^9$)$_2$, —$NR^9$C(═O)$R^{10}$, —$SO_2R^9$, or —$SO_2$N($R^9$)$_2$. In some embodiments, each $R^8$ is independently hydrogen, halogen, $C_1$-$C_6$alkyl, or $C_1$-$C_6$fluoroalkyl. In some embodiments, each $R^8$ is independently hydrogen or halogen.

In some embodiments, $R^{11}$ is halogen, substituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —C(═O)$R^{10}$, —$CO_2R^9$, —C(═O)N($R^9$)$_2$, —N($R^9$)$_2$, —$NR^9$C(═O)$R^{10}$, —$NR^9$C(═O)O$R^{10}$, —$NR^9$C(═O)N($R^9$)$_2$, —C($R^9$)═N—O$R^9$, —S$R^9$, —S(═O)$R^9$, —$SO_2R^9$, or —$SO_2$N($R^9$)$_2$. In some embodiments, $R^{11}$ is halogen, substituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —$CO_2R^9$, —C(═O)N($R^9$)$_2$, —N($R^9$)$_2$, —$NR^9$C(═O)$R^{10}$, —$NR^9$C(═O)O$R^{10}$, —$NR^9$C(═O)N($R^9$)$_2$, —C($R^9$)═N—O$R^9$, —S$R^9$, —S(═O)$R^9$, —$SO_2R^9$, or —$SO_2$N($R^9$)$_2$. In some embodiments, $R^{11}$ is halogen, substituted $C_1$-$C_6$alkyl, $C_1$-$C_6$fluoroalkyl, —CN, —$OR^9$, —$CO_2R^9$, —C(═O)N($R^9$)$_2$, —N($R^9$)$_2$, or —$NR^9$C(═O)$R^{10}$, substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl. In some embodiments, $R^{11}$ is halogen, substituted $C_1$-$C_6$alkyl, substituted or unsubstituted $C_1$-$C_6$fluoroalkyl, —CN, —$OR^9$, —$CO_2R^9$, —C(═O)N($R^9$)$_2$, —N($R^9$)$_2$, or —$NR^9$C(═O)$R^{10}$, or substituted or unsubstituted monocyclic carbocycle. In some embodiments, $R^{11}$ is halogen, substituted $C_1$-$C_6$alkyl, substituted or unsubstituted $C_1$-$C_6$fluoroalkyl, —CN, —$OR^9$, —$CO_2R^9$, —C(=O)N($R^9$)$_2$, —N($R^9$)$_2$, or —$NR^9$C(=O)$R^{10}$, or substituted or unsubstituted monocyclic $C_3$-$C_8$cycloalkyl. In some embodiments, $R^{11}$ is halogen, substituted $C_1$-$C_6$alkyl, substituted or unsubstituted $C_1$-$C_6$fluoroalkyl, —CN, —$OR^9$, or substituted or unsubstituted monocyclic cycloalkyl. In some embodiments, $R^{11}$ is halogen, substituted $C_1$-$C_6$alkyl, substituted or unsubstituted $C_1$-$C_6$fluoroalkyl, —CN, —$OR^9$, or substituted or unsubstituted monocyclic $C_3$-$C_8$cycloalkyl. In some embodiments, $R^{11}$ is halogen, substituted $C_1$-$C_6$alkyl, $C_1$-$C_6$fluoroalkyl, —CN, —$OR^9$, or substituted or unsubstituted monocyclic $C_3$-$C_8$cycloalkyl. In some embodiments, $R^{11}$ is halogen, substituted $C_1$-$C_6$alkyl, substituted or unsubstituted $C_1$-$C_6$fluoroalkyl, —CN, —$OR^9$. In some embodiments, $R^{11}$ is halogen, $C_1$-$C_6$fluoroalkyl, —CN, or —$OR^9$. In some embodiments, $R^{11}$ is —F, —Cl, —CN, —$CF_3$, —$OCH_3$, —$OCF_3$, or —$OCHF_2$. In some embodiments, $R^{11}$ is halogen. In some embodiments, $R^{11}$ is —F or —Cl. In some embodiments, $R^{11}$ is —F. In some embodiments, $R^{11}$ is —$C_1$.

In some embodiments, $R^{11}$ is taken together with an adjacent $R^8$ and the atoms connecting the $R^{11}$ and the adjacent $R^8$ to form a fused substituted or unsubstituted carbocycle, or a fused substituted or unsubstituted heterocycle. In some embodiments, $R^{11}$ is taken together with an adjacent $R^8$ and the atoms connecting the $R^{11}$ and the adjacent $R^8$ to form a fused substituted or unsubstituted $C_3$-$C_8$cycloalkyl, or a fused substituted or unsubstituted $C_2$-$C_5$heterocycloalkyl.

In some embodiments, $R^{12}$ is hydrogen, halogen, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted monocyclic carbocycle, substituted or unsubstituted monocyclic heterocycle, —CN, —$OR^9$, —$CO_2R^9$, —C(=O)N($R^9$)$_2$, —N($R^9$)$_2$, —$NR^9$C(=O)$R^{10}$, —$NR^9$C(=O)$OR^{10}$, —$NR^9$C(=O)N($R^9$)$_2$, —C($R^9$)=N—$OR^9$, —$SR^9$, —S(=O)$R^9$, —$SO_2R^9$, or —$SO_2$N($R^9$)$_2$.

In some embodiments, $R^{12}$ is hydrogen, halogen, $C_1$-$C_6$alkyl, $C_1$-$C_6$fluoroalkyl, —CN, —$OR^9$, —$CO_2R^9$, —C(=O)N($R^9$)$_2$, —N($R^9$)$_2$, or —$NR^9$C(=O)$R^{10}$, substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl. In some embodiments, $R^{12}$ is hydrogen, halogen, substituted or unsubstituted $C_1$-$C_6$alkyl, substituted or unsubstituted $C_1$-$C_6$fluoroalkyl, —CN, —$OR^9$, or substituted or unsubstituted monocyclic $C_3$-$C_8$cycloalkyl. In some embodiments, $R^{12}$ is hydrogen, halogen, $C_1$-$C_6$alkyl, $C_1$-$C_6$fluoroalkyl, —CN, or —$OR^9$. In some embodiments, $R^{12}$ is hydrogen, —F, —Cl, —CN, —$CH_3$, —$CF_3$, —$OCH_3$, —$OCF_3$, or —$OCHF_2$. In some embodiments, $R^{12}$ is hydrogen or halogen. In some embodiments, $R^{12}$ is hydrogen, —F, or —Cl.

In some embodiments, n is 0, 1, 2, or 3. In some embodiments, n is 0, 1, or 2. In some embodiments, n is 1, 2, or 3. In some embodiments, n is 2 or 3. In some embodiments, n is 0. In some embodiments, n is 1. In some embodiments, n is 2. In some embodiments, n is 3.

In some embodiments,

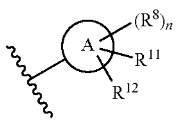

is

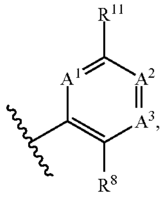

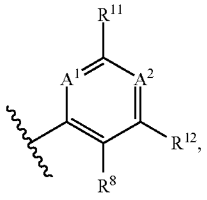

or

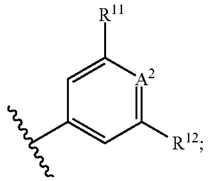

wherein $A^1$ and $A^2$ are each independently C—$R^8$ or N; and $A^3$ is C—$R^{12}$ or N. In some embodiments

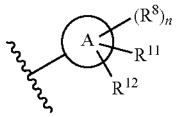

is

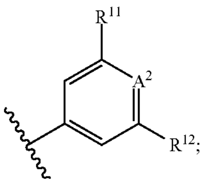

wherein $A^2$ is C—$R^8$ or N. In some embodiments,

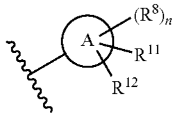

is

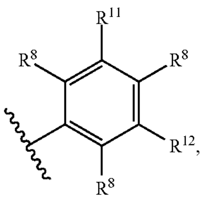

-continued

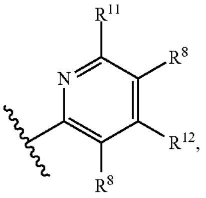

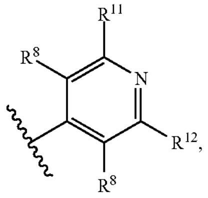

or

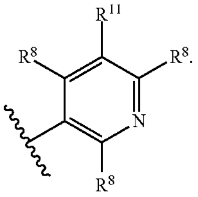

In some embodiments,

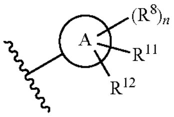

is

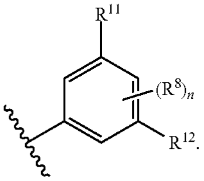

In some embodiments,

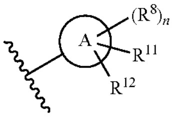

is

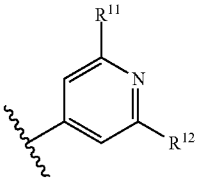

or

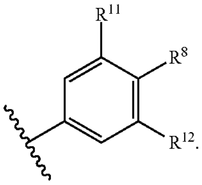

In some embodiments,

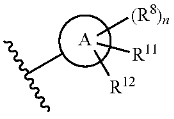

is

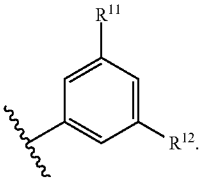

In some embodiments,

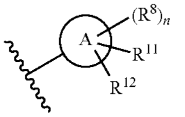

is

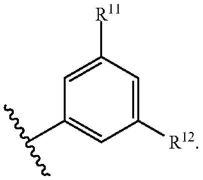

In some embodiments,

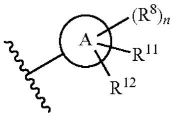

is

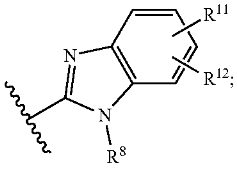

wherein $R^8$ is hydrogen, substituted or unsubstituted $C_1$-$C_6$alkyl, substituted or unsubstituted $C_1$-$C_6$fluoroalkyl, substituted or unsubstituted $C_3$-$C_6$cycloalkyl.

In some embodiments, $R^6$ and $R^7$ are as described for Formula (I).

In some embodiments, $R^7$ is hydrogen, substituted or unsubstituted $C_1$-$C_6$alkyl, substituted or unsubstituted $C_1$-$C_6$fluoroalkyl, substituted or unsubstituted $C_3$-$C_4$ cycloalkyl, or substituted or unsubstituted 3- or 4-membered heterocycloalkyl. In some embodiments, $R^7$ is hydrogen, substituted or unsubstituted $C_1$-$C_6$alkyl, or substituted or unsubstituted $C_1$-$C_6$fluoroalkyl. In some embodiments, $R^7$ is hydrogen or $C_1$-$C_6$alkyl.

In some embodiments, $R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or $-L^2-R^{6a}$;

$L^2$ is absent, substituted or unsubstituted $C_1$-$C_8$alkylene, or —$CHR^{6b}$—; $R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl; $R^{6b}$ is hydrogen, $C_1$-$C_6$alkyl, $C_1$-$C_6$fluoroalkyl, or substituted or unsubstituted $C_3$-$C_6$cycloalkyl.

In some embodiments, $R^6$ is substituted or unsubstituted $C_1$-$C_8$alkyl, substituted or unsubstituted $C_1$-$C_8$fluoroalkyl, or substituted or unsubstituted $C_1$-$C_8$heteroalkyl. In some embodiments, $R^6$ is $C_1$-$C_6$alkyl, $C_1$-$C_6$fluoroalkyl, or substituted or unsubstituted $C_1$-$C_6$heteroalkyl. In some embodiments, $R^6$ is substituted or unsubstituted $C_1$-$C_8$alkyl or substituted or unsubstituted $C_1$-$C_8$fluoroalkyl. In some embodiments, $R^6$ is substituted or unsubstituted $C_1$-$C_6$alkyl, or substituted or unsubstituted $C_1$-$C_6$fluoroalkyl. In some embodiments, $R^6$ is $C_1$-$C_6$alkyl or $C_1$-$C_6$fluoroalkyl.

In some embodiments, $R^6$ is -$L^2$-$R^{6a}$.

In some embodiments, $L^2$ is absent, substituted or unsubstituted $C_1$-$C_8$alkylene, or —$CHR^{6b}$—. In some embodiments, $L^2$ is absent, substituted or unsubstituted $C_1$-$C_6$alkylene, or —$CHR^{6b}$—. In some embodiments, $L^2$ is absent, $C_1$-$C_6$alkylene, or —$CHR^{6b}$—. In some embodiments, $L^2$ is absent, $C_1$-$C_4$alkylene, or —$CHR^{6b}$—. In some embodiments, $L^2$ is absent, —$CH_2$—, —$CH_2CH_2$—, —$CH_2CH_2CH_2$—, or —$CHR^{6b}$—. In some embodiments, $L^2$ is —$CH_2$—, —$CH_2CH_2$—, —$CH_2CH_2CH_2$—, or —$CHR^{6b}$—. In some embodiments, $L^2$ is —$CH_2$— or —$CHR^{6b}$—. In some embodiments, $L^2$ is —$CH_2$—, —$CH(CH_3)$— or —$CH(CF_3)$—.

In some embodiments, $R^{6b}$ is hydrogen, $C_1$-$C_6$alkyl, $C_1$-$C_6$fluoroalkyl, or substituted or unsubstituted $C_3$-$C_6$cycloalkyl. In some embodiments, $R^{6b}$ is hydrogen, $C_1$-$C_6$alkyl, $C_1$-$C_6$fluoroalkyl, or substituted or unsubstituted $C_3$-$C_4$cycloalkyl. In some embodiments, $R^{6b}$ is hydrogen, $C_1$-$C_6$alkyl, $C_1$-$C_6$fluoroalkyl, or $C_3$-$C_4$cycloalkyl. In some embodiments, $R^{6b}$ is hydrogen, $C_1$-$C_4$alkyl, $C_1$-$C_4$fluoroalkyl, or $C_3$-$C_4$cycloalkyl. In some embodiments, $R^{6b}$ is hydrogen, —$CH_3$, —$CH_2CH_3$, —$CH_2CH_2CH_3$, —$CH(CH_3)_2$, —$CHF_2$, —$CH_2F$, —$CF_3$, cyclopropyl, or cyclobutyl. In some embodiments, $R^{6b}$ is hydrogen, —$CH_3$, —$CHF_2$, —$CF_3$, cyclopropyl, or cyclobutyl. In some embodiments, $R^{6b}$ is hydrogen, —$CH_3$, —$CF_3$, or cyclopropyl. In some embodiments, $R^{6b}$ is hydrogen, —$CH_3$, or —$CF_3$.

In some embodiments, $R^{6a}$ is substituted or unsubstituted monocyclic $C_3$-$C_8$cycloalkyl, substituted or unsubstituted polycyclic $C_5$-$C_{10}$cycloalkyl, substituted or unsubstituted phenyl, substituted or unsubstituted indanyl, substituted or unsubstituted tetrahydronaphthyl, substituted or unsubstituted naphthyl, substituted or unsubstituted monocyclic $C_2$-$C_5$heterocycloalkyl, substituted or unsubstituted polycyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl. In some embodiments, $R^{6a}$ is substituted or unsubstituted monocyclic $C_3$-$C_6$cycloalkyl, substituted or unsubstituted bridged $C_5$-$C_{10}$cycloalkyl, substituted or unsubstituted spirocyclic $C_5$-$C_{10}$cycloalkyl, substituted or unsubstituted adamantyl, substituted or unsubstituted phenyl, substituted or unsubstituted indanyl, substituted or unsubstituted tetrahydronaphthyl, or substituted or unsubstituted naphthyl. In some embodiments, $R^{6a}$ is substituted or unsubstituted monocyclic $C_2$-$C_5$heterocycloalkyl, substituted or unsubstituted bridged $C_5$-$C_{10}$heterocycloalkyl, substituted or unsubstituted spirocyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl.

In some embodiments, $R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl. In some embodiments, $R^{6a}$ is substituted or unsubstituted monocyclic 3- or 4-membered monocyclic cycloalkyl, 3- or 4-membered monocyclic heterocycloalkyl, substituted or unsubstituted monocyclic or bicyclic $C_5$-$C_{10}$cycloalkyl, or substituted or unsubstituted 5- to 10-membered heteroaryl.

In some embodiments, $R^{6a}$ is substituted or unsubstituted $C_3$-$C_4$cycloalkyl, or substituted or unsubstituted 3- or 4-membered $C_2$-$C_3$heterocycloalkyl. In some embodiments, $R^{6a}$ is substituted or unsubstituted cyclopropyl, substituted or unsubstituted cyclobutyl, substituted or unsubstituted azetidinyl, or substituted or unsubstituted oxetanyl. In some embodiments, $R^{6a}$ is substituted or unsubstituted $C_3$-$C_4$cycloalkyl. In some embodiments, $R^{6a}$ is substituted or unsubstituted cyclopropyl or substituted or unsubstituted cyclobutyl. In some embodiments, $R^{6a}$ is substituted or unsubstituted cyclopropyl. In some embodiments, $R^{6a}$ is substituted or unsubstituted cyclobutyl.

In some embodiments, $R^6$ is substituted or unsubstituted $C_1$-$C_8$alkyl, substituted or unsubstituted $C_1$-$C_8$fluoroalkyl, substituted or unsubstituted $C_1$-$C_8$heteroalkyl, or -$L^2$-$R^{6a}$; $L^2$ is absent, substituted or unsubstituted $C_1$-$C_8$alkylene, or —$CHR^{6b}$—; $R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl; and $R^{6b}$ is hydrogen, $C_1$-$C_6$alkyl, $C_1$-$C_6$fluoroalkyl, or substituted or unsubstituted $C_3$-$C_6$cycloalkyl. In some embodiments, $R^6$ is $C_1$-$C_8$alkyl, $C_1$-$C_8$fluoroalkyl, substituted or unsubstituted $C_1$-$C_8$heteroalkyl, or -$L^2$-$R^{6a}$; $L^2$ is absent, $C_1$-$C_6$alkylene, or —$CHR^{6b}$—; $R^{6a}$ is substituted or unsubstituted monocyclic $C_3$-$C_8$cycloalkyl, substituted or unsubstituted polycyclic $C_5$-$C_{10}$cycloalkyl, substituted or unsubstituted phenyl, substituted or unsubstituted indanyl, substituted or unsubstituted tetrahydronaphthyl, substituted or unsubstituted naphthyl, substituted or unsubstituted monocyclic $C_2$-$C_5$heterocycloalkyl, substituted or unsubstituted polycyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl; and $R^{6b}$ is hydrogen, $C_1$-$C_6$alkyl, $C_1$-$C_6$fluoroalkyl, or substituted or unsubstituted $C_3$-$C_6$cycloalkyl.

In some embodiments, $R^6$ is $C_1$-$C_6$alkyl, $C_1$-$C_6$fluoroalkyl, substituted or unsubstituted $C_1$-$C_6$heteroalkyl, or -$L^2$-$R^{6a}$; $L^2$ is absent, $C_1$-$C_4$alkylene, or —$CHR^{6b}$—; and $R^{6b}$ is hydrogen, $C_1$-$C_4$alkyl, $C_1$-$C_4$fluoroalkyl, or substituted or unsubstituted $C_3$-$C_6$cycloalkyl. In some embodiments, $R^{6a}$ is substituted or unsubstituted monocyclic $C_3$-$C_6$cycloalkyl, substituted or unsubstituted bridged $C_5$-$C_{10}$cycloalkyl, substituted or unsubstituted spirocyclic $C_5$-$C_{10}$cycloalkyl, substituted or unsubstituted adamantyl, substituted or unsubstituted phenyl, substituted or unsubstituted indanyl, substituted or unsubstituted tetrahydronaphthyl, or substituted or unsubstituted naphthyl. In some embodiments, $R^{6a}$ is substituted or unsubstituted monocyclic $C_2$-$C_5$heterocycloalkyl, substituted or unsubstituted bridged $C_5$-$C_{10}$heterocycloalkyl, substituted or unsubstituted spirocyclic $C_5$-$C_{10}$heterocycloalkyl, substituted or unsubstituted monocyclic $C_1$-$C_5$heteroaryl or substituted or unsubstituted bicyclic $C_6$-$C_9$heteroaryl.

In some embodiments, $R^6$ is $C_1$-$C_6$alkyl, $C_1$-$C_6$fluoroalkyl, $C_1$-$C_6$heteroalkyl, or -$L^2$-$R^{6a}$; $L^2$ is absent, $C_1$-$C_4$alkylene, or —$CHR^{6b}$—; $R^{6a}$ is substituted or unsubstituted $C_3$-$C_4$cycloalkyl, or substituted or unsubstituted 3- or 4-membered $C_2$-$C_3$heterocycloalkyl; and $R^{6b}$ is hydrogen, $C_1$-$C_6$alkyl, $C_1$-$C_6$fluoroalkyl, or substituted or unsubstituted $C_3$-$C_4$cycloalkyl. In some embodiments, $R^6$ is $C_1$-$C_6$alkyl, $C_1$-$C_6$fluoroalkyl, $C_1$-$C_6$heteroalkyl, or -$L^2$-$R^{6a}$; $L^2$ is absent, —$CH_2$—, —$CH_2CH_2$—, —$CH_2CH_2CH_2$—, or —$CHR^{6b}$—; $R^{6a}$ is substituted or unsubstituted cyclopropyl, substituted or unsubstituted cyclobutyl, substituted or unsubstituted azetidinyl, or substituted or unsubstituted oxetanyl; and $R^{6b}$ is hydrogen, —$CH_3$, —$CH_2CH_3$, —$CH_2CH_2CH_3$, —$CH(CH_3)_2$, —$CHF_2$, —$CH_2F$, —$CF_3$, cyclopropyl, or cyclobutyl.

In some embodiments, $R^6$ and $R^7$ are taken together with the nitrogen to which they are attached to form a substituted or unsubstituted N-containing heterocycle. In some embodiments, $R^6$ and $R^7$ are taken together with the nitrogen to which they are attached to form a substituted or unsubstituted N-containing heterocycloalkyl. In some embodiments, $R^6$ and $R^7$ are taken together with the nitrogen to which they are attached to form a substituted or unsubstituted monocyclic N-containing heterocycloalkyl containing 1-2 N atoms, 0-2 O atoms and 0-1 S.

In some embodiments, X is N or CH;

Y is N or CH;

Z is N or C—$R^c$;

$R^c$ is hydrogen, halogen, —CN, —$N(R^9)_2$, —$OR^f$, $C_1$-$C_6$alkyl, $C_1$-$C_6$fluoroalkyl, $C_1$-$C_6$fluoroalkoxy, or substituted or unsubstituted $C_1$-$C_6$heteroalkyl;

$R^f$ is -$L^1$-$R^g$;

$L^1$ is absent, $C_1$-$C_6$alkylene, or $C_1$-$C_6$fluoroalkylene;

$R^g$ is hydrogen, substituted or unsubstituted $C_3$-$C_6$cycloalkyl, substituted or unsubstituted phenyl, —$CO_2R^9$, or —$C(=O)N(R^9)_2$;

$R^1$ is hydrogen;

$R^2$ is hydrogen or $C_1$-$C_6$alkyl;

$R^L$ is $C_1$-$C_6$alkyl or $C_1$-$C_6$fluoroalkyl;

$R^6$ is $C_1$-$C_8$alkyl, $C_1$-$C_8$fluoroalkyl, or -$L^2$-$R^{6a}$.

$L^2$ is absent, $C_1$-$C_6$alkylene, or —$CHR^{6b}$—;

$R^{6a}$ is substituted or unsubstituted $C_3$-$C_{10}$cycloalkyl, substituted or unsubstituted $C_6$-$C_{10}$aryl, substituted or unsubstituted $C_2$-$C_{10}$heterocycloalkyl, or substituted or unsubstituted $C_1$-$C_9$heteroaryl;

$R^{6b}$ is hydrogen, $C_1$-$C_6$alkyl, $C_1$-$C_6$fluoroalkyl, or substituted or unsubstituted $C_3$-$C_6$cycloalkyl;

$R^7$ is hydrogen or $C_1$-$C_6$alkyl;

or $R^6$ and $R^7$ are taken together with the nitrogen to which they are attached to form a substituted or unsubstituted heterocycle.

In some embodiments, X is N or CH;

Y is N or CH;

Z is N or C—$R^c$;

$R^c$ is hydrogen, —F, —Cl, —CN, —$CH_3$, —$CF_3$, —$OCH_3$, —$OCH_2CH_3$, —$OCH_2CHF_2$, —$OCH_2CF_3$, —$OCH_2CH_2OCH_3$, —O-(cyclopropyl), —O—$CH_2$-(cyclopropyl), —O—$CH_2$-(phenyl), —$OCH_2CO_2H$, —$OCH_2CH_2CO_2H$, —$OCH_2CH_2CH_2CO_2H$, —$OCH_2CO_2CH_3$, —$OCH_2CH_2CO_2CH_3$, —$OCH_2CH_2CH_2CO_2CH_3$, —$OCH_2CO_2CH_2CH_3$, —$OCH_2CH_2CO_2CH_2CH_3$, or —$OCH_2CH_2CH_2CO_2CH_2CH_3$;

$R^1$ is hydrogen;

$R^2$ is hydrogen;

$R^L$ is $C_1$-$C_6$alkyl;

$R^6$ is $C_1$-$C_6$alkyl, $C_1$-$C_6$fluoroalkyl, or -$L^2$-$R^{6a}$.

$L^2$ is absent, $C_1$-$C_6$alkylene or —$CHR^{6b}$—;

$R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl;

$R^{6b}$ is hydrogen, $C_1$-$C_4$alkyl, $C_1$-$C_4$fluoroalkyl, or substituted or unsubstituted monocyclic $C_3$-$C_4$cycloalkyl;

$R^7$ is hydrogen or $C_1$-$C_6$alkyl;

or $R^6$ and $R^7$ are taken together with the nitrogen to which they are attached to form a substituted or unsubstituted heterocycle.

In some embodiments, the compound has the structure of Formula (A2), or a pharmaceutically acceptable salt, or solvate thereof:

Formula (A2)

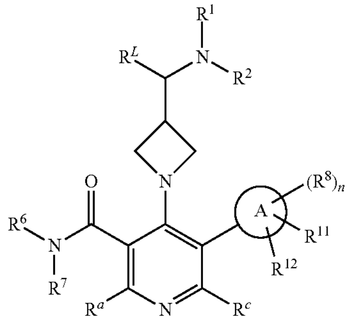

wherein:

Ring A is phenyl or pyridinyl;

$R^a$ and $R^c$ are each independently hydrogen, halogen, —CN, —$N(R^9)_2$, —$OR^e$, —$CO_2R^9$, —$C(=O)N(R^9)_2$, $C_1$-$C_6$alkyl, $C_1$-$C_6$fluoroalkyl, $C_1$-$C_6$fluoroalkoxy, substituted or unsubstituted monocyclic $C_3$-$C_6$cycloalkyl, or substituted or unsubstituted monocyclic $C_2$-$C_5$heterocycloalkyl;

$R^f$ is -$L^1$-$R^g$;

$L^1$ is absent, or $C_1$-$C_6$alkylene;

$R^9$ is hydrogen, substituted or unsubstituted $C_3$-$C_6$cycloalkyl, substituted or unsubstituted phenyl, —$CO_2R^9$, or —$C(=O)N(R^9)_2$, or substituted or unsubstituted monocyclic $C_2$-$C_5$heterocycloalkyl;

$R^1$ is hydrogen;

$R^2$ is hydrogen or $C_1$-$C_6$alkyl;

$R^L$ is $C_1$-$C_6$alkyl or $C_1$-$C_6$fluoroalkyl;

$R^6$ is $C_1$-$C_6$alkyl, $C_1$-$C_6$fluoroalkyl, or -$L^2$-$R^{6a}$.

$L^2$ is absent, $C_1$-$C_6$alkylene or —$CHR^{6b}$—;

$R^{6a}$ is substituted or unsubstituted monocyclic $C_3$-$C_4$cycloalkyl, substituted or unsubstituted monocyclic or bicyclic $C_5$-$C_{10}$cycloalkyl, substituted or unsubstituted $C_6$-$C_{10}$aryl, substituted or unsubstituted monocyclic $C_2$-$C_3$heterocycloalkyl, substituted or unsubstituted monocyclic or bicyclic $C_4$-$C_{10}$heterocycloalkyl, or substituted or unsubstituted $C_1$-$C_9$heteroaryl;

$R^{6b}$ is hydrogen, $C_1$-$C_4$alkyl, $C_1$-$C_4$fluoroalkyl, or substituted or unsubstituted monocyclic $C_3$-$C_4$cycloalkyl;

$R^7$ is hydrogen or $C_1$-$C_6$alkyl;

each $R^8$ is independently hydrogen, halogen, $C_1$-$C_6$alkyl, or $C_1$-$C_6$fluoroalkyl;

$R^{11}$ and $R^{12}$ are each independently hydrogen, halogen, $C_1$-$C_6$alkyl, $C_1$-$C_6$fluoroalkyl, —CN, —$OR^9$, —$CO_2R^9$, —C(=O)N($R^9$)$_2$, —N($R^9$)$_2$, or —$NR^9$C(=O)$R^{10}$, or substituted or unsubstituted monocyclic $C_3$-$C_8$cycloalkyl, substituted or unsubstituted phenyl, substituted or unsubstituted monocyclic $C_2$-$C_5$heterocycloalkyl, or substituted or unsubstituted monocyclic $C_1$-$C_5$heteroaryl;

each $R^9$ is independently hydrogen, substituted or unsubstituted $C_1$-$C_6$alkyl, or substituted or unsubstituted $C_1$-$C_6$fluoroalkyl;

or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl, or substituted or unsubstituted $C_1$-$C_6$fluoroalkyl.

n is 0-3.

In some embodiments, each $R^9$ is independently hydrogen, substituted or unsubstituted $C_1$-$C_6$alkyl, substituted or unsubstituted $C_1$-$C_6$fluoroalkyl, substituted or unsubstituted $C_3$-$C_7$cycloalkyl, or substituted or unsubstituted monocyclic 3- to 8-membered heterocycloalkyl; or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl, substituted or unsubstituted $C_1$-$C_6$fluoroalkyl, substituted or unsubstituted $C_3$-$C_7$cycloalkyl, or substituted or unsubstituted monocyclic 3- to 8-membered heterocycloalkyl. In some embodiments, each $R^9$ is independently hydrogen, substituted or unsubstituted $C_1$-$C_6$alkyl, or substituted or unsubstituted $C_1$-$C_6$fluoroalkyl; or two $R^9$ on the same N atom are taken together with the N atom to which they are attached to form a substituted or unsubstituted N-containing heterocycle; and each $R^{10}$ is independently substituted or unsubstituted $C_1$-$C_6$alkyl or substituted or unsubstituted $C_1$-$C_6$fluoroalkyl. In some embodiments, each $R^9$ is independently hydrogen, $C_1$-$C_6$alkyl, or $C_1$-$C_6$fluoroalkyl; or two $R^9$ on the same N atom are taken together with the N atom to which they are attached to form a substituted or unsubstituted N-containing heterocycle; and each $R^{10}$ is independently $C_1$-$C_6$alkyl or $C_1$-$C_6$fluoroalkyl.

In some embodiments, compounds described herein have the following structure:

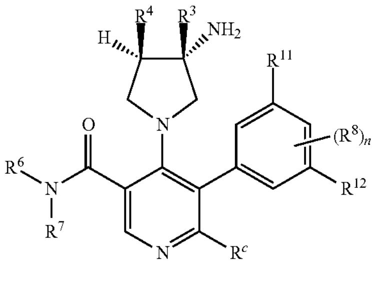

wherein,

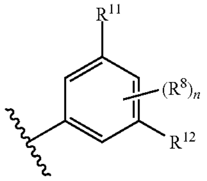

is as described in Table 1;

$R^3$ is as described in Table 1;

$R^4$ is as described in Table 1;

$R^4$ is as described in Table 1; and $NR^6R^7$ is as described in Table 1.

In some embodiments, compounds described herein have the following structure:

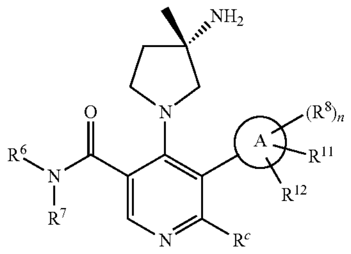

wherein,

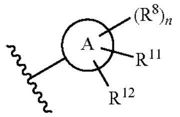

is as described in Table 2;

$R^c$ is as described in Table 2; and $NR^6R^7$ is as described in Table 2.

In some embodiments, compounds described herein have the following structure:

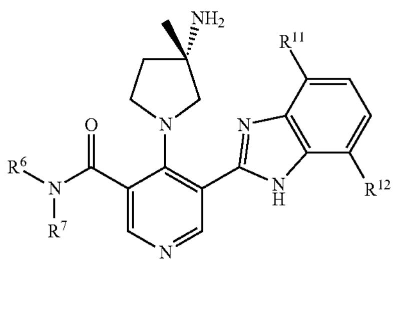

wherein, $R^{11}$ is as described in Table 3;

$R^{12}$ is as described in Table 3; and $NR^6R^7$ is as described in Table 3.

In some embodiments, compounds described herein have the following structure:

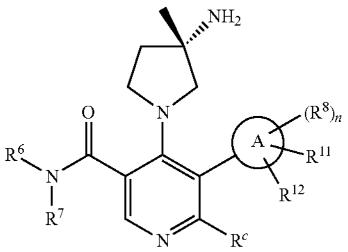

wherein,

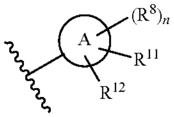

is as described in Table 4;

$R^c$ is as described in Table 4; and $NR^6R^7$ is as described in Table 4.

In some embodiments, compounds described herein have the following structure:

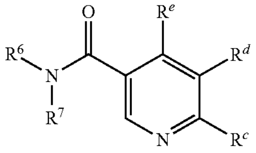

wherein, $R^c$ is as described in Table 5;

$R^d$ is as described in Table 5;

$R^c$ is as described in Table 5; and $NR^6R^7$ is as described in Table 5.

In some embodiments, compounds described herein have the following structure:

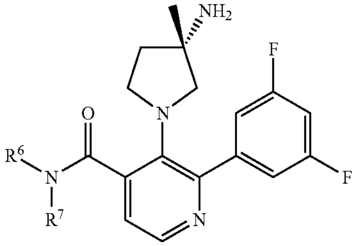

wherein, $NR^6R^7$ is as described in Table 6.

In some embodiments, compounds described herein have the following structure:

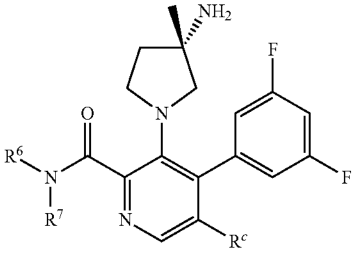

wherein, $R^c$ is as described in Table 7; and $NR^6R^7$ is as described in Table 7.

In some embodiments, compounds described herein have the following structure:

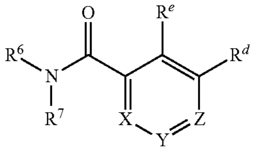

wherein,

X is N or C—$R^a$ as described herein,

Y is N or CH,

Z is N or C—$R^c$ as described herein, $R^d$ is

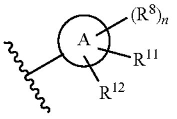

as described herein, $R^c$ is

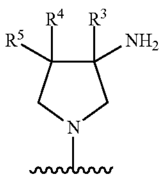

or

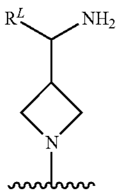

as described herein, and $R^6$ and $R^7$ are as described herein.

In some embodiments, $R^d$ is

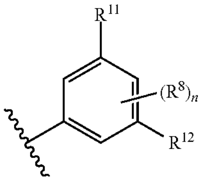

or

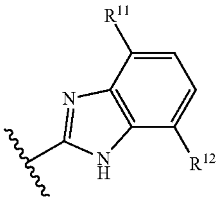

or H as described herein.

In some embodiments, X is N. In some embodiments, X is C—$R^a$. In some embodiments, X is CH.

In some embodiments, Y is N. In some embodiments, Y is CH.

In some embodiments, Z is N. In some embodiments, Z is C—$R^c$ as described in Table 1, Table 2, Table 3, Table 4, Table 5, Table 6, or Table 7. In some embodiments, Z is CH.

In some embodiments, X is CH, Y is N, and Z is C—$R^c$ as described herein as described in Table 1, Table 2, Table 3, Table 4, or Table 5.

In some embodiments, X is CH, Y is CH, and Z is N.

In some embodiments, X is N, Y is CH, and Z is C—$R^c$ as described herein as described in Table 7.

In some embodiments, $R^d$ is

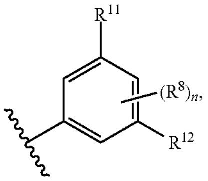

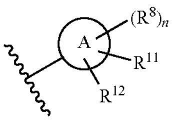

, or

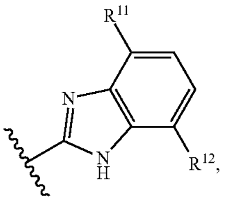

as described in Table 1, Table 2, Table 3, Table 4, Table 5, Table 6, or Table 7.

In some embodiments, $R^d$ is as

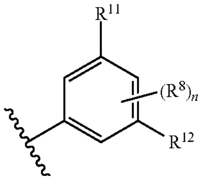

described in Table 1, Table 5, Table 6, or Table 7. In some embodiments, $R^d$ is

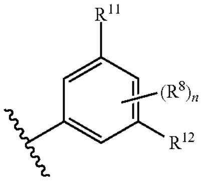

as described in Table 1. In some embodiments, $R^d$ is

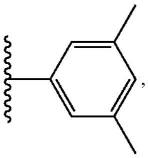

,

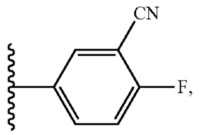

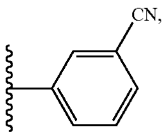

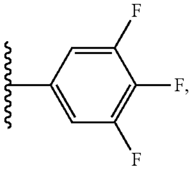

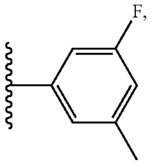

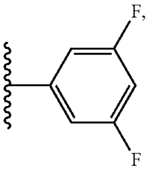

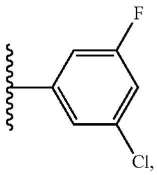

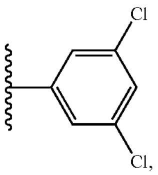

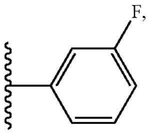

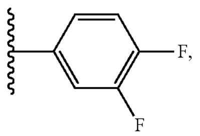

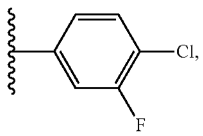

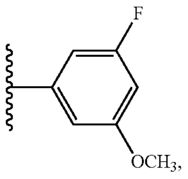

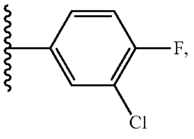

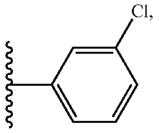

-continued
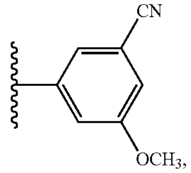
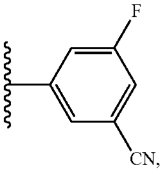
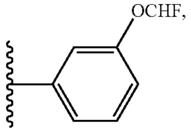
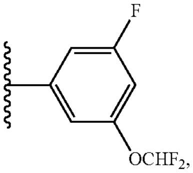
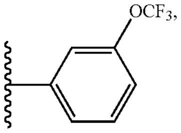
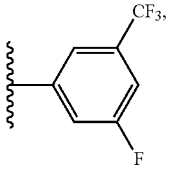
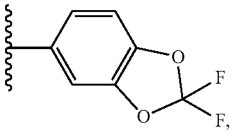
or
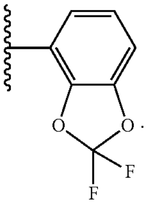
In some embodiments, $R^d$ is
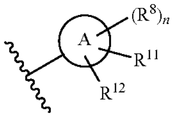
as described in Table 2. In some embodiments, $R^d$ is
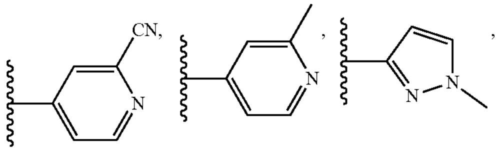
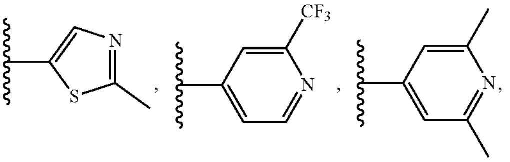
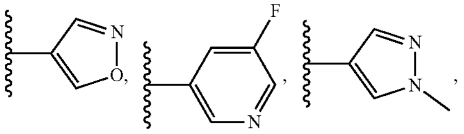
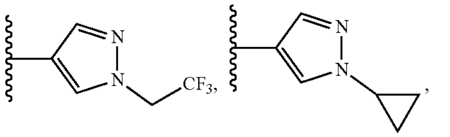
-continued
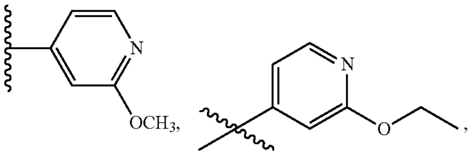
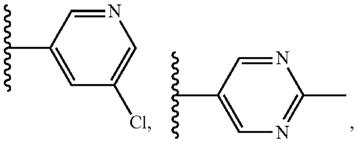
or
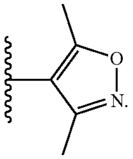
In some embodiments, $R^d$ is
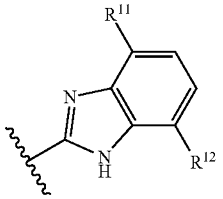
as described in Table 3. In some embodiments, $R^d$ is
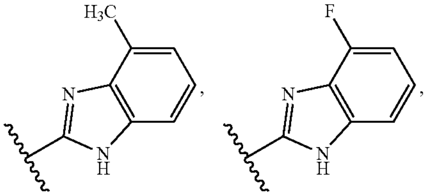
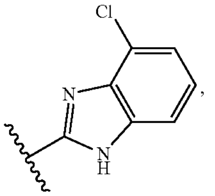
, or
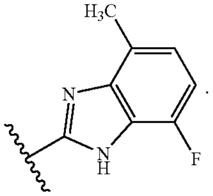
In some embodiments, $R^d$ is
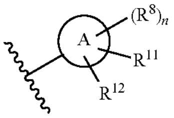

as described in Table 4. In some embodiments, $R^d$ is

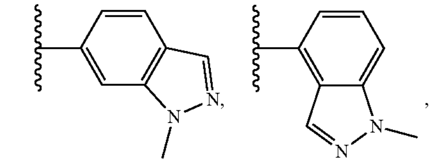

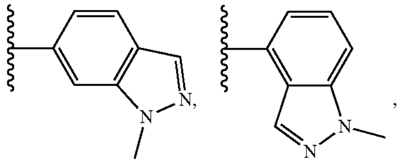

or

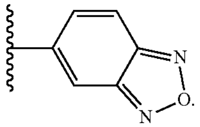

In some embodiments, $R^c$ is

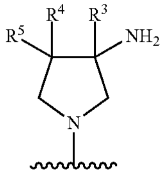

or

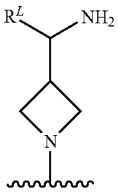

or as described in Table 1, Table 2, Table 3, Table 4, Table 5, Table 6, or Table 7.

In some embodiments, $R^c$ is

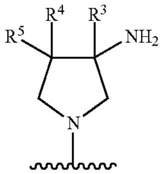

as described in Table 1, Table 2, Table 3, Table 4, Table 5, Table 6, or Table 7. In some embodiments, Re is

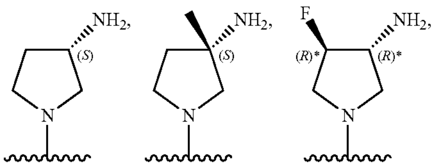

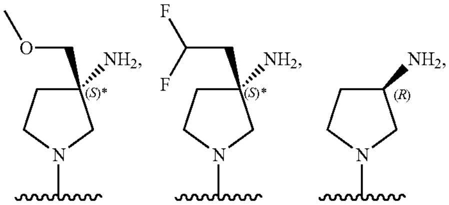

-continued

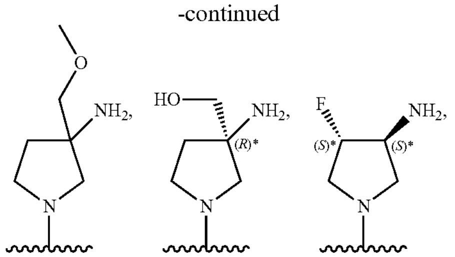

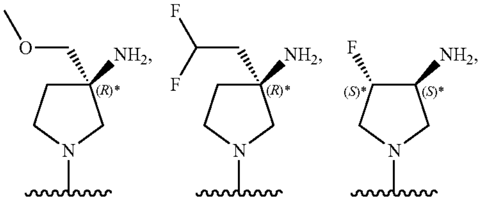

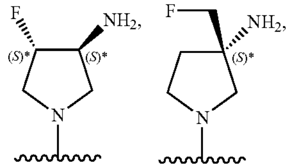

or

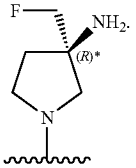

In some embodiments, $R^c$ is

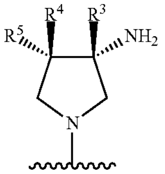

as described in Table 1, Table 2, Table 3, Table 4, Table 6, or Table 7. In some embodiments, $R^c$ is

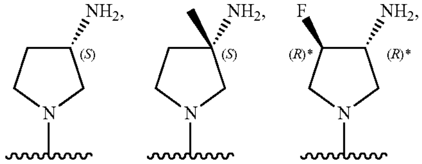

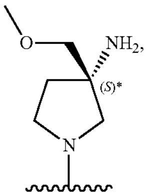

or

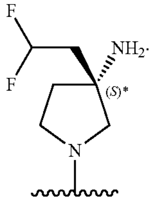

In some embodiments, $R^c$ is

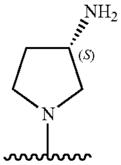

or

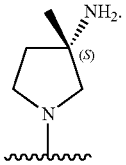

In some embodiments, $R^c$ is
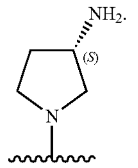
In some embodiments, $R^c$ is
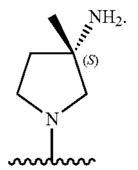
In some embodiments, $R^c$ is
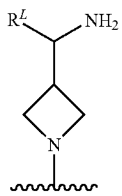
as described in Table 5. In some embodiments, $R^c$ is
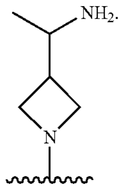 [SMILES: *N1CC(C(C)N)C1]
In some embodiments, $R^6$ and $R^7$ are as described in Table 1, Table 2, Table 3, Table 4, Table 5, Table 6, or Table 7. In some embodiments,
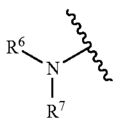
is as described in Table 1, Table 2, Table 3, Table 4, Table 5, Table 6, or Table 7. In some embodiments,
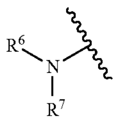
is
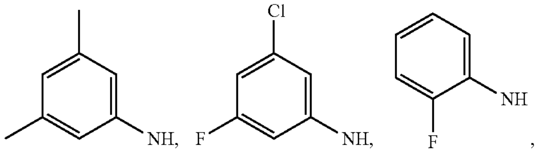
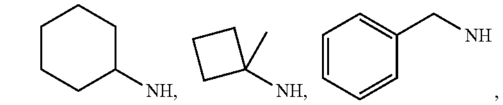
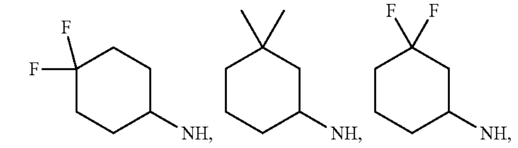
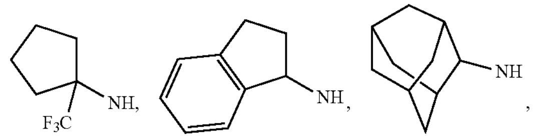
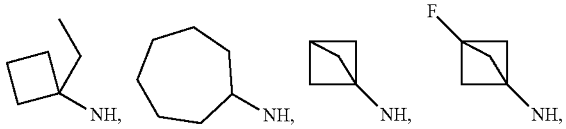
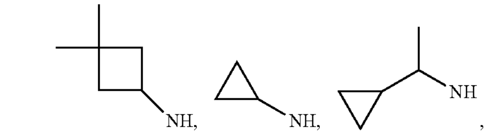
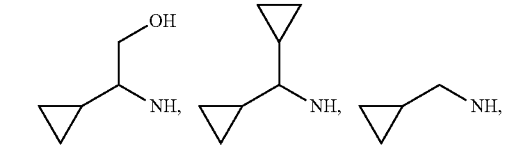
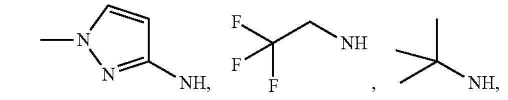
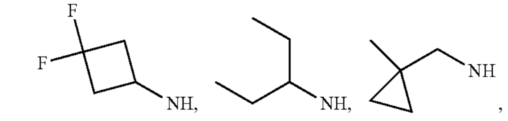
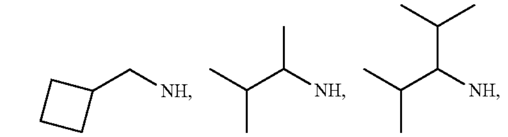
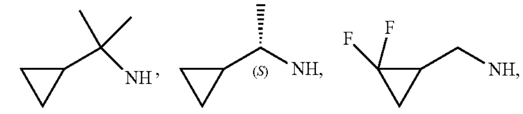
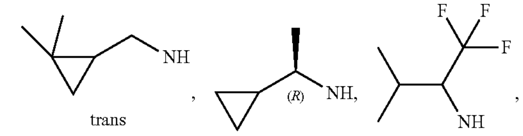
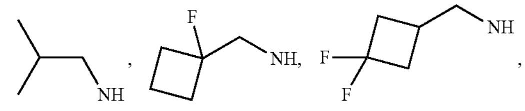

-continued
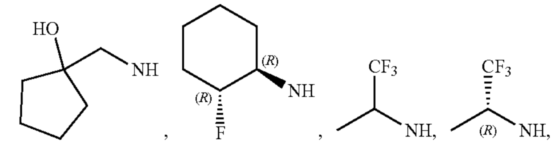
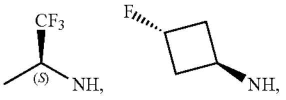
trans
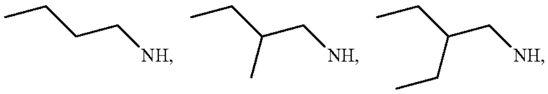
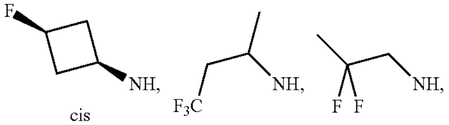
cis
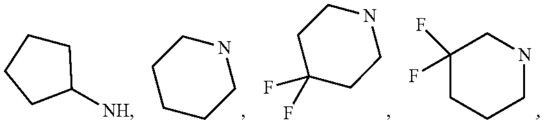
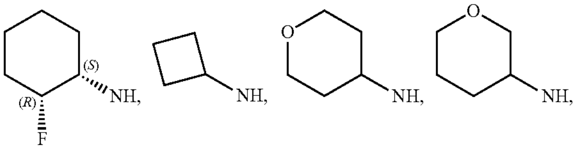
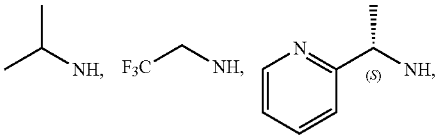
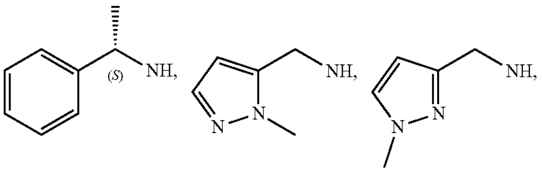
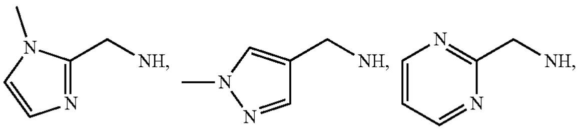
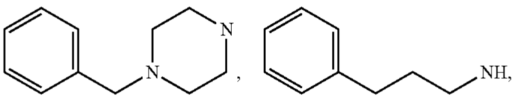
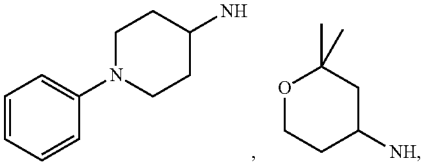
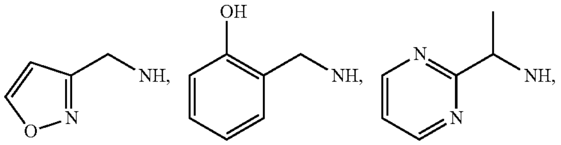
-continued
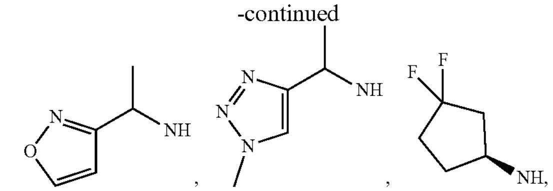
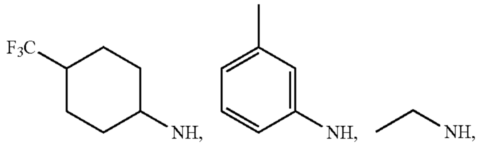
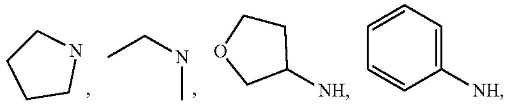
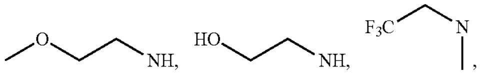
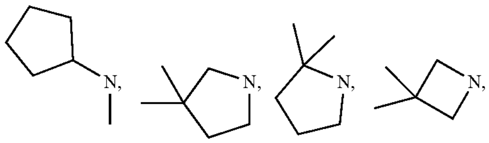
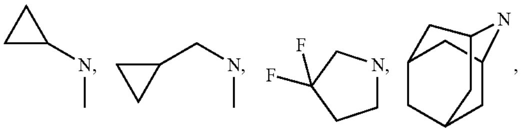
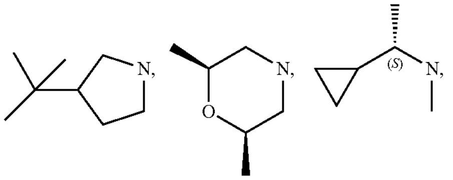
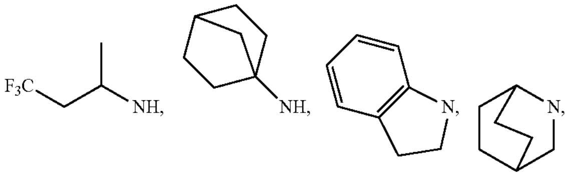
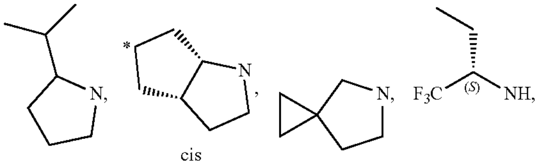
cis
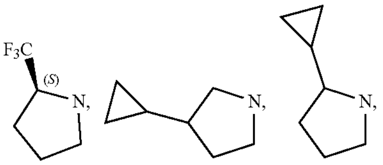
or
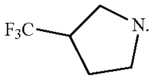
In some embodiments,
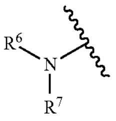

is

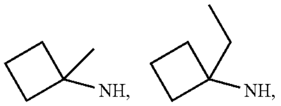

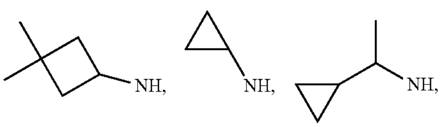

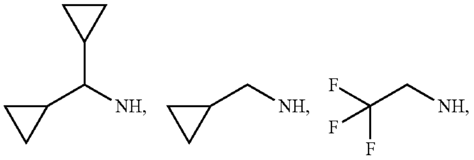

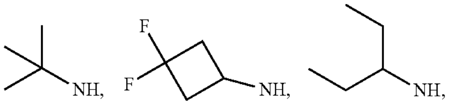

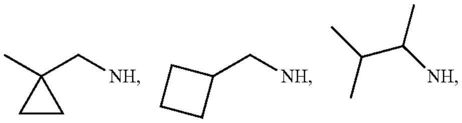

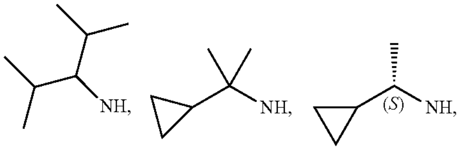

-continued

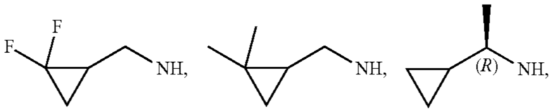

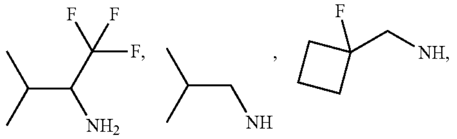

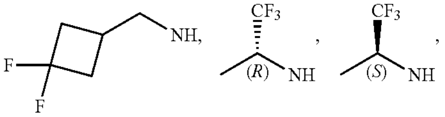

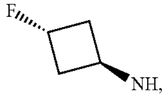

trans

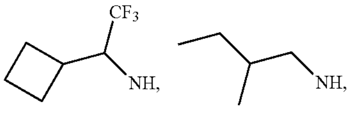

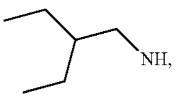

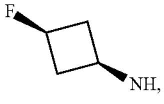

cis

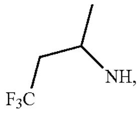

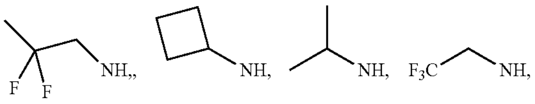

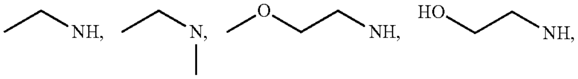

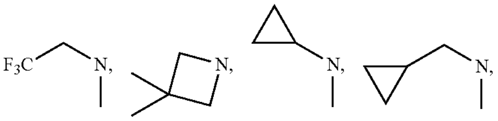

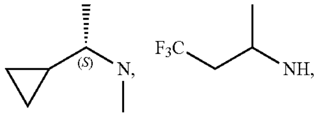

or

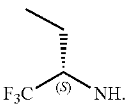

Any combination of the groups described above for the various variables is contemplated herein. Throughout the specification, groups and substituents thereof are chosen by one skilled in the field to provide stable moieties and compounds.

Exemplary compounds described herein include the compounds described in the following Tables:

TABLE 1
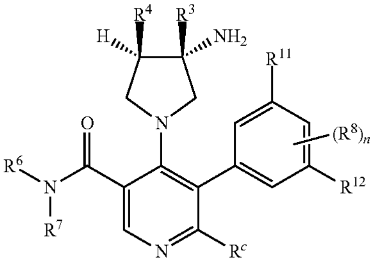
| Compd No. | $R^6R^7N$ | $R^4$ | $R^3$ | 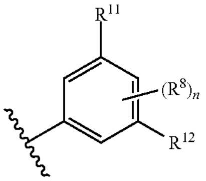 | $R^c$ |
|---|---|---|---|---|---|
| 1-1 | 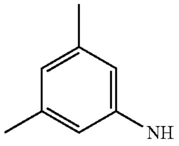 | H | H | 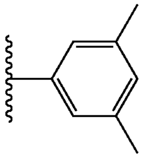 [SMILES: *c1cc(C)cc(C)c1] | H |
| 1-3 | 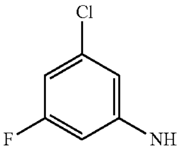 | H | H | 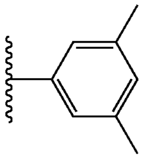 [SMILES: *c1cc(C)cc(C)c1] | H |
| 1-4 | 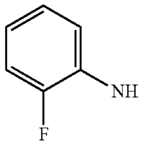 | H | $CH_3$ | 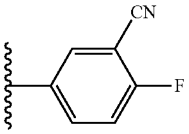 [SMILES: *c1ccc(F)c(C#N)c1] | H |
| 1-7 | 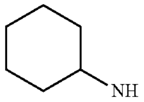 | H | H | 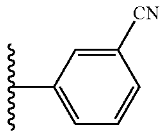 [SMILES: *c1cccc(C#N)c1] | H |
| 1-8 | 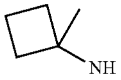 | H | H | 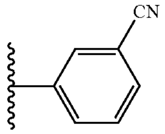 [SMILES: *c1cccc(C#N)c1] | H |
| 1-9 | 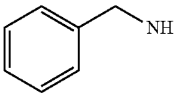 | H | H | 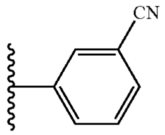 [SMILES: *c1cccc(C#N)c1] | H |
| 1-10 | 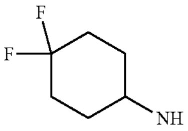 | H | $CH_3$ | 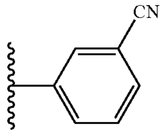 | H |

TABLE 1-continued
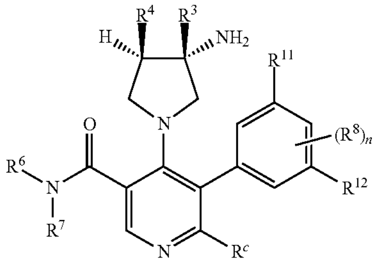
| Compd No. | $R^6R^7N$ | $R^4$ | $R^3$ | 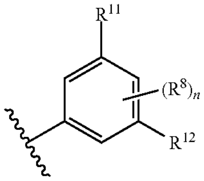 | $R^c$ |
|---|---|---|---|---|---|
| 1-11 | 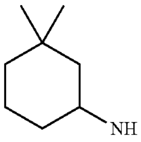 | H | $CH_3$ | 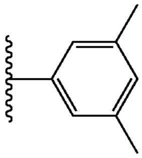 [SMILES: *c1cc(C)cc(C)c1] | H |
| 1-12 | 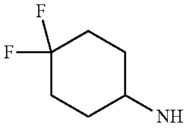 | H | $CH_3$ | 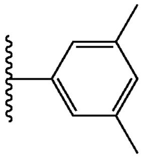 [SMILES: *c1cc(C)cc(C)c1] | H |
| 1-13 | 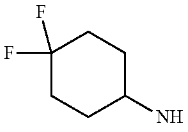 | H | $CH_3$ | 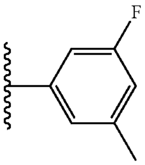 [SMILES: *c1cc(C)cc(F)c1] | H |
| 1-14 | 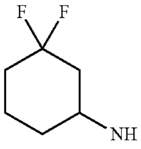 | H | $CH_3$ | 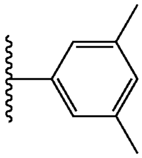 [SMILES: *c1cc(C)cc(C)c1] | H |
| 1-15 | 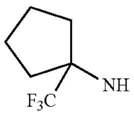 | H | $CH_3$ | 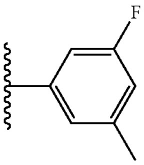 [SMILES: *c1cc(C)cc(F)c1] | H |
| 1-16 | 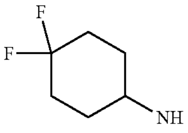 | H | $CH_3$ | 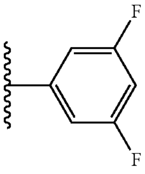 [SMILES: *c1cc(F)cc(F)c1] | H |

TABLE 1-continued
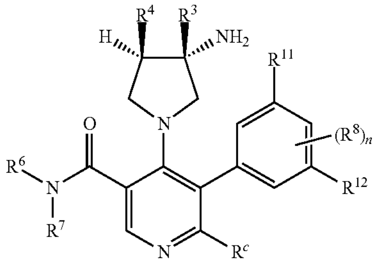
| Compd No. | $R^6R^7N$ | $R^4$ | $R^3$ | 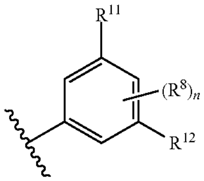 | $R^c$ |
|---|---|---|---|---|---|
| 1-17 | 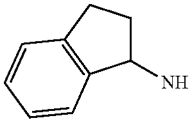 | H | $CH_3$ | 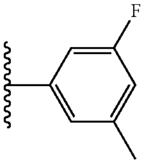 [SMILES: *c1cc(C)cc(F)c1] | H |
| 1-18 | 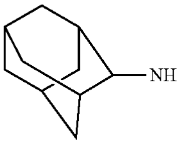 | H | $CH_3$ | 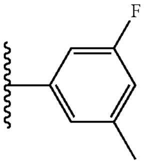 [SMILES: *c1cc(C)cc(F)c1] | H |
| 1-19 | 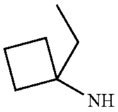 | H | $CH_3$ | 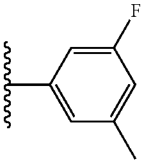 [SMILES: *c1cc(C)cc(F)c1] | H |
| 1-20 | 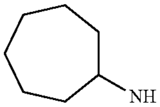 | H | $CH_3$ | 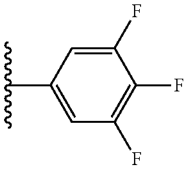 [SMILES: *c1cc(F)c(F)c(F)c1] | H |
| 1-21 | 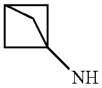 | H | $CH_3$ | 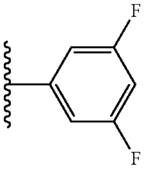 [SMILES: *c1cc(F)cc(F)c1] | H |
| 1-22 | 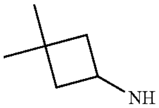 | H | $CH_3$ | 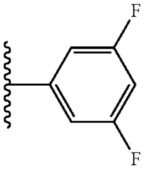 [SMILES: *c1cc(F)cc(F)c1] | H |

TABLE 1-continued
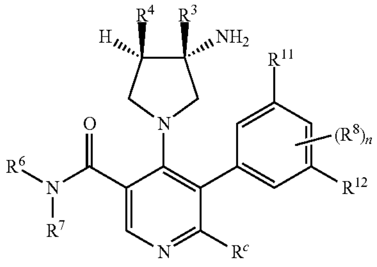
| Compd No. | $R^6R^7N$ | $R^4$ | $R^3$ | 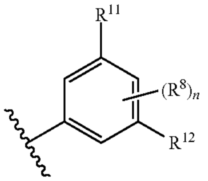 | $R^c$ |
|---|---|---|---|---|---|
| 1-23 | 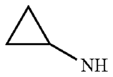 | H | $CH_3$ | 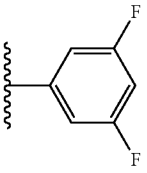 [SMILES: *c1cc(F)cc(F)c1] | H |
| 1-24 | 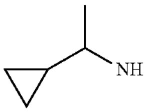 | H | $CH_3$ | 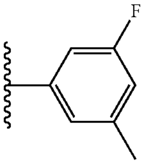 [SMILES: *c1cc(C)cc(F)c1] | H |
| 1-25 | 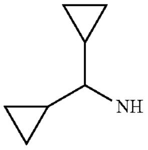 | H | $CH_3$ | 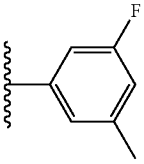 [SMILES: *c1cc(C)cc(F)c1] | H |
| 1-26 | 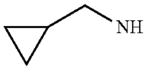 | H | $CH_3$ | 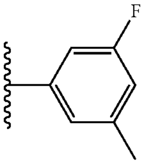 [SMILES: *c1cc(C)cc(F)c1] | H |
| 1-27 | 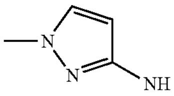 | H | $CH_3$ | 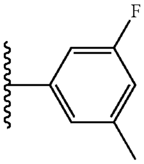 [SMILES: *c1cc(C)cc(F)c1] | H |
| 1-28 | 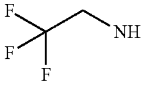 | H | $CH_3$ | 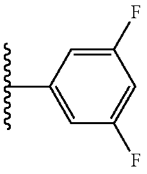 [SMILES: *c1cc(F)cc(F)c1] | H |

TABLE 1-continued
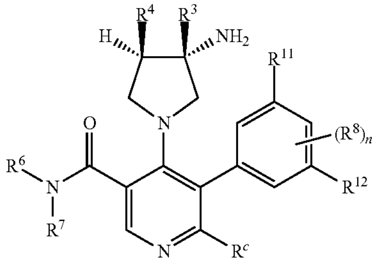
| Compd No. | $R^6R^7N$ | $R^4$ | $R^3$ | 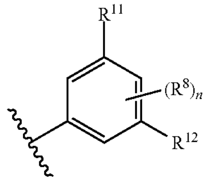 | $R^c$ |
|---|---|---|---|---|---|
| 1-29 | 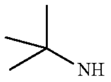 | H | $CH_3$ | 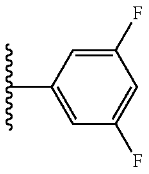 [SMILES: *c1cc(F)cc(F)c1] | H |
| 1-30 | 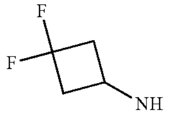 | H | $CH_3$ | 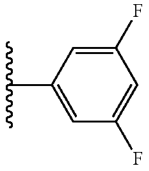 [SMILES: *c1cc(F)cc(F)c1] | H |
| 1-31 | 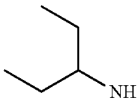 | H | $CH_3$ | 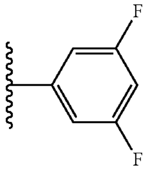 [SMILES: *c1cc(F)cc(F)c1] | H |
| 1-32 | 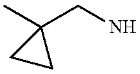 | H | $CH_3$ | 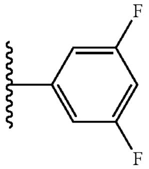 [SMILES: *c1cc(F)cc(F)c1] | H |
| 1-33 | 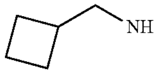 | H | $CH_3$ | 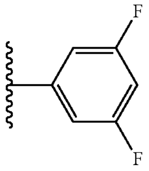 [SMILES: *c1cc(F)cc(F)c1] | H |
| 1-34 | 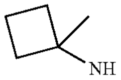 | H | $CH_3$ | 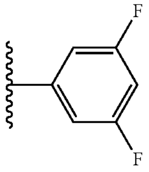 [SMILES: *c1cc(F)cc(F)c1] | H |

TABLE 1-continued
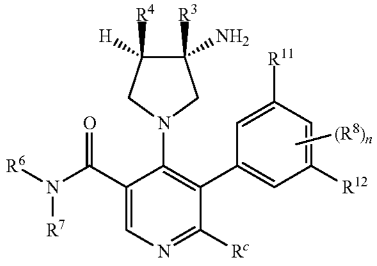
| Compd No. | $R^6R^7N$ | $R^4$ | $R^3$ | 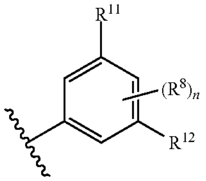 | $R^c$ |
|---|---|---|---|---|---|
| 1-35 | 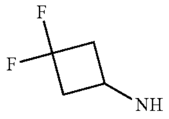 | H | $CH_3$ | 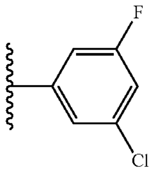 [SMILES: *c1cc(F)cc(Cl)c1] | H |
| 1-37 | 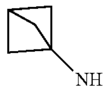 | F | H | 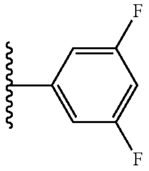 [SMILES: *c1cc(F)cc(F)c1] | H |
| 1-38 | 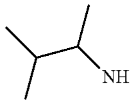 | H | $CH_3$ | 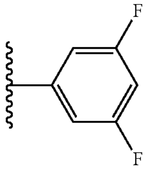 [SMILES: *c1cc(F)cc(F)c1] | H |
| 1-39 | 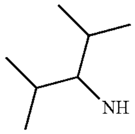 | H | $CH_3$ | 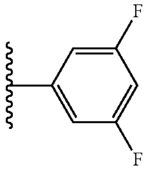 [SMILES: *c1cc(F)cc(F)c1] | H |
| 1-40 | 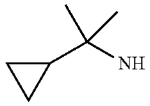 | H | $CH_3$ | 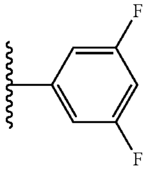 [SMILES: *c1cc(F)cc(F)c1] | H |
| 1-41 | 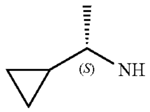 | H | $CH_3$ | 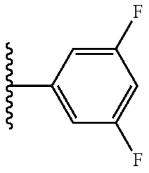 [SMILES: *c1cc(F)cc(F)c1] | H |

TABLE 1-continued
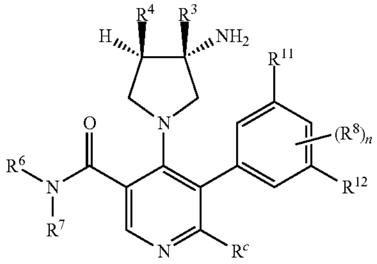
| Compd No. | $R^6R^7N$ | $R^4$ | $R^3$ | 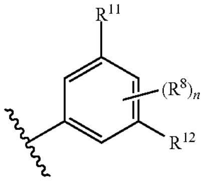 | $R^c$ |
|---|---|---|---|---|---|
| 1-42 | 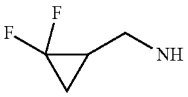 | H | $CH_3$ | 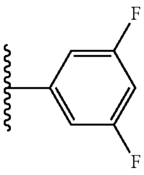 [SMILES: *c1cc(F)cc(F)c1] | H |
| 1-43 | 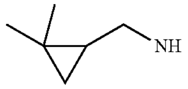 | H | $CH_3$ | 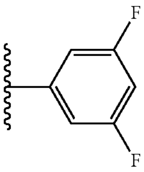 [SMILES: *c1cc(F)cc(F)c1] | H |
| 1-44 | 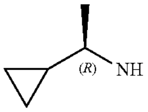 | H | $CH_3$ | 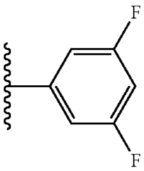 [SMILES: *c1cc(F)cc(F)c1] | H |
| 1-45 | 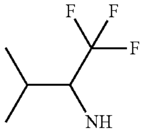 | H | $CH_3$ | 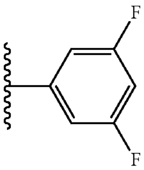 [SMILES: *c1cc(F)cc(F)c1] | H |
| 1-46 | 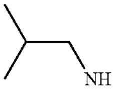 | H | $CH_3$ | 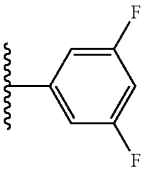 [SMILES: *c1cc(F)cc(F)c1] | H |
| 1-47 | 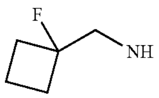 | H | $CH_3$ | 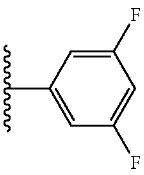 [SMILES: *c1cc(F)cc(F)c1] | H |

TABLE 1-continued
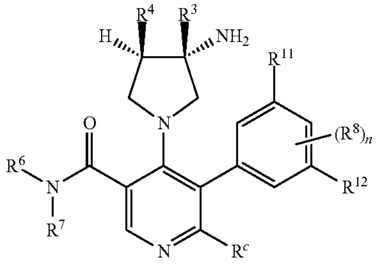
| Compd No. | $R^6R^7N$ | $R^4$ | $R^3$ | 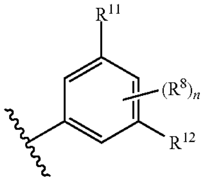 | $R^c$ |
|---|---|---|---|---|---|
| 1-48 | 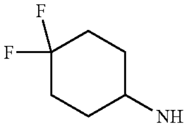 | H | $CH_3$ | 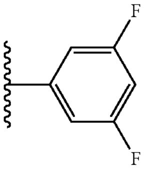 [SMILES: *c1cc(F)cc(F)c1] | CN |
| 1-49 | 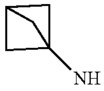 | H | $CH_3$ | 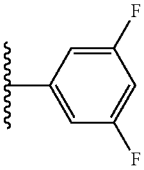 [SMILES: *c1cc(F)cc(F)c1] | CN |
| 1-50 | 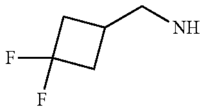 | H | $CH_3$ | 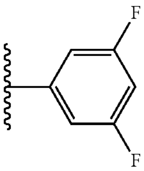 [SMILES: *c1cc(F)cc(F)c1] | H |
| 1-51 | 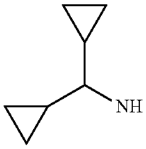 | H | $CH_3$ | 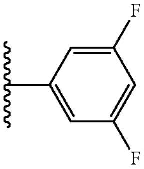 [SMILES: *c1cc(F)cc(F)c1] | H |
| 1-52 | trans 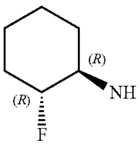 | H | $CH_3$ | 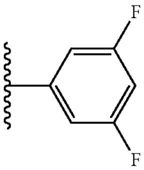 [SMILES: *c1cc(F)cc(F)c1] | H |
| 1-53 | 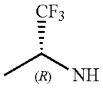 | H | $CH_3$ | 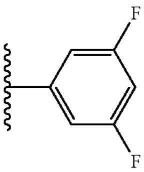 [SMILES: *c1cc(F)cc(F)c1] | H |

TABLE 1-continued
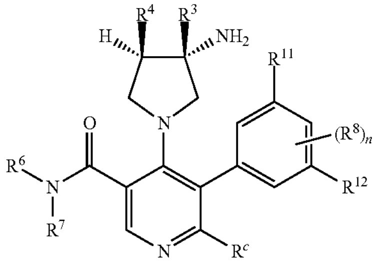
| Compd No. | $R^6R^7N$ | $R^4$ | $R^3$ | 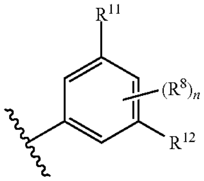 | $R^c$ |
|---|---|---|---|---|---|
| 1-54 | 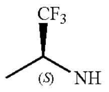 | H | $CH_3$ | 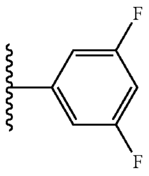 [SMILES: *c1cc(F)cc(F)c1] | H |
| 1-55 | 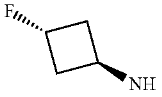 trans | H | $CH_3$ | 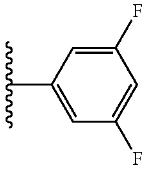 [SMILES: *c1cc(F)cc(F)c1] | H |
| 1-56 | 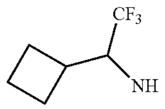 | H | $CH_3$ | 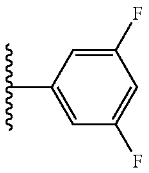 [SMILES: *c1cc(F)cc(F)c1] | H |
| 1-57 | 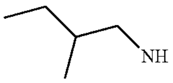 | H | $CH_3$ | 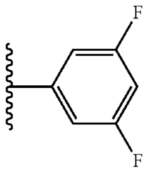 [SMILES: *c1cc(F)cc(F)c1] | H |
| 1-58 | 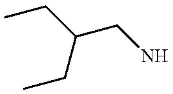 | H | $CH_3$ | 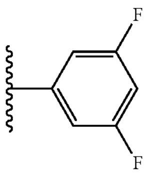 [SMILES: *c1cc(F)cc(F)c1] | H |
| 1-59 | 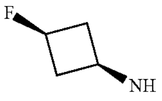 cis | H | $CH_3$ | 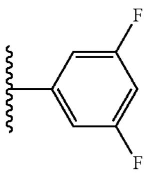 [SMILES: *c1cc(F)cc(F)c1] | H |

TABLE 1-continued
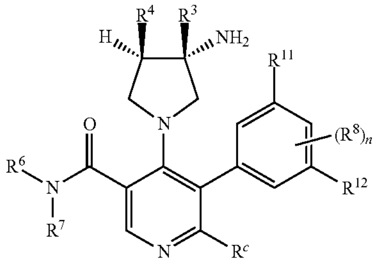
| Compd No. | $R^6R^7N$ | $R^4$ | $R^3$ | 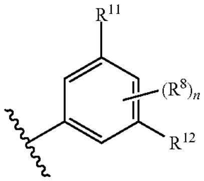 | $R^c$ |
|---|---|---|---|---|---|
| 1-60 | 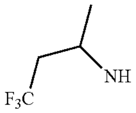 | H | $CH_3$ | 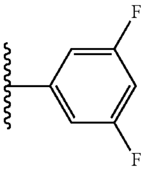 [SMILES: *c1cc(F)cc(F)c1] | H |
| 1-61 | 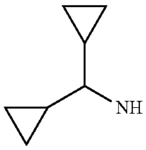 | H | H | 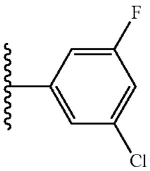 [SMILES: *c1cc(F)cc(Cl)c1] | H |
| 1-62 | 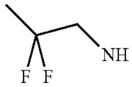 | H | $CH_3$ | 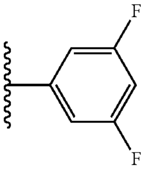 [SMILES: *c1cc(F)cc(F)c1] | H |
| 1-64 | 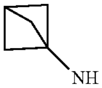 | H | H | 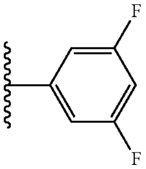 [SMILES: *c1cc(F)cc(F)c1] | CN |
| 1-65 | 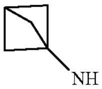 | H | H | 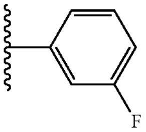 [SMILES: *c1cccc(F)c1] | CN |
| 1-66 | 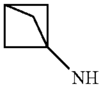 | H | H | 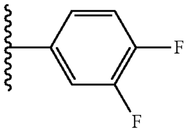 [SMILES: *c1ccc(F)c(F)c1] | CN |

TABLE 1-continued
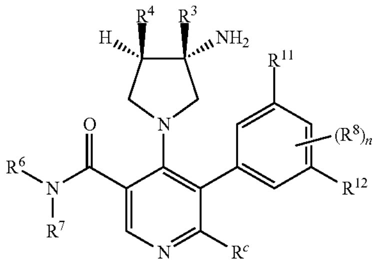
| Compd No. | $R^6R^7N$ | $R^4$ | $R^3$ | 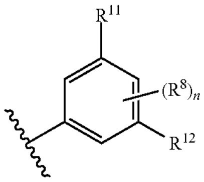 | $R^c$ |
|---|---|---|---|---|---|
| 1-67 | 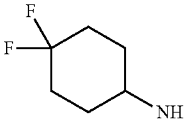 | H | H | 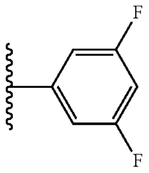 [SMILES: *c1cc(F)cc(F)c1] | CN |
| 1-68 | 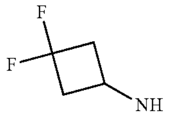 | H | H | 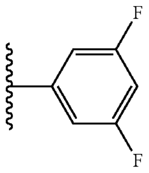 [SMILES: *c1cc(F)cc(F)c1] | CN |
| 1-69 | 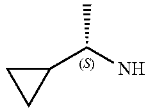 | H | H | 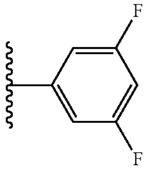 [SMILES: *c1cc(F)cc(F)c1] | CN |
| 1-70 | 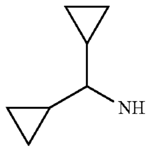 | H | H | 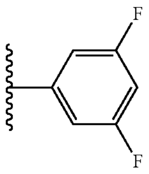 [SMILES: *c1cc(F)cc(F)c1] | CN |
| 1-71 | 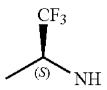 | H | H | 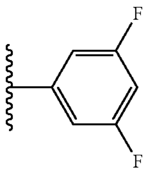 [SMILES: *c1cc(F)cc(F)c1] | CN |
| 1-72 | 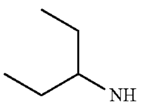 | H | H | 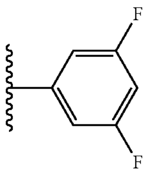 [SMILES: *c1cc(F)cc(F)c1] | CN |

TABLE 1-continued
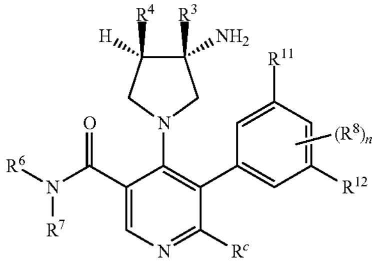
| Compd No. | $R^6R^7N$ | $R^4$ | $R^3$ | 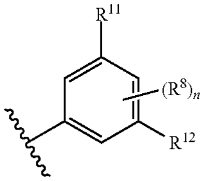 | $R^c$ |
|---|---|---|---|---|---|
| 1-73 | 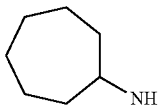 | H | H | 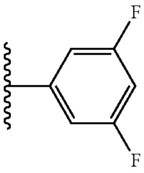 [SMILES: *c1cc(F)cc(F)c1] | CN |
| 1-74 | 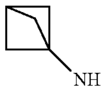 | H | $CH_3$ | 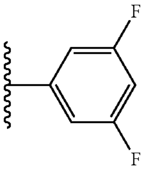 [SMILES: *c1cc(F)cc(F)c1] | $CH_3$ |
| 1-76 | 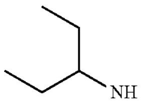 | H | $CH_3$ | 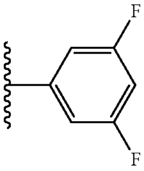 [SMILES: *c1cc(F)cc(F)c1] | CN |
| 1-77 | 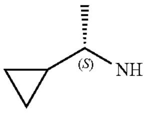 | H | $CH_3$ | 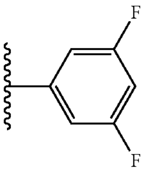 [SMILES: *c1cc(F)cc(F)c1] | CN |
| 1-78 | 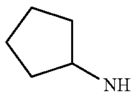 | H | $CH_3$ | 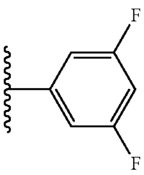 [SMILES: *c1cc(F)cc(F)c1] | CN |
| 1-79 | 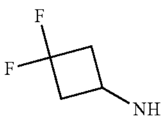 | H | $CH_3$ | 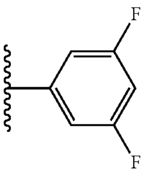 [SMILES: *c1cc(F)cc(F)c1] | CN |

TABLE 1-continued
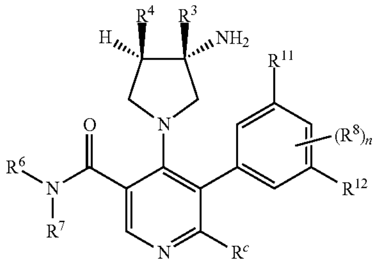
| Compd No. | $R^6R^7N$ | $R^4$ | $R^3$ | 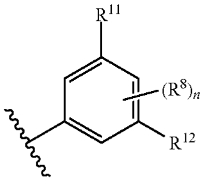 | $R^c$ |
|---|---|---|---|---|---|
| 1-80 | 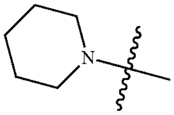 [SMILES: *N1CCCCC1] | H | H | 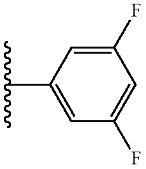 [SMILES: *c1cc(F)cc(F)c1] | CN |
| 1-81 | 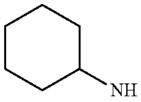 | H | H | 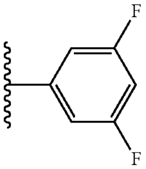 [SMILES: *c1cc(F)cc(F)c1] | CN |
| 1-82 | 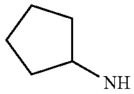 | H | H | 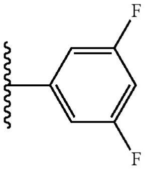 [SMILES: *c1cc(F)cc(F)c1] | CN |
| 1-83 | cis 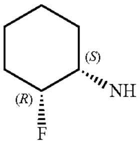 | H | $CH_3$ | 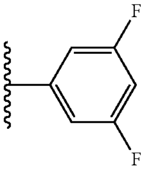 [SMILES: *c1cc(F)cc(F)c1] | H |
| 1-84 | 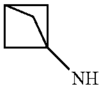 | H | H | 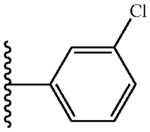 [SMILES: *c1cccc(Cl)c1] | CN |
| 1-85 | 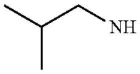 | H | $CH_3$ | 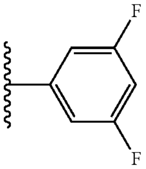 [SMILES: *c1cc(F)cc(F)c1] | CN |

TABLE 1-continued
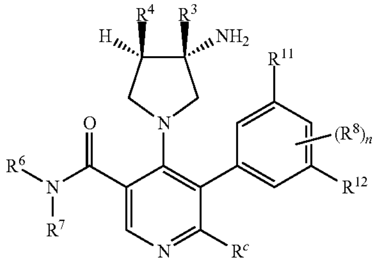
| Compd No. | $R^6R^7N$ | $R^4$ | $R^3$ | 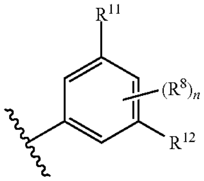 | $R^c$ |
|---|---|---|---|---|---|
| 1-86 | 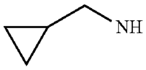 | H | $CH_3$ | 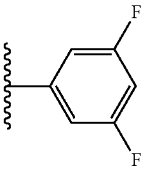 [SMILES: *c1cc(F)cc(F)c1] | CN |
| 1-87 | 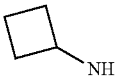 | H | $CH_3$ | 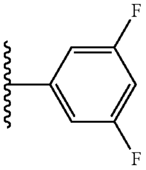 [SMILES: *c1cc(F)cc(F)c1] | CN |
| 1-88 | 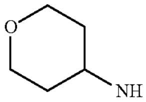 | H | $CH_3$ | 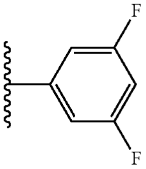 [SMILES: *c1cc(F)cc(F)c1] | CN |
| 1-89 | 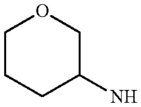 | H | $CH_3$ | 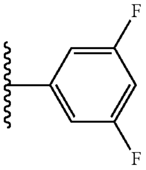 [SMILES: *c1cc(F)cc(F)c1] | CN |
| 1-90 | 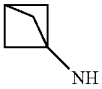 | H | H | 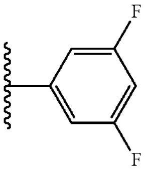 [SMILES: *c1cc(F)cc(F)c1] | CN |
| 1-91 | 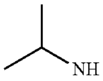 | H | $CH_3$ | 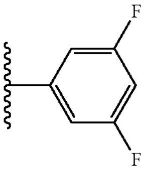 [SMILES: *c1cc(F)cc(F)c1] | CN |

TABLE 1-continued
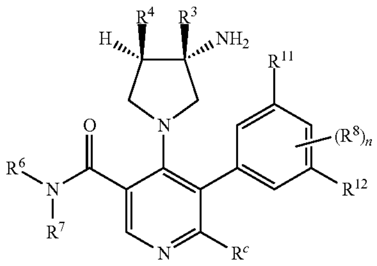
| Compd No. | $R^6R^7N$ | $R^4$ | $R^3$ | 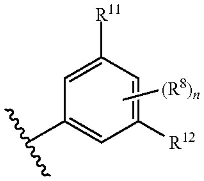 | $R^c$ |
|---|---|---|---|---|---|
| 1-92 | 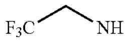 | H | $CH_3$ | 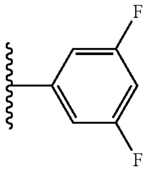 [SMILES: *c1cc(F)cc(F)c1] | CN |
| 1-93 | 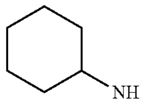 | H | $CH_3$ | 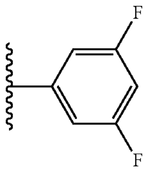 [SMILES: *c1cc(F)cc(F)c1] | CN |
| 1-94 | 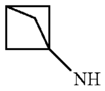 | H | $CH_3$ | 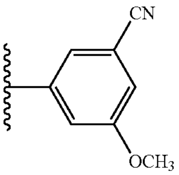 | H |
| 1-95 | 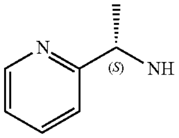 | H | H | 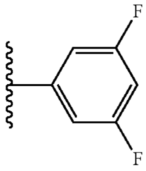 [SMILES: *c1cc(F)cc(F)c1] | CN |
| 1-96 | 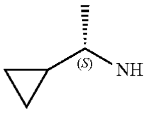 | H | $CH_3$ | 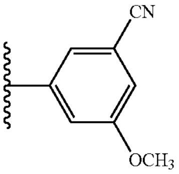 | H |
| 1-97 | 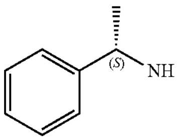 | H | H | 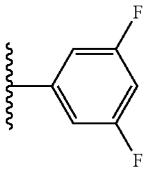 [SMILES: *c1cc(F)cc(F)c1] | CN |

TABLE 1-continued
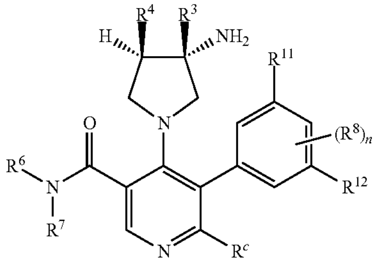
| Compd No. | $R^6R^7N$ | $R^4$ | $R^3$ | 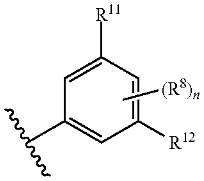 | $R^c$ |
|---|---|---|---|---|---|
| 1-98 | 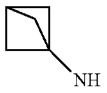 | H | $CH_2OH$ | 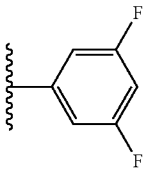 [SMILES: *c1cc(F)cc(F)c1] | CN |
| 1-101 | 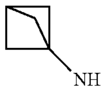 | F | H | 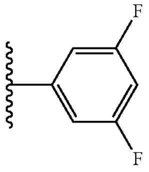 [SMILES: *c1cc(F)cc(F)c1] | CN |
| 1-103 | 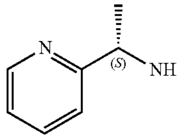 | H | $CH_3$ | 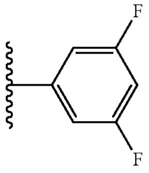 [SMILES: *c1cc(F)cc(F)c1] | CN |
| 1-104 | 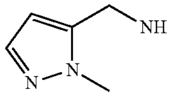 | H | $CH_3$ | 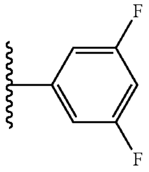 [SMILES: *c1cc(F)cc(F)c1] | CN |
| 1-105 | 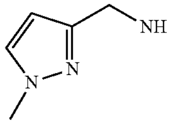 | H | $CH_3$ | 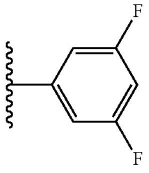 [SMILES: *c1cc(F)cc(F)c1] | CN |
| 1-106 | 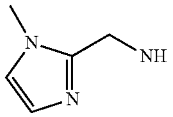 | H | $CH_3$ | 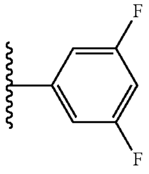 [SMILES: *c1cc(F)cc(F)c1] | CN |

TABLE 1-continued
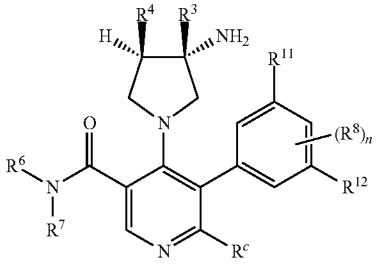
| Compd No. | $R^6R^7N$ | $R^4$ | $R^3$ | 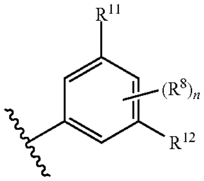 | $R^c$ |
|---|---|---|---|---|---|
| 1-107 | 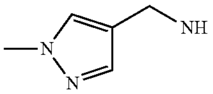 | H | $CH_3$ | 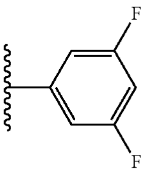 [SMILES: *c1cc(F)cc(F)c1] | CN |
| 1-108 | 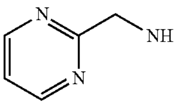 | H | $CH_3$ | 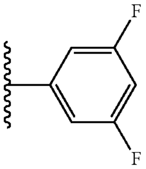 [SMILES: *c1cc(F)cc(F)c1] | CN |
| 1-109 | 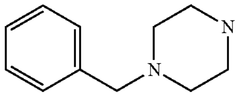 | H | $CH_3$ | 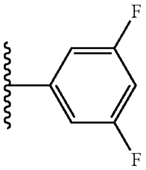 [SMILES: *c1cc(F)cc(F)c1] | CN |
| 1-110 | 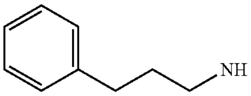 | H | $CH_3$ | 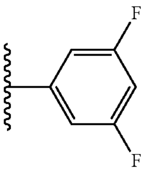 [SMILES: *c1cc(F)cc(F)c1] | CN |
| 1-111 | 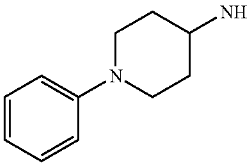 | H | $CH_3$ | 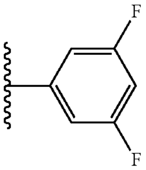 [SMILES: *c1cc(F)cc(F)c1] | CN |
| 1-112 | 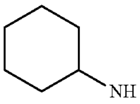 | H | $CH_3$ | 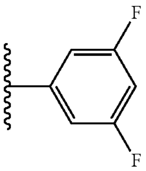 [SMILES: *c1cc(F)cc(F)c1] | H |

TABLE 1-continued
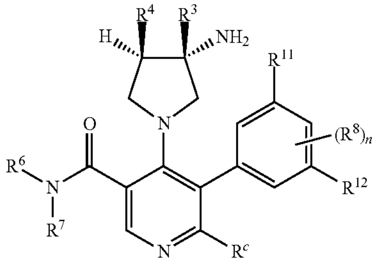
| Compd No. | $R^6R^7N$ | $R^4$ | $R^3$ | 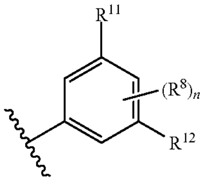 | $R^c$ |
|---|---|---|---|---|---|
| 1-113 | 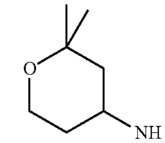 | H | $CH_3$ | 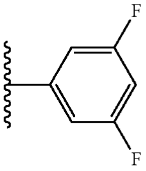 [SMILES: *c1cc(F)cc(F)c1] | CN |
| 1-114 | 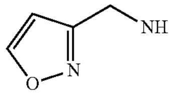 | H | $CH_3$ | 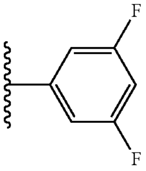 [SMILES: *c1cc(F)cc(F)c1] | CN |
| 1-115 | 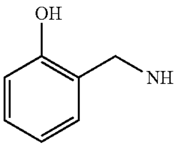 | H | $CH_3$ | 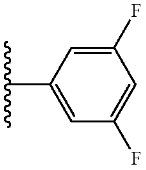 [SMILES: *c1cc(F)cc(F)c1] | CN |
| 1-116 | 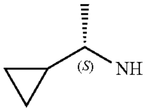 | H | $CH_2OMe$ | 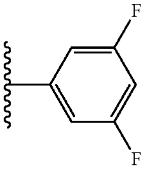 [SMILES: *c1cc(F)cc(F)c1] | CN |
| 1-118 | 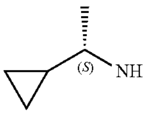 | H | $CH_2CHF_2$ | 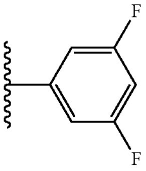 [SMILES: *c1cc(F)cc(F)c1] | CN |
| 1-120 | 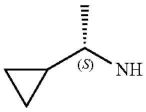 | H | $CH_3$ | 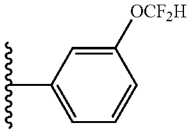 | CN |

TABLE 1-continued
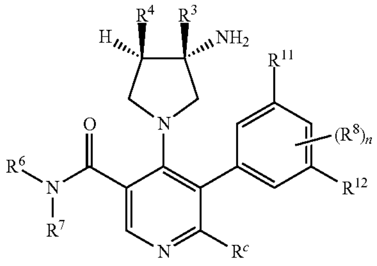
| Compd No. | $R^6R^7N$ | $R^4$ | $R^3$ | 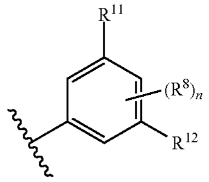 | $R^c$ |
|---|---|---|---|---|---|
| 1-122 | 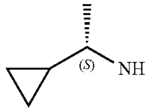 | H | $CH_3$ | 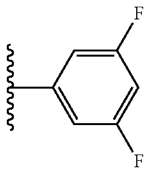 [SMILES: *c1cc(F)cc(F)c1] | $CH_3$ |
| 1-123 | 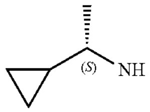 | H | $CH_3$ | 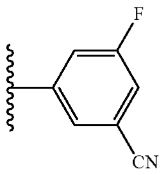 [SMILES: *c1cc(F)cc(C#N)c1] | $CH_3$ |
| 1-124 | 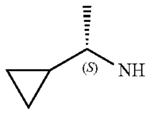 | H | $CH_3$ | 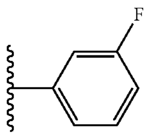 [SMILES: *c1cccc(F)c1] | $CH_3$ |
| 1-125 | 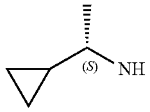 | H | $CH_3$ | 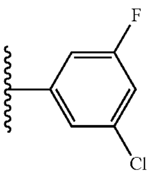 [SMILES: *c1cc(F)cc(Cl)c1] | $CH_3$ |
| 1-126 | 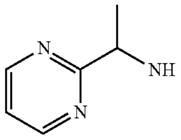 | H | $CH_3$ | 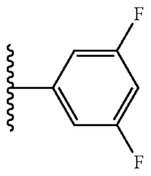 [SMILES: *c1cc(F)cc(F)c1] | CN |
| 1-127 | 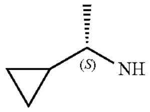 | H | $CH_3$ | 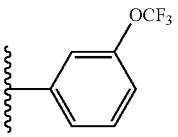 [SMILES: *c1cccc(OC(F)(F)F)c1] | CN |

TABLE 1-continued
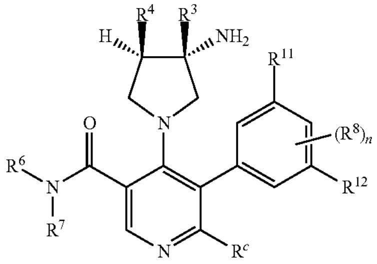
| Compd No. | $R^6R^7N$ | $R^4$ | $R^3$ | 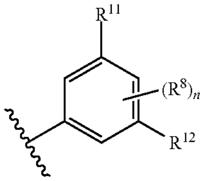 | $R^c$ |
|---|---|---|---|---|---|
| 1-130 | 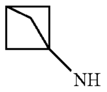 | H | $CH_3$ | 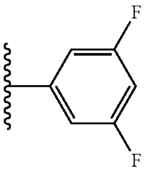 [SMILES: *c1cc(F)cc(F)c1] | $OCH_3$ |
| 1-132 | 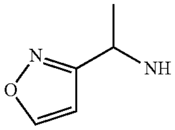 | H | $CH_3$ | 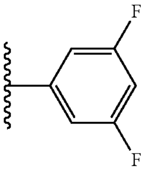 [SMILES: *c1cc(F)cc(F)c1] | CN |
| 1-133 | 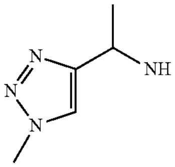 | H | $CH_3$ | 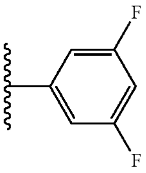 [SMILES: *c1cc(F)cc(F)c1] | CN |
| 1-135 | 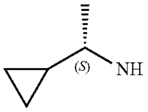 | F | H | 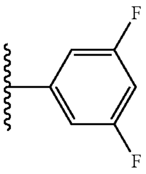 [SMILES: *c1cc(F)cc(F)c1] | CN |
| 1-137 | 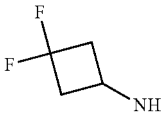 | H | $CH_3$ | 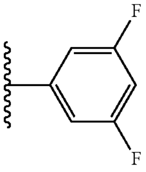 [SMILES: *c1cc(F)cc(F)c1] | $OCH_3$ |
| 1-138 | 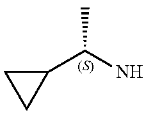 | F | H | 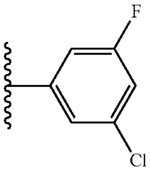 | CN |

TABLE 1-continued
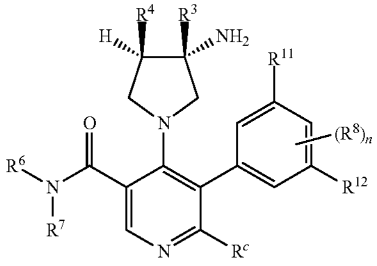
| Compd No. | $R^6R^7N$ | $R^4$ | $R^3$ | 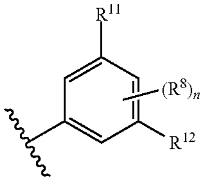 | $R^c$ |
|---|---|---|---|---|---|
| 1-140 | 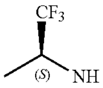 | H | $CH_3$ | 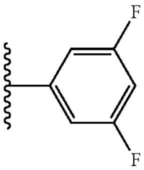 [SMILES: *c1cc(F)cc(F)c1] | $OCH_3$ |
| 1-141 | 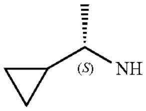 | H | $CH_3$ | 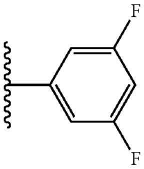 [SMILES: *c1cc(F)cc(F)c1] | $OCH_3$ |
| 1-143 | 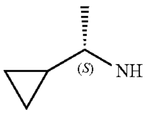 | H | $CH_3$ | 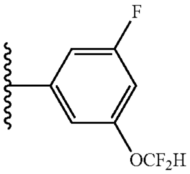 | H |
| 1-144 | 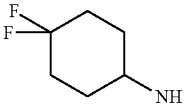 | H | $CH_3$ | 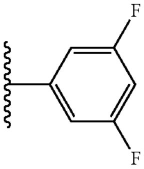 [SMILES: *c1cc(F)cc(F)c1] | $OCH_3$ |
| 1-145 | 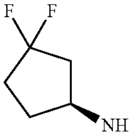 | H | $CH_3$ | 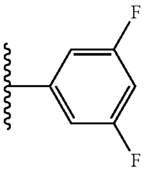 [SMILES: *c1cc(F)cc(F)c1] | $OCH_3$ |
| 1-146 | 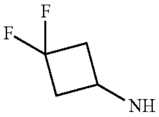 | H | $CH_3$ | 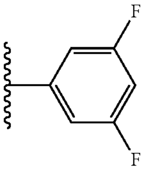 [SMILES: *c1cc(F)cc(F)c1] | $CH_3$ |

TABLE 1-continued
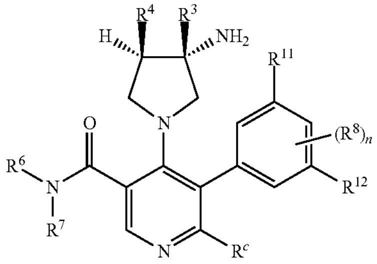
| Compd No. | $R^6R^7N$ | $R^4$ | $R^3$ | 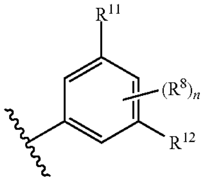 | $R^c$ |
|---|---|---|---|---|---|
| 1-147 | 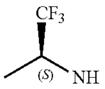 | H | $CH_3$ | 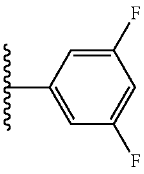 [SMILES: *c1cc(F)cc(F)c1] | $CH_3$ |
| 1-149 | 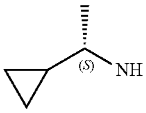 | H | $CH_3$ | 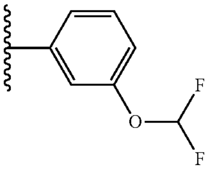 [SMILES: *c1cccc(OC(F)F)c1] | H |
| 1-150 | 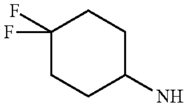 | H | H | 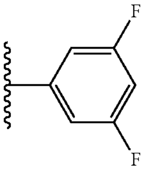 [SMILES: *c1cc(F)cc(F)c1] | $OCH_3$ |
| 1-151 | 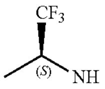 | H | H | 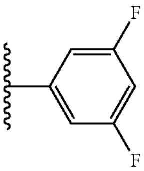 [SMILES: *c1cc(F)cc(F)c1] | $OCH_3$ |
| 1-152 | 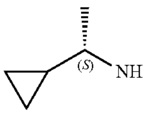 | H | H | 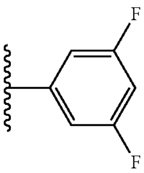 [SMILES: *c1cc(F)cc(F)c1] | $OCH_3$ |
| 1-153 | 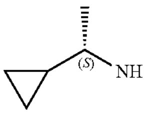 | H | $CH_3$ | 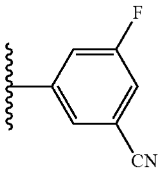 [SMILES: *c1cc(F)cc(C#N)c1] | $OCH_3$ |

TABLE 1-continued
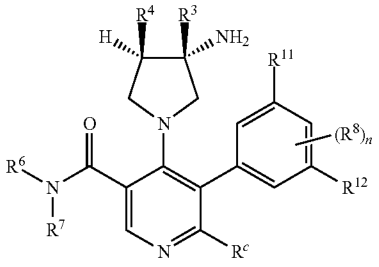
| Compd No. | $R^6R^7N$ | $R^4$ | $R^3$ | 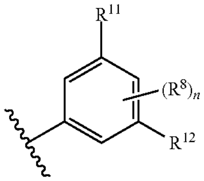 | $R^c$ |
|---|---|---|---|---|---|
| 1-154 | 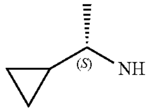 | H | $CH_3$ | 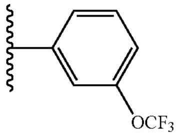 | $OCH_3$ |
| 1-164 | 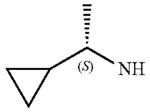 | H | $CH_3$ | 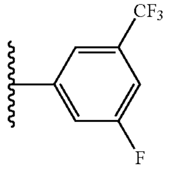 [SMILES: *c1cc(F)cc(C(F)(F)F)c1] | $OCH_3$ |
| 1-165 | 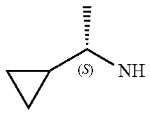 | H | $CH_3$ | 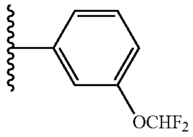 | $OCH_3$ |
| 1-168 | 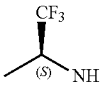 | H | $CH_3$ | 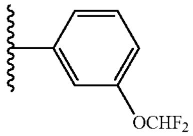 | CN |
| 1-171 | 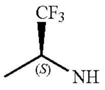 | H | $CH_3$ | 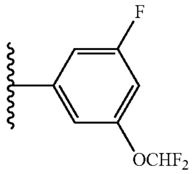 [SMILES: *c1cc(F)cc(OC(F)F)c1] | $CH_3$ |
| 1-172 | 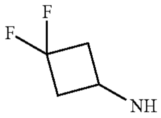 | H | $CH_3$ | 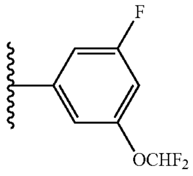 [SMILES: *c1cc(F)cc(OC(F)F)c1] | $CH_3$ |

TABLE 1-continued
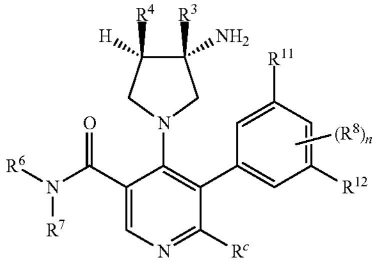
| Compd No. | $R^6R^7N$ | $R^4$ | $R^3$ | 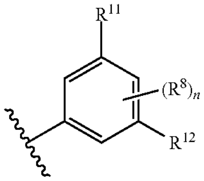 | $R^c$ |
|---|---|---|---|---|---|
| 1-173 | 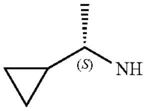 | H | $CH_3$ | 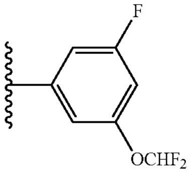 [SMILES: *c1cc(F)cc(OC(F)F)c1] | $CH_3$ |
| 1-174 | 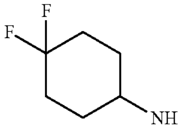 | H | $CH_3$ | 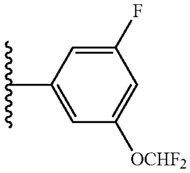 [SMILES: *c1cc(F)cc(OC(F)F)c1] | $CH_3$ |
| 1-176 | 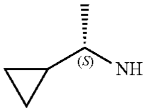 | H | $CH_3$ | 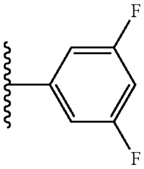 [SMILES: *c1cc(F)cc(F)c1] | $OCH_2CH_3$ |
| 1-177 | 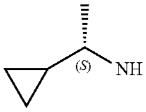 | H | $CH_3$ | 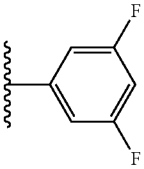 [SMILES: *c1cc(F)cc(F)c1] | $OCH_2CHF_2$ |
| 1-178 | 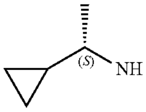 | H | $CH_3$ | 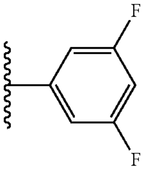 [SMILES: *c1cc(F)cc(F)c1] | 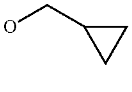 |
| 1-179 | 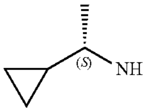 | H | $CH_3$ | 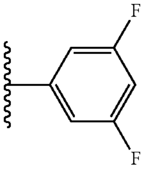 [SMILES: *c1cc(F)cc(F)c1] | $OCH_2CH_2OCH_3$ |

TABLE 1-continued
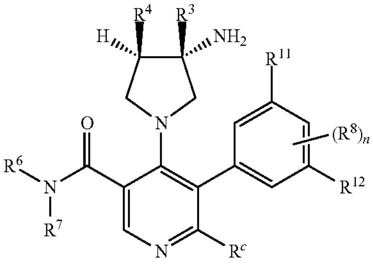
| Compd No. | $R^6R^7N$ | $R^4$ | $R^3$ | 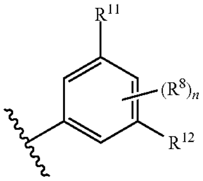 | $R^c$ |
|---|---|---|---|---|---|
| 1-180 | 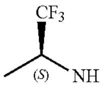 | H | $CH_3$ | 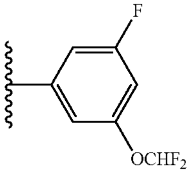 [SMILES: *c1cc(F)cc(OC(F)F)c1] | CN |
| 1-181 | 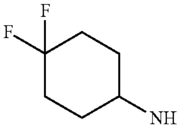 | H | $CH_3$ | 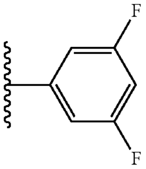 [SMILES: *c1cc(F)cc(F)c1] | $CH_3$ |
| 1-188 | 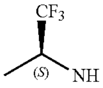 | H | $CH_3$ | 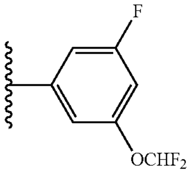 [SMILES: *c1cc(F)cc(OC(F)F)c1] | $OCH_3$ |
| 1-189 | 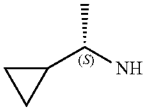 | H | $CH_3$ | 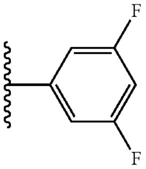 [SMILES: *c1cc(F)cc(F)c1] | $CF_3$ |
| 1-190 | 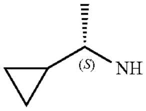 | H | $CH_3$ | 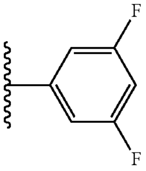 [SMILES: *c1cc(F)cc(F)c1] | $OCH_2CF_3$ |
| 1-191 | 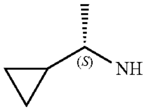 | H | $CH_3$ | 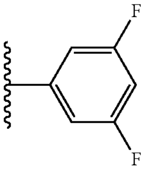 [SMILES: *c1cc(F)cc(F)c1] | 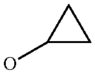 |

TABLE 1-continued
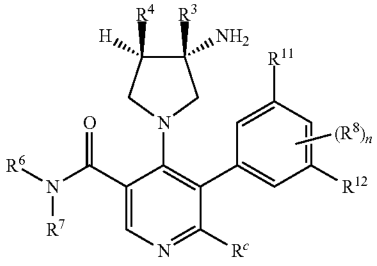
| Compd No. | $R^6R^7N$ | $R^4$ | $R^3$ | 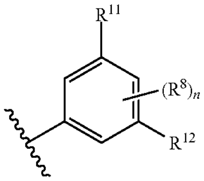 | $R^c$ |
|---|---|---|---|---|---|
| 1-192 | 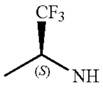 | H | $CH_3$ | 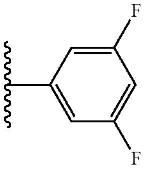 [SMILES: *c1cc(F)cc(F)c1] | CN |
| 1-193 | 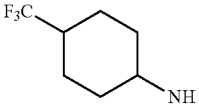 | H | H | 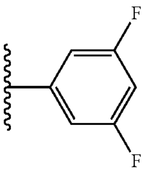 [SMILES: *c1cc(F)cc(F)c1] | $OCH_3$ |
| 1-194 | 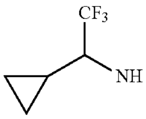 | H | H | 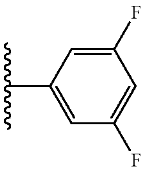 [SMILES: *c1cc(F)cc(F)c1] | $OCH_3$ |
| 1-175 | 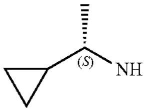 | H | $CH_3$ | 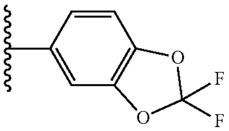 [SMILES: *c1ccc2c(c1)OC(F)(F)O2] | H |
| 1-163 | 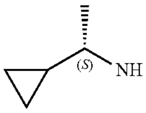 | H | $CH_3$ | 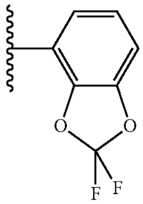 [SMILES: *c1cccc2c1OC(F)(F)O2] | H |
| 1-184 | 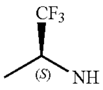 | H | $CH_3$ | 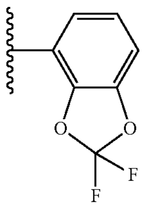 [SMILES: *c1cccc2c1OC(F)(F)O2] | $OCH_3$ |

TABLE 1-continued
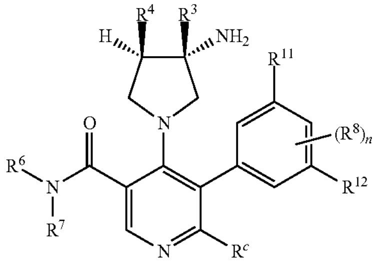
| Compd No. | $R^6R^7N$ | $R^4$ | $R^3$ | 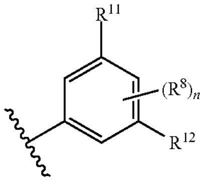 | $R^c$ |
|---|---|---|---|---|---|
| 1-195 | 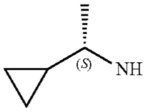 | H | $CH_3$ | 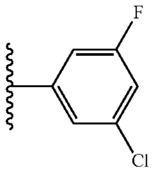 [SMILES: *c1cc(F)cc(Cl)c1] | $CF_3$ |
| 1-196 | 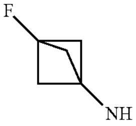 | H | H | 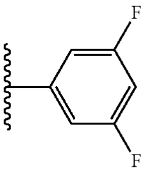 [SMILES: *c1cc(F)cc(F)c1] | $OCH_3$ |
| 1-197 | 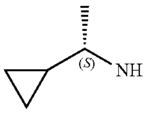 | H | $CH_3$ | 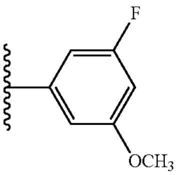 [SMILES: *c1cc(F)cc(OC)c1] | $CF_3$ |
| 1-198 | 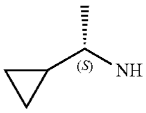 | H | H | 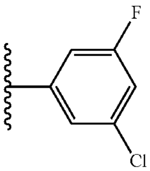 [SMILES: *c1cc(F)cc(Cl)c1] | $CF_3$ |
| 1-199 | 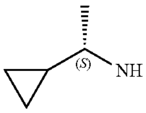 | H | H | 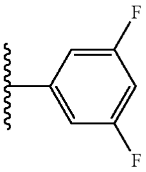 [SMILES: *c1cc(F)cc(F)c1] | $CF_3$ |
| 1-200 | 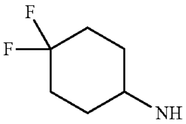 | H | H | 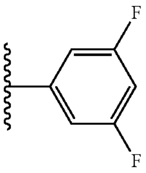 [SMILES: *c1cc(F)cc(F)c1] | $OCH_2COOEt$ |

TABLE 1-continued
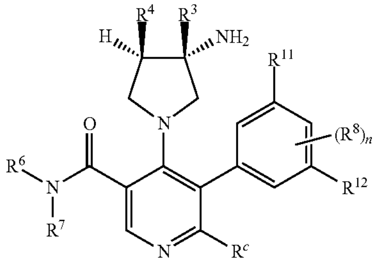
| Compd No. | $R^6R^7N$ | $R^4$ | $R^3$ | 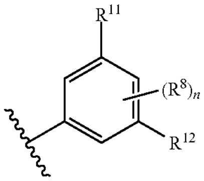 | $R^c$ |
|---|---|---|---|---|---|
| 1-201 | 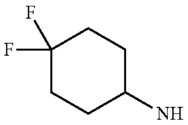 | H | H | 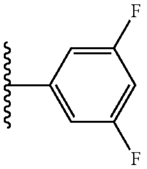 [SMILES: *c1cc(F)cc(F)c1] | $OCH_2CH_2COOEt$ |
| 1-202 | 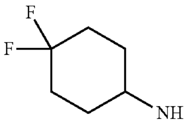 | H | H | 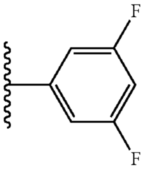 [SMILES: *c1cc(F)cc(F)c1] | $OCH_2CH_2CH_2COOEt$ |
| 1-203 | 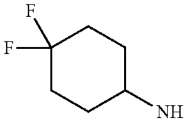 | H | H | 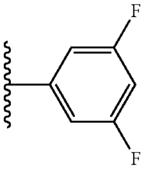 [SMILES: *c1cc(F)cc(F)c1] | $OCH_2COOH$ |
| 1-204 | 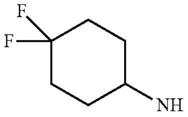 | H | H | 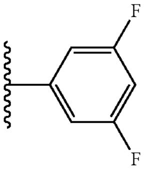 [SMILES: *c1cc(F)cc(F)c1] | $OCH_2CH_2COOH$ |
| 1-205 | 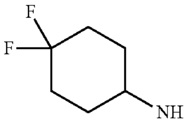 | H | H | 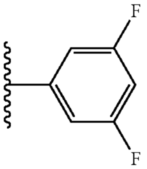 [SMILES: *c1cc(F)cc(F)c1] | $OCH_2CH_2CH_2OOH$ |
| 1-209 | 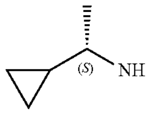 | H | $CH_3$ | 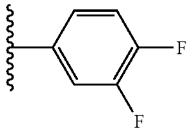 | $CF_3$ |

TABLE 1-continued
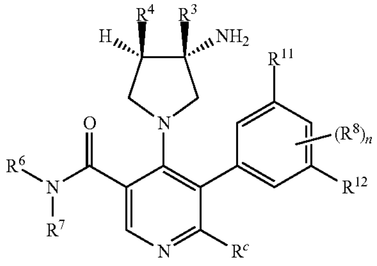
| Compd No. | $R^6R^7N$ | $R^4$ | $R^3$ | 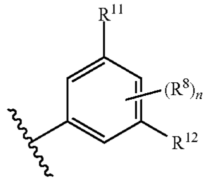 | $R^c$ |
|---|---|---|---|---|---|
| 1-210 | 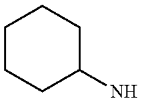 | H | $CH_3$ | 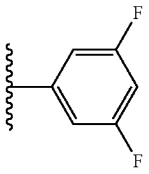 [SMILES: *c1cc(F)cc(F)c1] | $CF_3$ |
| 1-211 | 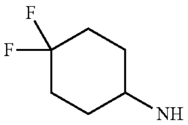 | H | $CH_3$ | 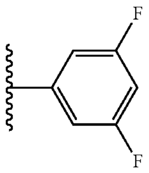 [SMILES: *c1cc(F)cc(F)c1] | $CF_3$ |
| 1-212 | 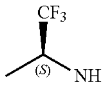 | H | H | 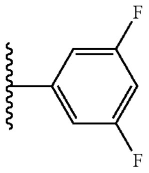 [SMILES: *c1cc(F)cc(F)c1] | $CF_3$ |
| 1-213 | 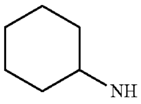 | H | H | 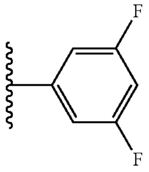 [SMILES: *c1cc(F)cc(F)c1] | $CF_3$ |
| 1-214 | 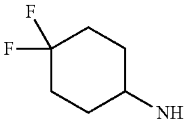 | H | H | 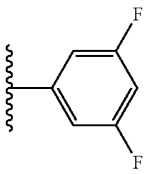 [SMILES: *c1cc(F)cc(F)c1] | $CF_3$ |
| 1-215 | 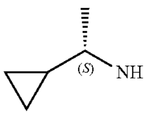 | H | H | 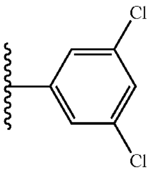 | $CF_3$ |

TABLE 1-continued
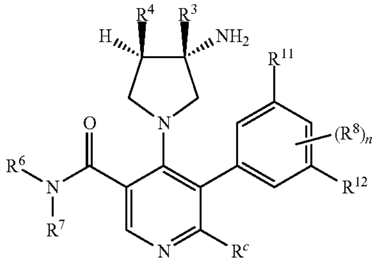
| Compd No. | $R^6R^7N$ | $R^4$ | $R^3$ | 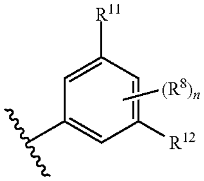 | $R^c$ |
|---|---|---|---|---|---|
| 1-216 | 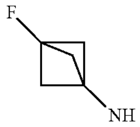 | H | H | 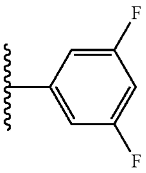 [SMILES: *c1cc(F)cc(F)c1] | $CF_3$ |
| 1-217 | 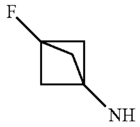 | H | $CH_3$ | 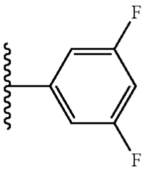 [SMILES: *c1cc(F)cc(F)c1] | $CF_3$ |
| 1-218 | 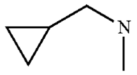 | H | $CH_3$ | 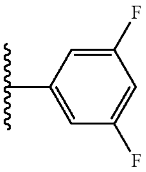 [SMILES: *c1cc(F)cc(F)c1] | CN |
| 1-219 | 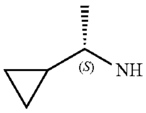 | H | $CH_3$ | 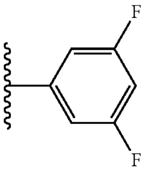 [SMILES: *c1cc(F)cc(F)c1] | CN |
| 1-222 | 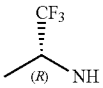 | H | $CH_3$ | 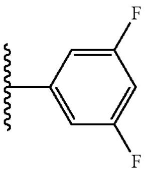 [SMILES: *c1cc(F)cc(F)c1] | CN |
| 1-223 | 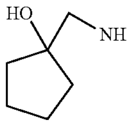 | H | $CH_3$ | 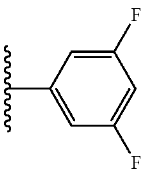 [SMILES: *c1cc(F)cc(F)c1] | $CH_3$ |

TABLE 1-continued
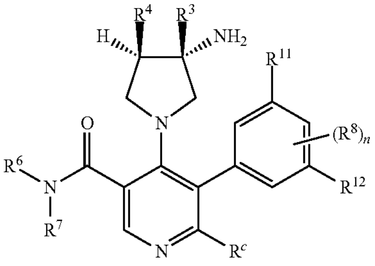
| Compd No. | $R^6R^7N$ | $R^4$ | $R^3$ | 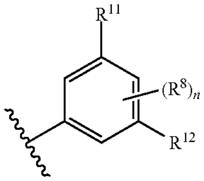 | $R^c$ |
|---|---|---|---|---|---|
| 1-224 | 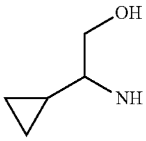 | H | $CH_3$ | 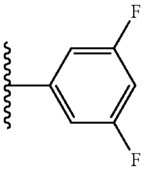 [SMILES: *c1cc(F)cc(F)c1] | $CH_3$ |
| 1-225 | 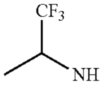 | H | H | 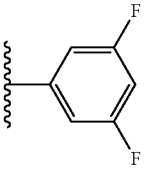 [SMILES: *c1cc(F)cc(F)c1] | CN |
| 1-226 | 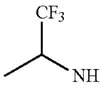 | H | H | 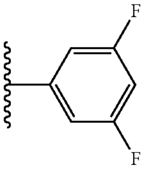 [SMILES: *c1cc(F)cc(F)c1] | CN |
| 1-227 | 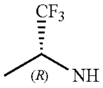 | H | H | 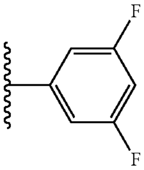 [SMILES: *c1cc(F)cc(F)c1] | CN |
| 1-228 | 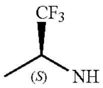 | H | $CH_3$ | 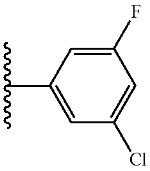 [SMILES: *c1cc(F)cc(Cl)c1] | $OCH_3$ |
| 1-229 | 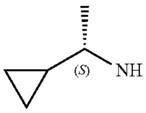 | H | $CH_3$ | 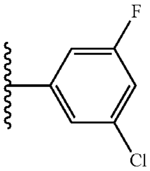 [SMILES: *c1cc(F)cc(Cl)c1] | $OCH_3$ |

TABLE 1-continued
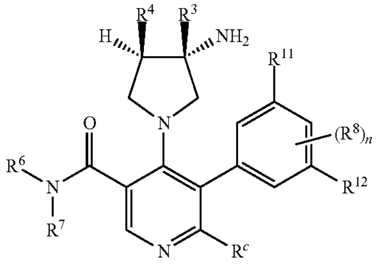
| Compd No. | $R^6R^7N$ | $R^4$ | $R^3$ | 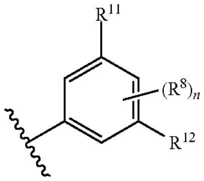 | $R^c$ |
|---|---|---|---|---|---|
| 1-230 | 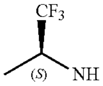 | H | H | 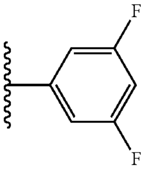 [SMILES: *c1cc(F)cc(F)c1] | $CH_3$ |
| 1-231 | 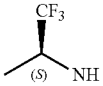 | H | H | 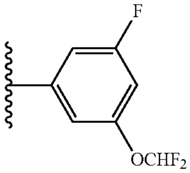 [SMILES: *c1cc(F)cc(OC(F)F)c1] | $CH_3$ |
| 1-232 | 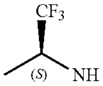 | H | H | 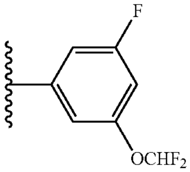 [SMILES: *c1cc(F)cc(OC(F)F)c1] | $CH_3$ |
| 1-233 | 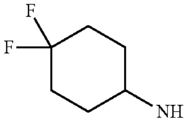 | H | H | 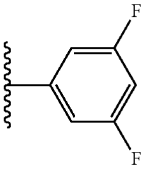 [SMILES: *c1cc(F)cc(F)c1] | $CH_3$ |
| 1-234 | 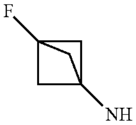 | H | $CH_3$ | 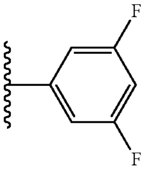 [SMILES: *c1cc(F)cc(F)c1] | CN |
| 1-235 | 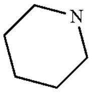 | H | H | 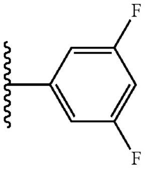 [SMILES: *c1cc(F)cc(F)c1] | $OCH_3$ |

TABLE 1-continued
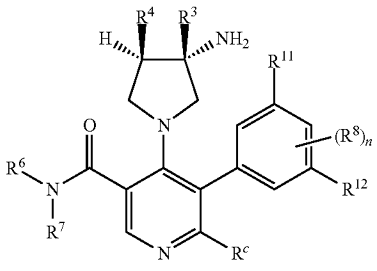
| Compd No. | $R^6R^7N$ | $R^4$ | $R^3$ | 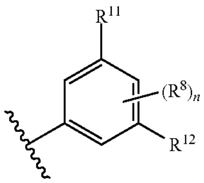 | $R^c$ |
|---|---|---|---|---|---|
| 1-236 | 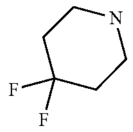 | H | H | 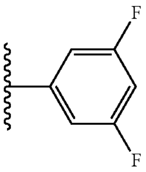 [SMILES: *c1cc(F)cc(F)c1] | $OCH_3$ |
| 1-237 | 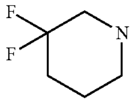 | H | H | 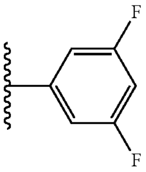 [SMILES: *c1cc(F)cc(F)c1] | $OCH_3$ |
| 1-238 | 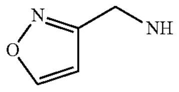 | H | $CH_3$ | 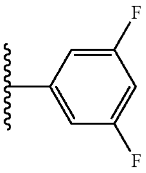 [SMILES: *c1cc(F)cc(F)c1] | $OCH_3$ |
| 1-239 | 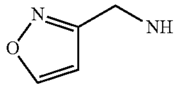 | H | $CH_3$ | 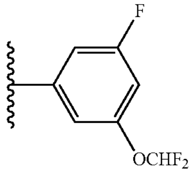 | $OCH_3$ |
| 1-240 | 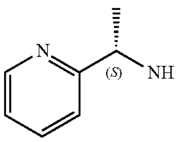 | H | $CH_3$ | 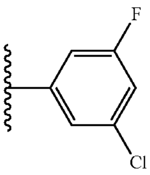 [SMILES: *c1cc(F)cc(Cl)c1] | $OCH_3$ |
| 1-241 | 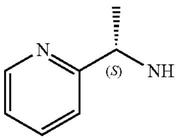 | H | $CH_3$ | 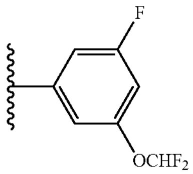 | $OCH_3$ |

TABLE 1-continued
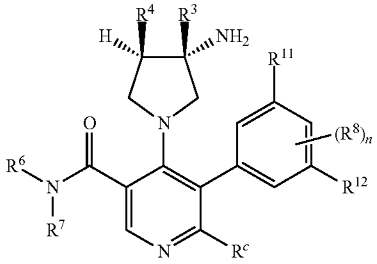
| Compd No. | $R^6R^7N$ | $R^4$ | $R^3$ | 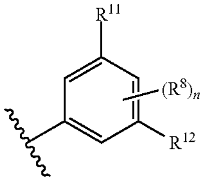 | $R^c$ |
|---|---|---|---|---|---|
| 1-242 | 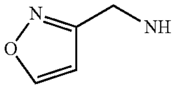 | H | $CH_3$ | 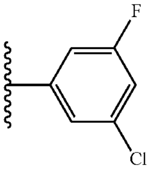 | $CH_3$ |
| 1-243 | 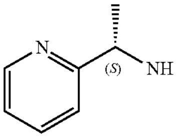 | H | $CH_3$ | 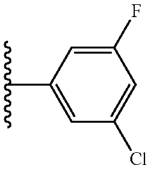 [SMILES: *c1cc(F)cc(Cl)c1] | $CH_3$ |
| 1-244 | 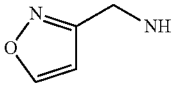 | H | $CH_3$ | 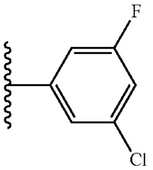 [SMILES: *c1cc(F)cc(Cl)c1] | CN |
| 1-245 | 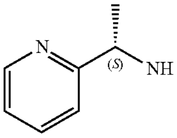 | H | $CH_3$ | 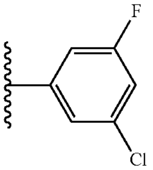 | CN |
| 1-246 | 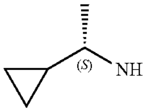 | H | $CH_3$ | 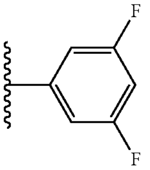 [SMILES: *c1cc(F)cc(F)c1] | $OCH_2CH_2OH$ |
| 1-247 | 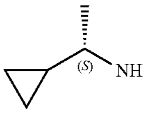 | H | $CH_3$ | 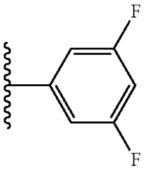 [SMILES: *c1cc(F)cc(F)c1] | $OCH_2COOH$ |

TABLE 1-continued
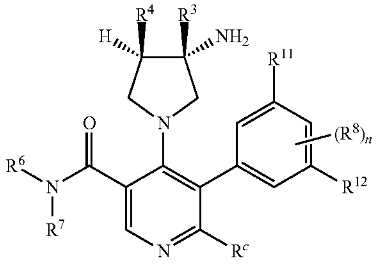
| Compd No. | $R^6R^7N$ | $R^4$ | $R^3$ | 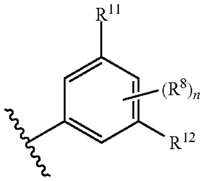 | $R^c$ |
|---|---|---|---|---|---|
| 1-259 | 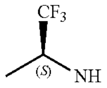 | H | $CH_3$ | 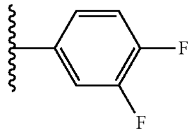 | $OCH_3$ |
| 1-260 | 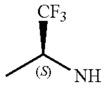 | H | $CH_3$ | 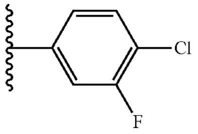 [SMILES: *c1ccc(Cl)c(F)c1] | $OCH_3$ |
| 1-261 | 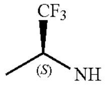 | H | $CH_3$ | 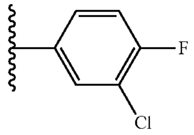 [SMILES: *c1ccc(F)c(Cl)c1] | $OCH_3$ |
| 1-262 | 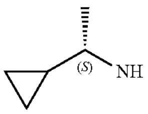 | H | $CH_3$ | 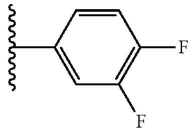 [SMILES: *c1ccc(F)c(F)c1] | $OCH_3$ |
| 1-263 | 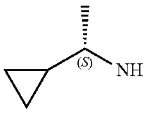 | H | $CH_3$ | 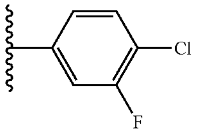 [SMILES: *c1ccc(Cl)c(F)c1] | $OCH_3$ |
| 1-264 | 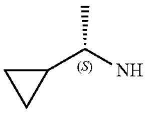 | H | $CH_3$ | 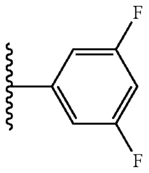 [SMILES: *c1cc(F)cc(F)c1] | $OCH_2CH_2COOH$ |
| 1-265 | 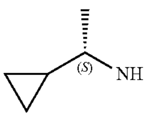 | H | $CH_3$ | 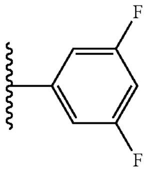 [SMILES: *c1cc(F)cc(F)c1] | OCH2CH2CH2COOH |

TABLE 1-continued
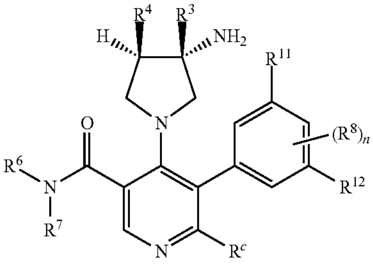
| Compd No. | $R^6R^7N$ | $R^4$ | $R^3$ | 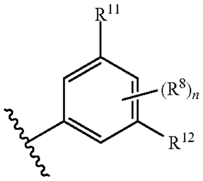 | $R^c$ |
|---|---|---|---|---|---|
| 1-266 | 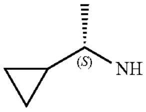 | H | $CH_3$ | 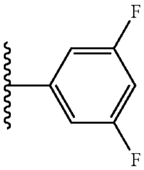 [SMILES: *c1cc(F)cc(F)c1] | 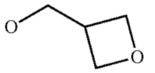 |
| 1-267 | 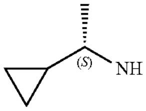 | H | $CH_3$ | 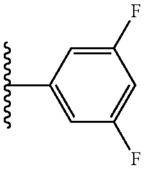 [SMILES: *c1cc(F)cc(F)c1] | 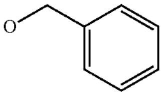 |
| 1-268 | 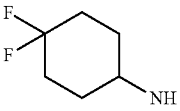 | H | $CH_3$ | 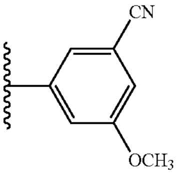 | $CH_3$ |
| 1-269 | 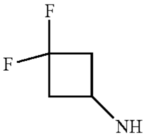 | H | $CH_3$ | 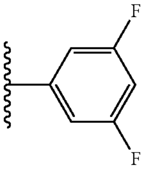 [SMILES: *c1cc(F)cc(F)c1] | $CH_3$ |
| 1-272 | 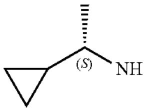 | H | H | 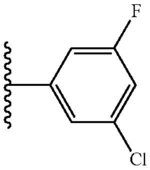 | $CH_3$ |
| 1-273 | 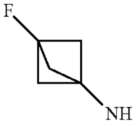 | H | $CH_3$ | 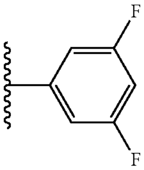 [SMILES: *c1cc(F)cc(F)c1] | $OCH_3$ |

TABLE 1-continued
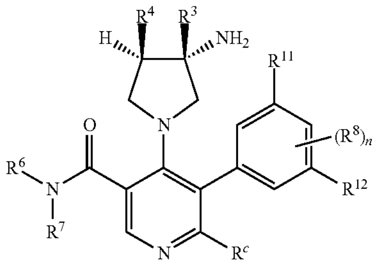
| Compd No. | $R^6R^7N$ | $R^4$ | $R^3$ | 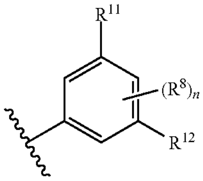 | $R^c$ |
|---|---|---|---|---|---|
| 1-275 | 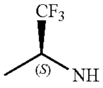 | H | $CH_3$ | 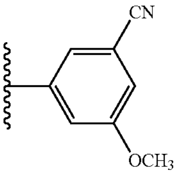 | $CH_3$ |
| 1-276 | 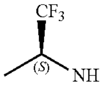 | H | H | 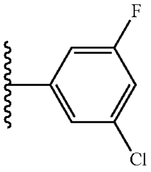 [SMILES: *c1cc(F)cc(Cl)c1] | $CH_3$ |
| 1-277 | 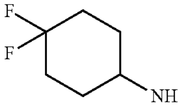 | H | H | 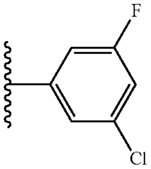 [SMILES: *c1cc(F)cc(Cl)c1] | $CH_3$ |
| 1-278 | 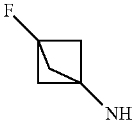 | H | H | 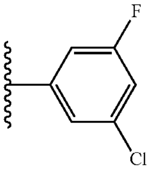 [SMILES: *c1cc(F)cc(Cl)c1] | $CH_3$ |
| 1-279 | 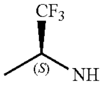 | H | $CH_3$ | 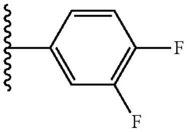 | $CH_3$ |
| 1-280 | 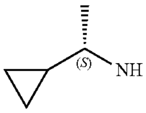 | H | $CH_3$ | 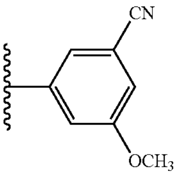 [SMILES: *c1cc(C#N)cc(OC)c1] | $CH_3$ |

TABLE 1-continued
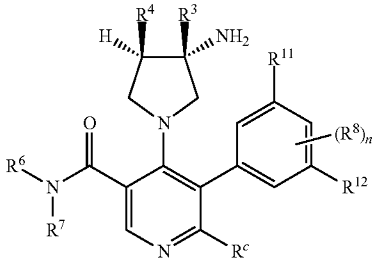
| Compd No. | $R^6R^7N$ | $R^4$ | $R^3$ | 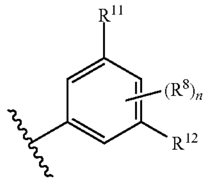 | $R^c$ |
|---|---|---|---|---|---|
| 1-281 | 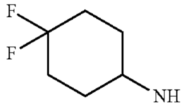 | H | $CH_3$ | 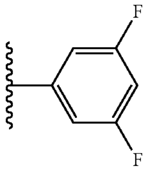 [SMILES: *c1cc(F)cc(F)c1] | 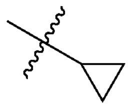 [SMILES: *C1CC1] |
| 1-282 | 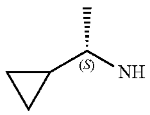 | H | H | 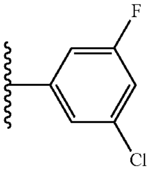 | $OCH_3$ |
| 1-283 | 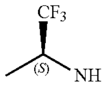 | H | H | 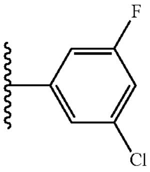 | $OCH_3$ |
| 1-284 | 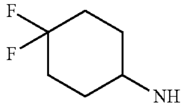 | H | H | 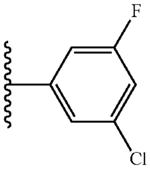 [SMILES: *c1cc(F)cc(Cl)c1] | $OCH_3$ |
| 1-285 | 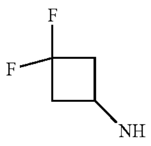 | H | H | 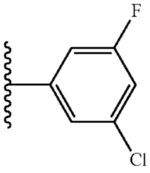 [SMILES: *c1cc(F)cc(Cl)c1] | $OCH_3$ |
| 1-286 | 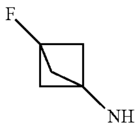 | H | H | 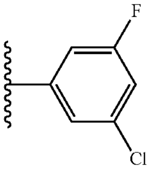 [SMILES: *c1cc(F)cc(Cl)c1] | $OCH_3$ |

TABLE 1-continued

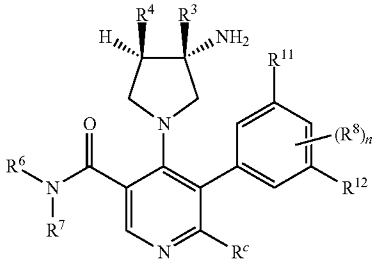

| Compd No. | $R^6R^7N$ | $R^4$ | $R^3$ | 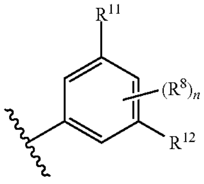 | $R^c$ |
|---|---|---|---|---|---|
| 1-287 | 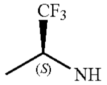 | H | $CH_3$ | 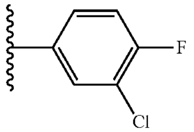 [SMILES: *c1ccc(F)c(Cl)c1] | $CH_3$ |
| 1-288 | 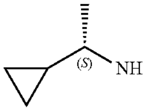 | H | $CH_3$ | 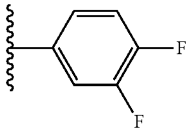 | $CH_3$ |
| 1-289 | 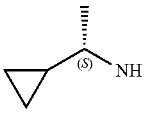 | H | $CH_3$ | 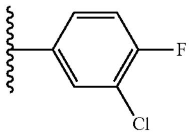 | $CH_3$ |
| 1-290 | 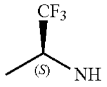 | H | $CH_3$ | 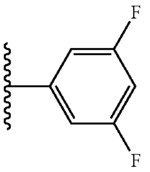 [SMILES: *c1cc(F)cc(F)c1] | 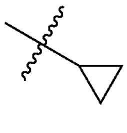 [SMILES: *C1CC1] |

Compounds in Table 1 are named:

1-1: 4-[(3 S)-3-aminopyrrolidin-1-yl]-N,5-bis(3,5-dimethylphenyl)pyridine-3-carboxamide;

1-3: 4-[(3 S)-3-aminopyrrolidin-1-yl]-N-(3-chloro-5-fluorophenyl)-5-(3,5-dimethylphenyl)pyridine-3-carboxamide;

1-4: 4-[(3S)-3-amino-3-methylpyrrolidin-1-yl]-5-(3-cyano-4-fluorophenyl)-N-(2-fluorophenyl)pyridine-3-carboxamide;

1-7: 4-[(3S)-3-aminopyrrolidin-1-yl]-5-(3-cyanophenyl)-N-cyclohexylpyridine-3-carboxamide;

1-8: 4-[(3S)-3-aminopyrrolidin-1-yl]-5-(3-cyanophenyl)-N-(1-methylcyclobutyl)pyridine-3-carboxamide;

1-9: 4-[(3S)-3-aminopyrrolidin-1-yl]-N-benzyl-5-(3-cyanophenyl)pyridine-3-carboxamide;

1-10: 4-[(3S)-3-amino-3-methylpyrrolidin-1-yl]-5-(3-cyanophenyl)-N-(4,4-difluorocyclohexyl)pyridine-3-carboxamide;

1-11: 4-[(3S)-3-amino-3-methylpyrrolidin-1-yl]-N-(3,3-dimethylcyclohexyl)-5-(3,5-dimethylphenyl)pyridine-3-carboxamide;

1-12: 4-[(3S)-3-amino-3-methylpyrrolidin-1-yl]-N-(4,4-difluorocyclohexyl)-5-(3,5-dimethylphenyl)pyridine-3-carboxamide;

1-13: 4-[(3S)-3-amino-3-methylpyrrolidin-1-yl]-N-(4,4-difluorocyclohexyl)-5-(3-fluoro-5-methylphenyl)pyridine-3-carboxamide;

1-14: 4-[(3S)-3-amino-3-methylpyrrolidin-1-yl]-N-(3,3-difluorocyclohexyl)-5-(3,5-dimethylphenyl)pyridine-3-carboxamide;

1-15: 4-[(3S)-3-amino-3-methylpyrrolidin-1-yl]-5-(3-fluoro-5-methylphenyl)-N-[1-(trifluoromethyl)cyclopentyl]pyridine-3-carboxamide;

1-16: 4-[(3S)-3-amino-3-methylpyrrolidin-1-yl]-N-(4,4-difluorocyclohexyl)-5-(3,5-difluorophenyl)pyridine-3-carboxamide;

1-17: 4-[(3S)-3-amino-3-methylpyrrolidin-1-yl]-N-(2,3-dihydro-1H-inden-1-yl)-5-(3-fluoro-5-methylphenyl)pyridine-3-carboxamide;

1-18: N-(adamantan-2-yl)-4-[(3S)-3-amino-3-methylpyrrolidin-1-yl]-5-(3-fluoro-5-methylphenyl)pyridine-3-carboxamide;

1-19: 4-[(3S)-3-amino-3-methylpyrrolidin-1-yl]-N-(1-ethylcyclobutyl)-5-(3-fluoro-5-methylphenyl)pyridine-3-carboxamide;

1-20: 4-[(3S)-3-amino-3-methylpyrrolidin-1-yl]-N-(4,4-difluorocyclohexyl)-5-(3,4,5-trifluorophenyl)pyridine-3-carboxamide;

1-21: 4-[(3S)-3-amino-3-methylpyrrolidin-1-yl]-N-{bicyclo[1.1.1]pentan-1-yl}-5-(3,5-difluorophenyl)pyridine-3-carboxamide;

1-22: 4-[(3S)-3-amino-3-methylpyrrolidin-1-yl]-5-(3,5-difluorophenyl)-N-(3,3-dimethylcyclobutyl)pyridine-3-carboxamide;

1-23: 4-[(3S)-3-amino-3-methylpyrrolidin-1-yl]-N-cyclopropyl-5-(3,5-difluorophenyl)pyridine-3-carboxamide;

1-24: 4-[(3S)-3-amino-3-methylpyrrolidin-1-yl]-N-(1-cyclopropylethyl)-5-(3-fluoro-5-methylphenyl)pyridine-3-carboxamide;

1-25: 4-[(3S)-3-amino-3-methylpyrrolidin-1-yl]-N-(dicyclopropylmethyl)-5-(3-fluoro-5-methylphenyl)pyridine-3-carboxamide;

1-26: 4-[(3S)-3-amino-3-methylpyrrolidin-1-yl]-N-(cyclopropylmethyl)-5-(3-fluoro-5-methylphenyl)pyridine-3-carboxamide;

1-27: 4-[(3S)-3-amino-3-methylpyrrolidin-1-yl]-5-(3-fluoro-5-methylphenyl)-N-(1-methyl-1H-pyrazol-3-yl)pyridine-3-carboxamide;

1-28: 4-[(3S)-3-amino-3-methylpyrrolidin-1-yl]-5-(3,5-difluorophenyl)-N-(2,2,2-trifluoroethyl)pyridine-3-carboxamide;

1-29: 4-[(3S)-3-amino-3-methylpyrrolidin-1-yl]-N-tert-butyl-5-(3,5-difluorophenyl)pyridine-3-carboxamide;

1-30: 4-[(3S)-3-amino-3-methylpyrrolidin-1-yl]-N-(3,3-difluorocyclobutyl)-5-(3,5-difluorophenyl)pyridine-3-carboxamide;

1-31: 4-[(3S)-3-amino-3-methylpyrrolidin-1-yl]-5-(3,5-difluorophenyl)-N-(pentan-3-yl)pyridine-3-carboxamide;

1-32: 4-[(3S)-3-amino-3-methylpyrrolidin-1-yl]-5-(3,5-difluorophenyl)-N-[(1-methylcyclopropyl)methyl]pyridine-3-carboxamide;

1-33: 4-[(3S)-3-amino-3-methylpyrrolidin-1-yl]-N-(cyclobutylmethyl)-5-(3,5-difluorophenyl)pyridine-3-carboxamide;

1-34: 4-[(3S)-3-amino-3-methylpyrrolidin-1-yl]-5-(3,5-difluorophenyl)-N-(1-methylcyclobutyl)pyridine-3-carboxamide;

1-35: 4-[(3S)-3-amino-3-methylpyrrolidin-1-yl]-5-(3-chloro-5-fluorophenyl)-N-(3,3-difluorocyclobutyl)pyridine-3-carboxamide;

1-37: 4-[(3R,4R)-3-amino-4-fluoropyrrolidin-1-yl]-N-{bicyclo[1.1.1]pentan-1-yl}-5-(3,5-difluorophenyl)pyridine-3-carboxamide;

1-38: 4-[(3S)-3-amino-3-methylpyrrolidin-1-yl]-5-(3,5-difluorophenyl)-N-(3-methylbutan-2-yl)pyridine-3-carboxamide;

1-39: 4-[(3S)-3-amino-3-methylpyrrolidin-1-yl]-5-(3,5-difluorophenyl)-N-(2,4-dimethylpentan-3-yl)pyridine-3-carboxamide;

1-40: 4-[(3S)-3-amino-3-methylpyrrolidin-1-yl]-N-(2-cyclopropylpropan-2-yl)-5-(3,5-difluorophenyl)pyridine-3-carboxamide;

1-41: 4-[(3S)-3-amino-3-methylpyrrolidin-1-yl]-N-[(1S)-1-cyclopropylethyl]-5-(3,5-difluorophenyl)pyridine-3-carboxamide;

1-42: 4-[(3S)-3-amino-3-methylpyrrolidin-1-yl]-N-[(2,2-difluorocyclopropyl)methyl]-5-(3,5-difluorophenyl)pyridine-3-carboxamide;

1-43: 4-[(3S)-3-amino-3-methylpyrrolidin-1-yl]-5-(3,5-difluorophenyl)-N-[(2,2-dimethylcyclopropyl)methyl]pyridine-3-carboxamide;

1-44: 4-[(3S)-3-amino-3-methylpyrrolidin-1-yl]-N-[(1R)-1-cyclopropylethyl]-5-(3,5-difluorophenyl)pyridine-3-carboxamide;

1-45: 4-[(3S)-3-amino-3-methylpyrrolidin-1-yl]-5-(3,5-difluorophenyl)-N-(1,1,1-trifluoro-3-methylbutan-2-yl)pyridine-3-carboxamide;

1-46: 4-[(3S)-3-amino-3-methylpyrrolidin-1-yl]-5-(3,5-difluorophenyl)-N-(2-methylpropyl)pyridine-3-carboxamide;

1-47: 4-[(3S)-3-amino-3-methylpyrrolidin-1-yl]-5-(3,5-difluorophenyl)-N-[(1-fluorocyclobutyl)methyl]pyridine-3-carboxamide;

1-48: 4-[(3S)-3-amino-3-methylpyrrolidin-1-yl]-6-cyano-N-(4,4-difluorocyclohexyl)-5-(3,5-difluorophenyl)pyridine-3-carboxamide;

1-49: 4-[(3S)-3-amino-3-methylpyrrolidin-1-yl]-N-{bicyclo[1.1.1]pentan-1-yl}-6-cyano-5-(3,5-difluorophenyl)pyridine-3-carboxamide;

1-50: 4-[(3S)-3-amino-3-methylpyrrolidin-1-yl]-N-[(3,3-difluorocyclobutyl)methyl]-5-(3,5-difluorophenyl)pyridine-3-carboxamide;

1-51: 4-[(3S)-3-amino-3-methylpyrrolidin-1-yl]-N-(dicyclopropylmethyl)-5-(3,5-difluorophenyl)pyridine-3-carboxamide;

1-52: 4-[(3S)-3-amino-3-methylpyrrolidin-1-yl]-5-(3,5-difluorophenyl)-N-[trans-2-fluorocyclohexyl]pyridine-3-carboxamide;

1-53: 4-[(3S)-3-amino-3-methylpyrrolidin-1-yl]-5-(3,5-difluorophenyl)-N-[(2R)-1,1,1-trifluoropropan-2-yl]pyridine-3-carboxamide;

1-54: 4-[(3S)-3-amino-3-methylpyrrolidin-1-yl]-5-(3,5-difluorophenyl)-N-[(2S)-1,1,1-trifluoropropan-2-yl]pyridine-3-carboxamide;

1-55: 4-[(3S)-3-amino-3-methylpyrrolidin-1-yl]-5-(3,5-difluorophenyl)-N-[(trans-3-fluorocyclobutyl]pyridine-3-carboxamide;

1-56: 4-[(3S)-3-amino-3-methylpyrrolidin-1-yl]-N-(1-cyclobutyl-2,2,2-trifluoroethyl)-5-(3,5-difluorophenyl)pyridine-3-carboxamide;

1-57: 4-[(3S)-3-amino-3-methylpyrrolidin-1-yl]-5-(3,5-difluorophenyl)-N-(2-methylbutyl)pyridine-3-carboxamide;

1-58: 4-[(3S)-3-amino-3-methylpyrrolidin-1-yl]-5-(3,5-difluorophenyl)-N-(2-ethylbutyl)pyridine-3-carboxamide;

1-59: 4-[(3S)-3-amino-3-methylpyrrolidin-1-yl]-5-(3,5-difluorophenyl)-N-[cis-3-fluorocyclobutyl]pyridine-3-carboxamide;

1-60: 4-[(3S)-3-amino-3-methylpyrrolidin-1-yl]-5-(3,5-difluorophenyl)-N-(4,4,4-trifluorobutan-2-yl)pyridine-3-carboxamide;

1-61: 4-[(3S)-3-aminopyrrolidin-1-yl]-5-(3-chloro-5-fluorophenyl)-N-(dicyclopropylmethyl)pyridine-3-carboxamide;

1-62: 4-[(3S)-3-amino-3-methylpyrrolidin-1-yl]-5-(3,5-difluorophenyl)-N-(2,2-difluoropropyl)pyridine-3-carboxamide;

1-64: 4-[(3S)-3-aminopyrrolidin-1-yl]-N-{bicyclo[1.1.1]pentan-1-yl}-6-cyano-5-(3,5-difluorophenyl)pyridine-3-carboxamide;

1-65: 4-[(3S)-3-aminopyrrolidin-1-yl]-N-{bicyclo[1.1.1]pentan-1-yl}-6-cyano-5-(3-fluorophenyl)pyridine-3-carboxamide;

1-66: 4-[(3S)-3-aminopyrrolidin-1-yl]-N-{bicyclo[1.1.1]pentan-1-yl}-6-cyano-5-(3,4-difluorophenyl)pyridine-3-carboxamide;

1-67: 4-[(3S)-3-aminopyrrolidin-1-yl]-6-cyano-N-(4,4-difluorocyclohexyl)-5-(3,5-difluorophenyl)pyridine-3-carboxamide;

1-68: 4-[(3S)-3-aminopyrrolidin-1-yl]-6-cyano-N-(3,3-difluorocyclobutyl)-5-(3,5-difluorophenyl)pyridine-3-carboxamide;

1-69: 4-[(3S)-3-aminopyrrolidin-1-yl]-6-cyano-N-[(1S)-1-cyclopropylethyl]-5-(3,5-difluorophenyl)pyridine-3-carboxamide;

1-70: 4-[(3S)-3-aminopyrrolidin-1-yl]-6-cyano-N-(dicyclopropylmethyl)-5-(3,5-difluorophenyl)pyridine-3-carboxamide;

1-71: 4-[(3S)-3-aminopyrrolidin-1-yl]-6-cyano-5-(3,5-difluorophenyl)-N-[(2S)-1,1,1-trifluoropropan-2-yl]pyridine-3-carboxamide;

1-72: 4-[(3S)-3-aminopyrrolidin-1-yl]-6-cyano-5-(3,5-difluorophenyl)-N-(pentan-3-yl)pyridine-3-carboxamide;

1-73: 4-[(3S)-3-aminopyrrolidin-1-yl]-6-cyano-N-cycloheptyl-5-(3,5-difluorophenyl)pyridine-3-carboxamide;

1-74: 4-[(3S)-3-amino-3-methylpyrrolidin-1-yl]-N-{bicyclo[1.1.1]pentan-1-yl}-5-(3,5-difluorophenyl)-6-methylpyridine-3-carboxamide;

1-76: 4-[(3S)-3-amino-3-methylpyrrolidin-1-yl]-6-cyano-5-(3,5-difluorophenyl)-N-(pentan-3-yl)pyridine-3-carboxamide;

1-77: 4-[(3S)-3-amino-3-methylpyrrolidin-1-yl]-6-cyano-N-[(1S)-1-cyclopropylethyl]-5-(3,5-difluorophenyl)pyridine-3-carboxamide;

1-78: 4-[(3S)-3-amino-3-methylpyrrolidin-1-yl]-6-cyano-N-cyclopentyl-5-(3,5-difluorophenyl)pyridine-3-carboxamide;

1-79: 4-[(3S)-3-amino-3-methylpyrrolidin-1-yl]-6-cyano-N-(3,3-difluorocyclobutyl)-5-(3,5-difluorophenyl)pyridine-3-carboxamide;

1-80: 4-[(3S)-3-aminopyrrolidin-1-yl]-3-(3,5-difluorophenyl)-5-(piperidine-1-carbonyl)pyridine-2-carbonitrile;

1-81: 4-[(3S)-3-aminopyrrolidin-1-yl]-6-cyano-N-cyclohexyl-5-(3,5-difluorophenyl)pyridine-3-carboxamide;

1-82: 4-[(3S)-3-aminopyrrolidin-1-yl]-6-cyano-N-cyclopentyl-5-(3,5-difluorophenyl)pyridine-3-carboxamide;

1-83: 4-[(3S)-3-amino-3-methylpyrrolidin-1-yl]-5-(3,5-difluorophenyl)-N-[cis-2-fluorocyclohexyl]pyridine-3-carboxamide;

1-84: 4-[(3S)-3-aminopyrrolidin-1-yl]-N-{bicyclo[1.1.1]pentan-1-yl}-5-(3-chlorophenyl)-6-cyanopyridine-3-carboxamide;

1-85: 4-[(3S)-3-amino-3-methylpyrrolidin-1-yl]-6-cyano-5-(3,5-difluorophenyl)-N-(2-methylpropyl)pyridine-3-carboxamide;

1-86: 4-[(3S)-3-amino-3-methylpyrrolidin-1-yl]-6-cyano-N-(cyclopropylmethyl)-5-(3,5-difluorophenyl)pyridine-3-carboxamide;

1-87: 4-[(3S)-3-amino-3-methylpyrrolidin-1-yl]-6-cyano-N-cyclobutyl-5-(3,5-difluorophenyl)pyridine-3-carboxamide;

1-88: 4-[(3S)-3-amino-3-methylpyrrolidin-1-yl]-6-cyano-5-(3,5-difluorophenyl)-N-(oxan-4-yl)pyridine-3-carboxamide;

1-89: 4-[(3S)-3-amino-3-methylpyrrolidin-1-yl]-6-cyano-5-(3,5-difluorophenyl)-N-(oxan-3-yl)pyridine-3-carboxamide;

1-90: 4-[(3S)-3-aminopyrrolidin-1-yl]-N-{bicyclo[1.1.1]pentan-1-yl}-5-(3-chloro-5-fluorophenyl)-6-cyanopyridine-3-carboxamide;

1-91: 4-[(3S)-3-amino-3-methylpyrrolidin-1-yl]-6-cyano-5-(3,5-difluorophenyl)-N-(propan-2-yl)pyridine-3-carboxamide;

1-92: 4-[(3S)-3-amino-3-methylpyrrolidin-1-yl]-6-cyano-5-(3,5-difluorophenyl)-N-(2,2,2-trifluoroethyl)pyridine-3-carboxamide;

1-93: 4-[(3S)-3-amino-3-methylpyrrolidin-1-yl]-6-cyano-N-cyclohexyl-5-(3,5-difluorophenyl)pyridine-3-carboxamide;

1-94: 4-[(3S)-3-amino-3-methylpyrrolidin-1-yl]-N-{bicyclo[1.1.1]pentan-1-yl}-5-(3-cyano-5-methoxyphenyl)pyridine-3-carboxamide;

1-95: 4-[(3S)-3-aminopyrrolidin-1-yl]-6-cyano-5-(3,5-difluorophenyl)-N-[(1S)-1-(pyridin-2-yl)ethyl]pyridine-3-carboxamide;

1-96: 4-[(3S)-3-amino-3-methylpyrrolidin-1-yl]-5-(3-cyano-5-methoxyphenyl)-N-[(1S)-1-cyclopropylethyl]pyridine-3-carboxamide;

1-97: 4-[(3S)-3-aminopyrrolidin-1-yl]-6-cyano-5-(3,5-difluorophenyl)-N-[(1S)-1-phenylethyl]pyridine-3-carboxamide;

1-98: 4-[(3S)-3-amino-3-(hydroxymethyl)pyrrolidin-1-yl]-N-{bicyclo[1.1.1]pentan-1-yl}-6-cyano-5-(3,5-difluorophenyl)pyridine-3-carboxamide;

1-101: 4-[(3R,4R)-3-amino-4-fluoropyrrolidin-1-yl]-N-{bicyclo[1.1.1]pentan-1-yl}-6-cyano-5-(3,5-difluorophenyl)pyridine-3-carboxamide;

1-103: 4-[(3S)-3-amino-3-methylpyrrolidin-1-yl]-6-cyano-5-(3,5-difluorophenyl)-N-[(1S)-1-(pyridin-2-yl)ethyl]pyridine-3-carboxamide;

1-104: 4-[(3S)-3-amino-3-methylpyrrolidin-1-yl]-6-cyano-5-(3,5-difluorophenyl)-N-[(1-methyl-1H-pyrazol-5-yl)methyl]pyridine-3-carboxamide;

1-105: 4-[(3S)-3-amino-3-methylpyrrolidin-1-yl]-6-cyano-5-(3,5-difluorophenyl)-N-[(1-methyl-1H-pyrazol-3-yl)methyl]pyridine-3-carboxamide;

1-106: 4-[(3S)-3-amino-3-methylpyrrolidin-1-yl]-6-cyano-5-(3,5-difluorophenyl)-N-[(1-methyl-1H-imidazol-2-yl)methyl]pyridine-3-carboxamide;

1-107: 4-[(3S)-3-amino-3-methylpyrrolidin-1-yl]-6-cyano-5-(3,5-difluorophenyl)-N-[(1-methyl-1H-pyrazol-4-yl)methyl]pyridine-3-carboxamide;

1-108: 4-[(3S)-3-amino-3-methylpyrrolidin-1-yl]-6-cyano-5-(3,5-difluorophenyl)-N-[(pyrimidin-2-yl)methyl]pyridine-3-carboxamide;

1-109: 4-[(3S)-3-aminopyrrolidin-1-yl]-5-(4-benzylpiperazine-1-carbonyl)-3-(3,5-difluorophenyl)pyridine-2-carbonitrile;

1-110: 4-[(3S)-3-aminopyrrolidin-1-yl]-6-cyano-5-(3,5-difluorophenyl)-N-(3-phenylpropyl)pyridine-3-carboxamide;

1-111: 4-[(3S)-3-aminopyrrolidin-1-yl]-6-cyano-5-(3,5-difluorophenyl)-N-(1-phenylpiperidin-4-yl)pyridine-3-carboxamide;

1-112: 4-[(3S)-3-amino-3-methylpyrrolidin-1-yl]-N-cyclohexyl-5-(3,5-difluorophenyl)pyridine-3-carboxamide;

1-113: 4-[(3S)-3-amino-3-methylpyrrolidin-1-yl]-6-cyano-5-(3,5-difluorophenyl)-N-(2,2-dimethyloxan-4-yl)pyridine-3-carboxamide;

1-114: 4-[(3S)-3-amino-3-methylpyrrolidin-1-yl]-6-cyano-5-(3,5-difluorophenyl)-N-[(1,2-oxazol-3-yl)methyl]pyridine-3-carboxamide;

1-115: 4-[(3S)-3-amino-3-methylpyrrolidin-1-yl]-6-cyano-5-(3,5-difluorophenyl)-N-[(2-hydroxyphenyl)methyl]pyridine-3-carboxamide;

1-116: 4-[(3R)-3-amino-3-(methoxymethyl)pyrrolidin-1-yl]-6-cyano-N-[(1S)-1-cyclopropylethyl]-5-(3,5-difluorophenyl)pyridine-3-carboxamide;

1-118: 4-[(3S)-3-amino-3-(2,2-difluoroethyl)pyrrolidin-1-yl]-6-cyano-N-[(1S)-1-cyclopropylethyl]-5-(3,5-difluorophenyl)pyridine-3-carboxamide;

1-120: 4-[(3S)-3-amino-3-methylpyrrolidin-1-yl]-6-cyano-N-[(1S)-1-cyclopropylethyl]-5-[3-(difluoromethoxy)phenyl]pyridine-3-carboxamide;

1-122: 4-[(3S)-3-amino-3-methylpyrrolidin-1-yl]-N-[(1S)-1-cyclopropylethyl]-5-(3,5-difluorophenyl)-6-methylpyridine-3-carboxamide;

1-123: 4-[(3S)-3-amino-3-methylpyrrolidin-1-yl]-5-(3-cyano-5-fluorophenyl)-N-[(1S)-1-cyclopropylethyl]-6-methylpyridine-3-carboxamide;

1-124: 4-[(3S)-3-amino-3-methylpyrrolidin-1-yl]-N-[(1S)-1-cyclopropylethyl]-5-(3-fluorophenyl)-6-methylpyridine-3-carboxamide;

1-125: 4-[(3S)-3-amino-3-methylpyrrolidin-1-yl]-5-(3-chloro-5-fluorophenyl)-N-[(1S)-1-cyclopropylethyl]-6-methylpyridine-3-carboxamide;

1-126: 4-[(3S)-3-amino-3-methylpyrrolidin-1-yl]-6-cyano-5-(3,5-difluorophenyl)-N-[1-(pyrimidin-2-yl)ethyl]pyridine-3-carboxamide;

1-127: 4-[(3S)-3-amino-3-methylpyrrolidin-1-yl]-6-cyano-N-[(1S)-1-cyclopropylethyl]-5-[3-(trifluoromethoxy)phenyl]pyridine-3-carboxamide;

1-130: 4-[(3S)-3-amino-3-methylpyrrolidin-1-yl]-N-{bicyclo[1.1.1]pentan-1-yl}-5-(3,5-difluorophenyl)-6-methoxypyridine-3-carboxamide;

1-132: 4-[(3S)-3-amino-3-methylpyrrolidin-1-yl]-6-cyano-5-(3,5-difluorophenyl)-N-[1-(1,2-oxazol-3-yl)ethyl]pyridine-3-carboxamide;

1-133: 4-[(3S)-3-amino-3-methylpyrrolidin-1-yl]-6-cyano-5-(3,5-difluorophenyl)-N-[1-(1-methyl-1H-1,2,3-triazol-4-yl)ethyl]pyridine-3-carboxamide;

1-135: 4-[(3R,4R)-3-amino-4-fluoropyrrolidin-1-yl]-6-cyano-N-[(1S)-1-cyclopropylethyl]-5-(3,5-difluorophenyl)pyridine-3-carboxamide;

1-137: 4-[(3S)-3-amino-3-methylpyrrolidin-1-yl]-N-(3,3-difluorocyclobutyl)-5-(3,5-difluorophenyl)-6-methoxypyridine-3-carboxamide;

1-138: 4-[(3R,4R)-3-amino-4-fluoropyrrolidin-1-yl]-5-(3-chloro-5-fluorophenyl)-6-cyano-N-[(1S)-1-cyclopropylethyl]pyridine-3-carboxamide;

1-140: 4-[(3S)-3-amino-3-methylpyrrolidin-1-yl]-5-(3,5-difluorophenyl)-6-methoxy-N-[(2S)-1,1,1-trifluoropropan-2-yl]pyridine-3-carboxamide;

1-141: 4-[(3S)-3-amino-3-methylpyrrolidin-1-yl]-N-[(1S)-1-cyclopropylethyl]-5-(3,5-difluorophenyl)-6-methoxypyridine-3-carboxamide;

1-143: 4-[(3S)-3-amino-3-methylpyrrolidin-1-yl]-N-[(1S)-1-cyclopropylethyl]-5-[3-(difluoromethoxy)-5-fluorophenyl]pyridine-3-carboxamide;

1-144: 4-[(3S)-3-amino-3-methylpyrrolidin-1-yl]-N-(4,4-difluorocyclohexyl)-5-(3,5-difluorophenyl)-6-methoxypyridine-3-carboxamide;

1-145: 4-[(3S)-3-amino-3-methylpyrrolidin-1-yl]-N-[(1S)-3,3-difluorocyclopentyl]-5-(3,5-difluorophenyl)-6-methoxypyridine-3-carboxamide;

1-146: 4-[(3S)-3-amino-3-methylpyrrolidin-1-yl]-N-(3,3-difluorocyclobutyl)-5-(3,5-difluorophenyl)-6-methylpyridine-3-carboxamide;

1-147: 4-[(3S)-3-amino-3-methylpyrrolidin-1-yl]-5-(3,5-difluorophenyl)-6-methyl-N-[(2S)-1,1,1-trifluoropropan-2-yl]pyridine-3-carboxamide;

1-149: 4-[(3S)-3-amino-3-methylpyrrolidin-1-yl]-N-[(1S)-1-cyclopropylethyl]-5-[3-(difluoromethoxy)phenyl]pyridine-3-carboxamide;

1-150: 4-[(3S)-3-aminopyrrolidin-1-yl]-N-(4,4-difluorocyclohexyl)-5-(3,5-difluorophenyl)-6-methoxypyridine-3-carboxamide;

1-151: 4-[(3S)-3-aminopyrrolidin-1-yl]-5-(3,5-difluorophenyl)-6-methoxy-N-[(2S)-1,1,1-trifluoropropan-2-yl]pyridine-3-carboxamide;

1-152: 4-[(3S)-3-aminopyrrolidin-1-yl]-N-[(1S)-1-cyclopropylethyl]-5-(3,5-difluorophenyl)-6-methoxypyridine-3-carboxamide;

1-153: 4-[(3S)-3-amino-3-methylpyrrolidin-1-yl]-5-(3-cyano-5-fluorophenyl)-N-[(1S)-1-cyclopropylethyl]-6-methoxypyridine-3-carboxamide;

1-154: 4-[(3S)-3-amino-3-methylpyrrolidin-1-yl]-N-[(1S)-1-cyclopropylethyl]-6-methoxy-5-[3-(trifluoromethoxy)phenyl]pyridine-3-carboxamide;

1-163: 4-[(3S)-3-amino-3-methylpyrrolidin-1-yl]-N-[(1S)-1-cyclopropylethyl]-5-(2,2-difluoro-2H-1,3-benzodioxol-4-yl)pyridine-3-carboxamide;

1-164: 4-[(3S)-3-amino-3-methylpyrrolidin-1-yl]-N-[(1S)-1-cyclopropylethyl]-5-[3-fluoro-5-(trifluoromethyl)phenyl]-6-methoxypyridine-3-carboxamide;

1-165: 4-[(3S)-3-amino-3-methylpyrrolidin-1-yl]-N-[(1S)-1-cyclopropylethyl]-5-[3-(difluoromethoxy)phenyl]-6-methoxypyridine-3-carboxamide;

1-168: 4-[(3S)-3-amino-3-methylpyrrolidin-1-yl]-6-cyano-5-[3-(difluoromethoxy)phenyl]-N-[(2S)-1,1,1-trifluoropropan-2-yl]pyridine-3-carboxamide;

1-171: 4-[(3S)-3-amino-3-methylpyrrolidin-1-yl]-5-[3-(difluoromethoxy)-5-fluorophenyl]-6-methyl-N-[(2S)-1,1,1-trifluoropropan-2-yl]pyridine-3-carboxamide;

1-172: 4-[(3S)-3-amino-3-methylpyrrolidin-1-yl]-N-(3,3-difluorocyclobutyl)-5-[3-(difluoromethoxy)-5-fluorophenyl]-6-methylpyridine-3-carboxamide;

1-173: 4-[(3S)-3-amino-3-methylpyrrolidin-1-yl]-N-[(1S)-1-cyclopropylethyl]-5-[3-(difluoromethoxy)-5-fluorophenyl]-6-methylpyridine-3-carboxamide;

1-174: 4-[(3S)-3-amino-3-methylpyrrolidin-1-yl]-N-(4,4-difluorocyclohexyl)-5-[3-(difluoromethoxy)-5-fluorophenyl]-6-methylpyridine-3-carboxamide;

1-175: 4-[(3S)-3-amino-3-methylpyrrolidin-1-yl]-N-[(1S)-1-cyclopropylethyl]-5-(2,2-difluoro-2H-1,3-benzodioxol-5-yl)pyridine-3-carboxamide;

1-176: 4-[(3S)-3-amino-3-methylpyrrolidin-1-yl]-N-[(1S)-1-cyclopropylethyl]-5-(3,5-difluorophenyl)-6-ethoxypyridine-3-carboxamide;

1-177: 4-[(3S)-3-amino-3-methylpyrrolidin-1-yl]-N-[(1S)-1-cyclopropylethyl]-6-(2,2-difluoroethoxy)-5-(3,5-difluorophenyl)pyridine-3-carboxamide;

1-178: 4-[(3S)-3-amino-3-methylpyrrolidin-1-yl]-N-[(1S)-1-cyclopropylethyl]-6-(cyclopropylmethoxy)-5-(3,5-difluorophenyl)pyridine-3-carboxamide;

1-179: 4-[(3S)-3-amino-3-methylpyrrolidin-1-yl]-N-[(1S)-1-cyclopropylethyl]-5-(3,5-difluorophenyl)-6-(2-methoxyethoxy)pyridine-3-carboxamide;

1-180: 4-[(3S)-3-amino-3-methylpyrrolidin-1-yl]-6-cyano-5-[3-(difluoromethoxy)-5-fluorophenyl]-N-[(2S)-1,1,1-trifluoropropan-2-yl]pyridine-3-carboxamide;

1-181: 4-[(3S)-3-amino-3-methylpyrrolidin-1-yl]-N-(4,4-difluorocyclohexyl)-5-(3,5-difluorophenyl)-6-methylpyridine-3-carboxamide;

1-184: 4-[(3S)-3-amino-3-methylpyrrolidin-1-yl]-5-(2,2-difluoro-2H-1,3-benzodioxol-4-yl)-6-methoxy-N-[(2S)-1,1,1-trifluoropropan-2-yl]pyridine-3-carboxamide;

1-188: 4-[(3S)-3-amino-3-methylpyrrolidin-1-yl]-5-[3-(difluoromethoxy)-5-fluorophenyl]-6-methoxy-N-[(2S)-1,1,1-trifluoropropan-2-yl]pyridine-3-carboxamide;

1-189: 4-[(3S)-3-amino-3-methylpyrrolidin-1-yl]-N-[(1S)-1-cyclopropylethyl]-5-(3,5-difluorophenyl)-6-(trifluoromethyl)pyridine-3-carboxamide;

1-190: 4-[(3S)-3-amino-3-methylpyrrolidin-1-yl]-N-[(1S)-1-cyclopropylethyl]-5-(3,5-difluorophenyl)-6-(2,2,2-trifluoroethoxy)pyridine-3-carboxamide;

1-191: 4-[(3S)-3-amino-3-methylpyrrolidin-1-yl]-6-cyclopropoxy-N-[(1S)-1-cyclopropylethyl]-5-(3,5-difluorophenyl)pyridine-3-carboxamide;

1-192: 4-[(3S)-3-amino-3-methylpyrrolidin-1-yl]-6-cyano-5-(3,5-difluorophenyl)-N-[(2S)-1,1,1-trifluoropropan-2-yl]pyridine-3-carboxamide;

1-193: 4-[(3S)-3-aminopyrrolidin-1-yl]-5-(3,5-difluorophenyl)-6-methoxy-N-[4-(trifluoromethyl)cyclohexyl]pyridine-3-carboxamide;

1-194: 4-[(3S)-3-aminopyrrolidin-1-yl]-N-(1-cyclopropyl-2,2,2-trifluoroethyl)-5-(3,5-difluorophenyl)-6-methoxypyridine-3-carboxamide;

1-195: 4-[(3S)-3-amino-3-methylpyrrolidin-1-yl]-5-(3-chloro-5-fluorophenyl)-N-[(1S)-1-cyclopropylethyl]-6-(trifluoromethyl)pyridine-3-carboxamide;

1-196: 4-[(3S)-3-aminopyrrolidin-1-yl]-5-(3,5-difluorophenyl)-N-{3-fluorobicyclo[1.1.1]pentan-1-yl}-6-methoxypyridine-3-carboxamide;

1-197: 4-[(3S)-3-amino-3-methylpyrrolidin-1-yl]-5-(3-cyano-5-methoxyphenyl)-N-[(1S)-1-cyclopropylethyl]-6-(trifluoromethyl)pyridine-3-carboxamide;

1-198: 4-[(3S)-3-aminopyrrolidin-1-yl]-5-(3-chloro-5-fluorophenyl)-N-[(1S)-1-cyclopropylethyl]-6-(trifluoromethyl)pyridine-3-carboxamide;

1-199: 4-[(3S)-3-aminopyrrolidin-1-yl]-N-[(1S)-1-cyclopropylethyl]-5-(3,5-difluorophenyl)-6-(trifluoromethyl)pyridine-3-carboxamide;

1-200: ethyl 2-({4-[(3S)-3-aminopyrrolidin-1-yl]-5-[(4,4-difluorocyclohexyl)carbamoyl]-3-(3,5-difluorophenyl)pyridin-2-yl}oxy)acetate;

1-201: ethyl 3-({4-[(3S)-3-aminopyrrolidin-1-yl]-5-[(4,4-difluorocyclohexyl)carbamoyl]-3-(3,5-difluorophenyl)pyridin-2-yl}oxy)propanoate;

1-202: ethyl 4-({4-[(3S)-3-aminopyrrolidin-1-yl]-5-[(4,4-difluorocyclohexyl)carbamoyl]-3-(3,5-difluorophenyl)pyridin-2-yl}oxy)butanoate;

1-203: 2-({4-[(3S)-3-aminopyrrolidin-1-yl]-5-[(4,4-difluorocyclohexyl)carbamoyl]-3-(3,5-difluorophenyl)pyridin-2-yl}oxy)acetic acid 1-204: 3-({4-[(3S)-3-aminopyrrolidin-1-yl]-5-[(4,4-difluorocyclohexyl)carbamoyl]-3-(3,5-difluorophenyl)pyridin-2-yl}oxy)propanoic acid;

1-205: 4-({4-[(3S)-3-aminopyrrolidin-1-yl]-5-[(4,4-difluorocyclohexyl)carbamoyl]-3-(3,5-difluorophenyl)pyridin-2-yl}oxy)butanoic acid;

1-209: 4-[(3S)-3-amino-3-methylpyrrolidin-1-yl]-N-[(1S)-1-cyclopropylethyl]-5-(3,4-difluorophenyl)-6-(trifluoromethyl)pyridine-3-carboxamide;

1-210: 4-[(3S)-3-amino-3-methylpyrrolidin-1-yl]-N-cyclohexyl-5-(3,5-difluorophenyl)-6-(trifluoromethyl)pyridine-3-carboxamide;

1-211: 4-[(3S)-3-amino-3-methylpyrrolidin-1-yl]-N-(4,4-difluorocyclohexyl)-5-(3,5-difluorophenyl)-6-(trifluoromethyl)pyridine-3-carboxamide;

1-212: 4-[(3S)-3-aminopyrrolidin-1-yl]-5-(3,5-difluorophenyl)-6-(trifluoromethyl)-N-[(2S)-1,1,1-trifluoropropan-2-yl]pyridine-3-carboxamide;

1-213: 4-[(3S)-3-aminopyrrolidin-1-yl]-N-cyclohexyl-5-(3,5-difluorophenyl)-6-(trifluoromethyl)pyridine-3-carboxamide;

1-214: 4-[(3S)-3-aminopyrrolidin-1-yl]-N-(4,4-difluorocyclohexyl)-5-(3,5-difluorophenyl)-6-(trifluoromethyl)pyridine-3-carboxamide;

1-215: 4-[(3S)-3-aminopyrrolidin-1-yl]-N-[(1S)-1-cyclopropylethyl]-5-(3,5-dichlorophenyl)-6-(trifluoromethyl)pyridine-3-carboxamide;

1-216: 4-[(3S)-3-aminopyrrolidin-1-yl]-5-(3,5-difluorophenyl)-N-{3-fluorobicyclo[1.1.1]pentan-1-yl}-6-(trifluoromethyl)pyridine-3-carboxamide;

1-217: 4-[(3S)-3-amino-3-methylpyrrolidin-1-yl]-5-(3,5-difluorophenyl)-N-{3-fluorobicyclo[1.1.1]pentan-1-yl}-6-(trifluoromethyl)pyridine-3-carboxamide;

1-218: 4-[(3S)-3-amino-3-methylpyrrolidin-1-yl]-6-cyano-N-(cyclopropylmethyl)-5-(3,5-difluorophenyl)-N-methylpyridine-3-carboxamide;

1-219: 4-[(3S)-3-amino-3-methylpyrrolidin-1-yl]-6-cyano-N-[(1S)-1-cyclopropylethyl]-5-(3,5-difluorophenyl)-N-methylpyridine-3-carboxamide;

1-222: 4-[(3S)-3-amino-3-methylpyrrolidin-1-yl]-6-cyano-5-(3,5-difluorophenyl)-N-[(2R)-1,1,1-trifluoropropan-2-yl]pyridine-3-carboxamide;

1-223: 4-[(3S)-3-amino-3-methylpyrrolidin-1-yl]-5-(3,5-difluorophenyl)-N-[(1-hydroxycyclopentyl)methyl]-6-methylpyridine-3-carboxamide;

1-224: 4-[(3S)-3-amino-3-methylpyrrolidin-1-yl]-N-(1-cyclopropyl-2-hydroxyethyl)-5-(3,5-difluorophenyl)-6-methylpyridine-3-carboxamide;

1-225: 4-(3-aminopyrrolidin-1-yl)-6-cyano-5-(3,5-difluorophenyl)-N-(1,1,1-trifluoropropan-2-yl)pyridine-3-carboxamide;

1-226: 4-[(3S)-3-aminopyrrolidin-1-yl]-6-cyano-5-(3,5-difluorophenyl)-N-(1,1,1-trifluoropropan-2-yl)pyridine-3-carboxamide;

1-227: 4-[(3R)-3-aminopyrrolidin-1-yl]-6-cyano-5-(3,5-difluorophenyl)-N-[(2R)-1,1,1-trifluoropropan-2-yl]pyridine-3-carboxamide;

1-228: 4-[(3S)-3-amino-3-methylpyrrolidin-1-yl]-5-(3-chloro-5-fluorophenyl)-6-methoxy-N-[(2S)-1,1,1-trifluoropropan-2-yl]pyridine-3-carboxamide;

1-229: 4-[(3S)-3-amino-3-methylpyrrolidin-1-yl]-5-(3-chloro-5-fluorophenyl)-N-[(1S)-1-cyclopropylethyl]-6-methoxypyridine-3-carboxamide;

1-230: 4-[(3S)-3-aminopyrrolidin-1-yl]-5-(3,5-difluorophenyl)-6-methyl-N-[(2S)-1,1,1-trifluoropropan-2-yl]pyridine-3-carboxamide;

1-231: 4-[(3S)-3-aminopyrrolidin-1-yl]-5-[3-(difluoromethoxy)-5-fluorophenyl]-6-methyl-N-[(2S)-1,1,1-trifluoropropan-2-yl]pyridine-3-carboxamide;

1-232: 4-[(3S)-3-aminopyrrolidin-1-yl]-5-[3-(difluoromethoxy)phenyl]-6-methyl-N-[(2S)-1,1,1-trifluoropropan-2-yl]pyridine-3-carboxamide;

1-233: 4-[(3S)-3-aminopyrrolidin-1-yl]-N-(4,4-difluorocyclohexyl)-5-(3,5-difluorophenyl)-6-methylpyridine-3-carboxamide;

1-234: 4-[(3S)-3-amino-3-methylpyrrolidin-1-yl]-6-cyano-5-(3,5-difluorophenyl)-N-{3-fluorobicyclo[1.1.1]pentan-1-yl}pyridine-3-carboxamide;

1-235: (3S)-1-[3-(3,5-difluorophenyl)-2-methoxy-5-(piperidine-1-carbonyl)pyridin-4-yl]pyrrolidin-3-amine;

1-236: (3S)-1-[3-(3,5-difluorophenyl)-5-(4,4-difluoropiperidine-1-carbonyl)-2-methoxypyridin-4-yl]pyrrolidin-3-amine;

1-237: (3S)-1-[3-(3,5-difluorophenyl)-5-(3,3-difluoropiperidine-1-carbonyl)-2-methoxypyridin-4-yl]pyrrolidin-3-amine;

1-238: 4-[(3S)-3-amino-3-methylpyrrolidin-1-yl]-5-(3-chloro-5-fluorophenyl)-6-methoxy-N-[(1,2-oxazol-3-yl)methyl]pyridine-3-carboxamide;

1-239: 4-[(3S)-3-amino-3-methylpyrrolidin-1-yl]-5-[3-(difluoromethoxy)-5-fluorophenyl]-6-methoxy-N-[(1,2-oxazol-3-yl)methyl]pyridine-3-carboxamide;

1-240: 4-[(3S)-3-amino-3-methylpyrrolidin-1-yl]-5-(3-chloro-5-fluorophenyl)-6-methoxy-N-[(1S)-1-(pyridin-2-yl)ethyl]pyridine-3-carboxamide;

1-241: 4-[(3S)-3-amino-3-methylpyrrolidin-1-yl]-5-[3-(difluoromethoxy)-5-fluorophenyl]-6-methoxy-N-[(1S)-1-(pyridin-2-yl)ethyl]pyridine-3-carboxamide;

1-242: 4-[(3S)-3-amino-3-methylpyrrolidin-1-yl]-5-(3-chloro-5-fluorophenyl)-6-methyl-N-[(1,2-oxazol-3-yl)methyl]pyridine-3-carboxamide;

1-243: 4-[(3S)-3-amino-3-methylpyrrolidin-1-yl]-5-(3-chloro-5-fluorophenyl)-6-methyl-N-[(1S)-1-(pyridin-2-yl)ethyl]pyridine-3-carboxamide;

1-244: 4-[(3S)-3-amino-3-methylpyrrolidin-1-yl]-5-(3-chloro-5-fluorophenyl)-6-cyano-N-[(1,2-oxazol-3-yl)methyl]pyridine-3-carboxamide;

1-245: 4-[(3S)-3-amino-3-methylpyrrolidin-1-yl]-5-(3-chloro-5-fluorophenyl)-6-cyano-N-[(1 S)-1-(pyridin-2-yl)ethyl]pyridine-3-carboxamide;

1-246: 4-[(3S)-3-amino-3-methylpyrrolidin-1-yl]-N-[(1S)-1-cyclopropylethyl]-5-(3,5-difluorophenyl)-6-(2-hydroxyethoxy)pyridine-3-carboxamide;

1-247: 2-({4-[(3S)-3-amino-3-methylpyrrolidin-1-yl]-5-{[(1S)-1-cyclopropylethyl]carbamoyl}-3-(3,5-difluorophenyl)pyridin-2-yl}oxy)acetic acid;

1-259: 4-[(3S)-3-amino-3-methylpyrrolidin-1-yl]-5-(3,4-difluorophenyl)-6-methoxy-N-[(2S)-1,1,1-trifluoropropan-2-yl]pyridine-3-carboxamide;

1-260: 4-[(3S)-3-amino-3-methylpyrrolidin-1-yl]-5-(4-chloro-3-fluorophenyl)-6-methoxy-N-[(2S)-1,1,1-trifluoropropan-2-yl]pyridine-3-carboxamide;

1-261: 4-[(3S)-3-amino-3-methylpyrrolidin-1-yl]-5-(3-chloro-4-fluorophenyl)-6-methoxy-N-[(2S)-1,1,1-trifluoropropan-2-yl]pyridine-3-carboxamide;

1-262: 4-[(3S)-3-amino-3-methylpyrrolidin-1-yl]-N-[(1S)-1-cyclopropylethyl]-5-(3,4-difluorophenyl)-6-methoxypyridine-3-carboxamide;

1-263: 4-[(3S)-3-amino-3-methylpyrrolidin-1-yl]-5-(4-chloro-3-fluorophenyl)-N-[(1S)-1-cyclopropylethyl]-6-methoxypyridine-3-carboxamide;

1-264: 3-({4-[(3S)-3-amino-3-methylpyrrolidin-1-yl]-5-{[(1S)-1-cyclopropylethyl]carbamoyl}-3-(3,5-difluorophenyl)pyridin-2-yl}oxy)propanoic acid;

1-265: 4-({4-[(3S)-3-amino-3-methylpyrrolidin-1-yl]-5-{[(1S)-1-cyclopropylethyl]carbamoyl}-3-(3,5-difluorophenyl)pyridin-2-yl}oxy)butanoic acid;

1-266: 4-[(3S)-3-amino-3-methylpyrrolidin-1-yl]-N-[(1S)-1-cyclopropylethyl]-5-(3,5-difluorophenyl)-6-[(oxetan-3-yl)methoxy]pyridine-3-carboxamide;

1-267: 4-[(3S)-3-amino-3-methylpyrrolidin-1-yl]-6-(benzyloxy)-N-[(1S)-1-cyclopropylethyl]-5-(3,5-difluorophenyl)pyridine-3-carboxamide;

1-268: 4-[(3S)-3-amino-3-methylpyrrolidin-1-yl]-5-(3-cyano-5-methoxyphenyl)-N-(4,4-difluorocyclohexyl)-6-methylpyridine-3-carboxamide;

1-269: 4-[(3S)-3-amino-3-methylpyrrolidin-1-yl]-5-(3-cyano-5-methoxyphenyl)-N-(3,3-difluorocyclobutyl)-6-methylpyridine-3-carboxamide;

1-272: 4-[(3S)-3-aminopyrrolidin-1-yl]-5-(3-chloro-5-fluorophenyl)-N-[(1S)-1-cyclopropylethyl]-6-methylpyridine-3-carboxamide;

1-273: 4-[(3S)-3-amino-3-methylpyrrolidin-1-yl]-5-(3,5-difluorophenyl)-N-{3-fluorobicyclo[1.1.1]pentan-1-yl}-6-methoxypyridine-3-carboxamide;

1-275: 4-[(3S)-3-amino-3-methylpyrrolidin-1-yl]-5-(3-cyano-5-methoxyphenyl)-6-methyl-N-[(2S)-1,1,1-trifluoropropan-2-yl]pyridine-3-carboxamide;

1-276: 4-[(3S)-3-aminopyrrolidin-1-yl]-5-(3-chloro-5-fluorophenyl)-6-methyl-N-[(2S)-1,1,1-trifluoropropan-2-yl]pyridine-3-carboxamide;

1-277: 4-[(3S)-3-aminopyrrolidin-1-yl]-5-(3-chloro-5-fluorophenyl)-N-(4,4-difluorocyclohexyl)-6-methylpyridine-3-carboxamide;

1-278: 4-[(3S)-3-aminopyrrolidin-1-yl]-5-(3-chloro-5-fluorophenyl)-N-{3-fluorobicyclo[1.1.1]pentan-1-yl}-6-methylpyridine-3-carboxamide;

1-279: 4-[(3S)-3-amino-3-methylpyrrolidin-1-yl]-5-(3,4-difluorophenyl)-6-methyl-N-[(2S)-1,1,1-trifluoropropan-2-yl]pyridine-3-carboxamide;

1-280: 4-[(3S)-3-amino-3-methylpyrrolidin-1-yl]-5-(3-cyano-5-methoxyphenyl)-N-[(1S)-1-cyclopropylethyl]-6-methylpyridine-3-carboxamide;

1-281: 4-[(3S)-3-amino-3-methylpyrrolidin-1-yl]-6-cyclopropyl-N-(4,4-difluorocyclohexyl)-5-(3,5-difluorophenyl)pyridine-3-carboxamide;

1-282: 4-[(3S)-3-aminopyrrolidin-1-yl]-5-(3-chloro-5-fluorophenyl)-N-[(1S)-1-cyclopropylethyl]-6-methoxypyridine-3-carboxamide;

1-283: 4-[(3S)-3-aminopyrrolidin-1-yl]-5-(3-chloro-5-fluorophenyl)-6-methoxy-N-[(2S)-1,1,1-trifluoropropan-2-yl]pyridine-3-carboxamide;

1-284: 4-[(3S)-3-aminopyrrolidin-1-yl]-5-(3-chloro-5-fluorophenyl)-N-(4,4-difluorocyclohexyl)-6-methoxypyridine-3-carboxamide;

1-285: 4-[(3S)-3-aminopyrrolidin-1-yl]-5-(3-chloro-5-fluorophenyl)-N-(3,3-difluorocyclobutyl)-6-methoxypyridine-3-carboxamide;

1-286: 4-[(3S)-3-aminopyrrolidin-1-yl]-5-(3-chloro-5-fluorophenyl)-N-{3-fluorobicyclo[1.1.1]pentan-1-yl}-6-methoxypyridine-3-carboxamide;

1-287: 4-[(3S)-3-amino-3-methylpyrrolidin-1-yl]-5-(3-chloro-4-fluorophenyl)-6-methyl-N-[(2S)-1,1,1-trifluoropropan-2-yl]pyridine-3-carboxamide;

1-288: 4-[(3S)-3-amino-3-methylpyrrolidin-1-yl]-N-[(1S)-1-cyclopropylethyl]-5-(3,4-difluorophenyl)-6-methylpyridine-3-carboxamide;

1-289: 4-[(3S)-3-amino-3-methylpyrrolidin-1-yl]-5-(3-chloro-4-fluorophenyl)-N-[(1S)-1-cyclopropylethyl]-6-methylpyridine-3-carboxamide;

1-290: 4-[(3S)-3-amino-3-methylpyrrolidin-1-yl]-6-cyclopropyl-5-(3,5-difluorophenyl)-N-[(2S)-1,1,1-trifluoropropan-2-yl]pyridine-3-carboxamide.

In some embodiments, provided herein is a pharmaceutically acceptable salt of a compound that is described in Table 1.

TABLE 2
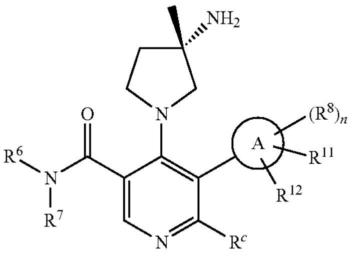
| Compd No. | $R^6R^7N$ | 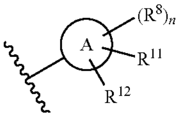 | $R^c$ |
|---|---|---|---|
| 1-5 | 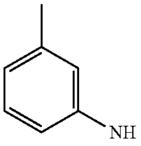 | 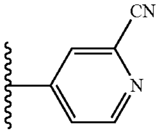 [SMILES: *c1ccnc(C#N)c1] | H |
| 1-6 | 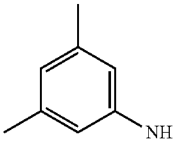 | 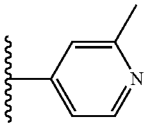 [SMILES: *c1ccnc(C)c1] | H |
| 1-121 | 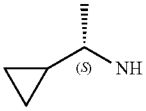 | 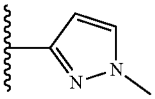 | CN |
| 1-128 | 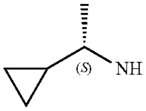 | 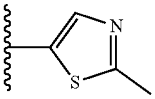 [SMILES: *c1cnc(C)s1] | CN |
| 1-129 | 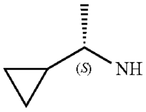 | 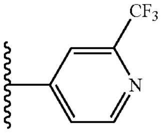 [SMILES: *c1ccnc(C(F)(F)F)c1] | CN |
| 1-131 | 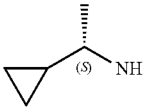 | 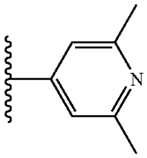 [SMILES: *c1cc(C)nc(C)c1] | H |
| 1-134 | 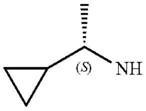 | 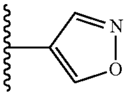 [SMILES: *c1cnoc1] | CN |
| 1-142 | 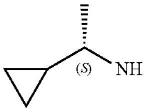 | 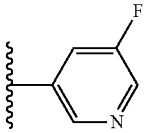 [SMILES: *c1cncc(F)c1] | H |
TABLE 2-continued
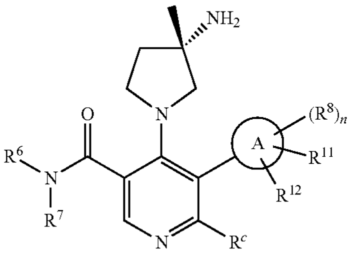
| Compd No. | $R^6R^7N$ | 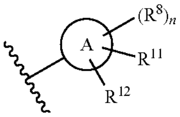 | $R^c$ |
|---|---|---|---|
| 1-148 | 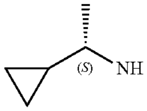 | 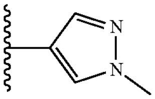 | $CH_3$ |
| 1-155 | 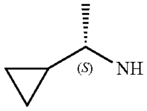 | 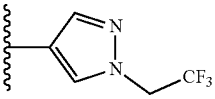 [SMILES: *c1cnn(CC(F)(F)F)c1] | $CH_3$ |
| 1-156 | 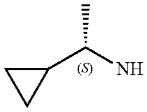 | 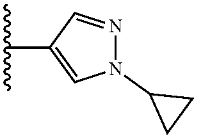 [SMILES: *c1cnn(C2CC2)c1] | $CH_3$ |
| 1-157 | 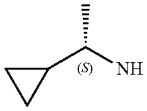 | 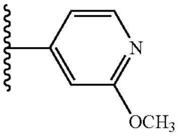 | $CH_3$ |
| 1-158 | 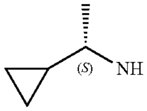 | 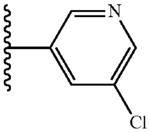 [SMILES: *c1cncc(Cl)c1] | $CH_3$ |
| 1-159 | 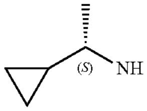 | 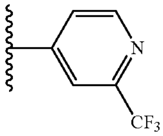 | $CH_3$ |
| 1-160 | 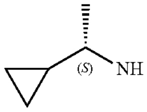 | 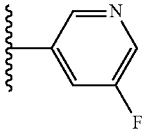 [SMILES: *c1cncc(F)c1] | $CH_3$ |
| 1-166 | 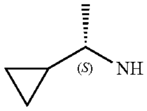 | 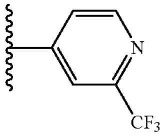 | $OCH_3$ |

TABLE 2-continued
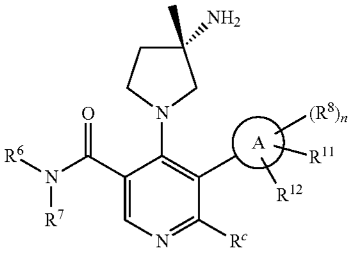
| Compd No. | $R^6R^7N$ | 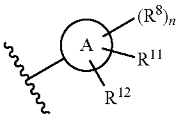 | $R^c$ |
|---|---|---|---|
| 1-167 | 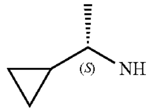 | 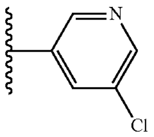 [SMILES: *c1cncc(Cl)c1] | $OCH_3$ |
| 1-169 | 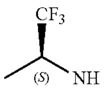 | 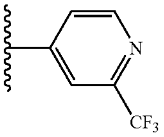 [SMILES: *c1ccnc(C(F)(F)F)c1] | CN |
| 1-170 | 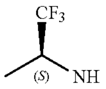 | 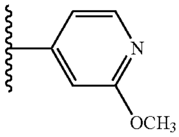 | CN |
| 1-185 | 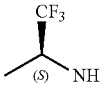 | 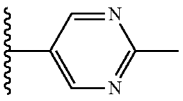 [SMILES: *c1cnc(C)nc1] | $OCH_3$ |
| 1-187 | 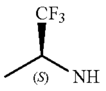 | 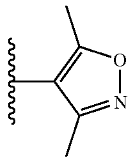 [SMILES: *c1c(C)noc1C] | $OCH_3$ |
| 1-206 | 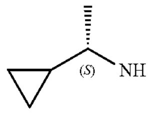 | 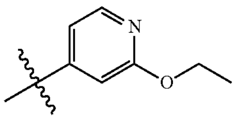 [SMILES: *c1ccnc(OCC)c1] | $CF_3$ |
| 1-208 | 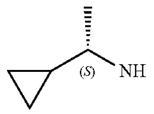 | 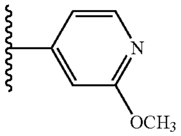 | $CF_3$ |
| 1-248 | 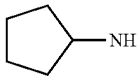 | 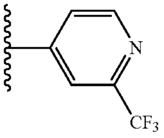 | CN |
TABLE 2-continued
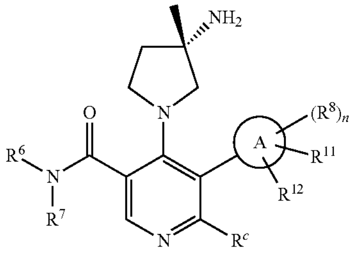
| Compd No. | $R^6R^7N$ | 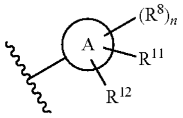 | $R^c$ |
|---|---|---|---|
| 1-249 | 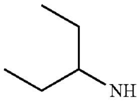 | 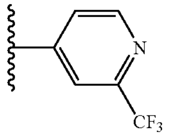 | CN |
| 1-250 | 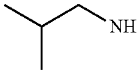 | 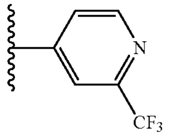 | CN |
| 1-251 | 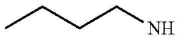 | 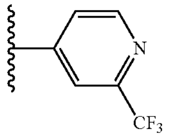 | CN |
| 1-252 | 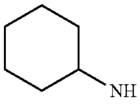 | 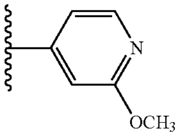 | CN |
| 1-253 | 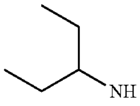 | 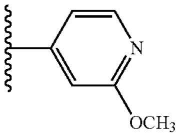 | CN |
| 1-254 | 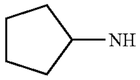 | 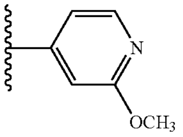 | CN |
| 1-255 | 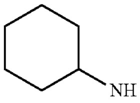 | 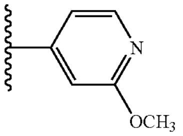 [SMILES: *c1ccnc(OC)c1] | $CH_3$ |
| 1-256 | 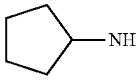 | 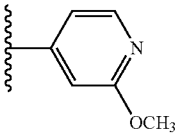 | $CH_3$ |

TABLE 2-continued

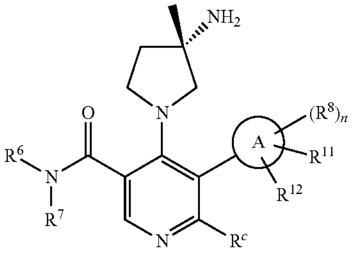

| Compd No. | $R^6R^7N$ | 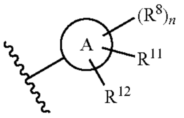 | $R^c$ |
|---|---|---|---|
| 1-257 | 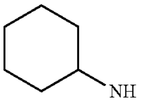 | 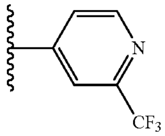 | $CH_3$ |
| 1-258 | 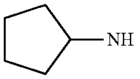 | 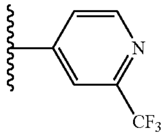 [SMILES: *c1ccnc(C(F)(F)F)c1] | $CH_3$ |
| 1-270 | 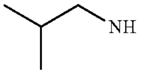 | 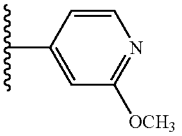 | CN |
| 1-271 | 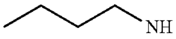 | 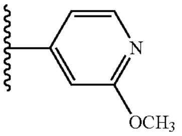 [SMILES: *c1ccnc(OC)c1] | CN |

Compounds in Table 2 are named:

1-5: 4-[(3S)-3-amino-3-methylpyrrolidin-1-yl]-2'-cyano-N-(3-methylphenyl)-[3,4'-bipyridine]-5-carboxamide;

1-6: 4-[(3S)-3-amino-3-methylpyrrolidin-1-yl]-N-(3,5-dimethylphenyl)-2'-methyl-[3,4'-bipyridine]-5-carboxamide;

1-121: 4-[(3S)-3-amino-3-methylpyrrolidin-1-yl]-6-cyano-N-[(1S)-1-cyclopropylethyl]-5-(1-methyl-1H-pyrazol-3-yl)pyridine-3-carboxamide;

1-128: 4-[(3S)-3-amino-3-methylpyrrolidin-1-yl]-6-cyano-N-[(1S)-1-cyclopropylethyl]-5-(2-methyl-1,3-thiazol-5-yl)pyridine-3-carboxamide;

1-129: 4-[(3S)-3-amino-3-methylpyrrolidin-1-yl]-2-cyano-N-[(1S)-1-cyclopropylethyl]-2'-(trifluoromethyl)-[3,4'-bipyridine]-5-carboxamide;

1-131: 4-[(3S)-3-amino-3-methylpyrrolidin-1-yl]-N-[(1S)-1-cyclopropylethyl]-2',6'-dimethyl-[3,4'-bipyridine]-5-carboxamide;

1-134: 4-[(3S)-3-amino-3-methylpyrrolidin-1-yl]-6-cyano-N-[(1S)-1-cyclopropylethyl]-5-(1,2-oxazol-4-yl)pyridine-3-carboxamide;

1-142: 4-[(3S)-3-amino-3-methylpyrrolidin-1-yl]-N-[(1S)-1-cyclopropylethyl]-5'-fluoro-[3,3'-bipyridine]-5-carboxamide;

1-148: 4-[(3S)-3-amino-3-methylpyrrolidin-1-yl]-N-[(1S)-1-cyclopropylethyl]-6-methyl-5-(1-methyl-1H-pyrazol-4-yl)pyridine-3-carboxamide;

1-155: 4-[(3S)-3-amino-3-methylpyrrolidin-1-yl]-N-[(1S)-1-cyclopropylethyl]-6-methyl-5-[1-(2,2,2-trifluoroethyl)-1H-pyrazol-4-yl]pyridine-3-carboxamide;

1-156: 4-[(3S)-3-amino-3-methylpyrrolidin-1-yl]-5-(1-cyclopropyl-1H-pyrazol-4-yl)-N-[(1S)-1-cyclopropylethyl]-6-methylpyridine-3-carboxamide;

1-157: 4-[(3S)-3-amino-3-methylpyrrolidin-1-yl]-N-[(1S)-1-cyclopropylethyl]-2'-methoxy-2-methyl-[3,4'-bipyridine]-5-carboxamide;

1-158: 4-[(3S)-3-amino-3-methylpyrrolidin-1-yl]-5'-chloro-N-[(1S)-1-cyclopropylethyl]-2-methyl-[3,3'-bipyridine]-5-carboxamide;

1-159: 4-[(3S)-3-amino-3-methylpyrrolidin-1-yl]-N-[(1S)-1-cyclopropylethyl]-2-methyl-2'-(trifluoromethyl)-[3,4'-bipyridine]-5-carboxamide;

1-160: 4-[(3S)-3-amino-3-methylpyrrolidin-1-yl]-N-[(1S)-1-cyclopropylethyl]-5'-fluoro-2-methyl-[3,3'-bipyridine]-5-carboxamide;

1-166: 4-[(3S)-3-amino-3-methylpyrrolidin-1-yl]-N-[(1S)-1-cyclopropylethyl]-2-methoxy-2'-(trifluoromethyl)-[3,4'-bipyridine]-5-carboxamide;

1-167: 4-[(3S)-3-amino-3-methylpyrrolidin-1-yl]-5'-chloro-N-[(1S)-1-cyclopropylethyl]-2-methoxy-[3,3'-bipyridine]-5-carboxamide;

1-169: 4-[(3S)-3-amino-3-methylpyrrolidin-1-yl]-2-cyano-2'-(trifluoromethyl)-N-[(2S)-1,1,1-trifluoropropan-2-yl]-[3,4'-bipyridine]-5-carboxamide;

1-170: 4-[(3S)-3-amino-3-methylpyrrolidin-1-yl]-2-cyano-2'-methoxy-N-[(2S)-1,1,1-trifluoropropan-2-yl]-[3,4'-bipyridine]-5-carboxamide;

1-185: 4-[(3S)-3-amino-3-methylpyrrolidin-1-yl]-6-methoxy-5-(2-methylpyrimidin-5-yl)-N-[(2S)-1,1,1-trifluoropropan-2-yl]pyridine-3-carboxamide;

1-187: 4-[(3S)-3-amino-3-methylpyrrolidin-1-yl]-5-(3,5-dimethyl-1,2-oxazol-4-yl)-6-methoxy-N-[(2S)-1,1,1-trifluoropropan-2-yl]pyridine-3-carboxamide;

1-206: 4-[(3S)-3-amino-3-methylpyrrolidin-1-yl]-N-[(1S)-1-cyclopropylethyl]-2'-ethoxy-2-(trifluoromethyl)-[3,4'-bipyridine]-5-carboxamide;

1-208: 4-[(3S)-3-amino-3-methylpyrrolidin-1-yl]-N-[(1S)-1-cyclopropylethyl]-2'-methoxy-2-(trifluoromethyl)-[3,4'-bipyridine]-5-carboxamide;

1-248: 4-[(3S)-3-amino-3-methylpyrrolidin-1-yl]-2-cyano-N-cyclopentyl-2'-(trifluoromethyl)-[3,4'-bipyridine]-5-carboxamide;

1-249: 4-[(3S)-3-amino-3-methylpyrrolidin-1-yl]-2-cyano-N-(pentan-3-yl)-2'-(trifluoromethyl)-[3,4'-bipyridine]-5-carboxamide;

1-250: 4-[(3S)-3-amino-3-methylpyrrolidin-1-yl]-2-cyano-N-(2-methylpropyl)-2'-(trifluoromethyl)-[3,4'-bipyridine]-5-carboxamide;

1-251: 4-[(3S)-3-amino-3-methylpyrrolidin-1-yl]-N-butyl-2-cyano-2'-(trifluoromethyl)-[3,4'-bipyridine]-5-carboxamide;

1-252: 4-[(3S)-3-amino-3-methylpyrrolidin-1-yl]-2-cyano-N-cyclohexyl-2'-methoxy-[3,4'-bipyridine]-5-carboxamide;

1-253: 4-[(3S)-3-amino-3-methylpyrrolidin-1-yl]-2-cyano-2'-methoxy-N-(pentan-3-yl)-[3,4'-bipyridine]-5-carboxamide;

1-254: 4-[(3S)-3-amino-3-methylpyrrolidin-1-yl]-2-cyano-N-cyclopentyl-2'-methoxy-[3,4'-bipyridine]-5-carboxamide;

1-255: 4-[(3S)-3-amino-3-methylpyrrolidin-1-yl]-N-cyclohexyl-2'-methoxy-2-methyl-[3,4'-bipyridine]-5-carboxamide;

1-256: 4-[(3S)-3-amino-3-methylpyrrolidin-1-yl]-N-cyclopentyl-2'-methoxy-2-methyl-[3,4'-bipyridine]-5-carboxamide;

1-257: 4-[(3S)-3-amino-3-methylpyrrolidin-1-yl]-N-cyclohexyl-2-methyl-2'-(trifluoromethyl)-[3,4'-bipyridine]-5-carboxamide;

1-258: 4-[(3S)-3-amino-3-methylpyrrolidin-1-yl]-N-cyclopentyl-2-methyl-2'-(trifluoromethyl)-[3,4'-bipyridine]-5-carboxamide;

1-270: 4-[(3S)-3-amino-3-methylpyrrolidin-1-yl]-2-cyano-2'-methoxy-N-(2-methylpropyl)-[3,4'-bipyridine]-5-carboxamide.

In some embodiments, provided herein is a pharmaceutically acceptable salt of a compound that is described in Table 2.

TABLE 3

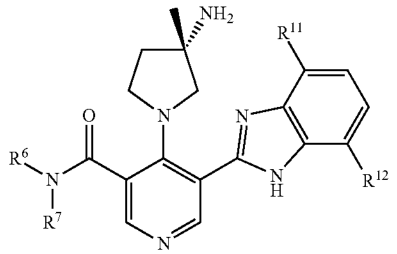

| Compd No. | $R^6R^7N$ | $R^{11}$ | $R^{12}$ |
|---|---|---|---|
| 2-1 | 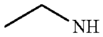 | $CH_3$ | H |
| 2-2 | 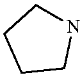 | $CH_3$ | H |
| 2-3 | 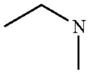 | $CH_3$ | H |
| 2-4 | 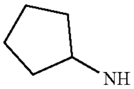 | $CH_3$ | H |
| 2-5 | 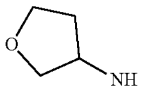 | $CH_3$ | H |
| 2-6 | 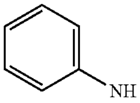 | $CH_3$ | H |
| 2-7 | 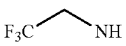 | $CH_3$ | H |
| 2-8 | 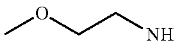 | $CH_3$ | H |
| 2-9 | 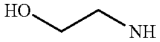 | $CH_3$ | H |
| 2-10 | 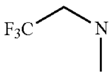 | $CH_3$ | H |
| 2-11 | 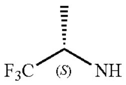 | $CH_3$ | H |

TABLE 3-continued

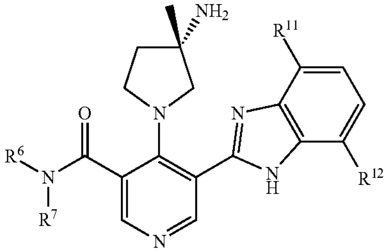

| Compd No. | $R^6R^7N$ | $R^{11}$ | $R^{12}$ |
|---|---|---|---|
| 2-12 | 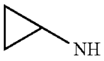 | $CH_3$ | H |
| 2-13 | 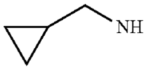 | $CH_3$ | H |
| 2-14 | 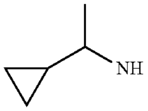 | $CH_3$ | H |
| 2-15 | 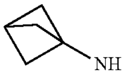 | $CH_3$ | H |
| 2-16 | 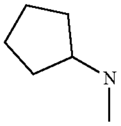 | $CH_3$ | H |
| 2-17 | 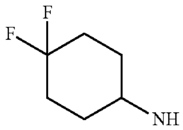 | $CH_3$ | H |
| 2-18 | 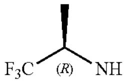 | $CH_3$ | H |
| 2-19 | 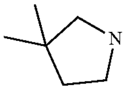 | $CH_3$ | H |
| 2-20 | 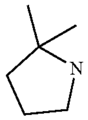 | $CH_3$ | H |
| 2-21 | 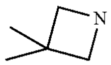 | $CH_3$ | H |
| 2-22 | 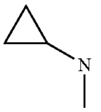 | $CH_3$ | H |
| 2-23 | 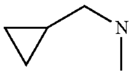 | $CH_3$ | H |

TABLE 3-continued
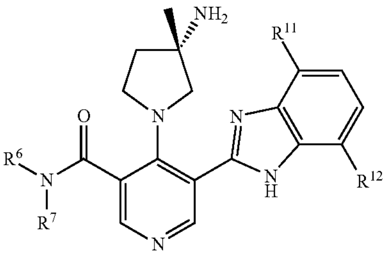
| Compd No. | $R^6R^7N$ | $R^{11}$ | $R^{12}$ |
|---|---|---|---|
| 2-24 | 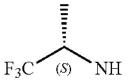 | F | H |
| 2-25 | 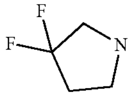 | $CH_3$ | H |
| 2-26 | 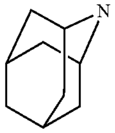 | $CH_3$ | H |
| 2-27 | 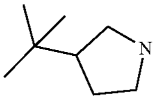 | $CH_3$ | H |
| 2-28 | 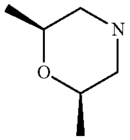 | $CH_3$ | H |
| 2-29 | 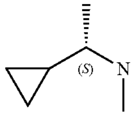 | $CH_3$ | F |
| 2-30 | 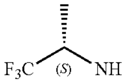 | $CH_3$ | F |
| 2-31 | 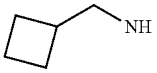 | $CH_3$ | H |
| 2-32 | 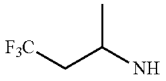 | $CH_3$ | H |
| 2-33 | 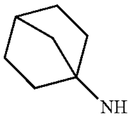 | $CH_3$ | H |
TABLE 3-continued
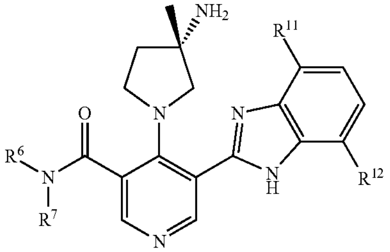
| Compd No. | $R^6R^7N$ | $R^{11}$ | $R^{12}$ |
|---|---|---|---|
| 2-34 | 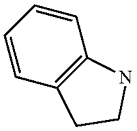 | $CH_3$ | H |
| 2-35 | 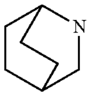 | $CH_3$ | H |
| 2-36 | 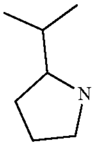 | $CH_3$ | H |
| 2-37 | 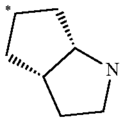 cis | $CH_3$ | H |
| 2-38 | 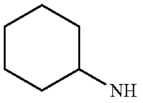 | $CH_3$ | H |
| 2-39 | 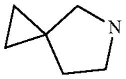 | $CH_3$ | H |
| 2-40 | 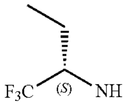 | $CH_3$ | H |
| 2-41 | 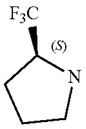 | $CH_3$ | H |
| 2-42 | 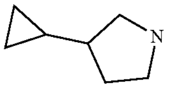 | $CH_3$ | H |
| 2-43 | 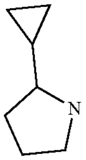 | $CH_3$ | H |

TABLE 3-continued

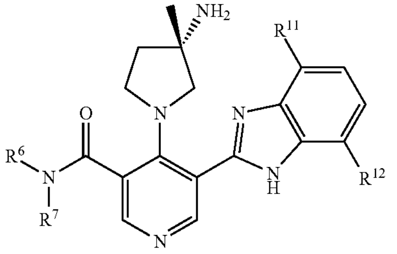

| Compd No. | $R^6R^7N$ | $R^{11}$ | $R^{12}$ |
|---|---|---|---|
| 2-44 | 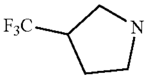 | $CH_3$ | H |
| 2-45 | 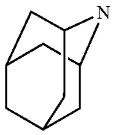 | Cl | H |

*racemic

Compounds in Table 3 are named:

2-1: 4-[(3S)-3-amino-3-methylpyrrolidin-1-yl]-N-ethyl-5-(4-methyl-1H-1,3-benzodiazol-2-yl)pyridine-3-carboxamide;

2-2: (3S)-3-methyl-1-[3-(4-methyl-1H-1,3-benzodiazol-2-yl)-5-(pyrrolidine-1-carbonyl)pyridin-4-yl]pyrrolidin-3-amine;

2-3: 4-[(3S)-3-amino-3-methylpyrrolidin-1-yl]-N-ethyl-N-methyl-5-(4-methyl-1H-1,3-benzodiazol-2-yl)pyridine-3-carboxamide;

2-4: 4-[(3S)-3-amino-3-methylpyrrolidin-1-yl]-N-cyclopentyl-5-(4-methyl-1H-1,3-benzodiazol-2-yl)pyridine-3-carboxamide;

2-5: 4-[(3S)-3-amino-3-methylpyrrolidin-1-yl]-5-(4-methyl-1H-1,3-benzodiazol-2-yl)-N-(oxolan-3-yl)pyridine-3-carboxamide;

2-6: 4-[(3S)-3-amino-3-methylpyrrolidin-1-yl]-5-(4-methyl-1H-1,3-benzodiazol-2-yl)-N-phenylpyridine-3-carboxamide;

2-7: 4-[(3S)-3-amino-3-methylpyrrolidin-1-yl]-5-(4-methyl-1H-1,3-benzodiazol-2-yl)-N-(2,2,2-trifluoroethyl)pyridine-3-carboxamide;

2-8: 4-[(3S)-3-amino-3-methylpyrrolidin-1-yl]-N-(2-methoxyethyl)-5-(4-methyl-1H-1,3-benzodiazol-2-yl)pyridine-3-carboxamide;

2-9: 4-[(3S)-3-amino-3-methylpyrrolidin-1-yl]-N-(2-hydroxyethyl)-5-(4-methyl-1H-1,3-benzodiazol-2-yl)pyridine-3-carboxamide;

2-10: 4-[(3S)-3-amino-3-methylpyrrolidin-1-yl]-N-methyl-5-(4-methyl-1H-1,3-benzodiazol-2-yl)-N-(2,2,2-trifluoroethyl)pyridine-3-carboxamide;

2-11: 4-[(3S)-3-amino-3-methylpyrrolidin-1-yl]-5-(4-methyl-1H-1,3-benzodiazol-2-yl)-N-[(2S)-1,1,1-trifluoropropan-2-yl]pyridine-3-carboxamide;

2-12: 4-[(3S)-3-amino-3-methylpyrrolidin-1-yl]-N-cyclopropyl-5-(4-methyl-1H-1,3-benzodiazol-2-yl)pyridine-3-carboxamide;

2-13: 4-[(3S)-3-amino-3-methylpyrrolidin-1-yl]-N-(cyclopropylmethyl)-5-(4-methyl-1H-1,3-benzodiazol-2-yl)pyridine-3-carboxamide;

2-14: 4-[(3S)-3-amino-3-methylpyrrolidin-1-yl]-N-(1-cyclopropylethyl)-5-(4-methyl-1H-1,3-benzodiazol-2-yl)pyridine-3-carboxamide;

2-15: 4-[(3S)-3-amino-3-methylpyrrolidin-1-yl]-N-{bicyclo[1,1,1]pentan-1-yl}-5-(4-methyl-1H-1,3-benzodiazol-2-yl)pyridine-3-carboxamide;

2-16: 4-[(3S)-3-amino-3-methylpyrrolidin-1-yl]-N-cyclopentyl-N-methyl-5-(4-methyl-1H-1,3-benzodiazol-2-yl)pyridine-3-carboxamide;

2-17: 4-[(3S)-3-amino-3-methylpyrrolidin-1-yl]-N-(4,4-difluorocyclohexyl)-5-(4-methyl-1H-1,3-benzodiazol-2-yl)pyridine-3-carboxamide;

2-18: 4-[(3S)-3-amino-3-methylpyrrolidin-1-yl]-5-(4-methyl-1H-1,3-benzodiazol-2-yl)-N-[(2R)-1,1,1-trifluoropropan-2-yl]pyridine-3-carboxamide;

2-19: (3S)-1-[3-(3,3-dimethylpyrrolidine-1-carbonyl)-5-(4-methyl-1H-1,3-benzodiazol-2-yl)pyridin-4-yl]-3-methylpyrrolidin-3-amine;

2-20: (3S)-1-[3-(2,2-dimethylpyrrolidine-1-carbonyl)-5-(4-methyl-1H-1,3-benzodiazol-2-yl)pyridin-4-yl]-3-methylpyrrolidin-3-amine;

2-21: (3S)-1-[3-(3,3-dimethylazetidine-1-carbonyl)-5-(4-methyl-1H-1,3-benzodiazol-2-yl)pyridin-4-yl]-3-methylpyrrolidin-3-amine;

2-22: 4-[(3S)-3-amino-3-methylpyrrolidin-1-yl]-N-cyclopropyl-N-methyl-5-(4-methyl-1H-1,3-benzodiazol-2-yl)pyridine-3-carboxamide;

2-23: 4-[(3S)-3-amino-3-methylpyrrolidin-1-yl]-N-(cyclopropylmethyl)-N-methyl-5-(4-methyl-1H-1,3-benzodiazol-2-yl)pyridine-3-carboxamide;

2-24: 4-[(3S)-3-amino-3-methylpyrrolidin-1-yl]-5-(4-fluoro-1H-1,3-benzodiazol-2-yl)-N-[(2S)-1,1,1-trifluoropropan-2-yl]pyridine-3-carboxamide;

2-25: (3S)-1-[3-(3,3-difluoropyrrolidine-1-carbonyl)-5-(4-methyl-1H-1,3-benzodiazol-2-yl)pyridin-4-yl]-3-methylpyrrolidin-3-amine;

2-26: (3S)-1-(3-{2-azatricyclo[3.3.1.1$^{3,7}$]decane-2-carbonyl}-5-(4-methyl-1H-1,3-benzodiazol-2-yl)pyridin-4-yl)-3-methylpyrrolidin-3-amine;

2-27: (3S)-1-[3-(3-tert-butylpyrrolidine-1-carbonyl)-5-(4-methyl-1H-1,3-benzodiazol-2-yl)pyridin-4-yl]-3-methylpyrrolidin-3-amine;

2-28: (3S)-1-{3-[(2R,6S)-2,6-dimethylmorpholine-4-carbonyl]-5-(4-methyl-1H-1,3-benzodiazol-2-yl)pyridin-4-yl}-3-methylpyrrolidin-3-amine;

2-29: 4-[(3S)-3-amino-3-methylpyrrolidin-1-yl]-N-[(1S)-1-cyclopropylethyl]-N-methyl-5-(4-methyl-1H-1,3-benzodiazol-2-yl)pyridine-3-carboxamide;

2-30: 4-[(3S)-3-amino-3-methylpyrrolidin-1-yl]-5-(7-fluoro-4-methyl-1H-1,3-benzodiazol-2-yl)-N-[(2S)-1,1,1-trifluoropropan-2-yl]pyridine-3-carboxamide;

2-31: 4-[(3S)-3-amino-3-methylpyrrolidin-1-yl]-N-(cyclobutylmethyl)-5-(4-methyl-1H-1,3-benzodiazol-2-yl)pyridine-3-carboxamide;

2-32: 4-[(3S)-3-amino-3-methylpyrrolidin-1-yl]-5-(4-methyl-1H-1,3-benzodiazol-2-yl)-N-(4,4,4-trifluorobutan-2-yl)pyridine-3-carboxamide;

2-33: 4-[(3S)-3-amino-3-methylpyrrolidin-1-yl]-N-{bicyclo[2.2.1]heptan-1-yl}-5-(4-methyl-1H-1,3-benzodiazol-2-yl)pyridine-3-carboxamide;

2-34: (3S)-1-[3-(2,3-dihydro-1H-indole-1-carbonyl)-5-(4-methyl-1H-1,3-benzodiazol-2-yl)pyridin-4-yl]-3-methylpyrrolidin-3-amine;

2-35: (3S)-1-(3-{2-azabicyclo[2.2.2]octane-2-carbonyl}-5-(4-methyl-1H-1,3-benzodiazol-2-yl)pyridin-4-yl)-3-methylpyrrolidin-3-amine;

2-36: (3S)-3-methyl-1-[3-(4-methyl-1H-1,3-benzodiazol-2-yl)-5-[2-(propan-2-yl)pyrrolidine-1-carbonyl]pyridin-4-yl]pyrrolidin-3-amine;

2-37: (3S)-1-{3-[(3aR)-octahydrocyclopenta[b]pyrrole-1-carbonyl]-5-(4-methyl-1H-1,3-benzodiazol-2-yl)pyridin-4-yl}-3-methylpyrrolidin-3-amine;

2-38: 4-[(3S)-3-amino-3-methylpyrrolidin-1-yl]-N-cyclohexyl-5-(4-methyl-1H-1,3-benzodiazol-2-yl)pyridine-3-carboxamide;

2-39: (3S)-1-(3-{5-azaspiro[2.4]heptane-5-carbonyl}-5-(4-methyl-1H-1,3-benzodiazol-2-yl)pyridin-4-yl)-3-methylpyrrolidin-3-amine;

2-40: 4-[(3S)-3-amino-3-methylpyrrolidin-1-yl]-5-(4-methyl-1H-1,3-benzodiazol-2-yl)-N-[(2S)-1,1,1-trifluorobutan-2-yl]pyridine-3-carboxamide;

2-41: (3S)-3-methyl-1-[3-(4-methyl-1H-1,3-benzodiazol-2-yl)-5-[(2S)-2-(trifluoromethyl)pyrrolidine-1-carbonyl]pyridin-4-yl]pyrrolidin-3-amine;

2-42: (3S)-1-[3-(3-cyclopropylpyrrolidine-1-carbonyl)-5-(4-methyl-1H-1,3-benzodiazol-2-yl)pyridin-4-yl]-3-methylpyrrolidin-3-amine;

2-43: (3S)-1-[3-(2-cyclopropylpyrrolidine-1-carbonyl)-5-(4-methyl-1H-1,3-benzodiazol-2-yl)pyridin-4-yl]-3-methylpyrrolidin-3-amine;

2-44: (3S)-3-methyl-1-[3-(4-methyl-1H-1,3-benzodiazol-2-yl)-5-[3-(trifluoromethyl)pyrrolidine-1-carbonyl]pyridin-4-yl]pyrrolidin-3-amine;

2-45: (3S)-1-(3-{2-azatricyclo[3.3.1.1$^{3,7}$]decane-2-carbonyl}-5-(7-chloro-1H-1,3-benzodiazol-2-yl)pyridin-4-yl)-3-methylpyrrolidin-3-amine.

In some embodiments, provided herein is a pharmaceutically acceptable salt of a compound that is described in Table 3.

TABLE 4

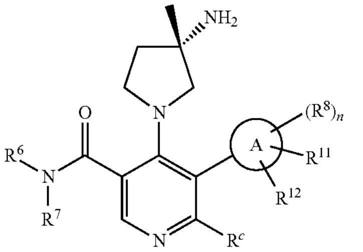

| Compd No. | $R^6R^7N$ | 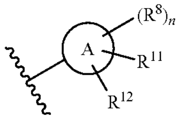 | $R^c$ |
|---|---|---|---|
| 1-161 | 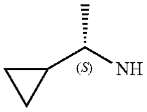 | 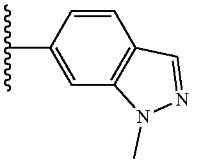 | H |
| 1-162 | 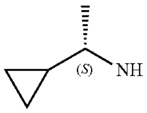 | 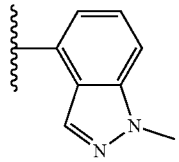 [SMILES: *c1cccc2c1cnn2C] | H |

TABLE 4-continued

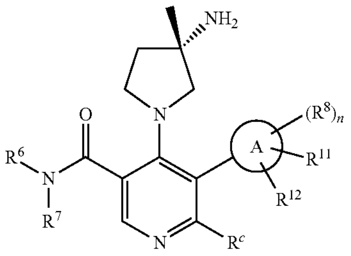

| Compd No. | $R^6R^7N$ | 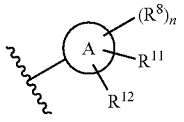 | $R^c$ |
|---|---|---|---|
| 1-182 | 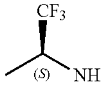 | 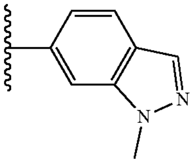 [SMILES: *c1ccc2cnn(C)c2c1] | $OCH_3$ |
| 1-183 | 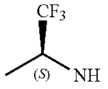 | 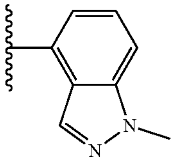 [SMILES: *c1cccc2c1cnn2C] | $OCH_3$ |
| 1-186 | 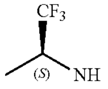 | 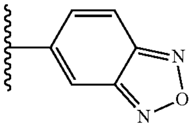 [SMILES: *c1ccc2nonc2c1] | $OCH_3$ |

Compounds in Table 4 are named:

1-161: 4-[(3S)-3-amino-3-methylpyrrolidin-1-yl]-N-[(1S)-1-cyclopropylethyl]-5-(1-methyl-1H-indazol-6-yl)pyridine-3-carboxamide;

1-162: 4-[(3S)-3-amino-3-methylpyrrolidin-1-yl]-N-[(1S)-1-cyclopropylethyl]-5-(1-methyl-1H-indazol-4-yl)pyridine-3-carboxamide;

1-182: 4-[(3S)-3-amino-3-methylpyrrolidin-1-yl]-6-methoxy-5-(1-methyl-1H-1,3-benzodiazol-6-yl)-N-[(2S)-1,1,1-trifluoropropan-2-yl]pyridine-3-carboxamide;

1-183: 4-[(3S)-3-amino-3-methylpyrrolidin-1-yl]-6-methoxy-5-(1-methyl-1H-indazol-4-yl)-N-[(2S)-1,1,1-trifluoropropan-2-yl]pyridine-3-carboxamide;

1-186: 4-[(3S)-3-amino-3-methylpyrrolidin-1-yl]-5-(2,1,3-benzoxadiazol-5-yl)-6-methoxy-N-[(2S)-1,1,1-trifluoropropan-2-yl]pyridine-3-carboxamide.

In some embodiments, provided herein is a pharmaceutically acceptable salt of a compound that is described in Table 4.

TABLE 5
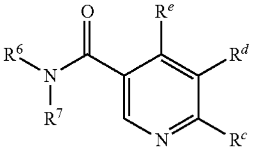
| Compd No. | $R^6R^7N$ | $R^e$ | $R^d$ | $R^c$ |
|---|---|---|---|---|
| 1-2 | 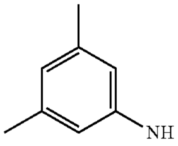 | 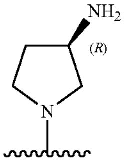 | 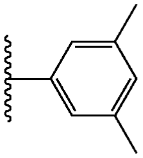 | H |
| 1-36 | 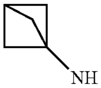 | 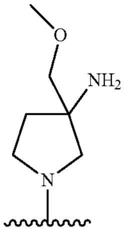 [SMILES: *N1CCC(N)(COC)C1] | 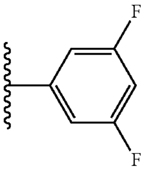 [SMILES: *c1cc(F)cc(F)c1] | H |
| 1-63 | 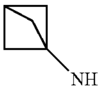 | 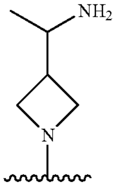 [SMILES: *N1CC(C(C)N)C1] | 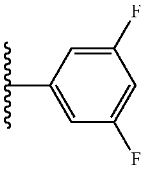 [SMILES: *c1cc(F)cc(F)c1] | H |
| 1-75 | 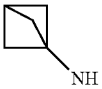 | 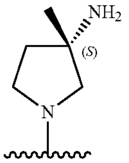 | H | CN |
| 1-99 | 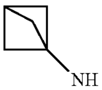 | 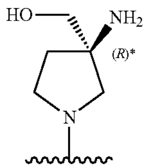 | 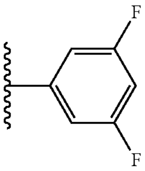 [SMILES: *c1cc(F)cc(F)c1] | CN |
| 1-100 | 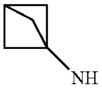 | 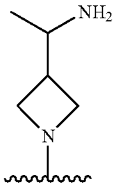 [SMILES: *N1CC(C(C)N)C1] | 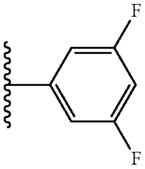 [SMILES: *c1cc(F)cc(F)c1] | CN |
| 1-102 | 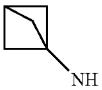 | 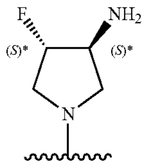 | 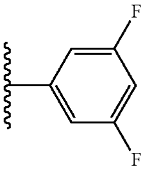 [SMILES: *c1cc(F)cc(F)c1] | CN |

TABLE 5-continued
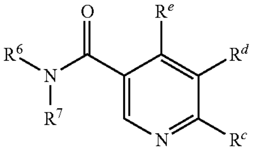
| Compd No. | $R^6R^7N$ | $R^e$ | $R^d$ | $R^c$ |
|---|---|---|---|---|
| 1-117 | 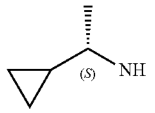 | 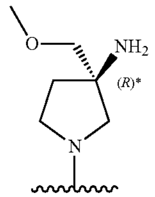 | 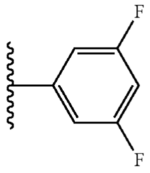 [SMILES: *c1cc(F)cc(F)c1] | CN |
| 1-119 | 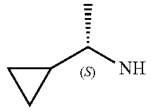 | 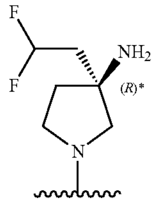 | 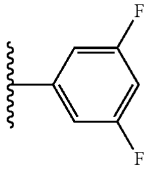 [SMILES: *c1cc(F)cc(F)c1] | CN |
| 1-136 | 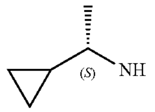 | 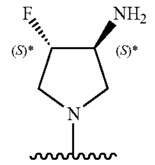 | 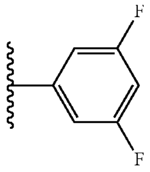 [SMILES: *c1cc(F)cc(F)c1] | CN |
| 1-139 | 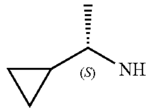 | 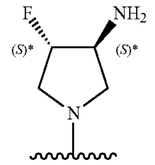 | 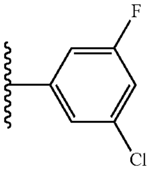 | CN |
| 1-220 | 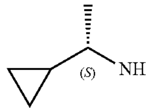 | 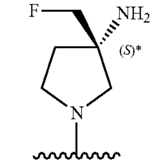 | 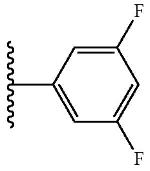 [SMILES: *c1cc(F)cc(F)c1] | CN |
| 1-221 | 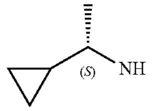 | 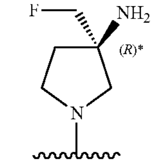 | 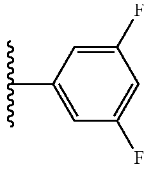 [SMILES: *c1cc(F)cc(F)c1] | CN |
| 1-274 | 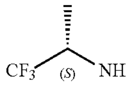 | 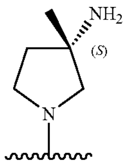 | Br | $OCH_3$ |
*absolute stereochemistry not determined Compounds in Table 5 are named:

1-2: 4-[(3R)-3-aminopyrrolidin-1-yl]-N,5-bis(3,5-dimethylphenyl)pyridine-3-carboxamide;

1-36: 4-[3-amino-3-(methoxymethyl)pyrrolidin-1-yl]-N—{bicyclo[1.1.1]pentan-1-yl}-5-(3,5-difluorophenyl)pyridine-3-carboxamide;

1-63: 4-[3-(1-aminoethyl)azetidin-1-yl]-N—{bicyclo[1.1.1]pentan-1-yl}-5-(3,5-difluorophenyl)pyridine-3-carboxamide;

1-75: 4-[(3S)-3-amino-3-methylpyrrolidin-1-yl]-N-{bicyclo[1.1.1]pentan-1-yl}-6-cyanopyridine-3-carboxamide;

1-99: 4-[(3R)-3-amino-3-(hydroxymethyl)pyrrolidin-1-yl]-N-{bicyclo[1.1.1]pentan-1-yl}-6-cyano-5-(3,5-difluorophenyl)pyridine-3-carboxamide;

1-100: 4-[3-(1-aminoethyl)azetidin-1-yl]-N-{bicyclo[1.1.1]pentan-1-yl}-6-cyano-5-(3,5-difluorophenyl)pyridine-3-carboxamide;

1-102: 4-[(3S,4S)-3-amino-4-fluoropyrrolidin-1-yl]-N-{bicyclo[1.1.1]pentan-1-yl}-6-cyano-5-(3,5-difluorophenyl)pyridine-3-carboxamide;

1-117: 4-[(3S)-3-amino-3-(methoxymethyl)pyrrolidin-1-yl]-6-cyano-N-[(1S)-1-cyclopropylethyl]-5-(3,5-difluorophenyl)pyridine-3-carboxamide;

1-119: 4-[(3R)-3-amino-3-(2,2-difluoroethyl)pyrrolidin-1-yl]-6-cyano-N-[(1S)-1-cyclopropylethyl]-5-(3,5-difluorophenyl)pyridine-3-carboxamide;

1-136: 4-[(3S,4S)-3-amino-4-fluoropyrrolidin-1-yl]-6-cyano-N-[(1S)-1-cyclopropylethyl]-5-(3,5-difluorophenyl)pyridine-3-carboxamide;

1-139: 4-[(3S,4S)-3-amino-4-fluoropyrrolidin-1-yl]-5-(3-chloro-5-fluorophenyl)-6-cyano-N-[(1S)-1-cyclopropylethyl]pyridine-3-carboxamide;

1-220: 4-[(3S)-3-amino-3-(fluoromethyl)pyrrolidin-1-yl]-6-cyano-N-[(1S)-1-cyclopropylethyl]-5-(3,5-difluorophenyl)pyridine-3-carboxamide;

1-221: 4-[(3R)-3-amino-3-(fluoromethyl)pyrrolidin-1-yl]-6-cyano-N-[(1S)-1-cyclopropylethyl]-5-(3,5-difluorophenyl)pyridine-3-carboxamide;

1-274: 4-[(3S)-3-amino-3-methylpyrrolidin-1-yl]-5-bromo-6-methoxy-N-[(2S)-1,1,1-trifluoropropan-2-yl]pyridine-3-carboxamide.

In some embodiments, provided herein is a pharmaceutically acceptable salt of a compound that is described in Table 5.

TABLE 6

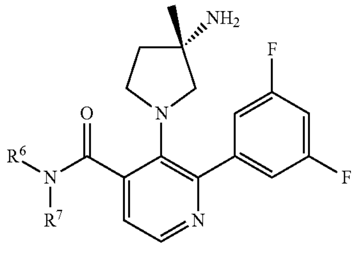

| Compd No. | $R^6R^7N$ |
|---|---|
| 3-1 | 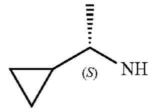 |

TABLE 6-continued

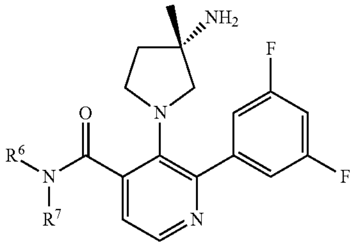

| Compd No. | $R^6R^7N$ |
|---|---|
| 3-2 | 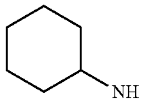 |
| 3-3 | 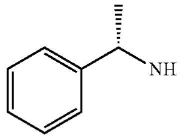 |
| 3-4 | 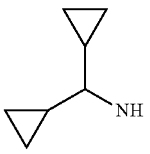 |
| 3-5 | 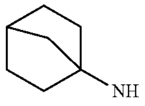 |
| 3-6 | 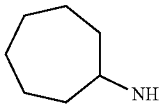 |
| 3-7 | 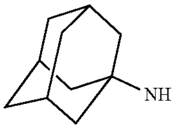 |
| 3-8 | 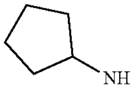 |

Compounds in Table 6 are named:

3-1: 3-[(3S)-3-amino-3-methylpyrrolidin-1-yl]-N-[(1S)-1-cyclopropylethyl]-2-(3,5-difluorophenyl)pyridine-4-carboxamide;

3-2: 3-[(3S)-3-amino-3-methylpyrrolidin-1-yl]-N-cyclohexyl-2-(3,5-difluorophenyl)pyridine-4-carboxamide;

3-3: 3-[(3S)-3-amino-3-methylpyrrolidin-1-yl]-2-(3,5-difluorophenyl)-N-[(1S)-1-phenylethyl]pyridine-4-carboxamide;

3-4: 3-[(3S)-3-amino-3-methylpyrrolidin-1-yl]-N-(dicyclopropylmethyl)-2-(3,5-difluorophenyl)pyridine-4-carboxamide;

3-5: 3-[(3S)-3-amino-3-methylpyrrolidin-1-yl]-N-{bicyclo[2.2.1]heptan-1-yl}-2-(3,5-difluorophenyl)pyridine-4-carboxamide;

3-6: 3-[(3S)-3-amino-3-methylpyrrolidin-1-yl]-N-cycloheptyl-2-(3,5-difluorophenyl)pyridine-4-carboxamide;

3-7: N-(adamantan-1-yl)-3-[(3S)-3-amino-3-methylpyrrolidin-1-yl]-2-(3,5-difluorophenyl)pyridine-4-carboxamide;

3-8: 3-[(3S)-3-amino-3-methylpyrrolidin-1-yl]-N-cyclopentyl-2-(3,5-difluorophenyl)pyridine-4-carboxamide.

In some embodiments, provided herein is a pharmaceutically acceptable salt of a compound that is described in Table 6.

TABLE 7

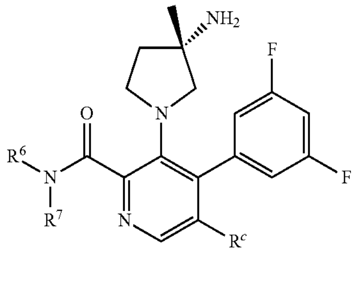

| Compd. No. | $R^6R^7N$ | $R^c$ |
|---|---|---|
| 4-1 | 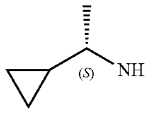 | Cl |
| 4-2 | 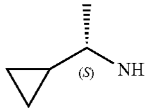 | $CH_3$ |
| 4-3 | 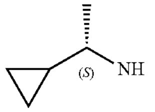 | CN |
| 4-4 | 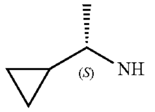 | $COOCH_3$ |
| 4-5 | 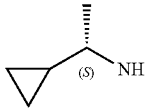 | $CONH_2$ |

Compounds in Table 7 are named:

4-1: 3-[(3S)-3-amino-3-methylpyrrolidin-1-yl]-5-chloro-N-[(1S)-1-cyclopropylethyl]-4-(3,5-difluorophenyl)pyridine-2-carboxamide;

4-2: 3-[(3S)-3-amino-3-methylpyrrolidin-1-yl]-N-[(1S)-1-cyclopropylethyl]-4-(3,5-difluorophenyl)-5-methylpyridine-2-carboxamide;

4-3: 3-[(3S)-3-amino-3-methylpyrrolidin-1-yl]-5-cyano-N-[(1S)-1-cyclopropylethyl]-4-(3,5-difluorophenyl)pyridine-2-carboxamide;

4-4: methyl 5-[(3S)-3-amino-3-methylpyrrolidin-1-yl]-6-{[(1S)-1-cyclopropylethyl]carbamoyl}-4-(3,5-difluorophenyl)pyridine-3-carboxylate;

4-5: 3-[(3S)-3-amino-3-methylpyrrolidin-1-yl]-N2-[(1S)-1-cyclopropylethyl]-4-(3,5-difluorophenyl)pyridine-2,5-dicarboxamide.

In some embodiments, provided herein is a pharmaceutically acceptable salt of a compound that is described in Table 7.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (–L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (–L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$ $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers, and the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

In some instances, heterocyclic rings may exist in tautomeric forms. In such situations, it is understood that the structures of said compounds are illustrated or named in one tautomeric form but could be illustrated or named in the alternative tautomeric form. The alternative tautomeric forms are expressly included in this disclosure, such as, for example, the structures illustrated below. For example, benzimidazoles or imidazoles could exist in the following tautomeric forms:

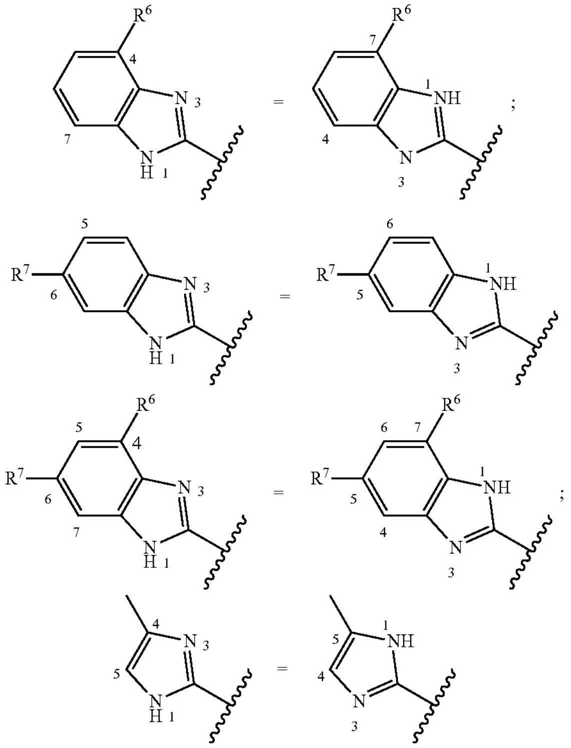

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

Scheme A

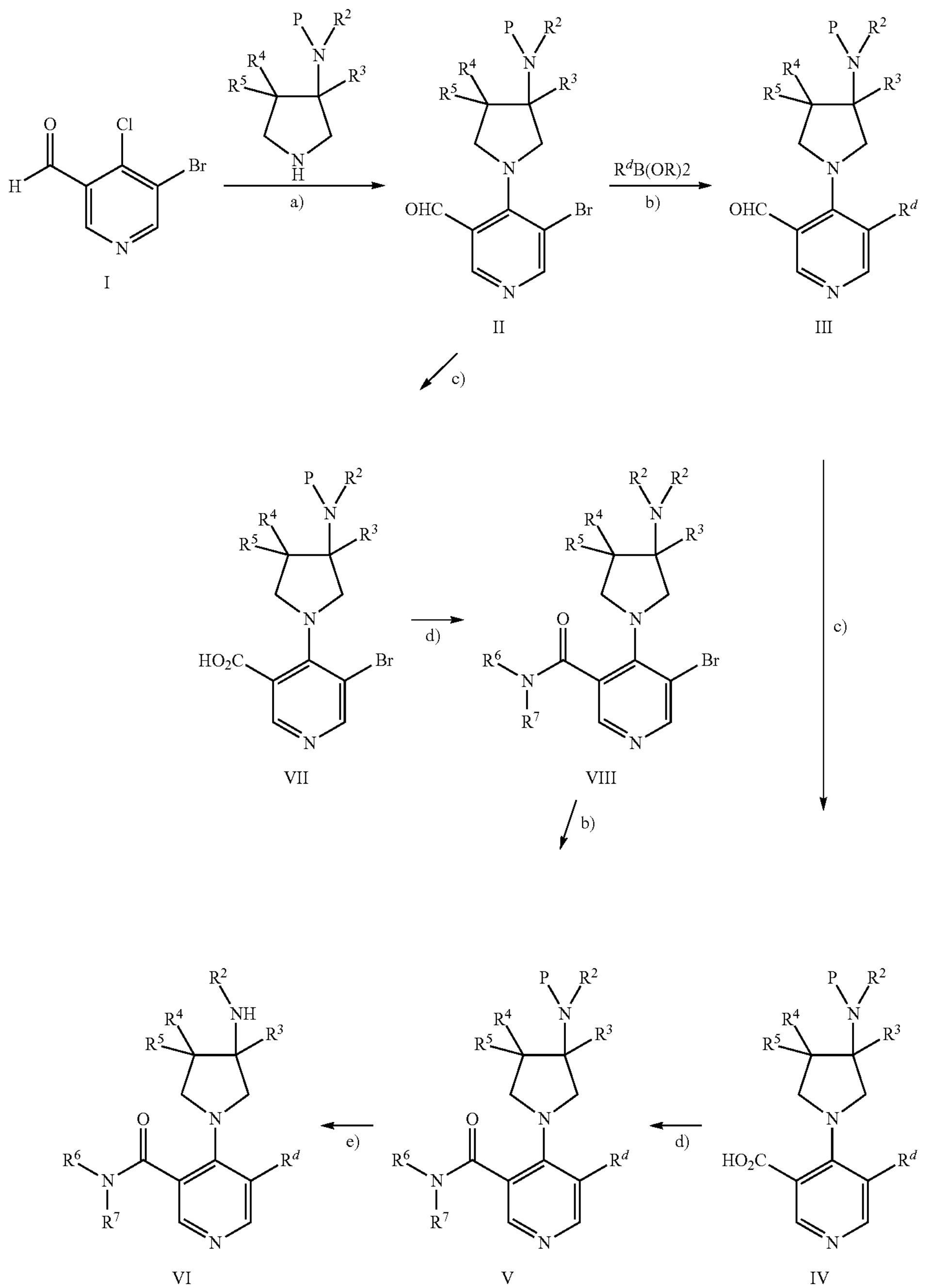

P = protecting group a) DIPEA, THF; b) Pd catalyst, base; c) $NaClO_2$, $NaH_2PO_4$, 2-methylbut-2-ene, t-BuOH/water; d) HATU, DIPEA, $R^6R^7NH$, DMF; e) de-protection Nucleophilic substitution of I with protected aminopyrrolidine afforded intermediate II, which was subsequently converted to intermediate III by an organometallic coupling reaction such as Suzuki-Miyaura reaction with a boronic acid ($R^dB(OH)_2$) or its ester or an organotrifluoroborate ($R^dBF_3K$). Aldehyde III was treated with oxidative reagents such as $NaClO_2$ to generate the corresponding acid IV, which was coupled with amines to produce amide intermediate V in the presence of coupling reagents such as HATU or 1-Chloro-N,N,2-trimethyl-1-propenylamine (Ghosez's reagent). Alternative, aldehyde II was treated with oxidative reagents such as $NaClO_2$ to generate acid VII, which could react with amines to produce amide intermediate VIII in the presence of coupling reagents such as HATU. This compound underwent organometallic coupling reaction such as Suzuki-Miyaura reaction to generate compound V. Removal of the protecting group using appropriate de-protection methods yielded final compound VI.

In some other embodiments, compounds described herein are prepared as described in Scheme B.

Scheme B
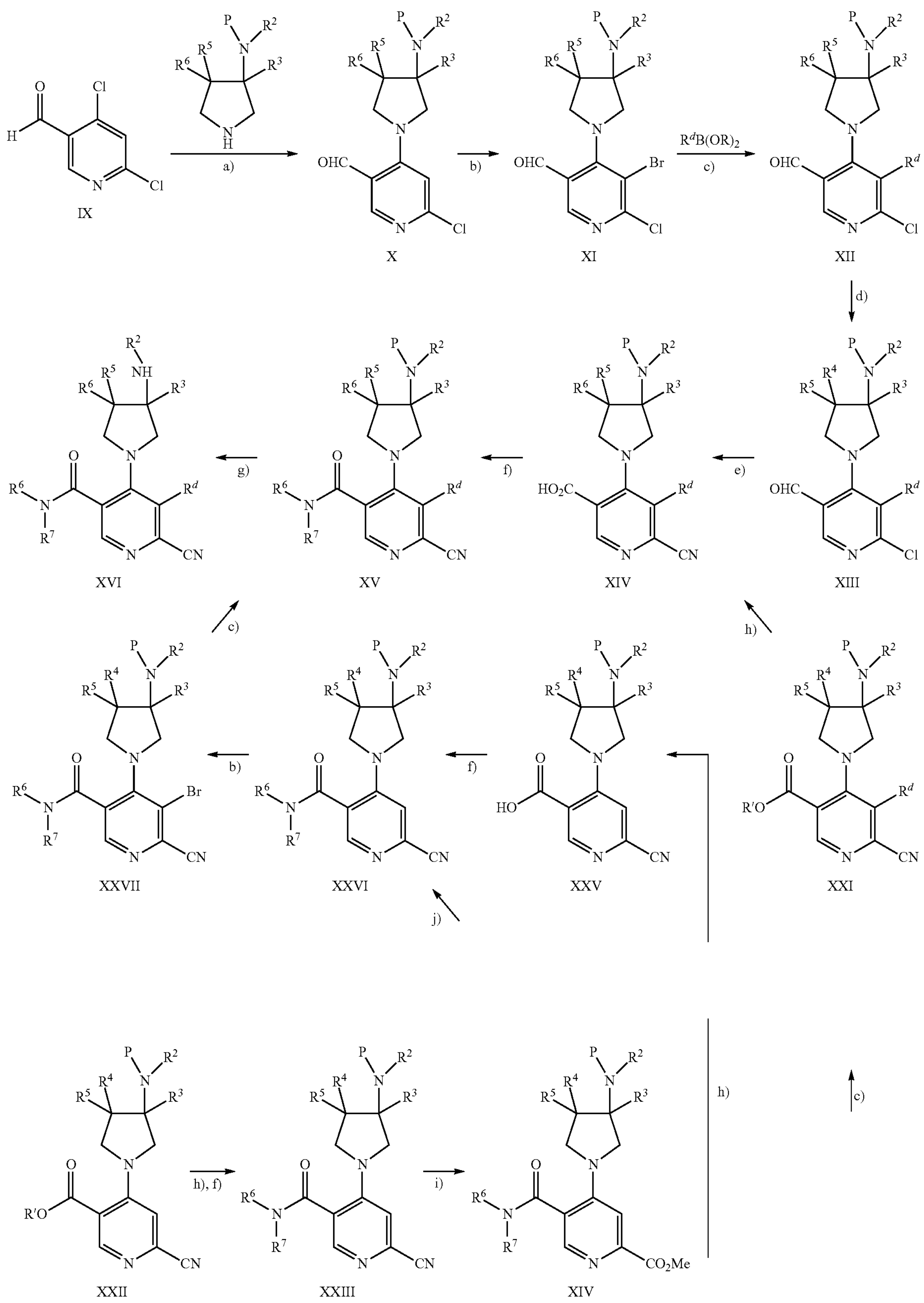

-continued

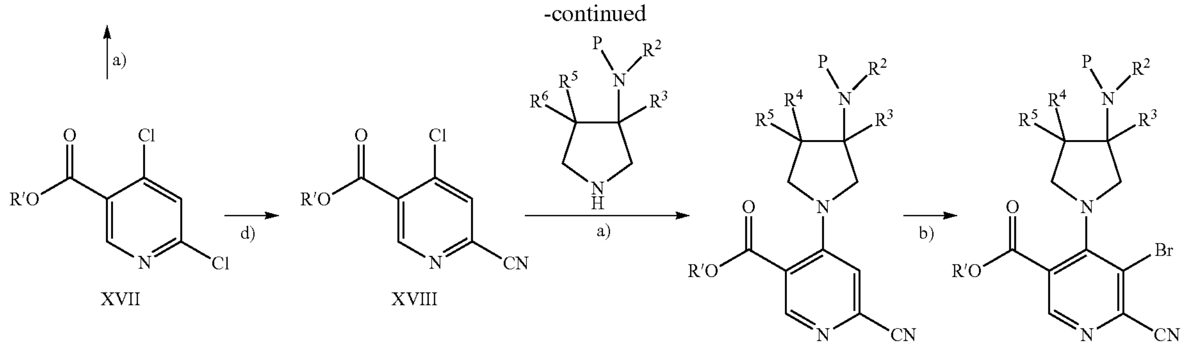

XVII XVIII XIX XX

P = protecting group a) TEA, MeCN; b) 1-bromopyrroidine-2,5-dione, HOAc; c) boronic acid/ester, Pd; d) $Zn(CN)_2$, Pd; e)$NaClO_2$, $NaH_2PO_4$, 2-methylbut-2-ene, t-BuOH/water; f) coupling agent, DIPEA, $R^6R^7NH$, DMF; g) de-protection; h) LiOH , MeOH/water; i) Pd, CO, MeOH; j) (1) $NH_3$, MeOH; (2) TFAA Nucleophilic substitution of IX with protected aminopyrrolidine afforded intermediate X, which was halogenated to afford compound XI. Subsequently, XI was converted to intermediate XII by an organometallic coupling reaction such as Suzuki-Miyaura reaction with a boronic acid ($R^dB(OH)_2$) or its ester or an organotrifluoroborate ($R^dBF_3K$). Compound XII was converted to nitrile XIII using an organometallic cyanation reaction, which was treated with oxidative reagents such as $NaClO_2$ to generate acid XIV. This compound could react with amines to produce amide XV in the presence of coupling reagents such as HATU. Alternatively, 4,6-dichloronicotinate XVII was converted to nitrile XVIII by an organometallic cyanation reaction, which underwent nucleophilic substitution with protected aminopyrrolidine to produce intermediate XIX. Subsequently, this compound was treated with halogenation reagents such as NBS or 1-bromopyrrolidine-2,5-dione to produce XX. Intermediate XX was converted to XXI using an organometallic coupling reaction such as Suzuki-Miyaura reaction, which was hydrolyzed to acid XIV in the presence of base. Intermediate XIX could also be converted to acid XXV, which was allowed to react with amines to generated amide XXVI. Subsequent halogenation followed by an organometallic coupling reaction such as Suzuki-Miyaura reaction produced intermediate XV. Intermediate XXVI was also synthesized using a different method. Nucleophilic substitution of XVII with protected aminopyrrolidine afforded intermediate XXII, which was hydrolyzed under basic conditions followed by coupling with appropriate amines to produce amides XXIII. This compound was subject to organometallic carbonylation conditions and the resulting ester XIV was converted to corresponding amides which could be readily dehydrated to nitrile XXVI. Removal of the protecting group of intermediate XV using appropriate de-protection methods yielded final compound XVI.

In some other embodiments, compounds described herein are prepared as described in Scheme C.

Scheme C

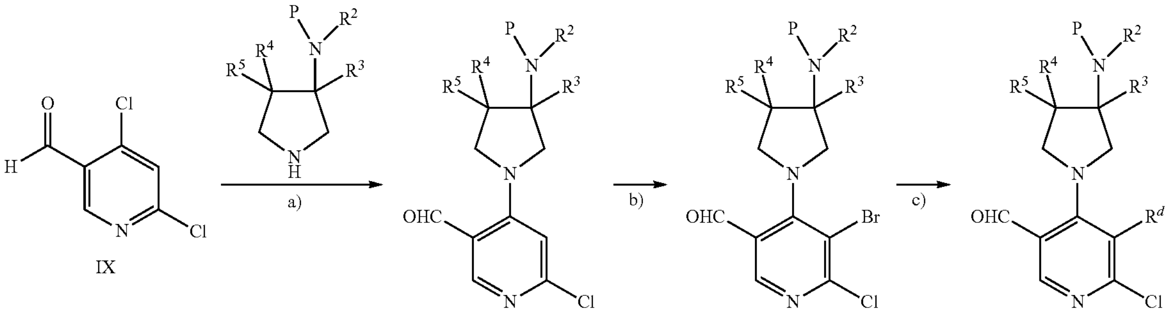

IX X XI XII

-continued

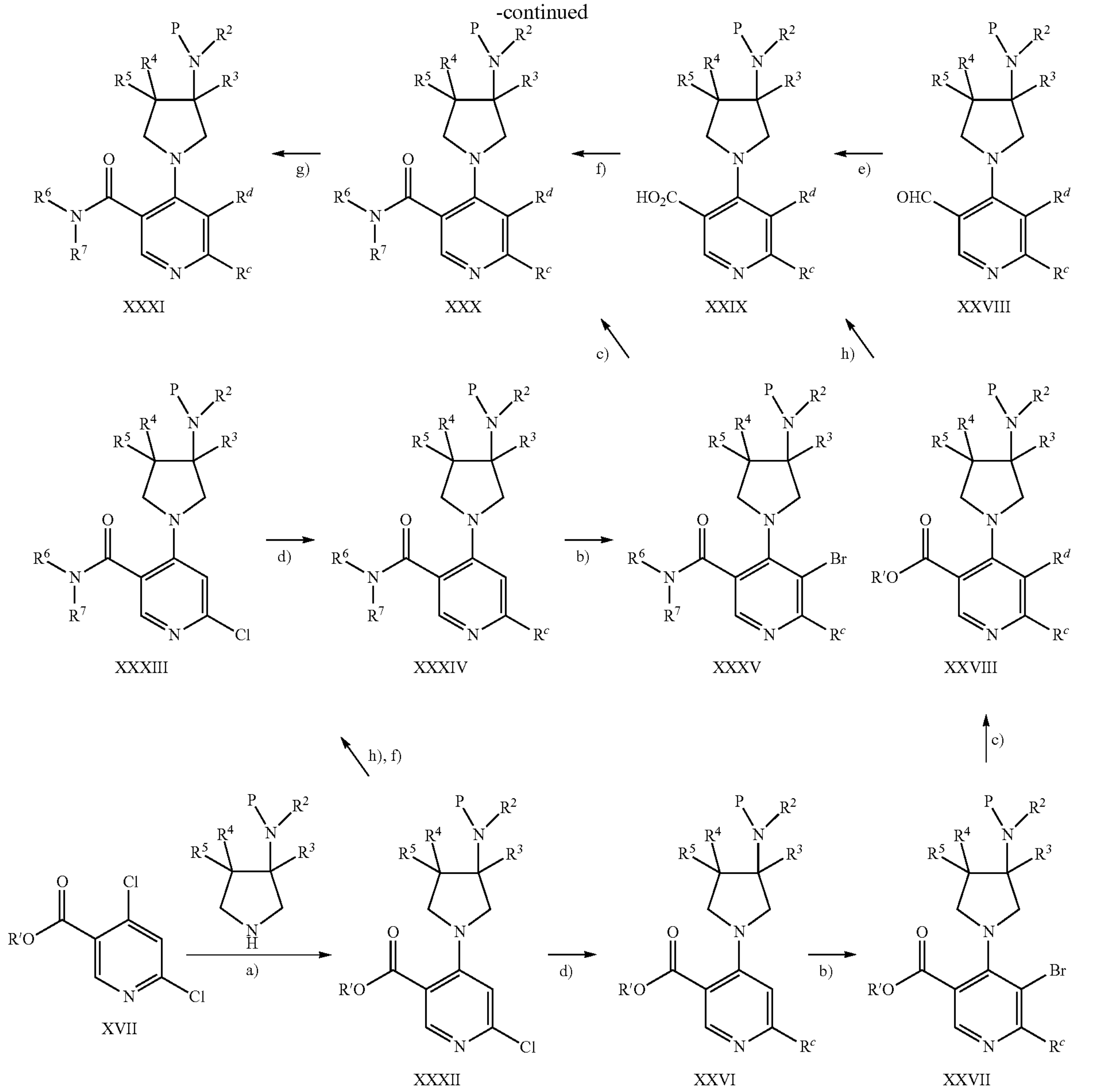

P = protecting group a) TEA, MeCN; b) 1-bromopyrrolidine-2,5-dione, HOAc; c) $R^dB(OR)_2$ or $R^dBF_3K$, Pd; d) $Zn(CN)_2$, Pd; e) $NaClO_2$, $NaH_2PO_4$, 2-methylbut-2-ene, t-BuOH/water; f) coupling reagent, DIPEA, $R^6R^7NH$, DMF, g) de-protection; h) LiOH, MeOH/water;

Nucleophilic substitution of IX with protected aminopyrrolidine afforded intermediate X, which was brominated to afford intermediate XI. Subsequently, compound XI was converted to intermediate XII by an organometallic coupling reaction such as Suzuki-Miyaura reaction, which underwent another organometallic coupling reaction to introduce $R^c$ group to afford XXVIII. This compound was treated with oxidative reagents such as $NaClO_2$ to generate acid XXIX, which could react with amines to produce amide XXX in the presence of coupling reagents such as HATU or Ghosez's reagent. Alternatively, nucleophilic substitution of 4,6-dichloronicotinate XVII with protected aminopyrrolidine afforded intermediate XXXII, which was hydrolyzed under basic conditions followed by coupling with amines to produce amides XXXIII. This compound was converted to intermediate XXXIV by an organometallic coupling reaction to introduce $R^c$ group. Halogenation of intermediate XXXIV led to the formation of intermediate XXXV, which could be converted to compound XXX by an organometallic coupling reaction such as Suzuki-Miyaura reaction. Alternatively, 4,6-dichloronicotinate XVII was converted to XXXII, then converted to XXXVI by an organometallic coupling reaction followed by halogenation to afforded compound XXVII. This compound was converted to intermediate XXXVIII by an organometallic coupling reaction such as Suzuki-Miyaura reaction, which was hydrolyzed to produce acid XXIX under basic conditions. Removing the protecting group of intermediate XXX using appropriate de-protection methods yielded final compound XXXI.

In some other embodiments, compounds described herein are prepared as described in Scheme D.

Scheme D
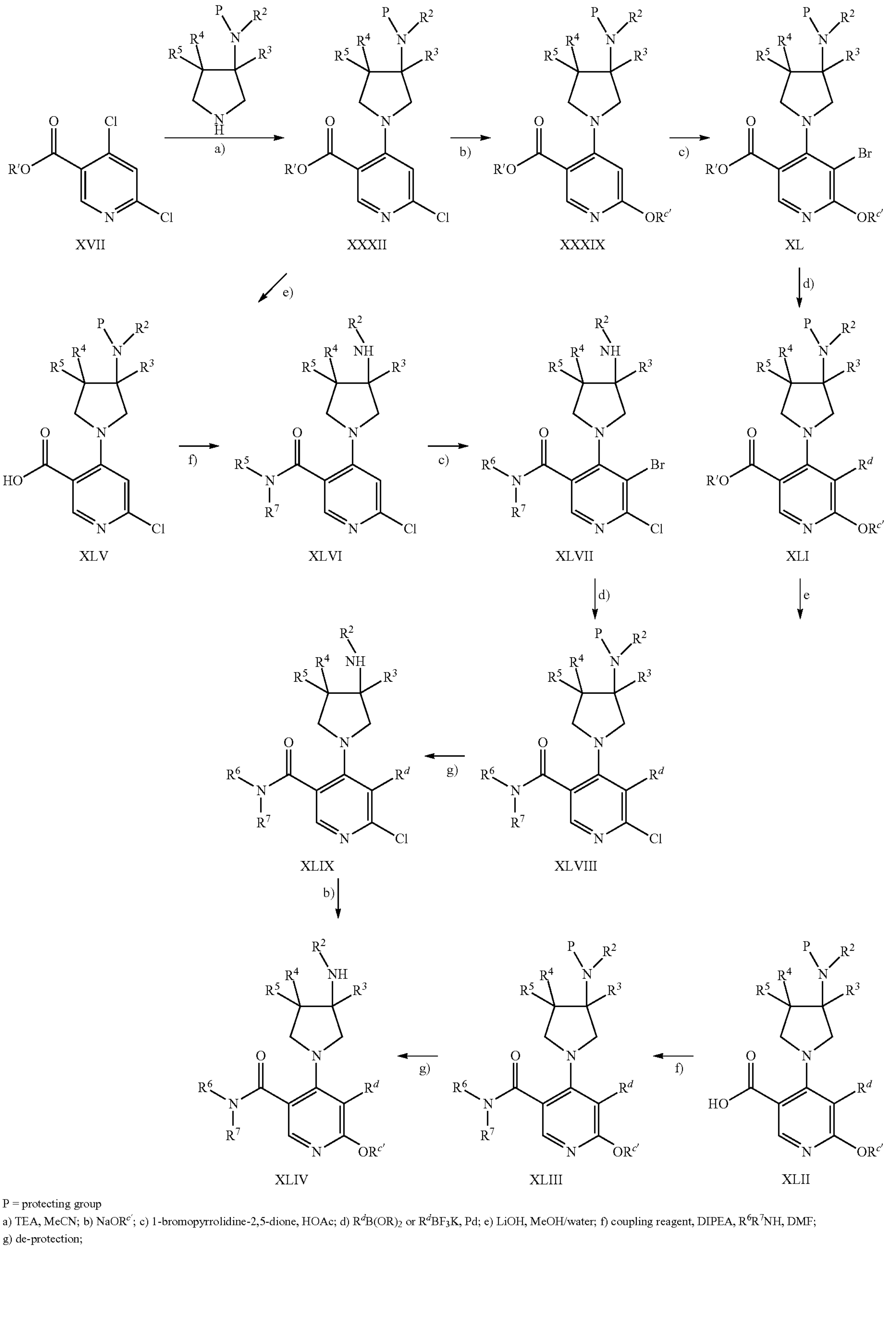
P = protecting group
a) TEA, MeCN; b) NaOR$^{c'}$; c) 1-bromopyrrolidine-2,5-dione, HOAc; d) $R^dB(OR)_2$ or $R^dBF_3K$, Pd; e) LiOH, MeOH/water; f) coupling reagent, DIPEA, $R^6R^7NH$, DMF; g) de-protection;

Nucleophilic substitution of 4,6-dichloronicotinate XVII with protected aminopyrrolidine afforded intermediate XXXII, which was treated with alkoxide with or without organometallic catalysts to generated compound XXXIX. Subsequent halogenation followed an organometallic coupling reaction such as Suzuki-Miyaura reaction afforded intermediate XLI. This compound was converted to acid XLII under basic conditions, which coupled with amines to produce amide XLIII in the presence of coupling reagents such as HATU or Ghosez's reagent. Removing the protecting group of intermediate XLIII using appropriate de-protection methods yielded final compound XLIV. Alternatively, ester XXXII was converted to acid XLV under basic conditions, which coupled with amines to produce amide XLVI in the presence of coupling reagents such as HATU or Ghosez's reagent. Subsequent halogenation followed by an organometallic coupling reaction such as Suzuki-Miyaura reaction afforded intermediate XLVIII. Removal of protecting group using appropriate de-protection methods followed by treating with alkoxide led to the formation of final compound XLIV.

In some other embodiments, compounds described herein are prepared as described in Scheme E.

Scheme E

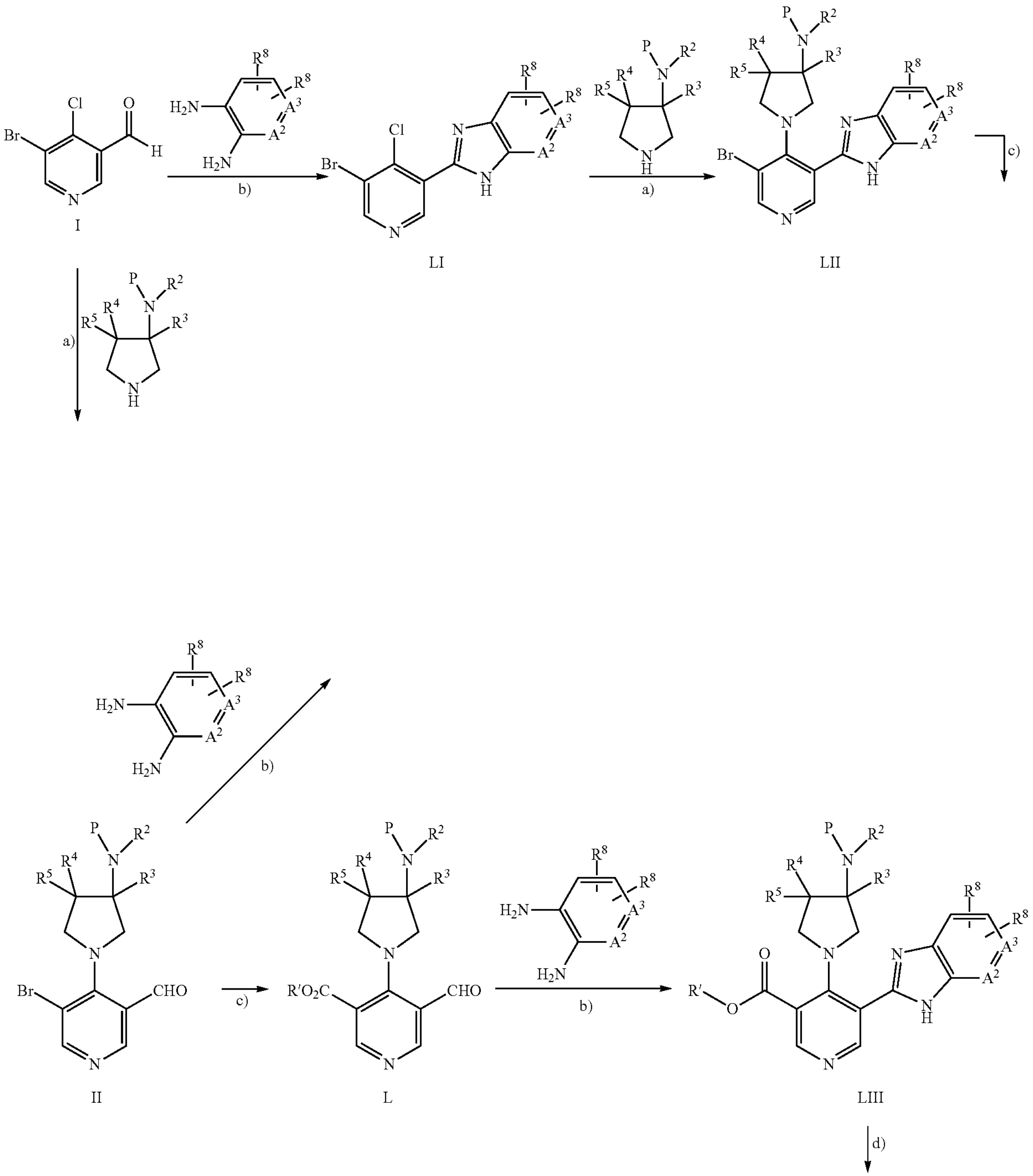

I LI LII II L LIII

-continued

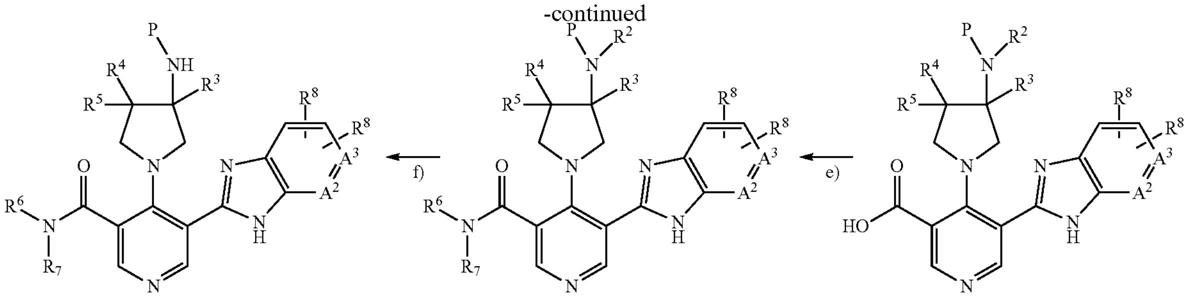

LVI LV LIV

P = protecting group a) TEA, MeCN; b) $Na_2S_2O_5$, DMSO; c) Pd, CO, R¢OH; d) NaOH; e) coupling reagent, DIPEA, $R^6R^7NH$, DMF; f) de-protection;

Nucleophilic substitution of I with protected aminopyrrolidine afforded intermediate II, which was treated with 1,2-diaminobenzenes by heating in wet DMF or NMP or DMSO or other solvents with or without $Na_2S_2O_5$ under atmospheric oxygen to yield benzimidazole LII. Subsequently, LII was converted to ester LIII by an organometallic carbonylation reaction. Alternative, compound II could be converted to ester L by an organometallic carbonylation reaction, which was treated with 1,2-diaminobenzenes by heating in wet DMF or NMP or DMSO or other solvents with or without $Na_2S_2O_5$ under atmospheric oxygen to yield benzimidazole LIII. Alternatively, aldehyde I could react with 1,2-diaminobenzenes by heating in wet DMF or NMP or DMSO or other solvents with or without $Na_2S_2O_5$ under atmospheric oxygen to yield imidazole LI, which underwent nucleophilic substitution with protected aminopyrrolidine to produce intermediate LII. Subsequently, ester LIII was converted to acid LIV under basic conditions, which was treated with amines to produce amide LV in the presence of coupling reagents such as HATU. Removal of the protecting group using appropriate de-protection methods yielded final compound LVI.

In some other embodiments, compounds described herein are prepared as described in Scheme F.

Scheme F

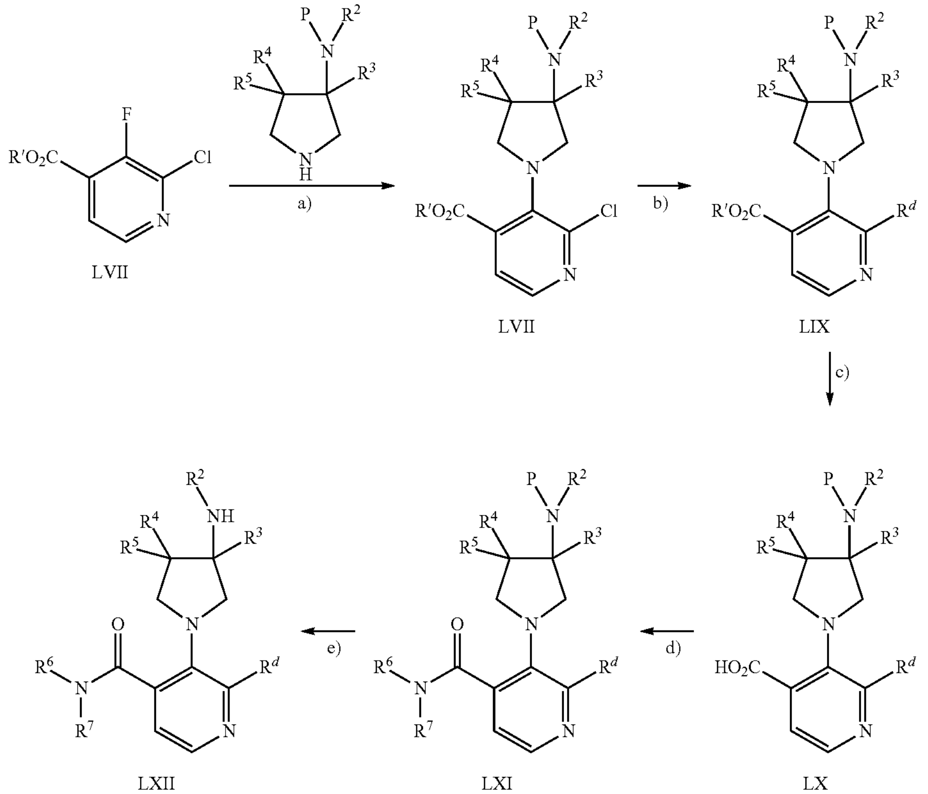

LVII LVII LIX

LXII LXI LX

P = protecting group a) K2CO3, dioxane; b) $R^dB(OR)_2$ or $R^dBF_3K$, Pd; c) LiOH, THF/water; d) HATU, DIPEA, $R^6R^7NH$, DMF; (e) de-protection;

Nucleophilic substitution of LVII with protected amino-pyrrolidine afforded intermediate LVIII, which was converted to compound LIX by an organometallic coupling reaction such as Suzuki-Miyaura reaction. Basic hydrolysis of ester LIX led to the formation of acid LX, which reacted with amines in the presence of amide coupling reagents such as HATU to produce intermediate LXI. Removal of the protecting group using appropriate de-protection methods yielded final compound LXII.

In some other embodiments, compounds described herein are prepared as described in Scheme G.

Scheme G

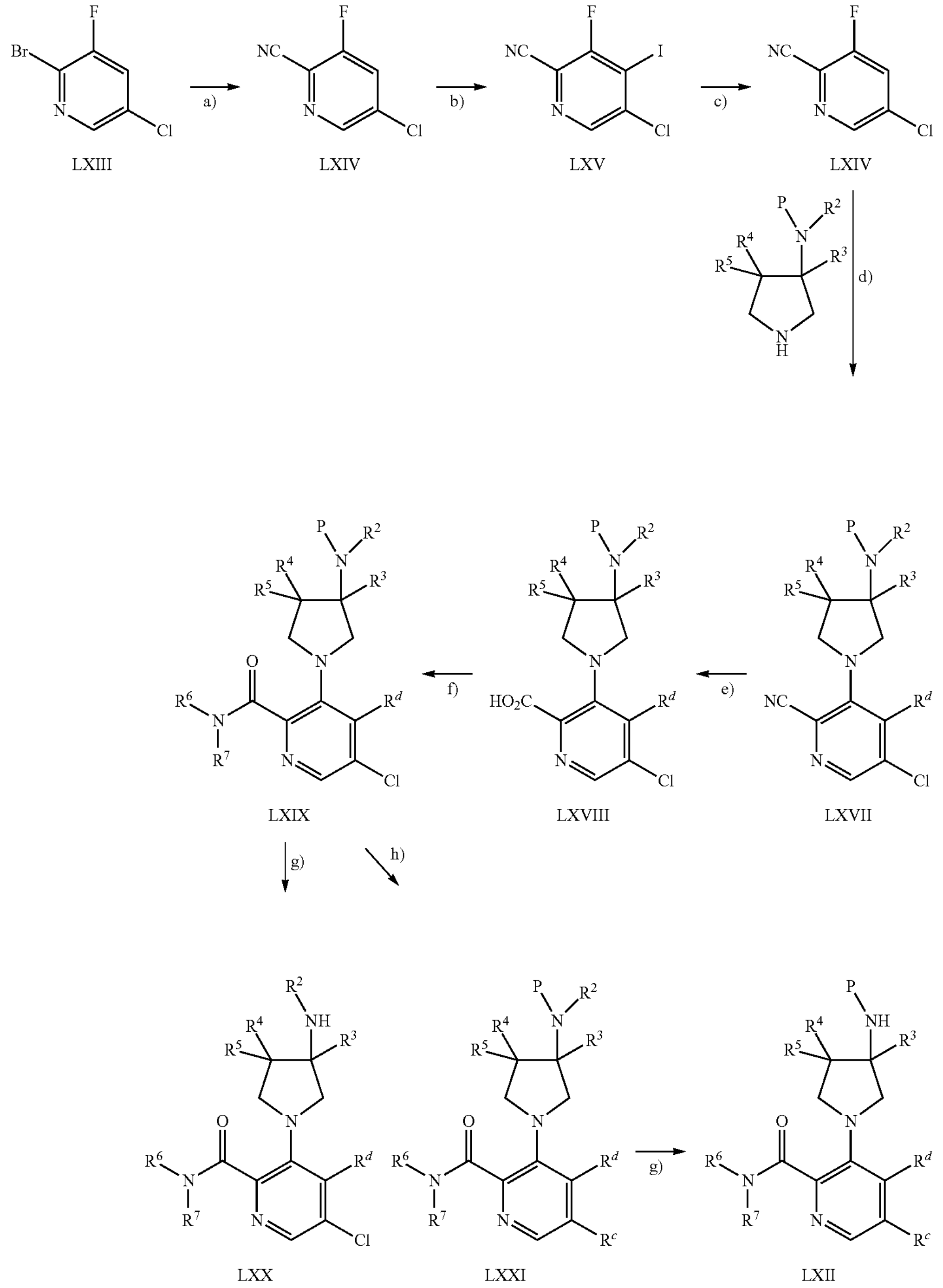

P = protecting group a) Pd, $Zn(CN)_2$; b) LDA, $I_2$; c) $R^dB(OR)_2$ or $R^dBF_3K$. Pd; d) DIPEA, MCN; e) KOH, EtOH/water; f) HATU, DIPEA, $R^6R^7NH$, DMF; g) de-protection; h) $R^cB(OR)_2$ or $R^cBF_3K$, Pd;

Transition-metal catalyzed cyanation of bromo-pyridine LXIII afforded nitrile intermediate LXIV, which underwent iodination to generate LXV in the presence of strong base such as LDA. Compound LXV was converted to intermediate LXVI by an organometallic coupling reaction such as Suzuki-Miyaura reaction. Subsequent nucleophilic substitution with protected aminopyrrolidine afforded intermediate LXVII, which was hydrolyzed to acid LXVIII under basic conditions. Compound LXVIII was treated with amines in the presence of coupling reagents such as HATU to produce amide LXIX. Removal of the protecting group using appropriate de-protection methods yielded final compound LXX. Compound LXIX could be converted to intermediate LXXI by an organometallic coupling reaction such as Suzuki-Miyaura reaction. Removal of the protecting group using appropriate de-protection methods yielded final compound LXXII.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, $—CH_2—$, $—CH_2CH_2—$, $—CH_2CH_2CH_2—$, $—CH_2CH_2CH_2CH_2—$, and the like. In some embodiments, an alkylene is $—CH_2—$.

An "alkoxy" group refers to a (alkyl)O— group, where alkyl is as defined herein.

The term "alkylamine" refers to the $—N(alkyl)_xH_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, $—CH_2OH$, $—CH_2CH_2OH$, $—CH_2CH_2CH_2OH$, $—CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, $—CH_2NH_2$, $—CH_2CH_2NH_2$, $—CH_2CH_2CH_2NH_2$, $—CH_2CH_2CH_2CH_2NH_2$, and the like.

The term "alkenyl" refers to a type of alkyl group in which at least one carbon-carbon double bond is present. In one embodiment, an alkenyl group has the formula $—C(R)=CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include $—CH=CH_2$, $—C(CH_3)=CH_2$, $—CH=CHCH_3$, $—C(CH_3)=CHCH_3$, and $—CH_2CH=CH_2$.

The term "alkynyl" refers to a type of alkyl group in which at least one carbon-carbon triple bond is present. In one embodiment, an alkenyl group has the formula $—C{\equiv}C—R$, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include $—C{\equiv}CH$, $—C{\equiv}CCH_3—C{\equiv}CCH_2CH_3$, $—CH_2C{\equiv}CH$.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbomyl and bicycle[1.1.1]pentyl. In some embodiments, a cycloalkyl is a $C_3$-$C_6$cycloalkyl. In some embodiments, a cycloalkyl is a $C_3$-$C_4$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl(both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, $—NH_2$, —NH(alkyl), $—N(alkyl)_2$, —OH, $—CO_2H$, $—CO_2$alkyl, $—C(═O)NH_2$, —C(═O)NH(alkyl), $—C(═O)N(alkyl)_2$, $—S(═O)_2NH_2$, $—S(═O)_2NH(alkyl)$, $—S(═O)_2N(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —$N(CH_3)_2$, —OH, —$CO_2H$, —$CO_2(C_1$-$C_4$alkyl), —C(═O)$NH_2$, —C(═O)NH($C_1$-$C_4$alkyl), —C(═O)N($C_1$-$C_4$alkyl$)_2$, —S(═O$)_2NH_2$, —S(═O$)_2$NH($C_1$-$C_4$alkyl), —S(═O$)_2$N($C_1$-$C_4$alkyl$)_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(═O)$C_1$-$C_4$alkyl, and —S(═O$)_2C_1$-$C_4$alkyl. In some embodiments, optional substituents are independently selected from halogen, —CN, —$NH_2$, —OH, —NH($CH_3$), —$N(CH_3)_2$, —$CH_3$, —$CH_2CH_3$, —$CHF_2$, —$CF_3$, —$OCH_3$, —$OCHF_2$, and —$OCF_3$. In some embodiments, substituted groups are substituted with one or two of the preceding groups. In some embodiments, an optional substituent on an aliphatic carbon atom (acyclic or cyclic) includes oxo (═O).

In some embodiments, each substituted alkyl, substituted fluoroalkyl, substituted heteroalkyl, substituted carbocycle, and substituted heterocycle is substituted with one or more $R^s$ groups independently selected from the group consisting of halogen, $C_1$-$C_6$alkyl, monocyclic carbocycle, monocyclic heterocycle, —CN, —$OR^{21}$, —$CO_2R^{21}$, —C(═O)N($R^{21})_2$, —N($R^{21})_2$, —$NR^{21}$C(═O)$R^{22}$, —$SR^{21}$, —S(═O)$R^{22}$, —$SO_2R^{22}$, or —$SO_2$N($R^{21})_2$; each $R^{21}$ is independently selected from hydrogen, $C_1$-$C_6$alkyl, $C_1$-$C_6$fluoroalkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl; or two $R^{21}$ groups are taken together with the N atom to which they are attached to form a N-containing heterocycle; each $R^{22}$ is independently selected from $C_1$-$C_6$alkyl, $C_1$-$C_6$fluoroalkyl, $C_1$-$C_6$heteroalkyl, $C_3$-$C_6$cycloalkyl, $C_2$-$C_6$heterocycloalkyl, phenyl, benzyl, 5-membered heteroaryl and 6-membered heteroaryl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch.

The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

As used above, and throughout the description of the invention, the following abbreviations, unless otherwise indicated, shall be understood to have the following meanings:

Abbreviations $Pd(PPh_3)_4$: tetrakis(triphenylphosphine)palladium(O);
$Pd_2(dba)_3 \cdot CHCl_3$: Tris(dibenzylideneacetone)dipalladium(O)-chloroform adduct;
$Pd(dppf)Cl_2$: [1,1'-bis(diphenylphosphino)ferrocene]palladium(II) dichloride;
$Pd(PPh_3)_2Cl_2$: bis(triphenylphosphine)palladium(II) dichloride;
PdAMphos or $Pd(amphos)Cl_2$: bis(di-tert-butyl(4-dimethylaminophenyl)phosphine)dichloropalladium(II);
$Pd(DtBPF)Cl_2$: [1,1'-Bis(di-tert-butylphosphino)ferrocene]dichloropalladium(II);
DIEA or DIPEA: N,N-diisopropylethylamine;
Prep-HPLC: preparative high performance liquid chromatography;
LCMS: Liquid chromatography-mass spectrometry;
MS: mass spectrometry;
AcOH: acetic acid;
TFA: trifluoroacetic acid;
HCl: hydrochloric acid or hydrochloride;
MeCN or $CH_3CN$ or ACN: acetonitrile;
$H_2O$: water;
DMSO: dimethyl sulfoxide;
DMF: dimethylformamide;
DCM: dichloromethane;
NBS: N-bromosuccinimide;
$Br_2$: bromine;
NCS: N-chlorosuccinimide;
rt: room temperature;

SST: somatostatin;
SSTR: somatostatin receptor;
hrs: hours;
h or hr: hour;
min: minute;
$N_2$: nitrogen gas;
mg: milligrams;
mL: milliliter;
eq. or equiv: equivalents;
mmol: millimole;
μmol: micromole;
ppts: precipitates;
$K_2CO_3$: potassium carbonate;
$NaClO_2$: sodium chlorite;
t-BuOH: tert-butyl alcohol;
EtOAc: ethyl acetate;
$Na_2SO_4$: sodium sulfate;
$NaHSO_4$: sodium bisulfate;
$Na_2S_2O_3$: sodium thiosulfate.

The following examples are provided for illustrative purposes only and not to limit the scope of the claims provided herein.

Synthesis of Compounds

Example 1. 4-[(3S)-3-aminopyrrolidin-1-yl]-N,5-bis(3,5-dimethylphenyl)pyridine-3-carboxamide (compound 1-1)

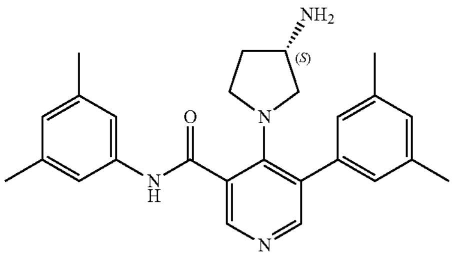

Step 1-1, preparation of tert-butyl (S)-(1-(3-(3,5-dimethylphenyl)-5-formylpyridin-4-yl)pyrrolidin-3-yl)carbamate: to a mixture of tert-butyl N-[(3S)-1-(3-bromo-5-formylpyridin-4-yl)pyrrolidin-3-yl]carbamate (120 mg, 1.0 Eq, 0.32 mmol, "Step 9-1, Example 9"), (3,5-dimethylphenyl)boronic acid (97 mg, 2.0 Eq, 0.65 mmol), $Pd_2(dba)_3 \cdot CHCl_3$ (33 mg, 0.10 Eq, 0.032 mmol), $P(t\text{-}Bu)_3 \cdot HBF_4$ (19 mg, 0.20 Eq, 0.064 mmol) and $K_3PO_4$ (206 mg, 3.0 Eq, 0.97 mmol) was added toluene (3.0 mL) and water (0.3 mL) under atmospheric nitrogen. The resulting mixture was stirred at 70° C. for 1 hour. The reaction solution was concentrated under vacuum and the remaining residue was purified by silica gel chromatography eluting with ethyl acetate/petroleum ether (1:1) to afford 100 mg of the title compound. MS $(M+H)^+$=396.5.

Step 1-2, preparation of (S)-4-(3-((tert-butoxycarbonyl)amino)pyrrolidin-1-yl)-5-(3,5-dimethylphenyl)nicotinic acid: to a round-bottom flask was added tert-butyl (S)-(1-(3-(3,5-dimethylphenyl)-5-formylpyridin-4-yl)pyrrolidin-3-yl)carbamate (100 mg, 1.0 Eq, 0.25 mmol), tert-butyl alcohol (4.2 mL), DCM (4.2 mL), $NaH_2PO_4$ (91 mg, 3.0 Eq, 0.76 mmol), 2-methylbut-2-ene (532 mg, 30 Eq, 7.59 mmol), water (1.4 mL), and $NaClO_2$ (46 mg, 2.0 Eq, 0.51 mmol). The resulting mixture was stirred at ambient temperature for 16 hours. The reaction mixture was concentrated under vacuum and the remaining residue was diluted with water (10 mL). The pH of resulting aqueous solution was adjusted to ~4 and solid product precipitated out. The resulting suspension was filtered and solid was collected and dried under vacuum. This resulted in 70 mg of the title compound as a yellow solid. MS $(M+H)^+$=412.5.

Step 1-3, preparation of tert-butyl (S)-(1-(3-(3,5-dimethylphenyl)-5-((3,5-dimethylphenyl)carbamoyl)pyridin-4-yl)pyrrolidin-3-yl)carbamate: to a DCM (3.0 mL) solution of (S)-4-(3-((tert-butoxycarbonyl)amino)pyrrolidin-1-yl)-5-(3,5-dimethylphenyl)nicotinic acid (50 mg, 1.0 Eq, 0.12 mmol) was added Ghosez's reagent (33 mg, 2.0 Eq, 0.24 mmol). The resulting mixture was stirred at ambient temperature for 10 min followed by the addition of pyridine (29 mg, 3.0 Eq, 0.36 mmol) and 3,5-dimethylaniline (18 mg, 1.2 Eq, 0.15 mmol). The reaction mixture was stirred at ambient temperature for 2 hours. The reaction crude was concentrated under vacuum and the remaining residue was purified by Prep-HPLC using the following conditions: Column, XBridge Shield PR18 OBD, 5 μm, 19×150 mm; mobile phase, water (10 mmol/L $NH_4HCO_3$+0.10% $NH_3 \cdot H_2O$) and ACN (46% Phase B up to 61% in 6 min); Detector, UV 220&254 nm. This resulted in 15 mg of the title compound as a light yellow solid. MS $(M+H)^+$=515.2.

Step 1-4, preparation of 4-[(3S)-3-aminopyrrolidin-1-yl]-N,5-bis(3,5-dimethylphenyl)pyridine-3-carboxamide: to a DCM (1.0 mL) solution of tert-butyl (S)-(1-(3-(3,5-dimethylphenyl)-5-((3,5-dimethylphenyl)carbamoyl)pyridin-4-yl)pyrrolidin-3-yl)carbamate was added TFA (1.0 mL). The resulting mixture was stirred at ambient temperature for 1 hour. The reaction crude was concentrated and dried under lyophilization to give 5.6 mg of the TFA salt of 4-[(3S)-3-aminopyrrolidin-1-yl]-N,5-bis(3,5-dimethylphenyl)pyridine-3-carboxamide as a light yellow solid. MS $(M+H)^+$=415.2.

The following compounds were prepared similarly to Example 1 with appropriate substituting reagents and substrates at different steps and they may require additional functional group modifications via well-known chemistry with appropriate reagents. The coupling reaction with aniline can be carried out using other coupling reagents such as HATU under appropriate conditions. Different salts, such as HCl or formic acid or TFA salt, may be obtained.

| Compound no. | MS $(M + H)^+$ |
|---|---|
| 1-2 | 415.3 |
| 1-3 | 439.1 |
| 1-4 | 434.2 |
| 1-5 | 413.2 |
| 1-6 | 416.1 |

Example 2. 4-[(3S)-3-amino-3-methylpyrrolidin-1-yl]-N-(4,4-difluorocyclohexyl)-5-(3,5-difluorophenyl)pyridine-3-carboxamide (compound 1-16)

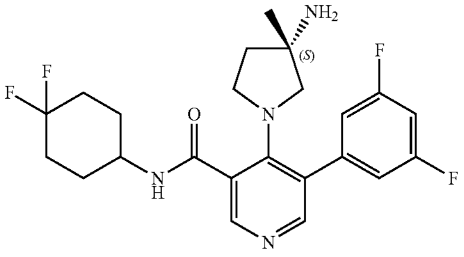

Step 2-1, preparation of tert-butyl N-[(3S)-1-(3-bromo-5-formylpyridin-4-yl)-3-methylpyrrolidin-3-yl]carbamate: to an MeCN solution (100 mL) of 5-bromo-4-chloropyridine-3-carbaldehyde (12 g, 1.0 Eq, 54 mmol) was added tert-butyl N-[(3S)-3-methylpyrrolidin-3-yl]carbamate (12 g, 1.1 Eq, 60 mmol) and DIPEA (21 g, 3.0 Eq, 160 mmol). The resulting solution was stirred at 70° C. for 24 hours. The reaction mixture was quenched water and extracted with ethyl acetate. The organic layers were combined, dried and concentrated. The remaining residue was purified by silica gel column chromatography eluting with petroleum ether/EtOAc (1:1) to afford tert-butyl (S)-(1-(3-bromo-5-formylpyridin-4-yl)-3-methylpyrrolidin-3-yl)carbamate (18 g, 86%) as a yellow solid. MS $(M+H)^+$=384.1, 386.1.

Step 2-2, preparation of (S)-5-bromo-4-(3-((tert-butoxycarbonyl)amino)-3-methylpyrrolidin-1-yl)nicotinic acid: to a tert-butyl alcohol solution (9.0 mL) tert-butyl (S)-(1-(3-bromo-5-formylpyridin-4-yl)-3-methylpyrrolidin-3-yl)carbamate (190 mg, 1.0 Eq, 0.49 mmol) was added 2-methylbut-2-ene (0.66 mL, 12 Eq, 5.9 mmol), sodium chlorite (0.43 g, 7.8 Eq, 3.8 mmol, wt. 85%), sodium dihydrogen phosphate (0.35 g, 5.9 Eq, 2.9 mmol) and water (2.8 mL).

The resulting mixture was stirred at ambient temperature for 1 hour. The reaction crude was concentrated to remove most tert-butyl alcohol and saturated $NaHSO_4$ (~2 mL) was added. The resulting aqueous solution was extracted with ethyl acetate (3×20 mL), and the organic layers were combined, dried and concentrated to give 160 mg of the title compound as a light yellow solid. This material was used for next step without further purification. MS $(M+H)^+$=400.1, 402.1.

Step 2-3, preparation of tert-butyl (S)-(1-(3-bromo-5-((4,4-difluorocyclohexyl)carbamoyl)pyridin-4-yl)-3-methylpyrrolidin-3-yl)carbamate: to a DMF (2.0 mL) solution of (S)-5-bromo-4-(3-((tert-butoxycarbonyl)amino)-3-methylpyrrolidin-1-yl)nicotinic acid (250 mg, 1.0 Eq, 0.63 mmol) was added HATU (356 mg, 1.5 Eq, 0.94 mmol), DIPEA (0.60 mL, 5.5 Eq, 3.4 mmol) and 4,4-difluorocyclohexan-1-amine hydrochloride (161 mg, 1.5 Eq, 0.94 mmol). The resulting mixture was stirred at ambient temperature for 0.5 hour. The reaction crude was purified by C18 reverse phase chromatography eluting with MeCN (0.1% TFA)/water (0.1% TFA) (5-60%). Pure fractions were combined, concentrated to remove most MeCN, neutralized with saturated $NaHCO_3$ (5 mL), added solid NaCl (15 g), and extracted with ethyl acetate (30 mL). Organic layer was dried with $MgSO_4$, filtered and concentrated to give 270 mg of the title compound. MS $(M+H)^+$=517.2, 519.2.

Step 2-4, preparation of tert-butyl (S)-(1-(3-((4,4-difluorocyclohexyl)carbamoyl)-5-(3,5-difluorophenyl)pyridin-4-yl)-3-methylpyrrolidin-3-yl)carbamate: to a mixture of tert-butyl (S)-(1-(3-bromo-5-((4,4-difluorocyclohexyl)carbamoyl)pyridin-4-yl)-3-methylpyrrolidin-3-yl)carbamate (90 mg, 1.0 Eq, 0.17 mmol), (3,5-difluorophenyl)boronic acid (55 mg, 2.0 Eq, 0.35 mmol), $K_2CO_3$ (72 mg, 3.0 Eq, 0.52 mmol) and Pd(amphos)$Cl_2$ (12 mg, 0.10 Eq, 0.017 mmol) was added dioxane (2.0 mL). Nitrogen gas was bubbled through the reaction solution for 1 min followed by the addition of water (0.20 mL). Nitrogen was bubbled for another 5 min. The resulting mixture was heated at 100° C. for 1 hour. The reaction crude was concentrated with silica gel and the remaining residue was purified by silica gel chromatography to give 66 mg of the title compound as a clear oil. MS $(M+H)^+$=551.4.

Step 2-5, preparation of (S)-4-(3-amino-3-methylpyrrolidin-1-yl)-N-(4,4-difluorocyclohexyl)-5-(3,5-difluorophenyl)nicotinamide: to a DCM (0.8 mL) solution of tert-butyl (S)-(1-(3-((4,4-difluorocyclohexyl)carbamoyl)-5-(3,5-difluorophenyl)pyridin-4-yl)-3-methylpyrrolidin-3-yl)carbamate (66 mg, 1.0 Eq, 0.12 mmol) was added TFA (0.8 mL). The resulting mixture was stirred at ambient temperature for 0.5 hour. The reaction crude was concentrated and the remaining residue was purified by C18 reverse phase chromatography eluting with MeCN (0.1% TFA)/water (0.1% TFA) (5-35%). Pure fractions were combined, neutralized with saturated $NaHCO_3$ (4 mL), added solid NaCl (8 g), and extracted with ethyl acetate (25 mL). Organic layer was dried with $MgSO_4$, filtered and concentrated with 1.0 M HCl in ethyl acetate (0.3 mL) to give 33 mg of the HCl salt of (S)-4-(3-amino-3-methylpyrrolidin-1-yl)-N-(4,4-difluorocyclohexyl)-5-(3,5-difluorophenyl)nicotinamide as a white solid. MS (M+H)+=451.2.

The following compounds were prepared similarly to Example 2 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-12 | 443.5 |
| 1-13 | 447.2 |
| 1-14 | 443.5 |
| 1-20 | 469.3 |
| 1-61 | 429.3 |
| 1-94 | 418.4 |
| 1-131 | 394.2 |
| 1-142 | 384.1 |
| 1-143 | 449.4 |
| 1-149 | 431.4 |
| 1-161 | 419.4 |
| 1-162 | 419.4 |
| 1-163 | 445.3 |
| 1-175 | 445.1 |

Example 3. 4-[(3S)-3-amino-3-methylpyrrolidin-1-yl]-N-(3,3-difluorocyclobutyl)-5-(3,5-difluorophenyl)pyridine-3-carboxamide (compound 1-30)

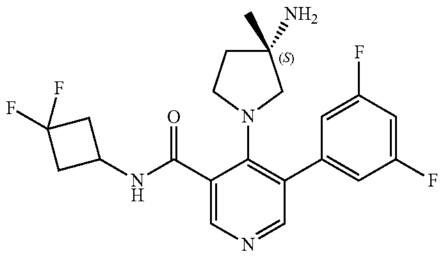

Step 3-1, preparation of tert-butyl (S)-(1-(3-(3,5-difluorophenyl)-5-formylpyridin-4-yl)-3-methylpyrrolidin-3-yl) carbamate: to a mixture of tert-butyl (S)-(1-(3-bromo-5-formylpyridin-4-yl)-3-methylpyrrolidin-3-yl)carbamate (380 mg, 1.0 Eq, 0.989 mmol, "Step 2-1, Example 2"), (3,5-difluorophenyl)boronic acid (312 mg, 2.0 Eq, 1.98 mmol), $K_2CO_3$ (410 mg, 3.0 Eq, 2.97 mmol) and Pd(amphos)$Cl_2$ (35 mg, 0.05 Eq, 0.050 mmol) was added dioxane (4.0 mL) and water (0.4 mL). Nitrogen was bubbled through the reaction solution for 5 min and the resulting mixture was heated at 100° C. for 1 hour. The reaction crude was concentrated with silica gel and the remaining residue was purified by silica gel chromatography to give 372 mg of the title compound as clear oil. MS $(M+H)^+$=418.1.

Step 3-2, preparation of (S)-4-(3-((tert-butoxycarbonyl) amino)-3-methylpyrrolidin-1-yl)-5-(3,5-difluorophenyl) nicotinic acid: to a tert-butyl alcohol solution (11 mL) of tert-butyl (S)-(1-(3-(3,5-difluorophenyl)-5-formylpyridin-4-yl)-3-methylpyrrolidin-3-yl)carbamate was added 2-methylbut-2-ene (1.2 mL, 12 Eq, 10.7 mmol), sodium chlorite (0.84 g, 8.9 Eq, 7.9 mmol, wt. 85%), sodium dihydrogen phosphate (0.75 g, 7.0 Eq, 6.3 mmol) and water (4.0 mL). The resulting mixture was stirred at ambient temperature for 1 hour. The reaction crude was concentrated to remove most tert-butyl alcohol and saturated $NaHSO_4$ (~3 mL) was added. The resulting aqueous solution was extracted with ethyl acetate (3×20 mL), and the organic layers were combined, dried and concentrated to give 370 mg of the title compound. This material was used for next step without further purification. MS $(M+H)^+$=434.3.

Step 3-3, preparation of tert-butyl (S)-(1-(3-((3,3-difluorocyclobutyl)carbamoyl)-5-(3,5-difluorophenyl)pyridin-4-yl)-3-methylpyrrolidin-3-yl)carbamate: to a DMF (0.6 mL) solution of (S)-4-(3-((tert-butoxycarbonyl)amino)-3-methylpyrrolidin-1-yl)-5-(3,5-difluorophenyl)nicotinic acid (44 mg, 1.0 Eq, 0.10 mmol) was added HATU (58 mg, 1.5 Eq, 0.15 mmol) and DIPEA (0.2 mL, 11 Eq, 1.0 mmol). The resulting mixture was stirred at ambient temperature for 5 min followed by the addition of 3,3-difluorocyclobutan-1-amine hydrochloride (44 mg, 3.0 Eq, 0.30 mmol). The resulting mixture was stirred at ambient temperature for 0.5 hour. The reaction crude was purified by C18 reverse phase chromatography eluting with MeCN (0.1% TFA)/water (0.1% TFA) (5-55%). Pure fractions were combined, concentrated to remove most MeCN, neutralized with saturated $NaHCO_3$ (3 mL), added solid NaCl (5 g), and extracted with ethyl acetate (2×10 mL). Organic layers were combined, dried with $MgSO_4$, filtered and concentrated to give 42 mg of the title compound. MS $(M+H)^+$=534.1.

Step 3-4, preparation of 4-[(3S)-3-amino-3-methylpyrrolidin-1-yl]-N-(3,3-difluorocyclobutyl)-5-(3,5-difluorophenyl)pyridine-3-carboxamide: to a DCM (0.7 mL) solution of tert-butyl (S)-(1-(3-((3,3-difluorocyclobutyl)carbamoyl)-5-(3,5-difluorophenyl)pyridin-4-yl)-3-methylpyrrolidin-3-yl) carbamate (42 mg, 1.0 Eq, 0.08 mmol) was added TFA (0.7 mL). The resulting mixture was stirred at ambient temperature for 0.5 hour. The reaction crude was concentrated, and the remaining residue was purified by C18 reverse phase chromatography eluting with MeCN (0.1% TFA)/water (0.1% TFA) (5-35%). Pure fractions were combined, neutralized with saturated $NaHCO_3$ (3 mL), added solid NaCl (5 g), and extracted with ethyl acetate (2×10 mL). Organic layers were combined, dried with $MgSO_4$, filtered and concentrated with 1.0 M HCl in ethyl acetate (0.10 mL) to give 25 mg of the HCl salt of 4-[(3S)-3-amino-3-methylpyrrolidin-1-yl]-N-(3,3-difluorocyclobutyl)-5-(3,5-difluorophenyl)pyridine-3-carboxamide as a white solid. MS $(M+H)^+$=423.2.

The following compounds were prepared similarly to Example 3 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-7 | 390.2 |
| 1-8 | 376.2 |
| 1-9 | 398.5 |
| 1-10 | 440.3 |
| 1-11 | 435.4 |
| 1-15 | 465.3 |
| 1-17 | 445.3 |
| 1-18 | 463.2 |
| 1-19 | 411.5 |
| 1-21 | 398.9, 399.1 |
| 1-22 | 415.4 |
| 1-23 | 373.2 |
| 1-24 | 397.0 |
| 1-25 | 423.3 |
| 1-26 | 382.9 |
| 1-27 | 409.5 |
| 1-28 | 415.3 |
| 1-29 | 389.5 |
| 1-31 | 403.3 |
| 1-32 | 401.4 |
| 1-33 | 401.2 |
| 1-34 | 401.1 |
| 1-35 | 439.3 |
| 1-36 | 429.2 |
| 1-37 | 403.2 |
| 1-38 | 403.5 |
| 1-39 | 431.5 |
| 1-40 | 415.3 |
| 1-41 | 401.1 |
| 1-42 | 423.0 |
| 1-43 | 415.2 |
| 1-44 | 401.1 |
| 1-45 | 457.3 |
| 1-46 | 389.3 |
| 1-47 | 419.2 |
| 1-50 | 437.2 |
| 1-51 | 427.3 |
| 1-52 | 433.3 |
| 1-53 | 429.3 |
| 1-55 | 405.3 |
| 1-56 | 469.4 |
| 1-57 | 403.4 |
| 1-58 | 417.4 |
| 1-59 | 405.3 |
| 1-60 | 443.5 |
| 1-62 | 411.4 |

-continued

| Compound no. | MS (M + H)$^+$ |
|---|---|
| 1-83 | 433.4 |
| 1-96 | 420.3 |
| 1-112 | 415.2 |

Example 4. 4-[(3S)-3-aminopyrrolidin-1-yl]-6-cyano-5-(3,5-difluorophenyl)-N-[(2S)-1,1,1-trifluoropropan-2-yl]pyridine-3-carboxamide (compound 1-71)

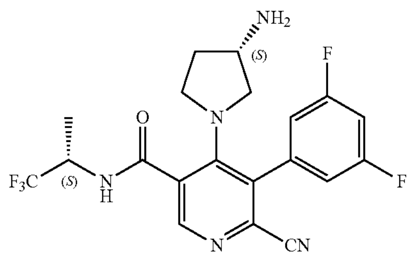

Step 4-1, preparation of tert-butyl (S)-(1-(2-chloro-5-formylpyridin-4-yl)pyrrolidin-3-yl)carbamate: to a DMF (70 mL) solution was added 4,6-dichloronicotinaldehyde (6.8 g, 1.0 Eq, 39 mmol), tert-butyl(S)-pyrrolidin-3-ylcarbamate (7.6 g, 1.1 Eq, 41 mmol) and TEA (16 mL, 3.1 Eq, 120 mmol). The resulting mixture was stirred at 50° C. for 4 hours. The reaction crude was quenched with water (100 mL) and extracted with ethyl acetate (3×40 mL). The organic layers were combined, washed with brine, dried and concentrated under vacuum. The remaining residue was purified by silica gel chromatography eluting with ethyl acetate/petroleum ether (⅓) to afford tert-butyl (S)-(1-(2-chloro-5-formylpyridin-4-yl)pyrrolidin-3-yl)carbamate (5.3 g, 42%) as a yellow solid. MS (M+H)$^+$=326.2.

Step 4-2, preparation of tert-butyl (S)-(1-(3-bromo-2-chloro-5-formylpyridin-4-yl)pyrrolidin-3-yl)carbamate: to an AcOH (60 mL) solution of tert-butyl (S)-(1-(2-chloro-5-formylpyridin-4-yl)pyrrolidin-3-yl)carbamate (5.3 g, 1.0 Eq, 16 mmol) was added NBS (3.1 g, 1.1 Eq, 17 mmol) at 10° C. The resulting mixture was stirred at the same temperature for 1 hour. The reaction mixture was quenched with saturated $NaHCO_3$ and extracted with ethyl acetate (3×40 mL). The organic layers were combined, washed with brine, dried and concentrated under vacuum. The remaining residue was purified by silica gel chromatography eluting with ethyl acetate/petroleum ether (¼) to afford tert-butyl (S)-(1-(3-bromo-2-chloro-5-formylpyridin-4-yl)pyrrolidin-3-yl) carbamate (3.5 g, 53%) as a yellow solid. MS (M+H)$^+$=404.1, 406.1.

Step 4-3, preparation of tert-butyl (S)-(1-(2-chloro-3-(3,5-difluorophenyl)-5-formylpyridin-4-yl)pyrrolidin-3-yl)carbamate: to a mixture of tert-butyl (S)-(1-(3-bromo-2-chloro-5-formylpyridin-4-yl)pyrrolidin-3-yl)carbamate (3.5 g, 1.0 Eq, 8.6 mmol), (3,5-difluorophenyl)boronic acid (0.88 Eq, 7.6 mmol, 1.2 g), Pd(DtBPF)$Cl_2$ (300 mg, 0.05 Eq, 0.46 mmol) and potassium phosphate (5.4 g, 2.9 Eq, 25 mmol) was added Toluene (140 mL) and water (14 mL) under atmospheric nitrogen. The resulting mixture was stirred at 40° C. for 2 hours. The reaction crude was concentrated under reduced pressure and the remaining residue was purified by silica gel column chromatography eluting with petroleum ether/EtOAc (3:1) to afford tert-butyl (S)-(1-(2-chloro-3-(3,5-difluorophenyl)-5-formylpyridin-4-yl)pyrrolidin-3-yl)carbamate (2.7 g, 71%) as a yellow solid. MS (M+H)$^+$=438.0, 440.0.

Step 4-4, preparation of tert-butyl (S)-(1-(2-cyano-3-(3,5-difluorophenyl)-5-formylpyridin-4-yl)pyrrolidin-3-yl)carbamate: to a mixture of tert-butyl (S)-(1-(2-chloro-3-(3,5-difluorophenyl)-5-formylpyridin-4-yl)pyrrolidin-3-yl) carbamate (2.7 g, 1.0 Eq, 6.2 mmol), $Pd_2(dba)_3 \cdot CHCl_3$ (310 mg, 0.05 Eq, 0.31 mmol), $Zn(CN)_2$ (1.4 g, 1.9 Eq, 12 mmol) and (9,9-dimethyl-9H-xanthene-4,5-diyl)bis(diphenylphosphane) (720 mg, 0.20 Eq, 1.24 mmol) was added DMF (30 mL) under atmospheric nitrogen. The resulting mixture was heated under microwave radiation conditions at 135° C. for 1 hour. The reaction crude was quenched with water (100 mL) and extracted with EtOAc (3×40 mL). Organic layers were combined, washed with brine, dried over anhydrous $Na_2SO_4$, filtered and concentrated under vacuum. The remaining residue was purified by silica gel chromatography eluting with petroleum ether/EtOAc (1:1) to afford tert-butyl (S)-(1-(2-cyano-3-(3,5-difluorophenyl)-5-formylpyridin-4-yl)pyrrolidin-3-yl)carbamate (2.2 g, 83%) as a yellow solid. MS (M+H)$^+$=429.2.

Step 4-5, preparation of (S)-4-(3-((tert-butoxycarbonyl)amino)pyrrolidin-1-yl)-6-cyano-5-(3,5-difluorophenyl) nicotinic acid: to a tert-butyl alcohol solution (20 mL) of (S)-(1-(2-cyano-3-(3,5-difluorophenyl)-5-formylpyridin-4-yl)pyrrolidin-3-yl)carbamate (2.4 g, 1.0 Eq, 5.1 mmol) was added sodium dihydrogen phosphate (2.4 g, 3.0 Eq, 15 mmol) 2-methylbut-2-ene (11.0 g, 31 Eq, 157 mmol), sodium chlorite (1.0 g, 2.2 Eq, 11 mmol) and water (6.6 mL). The resulting mixture was stirred at ambient temperature for 1 hour. The reaction mixture was quenched with saturated $NaHSO_4$ (50 mL) and extracted with ethyl acetate (3×40 mL). The organic layers were combined, washed with brine, dried and concentrated under vacuum to afford (S)-4-(3-((tert-butoxycarbonyl)amino)pyrrolidin-1-yl)-6-cyano-5-(3,5-difluorophenyl)nicotinic acid (2.0 g, 88%) as a yellow solid. This material was used for next step without purification. MS (M+H)$^+$=445.2.

Step 4-6, preparation of tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate: to a DMF solution (2.0 mL) of (S)-4-(3-((tert-butoxycarbonyl)amino) pyrrolidin-1-yl)-6-cyano-5-(3,5-difluorophenyl)nicotinic acid (70 mg, 1.0 Eq, 0.16 mmol) was added (S)-1,1,1-trifluoropropan-2-amine hydrochloride (35 mg, 1.5 Eq, 0.23 mmol), N-ethyl-N-isopropylpropan-2-amine (4.4 Eq, 0.70 mmol, 0.12 mL) and HATU (60 mg, 1.0 Eq, 0.16 mmol). The resulting mixture was stirred at ambient temperature for 2 hours. The reaction crude was purified by Prep-HPLC using the following conditions: SunFire Prep $C_{18}$ OBD Column, 19*150 mm 5 μm; mobile phase, Water (0.1% FA) and ACN (24.0% ACN up to 46.0% in 7 min); Total flow rate, 20 mL/min; Detector, UV 220 nm. This resulted in tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (45 mg, 53%) as a light yellow solid. MS (M+H)$^+$=540.3.

Step 4-7, preparation of 4-((S)-3-aminopyrrolidin-1-yl)-6-cyano-5-(3,5-difluorophenyl)-N—((S)-1,1,1-trifluoropropan-2-yl)nicotinamide: to a DCM solution (2.0 mL) of tert-butyl ((S)-1-(2-cyano-3-(3,5-difluorophenyl)-5-(((S)-1,1,1-trifluoropropan-2-yl)carbamoyl)pyridin-4-yl)pyrrolidin-3-yl)carbamate (45 mg, 1.0 Eq, 0.083 mmol) was added TFA (1.0 mL). The resulting mixture was stirred at ambient temperature for 2 hours. The reaction solution was concentrated and freeze-dried under vacuum to afford the TFA salt of 4-((S)-3-aminopyrrolidin-1-yl)-6-cyano-5-(3,5-difluorophenyl)-N—((S)-1,1,1-trifluoropropan-2-yl)nicotinamide bis(2,2,2-trifluoroacetate) (40.2 mg, 72%) as a light yellow solid. MS $(M+H)^+$=440.2.

The following compounds were prepared similarly to Example 4 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-48 | 476.3 |
| 1-49 | 424.2 |
| 1-64 | 410.2 |
| 1-65 | 392.2 |
| 1-66 | 410.2 |
| 1-67 | 462.2 |
| 1-68 | 434.2 |
| 1-69 | 412.2, |
| 1-70 | 438.2 |
| 1-72 | 414.2 |
| 1-73 | 440.2 |
| 1-76 | 428.3 |
| 1-78 | 426.2 |
| 1-79 | 448.1 |
| 1-80 | 412.3 |
| 1-81 | 426.3 |
| 1-82 | 412.3 |
| 1-84 | 408.2 |
| 1-85 | 414.2 |
| 1-86 | 412.2 |
| 1-87 | 412.2 |
| 1-88 | 442.2 |
| 1-89 | 442.2 |
| 1-90 | 426.1 |
| 1-91 | 400.2 |
| 1-92 | 440.2 |
| 1-93 | 440.2 |
| 1-95 | 449.3 |
| 1-97 | 448.1 |
| 1-98 | 440.2 |
| 1-99 | 440.2 |
| 1-100 | 424.2 |
| 1-101 | 428.2 |
| 1-102 | 428.2 |

Example 5. 4-[(3S)-3-amino-3-methylpyrrolidin-1-yl]-6-cyano-5-(3,5-difluorophenyl)-N-[(1S)-1-(pyridin-2-yl)ethyl]pyridine-3-carboxamide (compound 1-103)

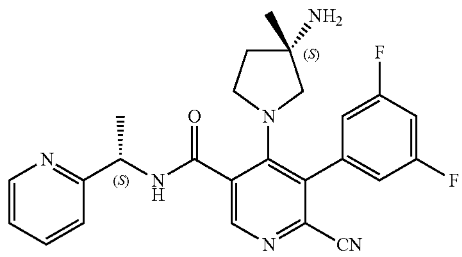

Step 5-1, preparation of ethyl 4-chloro-6-cyanonicotinate: to a mixture of ethyl 4,6-dichloronicotinate (200.0 g, 1.0 Eq, 909 mmol), zinc(II) cyanide (0.600 Eq, 545 mmol, 64 g), Tris(dibenzylideneacetone)dipalladium(0) chloroform adduct (9.41 g, 0.01 Eq, 9.09 mmol), (9,9-dimethyl-9H-xanthene-4,5-diyl)bis(diphenylphosphane) (10.5 g, 0.02 Eq, 18.1 mmol) was added DMF (1600 mL) under atmospheric nitrogen. The reaction mixture was stirred at 130° C. for 2 hours. The reaction mixture was poured into water (3000 mL), extracted with EtOAc (3×1000 mL). Organic layers were combined, washed with water (3×2000 mL) and brine (1000 mL), dried over anhydrous $Na_2SO_4$ and concentrated. The remaining residue was purified by silica gel chromatography eluting with petroleum ether/EtOAc/DCM (10/1/2). This resulted in a pure batch (78 g, 95% purity) and a less pure batch (63 g, 50% purity). MS $(M+H)^+$=211.1, 212.1.

Step 5-2, preparation of ethyl (S)-4-(3-((tert-butoxycarbonyl)amino)-3-methylpyrrolidin-1-yl)-6-cyanonicotinate: to a mixture of ethyl 4-chloro-6-cyanonicotinate (15 g, 1.0 Eq, 71 mmol), 2,3,4,6,7,8,9,10-octahydropyrimido[1,2-a]azepine (10 g, 0.92 Eq, 66 mmol) and tert-butyl (S)-(3-methylpyrrolidin-3-yl)carbamate (30 g, 2.1 Eq, 150 mmol) was added MeCN (200 mL). The resulting mixture was stirred at 50° C. for 1 hour. The reaction crude was quenched with water (100 mL) and extracted with EtOAc (3×40 mL). The organic layers were combined, washed with brine, dried and concentrated under vacuum. The remaining residue was purified by silica gel chromatography eluting with petroleum ether/EtOAc (3/1) to afford ethyl (S)-4-(3-((tert-butoxycarbonyl)amino)-3-methylpyrrolidin-1-yl)-6-cyanonicotinate (16.0 g, 60%) as a yellow solid. MS $(M+H)^+$=375.1.

Step 5-3, preparation of ethyl (S)-5-bromo-4-(3-((tert-butoxycarbonyl)amino)-3-methylpyrrolidin-1-yl)-6-cyanonicotinate: to a round-bottom flask was added ethyl (S)-4-(3-((tert-butoxycarbonyl)amino)-3-methylpyrrolidin-1-yl)-6-cyanonicotinate (3.0 g, 1.0 Eq, 8.0 mmol), AcOH (60 mL) and DCM (12 mL). At 0° C., 1,3,5-tribromo-1,3,5-triazinane-2,4,6-trione (5.8 g 2.0 Eq, 16 mmol) was added portion-wise. The resulting mixture was stirred at the same temperature for 30 min. The reaction crude was quenched with aqueous $NaHSO_3$ at 0° C. The resulting suspension was filtered, and the filtrate was extracted with EtOAc (3×100 mL). The organic layers were combined, and washed with water (3×30 mL) and aqueous $NaHCO_3$. The organic layer were dried and concentrated under vacuum. The remaining residue was purified by silica gel chromatography eluting with petroleum ether/EtOAc/(4/1) to afford ethyl (S)-5-bromo-4-(3-((tert-butoxycarbonyl)amino)-3-methylpyrrolidin-1-yl)-6-cyanonicotinate (2.2 g, 61%) as a yellow solid. MS $(M+H)^+$=453.0, 455.0.

Step 5-4, preparation of ethyl (S)-4-(3-((tert-butoxycarbonyl)amino)-3-methylpyrrolidin-1-yl)-6-cyano-5-(3,5-difluorophenyl)nicotinate: to a mixture of ethyl (S)-5-bromo-4-(3-((tert-butoxycarbonyl)amino)-3-methylpyrrolidin-1-yl)-6-cyanonicotinate (5.0 g, 1.0 Eq, 11 mmol), (3,5-difluorophenyl)boronic acid (3.5 g, 2.0 Eq, 22 mmol), potassium phosphate (7.2 g, 3.1 Eq, 34 mmol) and Pd(DtBPF)$Cl_2$ (350 mg, 0.049 Eq, 0.537 mmol) was added Toluene (50 mL) and water (5 mL) under atmospheric nitrogen. The resulting mixture was stirred at 80° C. for 1 hour. The reaction mixture was concentrated under reduced pressure and the remaining residue was purified by silica gel column chromatography eluting with petroleum ether/EtOAc (5:1) to afford ethyl (S)-4-(3-((tert-butoxycarbonyl)amino)-3-methylpyrrolidin-1-yl)-6-cyano-5-(3,5-difluorophenyl)nicotinate (4.4 g, 82%) as a yellow solid. MS $(M+H)^+$=487.4.

Step 5-5, preparation of (S)-4-(3-((tert-butoxycarbonyl)amino)-3-methylpyrrolidin-1-yl)-6-cyano-5-(3,5-difluorophenyl)nicotinic acid: to a MeOH solution (50 mL) of ethyl (S)-4-(3-((tert-butoxycarbonyl)amino)-3-methylpyrrolidin-1-yl)-6-cyano-5-(3,5-difluorophenyl)nicotinate (5.0 g, 1.0 Eq, 10 mmol) was added water (5.0 mL). The resulting mixture was cooled to 10° C. and lithium hydroxide (2.5 g, 10 Eq, 100 mmol) was added portion-wise. The reaction mixture was stirred at 50° C. for 3 hours. The reaction crude was concentrated under vacuum and saturated $NaHSO_4$ was added until the crude solution is acidic (pH 4-5). The resulting mixture was extracted with EtOAc (3×40 mL). Organic layers were combined, washed with water, dried and concentrated under vacuum to afford (S)-4-(3-((tert-butoxycarbonyl)amino)-3-methylpyrrolidin-1-yl)-6-cyano-5-(3,5-difluorophenyl)nicotinic acid (4.0 g, 85%) as a yellow solid. This material was used for next step without further purification. MS $(M+H)^+$=459.2.

Step 5-6, preparation of tert-butyl ((S)-1-(2-cyano-3-(3,5-difluorophenyl)-5-(((S)-1-(pyridin-2-yl)ethyl)carbamoyl)pyridin-4-yl)-3-methylpyrrolidin-3-yl)carbamate: to a mixture of (S)-4-(3-((tert-butoxycarbonyl)amino)-3-methylpyrrolidin-1-yl)-6-cyano-5-(3,5-difluorophenyl)nicotinic acid (90 mg, 1.0 Eq, 0.20 mmol), HATU (0.11 g, 1.5 Eq, 0.29 mmol) and (S)-1-(pyridin-2-yl)ethan-1-amine (36 mg, 1.50 Eq, 0.29 mmol) was added DMF (0.8 mL) and DIPEA (0.10 mL, 3.0 Eq, 0.59 mmol). The resulting mixture was stirred at ambient temperature for 0.5 hour. The reaction crude was purified by C18 reverse phase chromatography eluting with MeCN (0.1% TFA)/water (0.1% TFA) (5-65%). Pure fractions were combined, neutralized with saturated $NaHCO_3$ (3 mL), solid NaCl (5 g) was added, and extracted with ethyl acetate (20 mL). The organic layer was dried with $MgSO_4$, filtered and concentrated to give 75 mg of tert-butyl ((S)-1-(2-cyano-3-(3,5-difluorophenyl)-5-(((S)-1-(pyridin-2-yl)ethyl)carbamoyl)pyridin-4-yl)-3-methylpyrrolidin-3-yl)carbamate as a clean oil. MS (M+H)+=563.5.

Step 5-7, preparation of 4-((S)-3-amino-3-methylpyrrolidin-1-yl)-6-cyano-5-(3,5-difluorophenyl)-N—((S)-1-(pyridin-2-yl)ethyl)nicotinamide: to a DCM (0.6 mL) solution of tert-butyl ((S)-1-(2-cyano-3-(3,5-difluorophenyl)-5-(((S)-1-(pyridin-2-yl)ethyl)carbamoyl)pyridin-4-yl)-3-methylpyrrolidin-3-yl)carbamate (75 mg, 1.0 Eq, 0.13 mmol) was added TFA (0.6 mL). The resulting mixture was stirred at ambient temperature for 0.5 h. The reaction crude was concentrated, and the remaining residue was purified by C18 reverse phase chromatography eluting with MeCN (0.1% TFA)/water (0.1% TFA) (5-35%). Pure fractions were combined, neutralized with saturated $NaHCO_3$ (3 mL), added solid NaCl (5 g), and extracted with ethyl acetate (20 mL). The organic layer was dried with $MgSO_4$, filtered and concentrated with 1.0 M HCl in ethyl acetate (0.2 mL) to give the HCl salt of 4-((S)-3-amino-3-methylpyrrolidin-1-yl)-6-cyano-5-(3,5-difluorophenyl)-N—((S)-1-(pyridin-2-yl)ethyl)nicotinamide as a white solid. MS $(M+H)^+$=463.2.

The following compounds were prepared similarly to Example 5 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-104 | 452.2 |
| 1-105 | 452.2 |
| 1-106 | 452.2 |
| 1-107 | 452.2 |
| 1-108 | 450.2 |
| 1-109 | 503.2 |

-continued

| Compound no. | MS $(M + H)^+$ |
|---|---|
| 1-110 | 462.2 |
| 1-111 | 503.3 |
| 1-113 | 470.5 |
| 1-114 | 439.2 |
| 1-115 | 464.3 |
| 1-116 | 456.2 |
| 1-117 | 456.2 |
| 1-118 | 476.2 |
| 1-119 | 476.2 |
| 1-126 | 464.4 |
| 1-132 | 453.1 |
| 1-133 | 467.0 |
| 1-135 | 430.2 |
| 1-136 | 430.2 |
| 1-138 | 446.2 |
| 1-139 | 446.2 |
| 1-168 | 484.2 |
| 1-169 | 487.1 |
| 1-180 | 502.1 |
| 1-218 | 426.2 |
| 1-219 | 440.2 |
| 1-220 | 444.1 |
| 1-221 | 444.1 |
| 1-222 | 454.1 |
| 1-225 | 440.1 |
| 1-226 | 440.1 |
| 1-227 | 440.1 |
| 1-234 | 442.2 |
| 1-244 | 455.1 |
| 1-245 | 479.1 |
| 1-248 | 459.2 |
| 1-249 | 461.1 |
| 1-250 | 447.1 |
| 1-251 | 447.1 |
| 1-252 | 435.2 |
| 1-253 | 423.2 |
| 1-254 | 421.2 |
| 1-270 | 409.2 |
| 1-271 | 409.2 |

Example 6. 4-[3-(1-aminoethyl)azetidin-1-yl]-N-{bicyclo[1.1.1]pentan-1-yl}-5-(3,5-difluorophenyl)pyridine-3-carboxamide (compound 1-63)

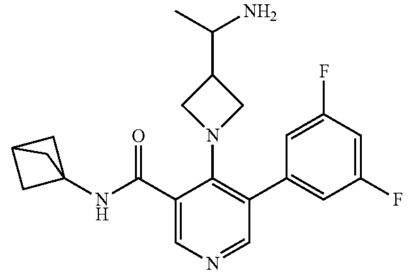 [SMILES: CC(N)C1CN(c2c(C(=O)NC34CC(C3)C4)cncc2-c2cc(F)cc(F)c2)C1]

Step 6-1, preparation of 1-(azetidin-3-yl)ethan-1-one: to a DCM (5 mL) solution of tert-butyl 3-acetylazetidine-1-carboxylate (500 mg, 1.0 Eq, 2.51 mmol) was added TFA (5 mL). The resulting mixture was stirred at ambient temperature for 3 hours. The reaction mixture was concentrated under reduced pressure. The mixture was diluted with water (30 mL) and saturated $NaHCO_3$ solution was added until pH is ~7.0. The resulting mixture was concentrated under reduced pressure and the remaining residue was washed with DCM/MeOH (3×50 mL). Organic layers were combined, dried over anhydrous $Na_2SO_4$, filtered and concentrated under vacuum. This resulted in 280 mg of 1-(azetidin- 3-yl)ethan-1-one (80% purity) as colorless oil. This material was used for next step without further purification.

Step 6-2, preparation of 4-(3-acetylazetidin-1-yl)-5-bromonicotinaldehyde: to a mixture of 1-(azetidin-3-yl)ethan-1-one (280 mg, 1.0 Eq, 2.3 mmol), 5-bromo-4-chloronicotinaldehyde (446 mg, 0.90 Eq, 2.02 mmol), N-ethyl-N-isopropylpropan-2-amine (1.00 g, 3.4 Eq, 7.74 mmol) was added MeCN (5 mL). The resulting mixture was stirred at 80° C. for 2 hours. The reaction mixture was concentrated under reduced pressure and the remaining residue was purified by silica gel chromatography eluting with petroleum ether/EtOAc (5:1) to afford 4-(3-acetylazetidin-1-yl)-5-bromonicotinaldehyde (250 mg, 39%) as colorless oil. MS $(M+H)^+$=285.0.

Step 6-3, preparation of 4-(3-acetylazetidin-1-yl)-5-(3,5-difluorophenyl)nicotinaldehyde: to a mixture of 4-(3-acetylazetidin-1-yl)-5-bromonicotinaldehyde (90 mg, 1.0 Eq, 0.32 mmol), (3,5-difluorophenyl)boronic acid (150 mg, 3.0 Eq, 0.95 mmol), potassium phosphate (200 mg, 3.0 Eq, 0.942 mmol), and dichloro[1,1'-bis(di-t-butylphosphino)ferrocene]palladium(II) (21 mg, 0.10 Eq, 0.032 mmol) was added 1,4-dioxane (1.0 mL) and Water (0.1 mL) under atmospheric nitrogen. The reaction mixture was stirred at 80° C. for 1 hour. The resulting mixture was concentrated under reduced pressure and the remaining residue was purified by silica gel chromatography. This resulted in 65 mg of 4-(3-acetylazetidin-1-yl)-5-(3,5-difluorophenyl)nicotinaldehyde (65%) as a yellow solid. MS (M+H)+=317.1.

Step 6-4, preparation of 4-(3-acetylazetidin-1-yl)-5-(3,5-difluorophenyl)nicotinic acid: to a tert-butyl alcohol (6.0 mL) solution of 4-(3-acetylazetidin-1-yl)-5-(3,5-difluorophenyl)nicotinaldehyde (150 mg, 1.0 Eq, 0.474 mmol) was added 2-methylbut-2-ene (1.66 g, 50 Eq, 23.7 mmol), sodium chlorite (86 mg, 2.0 Eq, 0.95 mmol), sodium dihydrogen phosphate dihydrate (222 mg, 3.0 Eq, 1.42 mmol) and water (2 mL). The resulting mixture was stirred at ambient temperature for 1 hour. The reaction mixture was purified by Prep-HPLC using the following conditions: Column, $C_{18}$; mobile phase, Water (0.1% TFA) and ACN (25% ACN up to 45% in 8 min); Total flow rate, 70 mL/min; Detector, UV 220 nm. This resulted in 120 mg of 4-(3-acetylazetidin-1-yl)-5-(3,5-difluorophenyl)nicotinic acid as colorless oil. MS $(M+H)^+$=333.1.

Step 6-5, preparation of 4-(3-acetylazetidin-1-yl)-N-(bicyclo[1.1.1]pentan-1-yl)-5-(3,5-difluorophenyl)nicotinamide: to a DMF (2.0 mL) solution of 4-(3-acetylazetidin-1-yl)-5-(3,5-difluorophenyl)nicotinic acid (120 mg, 1.0 Eq, 0.361 mmol) was added bicyclo[1.1.1]pentan-1-amine hydrochloride (65 mg, 1.5 Eq, 0.54 mmol), N-ethyl-N-isopropylpropan-2-amine (163 mg, 3.49 Eq, 1.26 mmol), and 2-(3H-[1,2,3]triazolo[4,5-b]pyridin-3-yl)-1,1,3,3-tetramethylisouronium hexafluorophosphate(V) (206 mg, 1.50 Eq, 0.54 mmol). The reaction mixture was stirred at ambient temperature for 1 hour. The reaction crude was purified by Prep-HPLC using the following conditions: Column, $C_{18}$; mobile phase, Water (0.1% TFA) and ACN (35% ACN up to 60% in 8 min); Total flow rate, 70 mL/min; Detector, UV 220 nm. This resulted in 4-(3-acetylazetidin-1-yl)-N-(bicyclo[1.1.1]pentan-1-yl)-5-(3,5-difluorophenyl)nicotinamide (110 mg, 76.6%) as a yellow solid. MS $(M+H)^+$=398.3.

Step 6-6, preparation of N-(bicyclo[1.1.1]pentan-1-yl)-5-(3,5-difluorophenyl)-4-(3-(1-((2,4-dimethoxybenzyl)amino)ethyl)azetidin-1-yl)nicotinamide: to a DCE (2.0 mL) solution of 4-(3-acetylazetidin-1-yl)-N-(bicyclo[1.1.1]pentan-1-yl)-5-(3,5-difluorophenyl)nicotinamide (100 mg, 1.0 Eq, 0.252 mmol) was added acetic acid (15 mg, 0.99 Eq, 0.25 mmol), (2,4-dimethoxyphenyl)methanamine (63 mg, 1.5 Eq, 0.38 mmol), and sodium triacetoxyhydroborate (160 mg 3.0 Eq, 0.755 mmol). The resulting mixture was stirred at ambient temperature for 6 hours. The reaction crude was concentrated under reduced pressure and the remaining residue was purified by Prep-HPLC using the following conditions: Column, $C_{18}$; mobile phase, Water (0.1% TFA) and ACN (30% ACN up to 60% in 8 min); Total flow rate, 70 mL/min; Detector, UV 220 nm. This resulted in N-(bicyclo[1.1.1]pentan-1-yl)-5-(3,5-difluorophenyl)-4-(3-(1-((2,4-dimethoxybenzyl)amino)ethyl)azetidin-1-yl)nicotinamide (110 mg, 72%, 90% purity) as yellow oil. MS $(M+H)^+$=549.3.

Step 6-7, preparation of 4-(3-(1-aminoethyl)azetidin-1-yl)-N-(bicyclo[1.1.1]pentan-1-yl)-5-(3,5-difluorophenyl)nicotinamide: N-(bicyclo[1.1.1]pentan-1-yl)-5-(3,5-difluorophenyl)-4-(3-(1-((2,4-dimethoxybenzyl)amino)ethyl)azetidin-1-yl)nicotinamide (100 mg, 1.0 Eq, 0.182 mmol) was combined with TFA (2.0 mL) and the resulting mixture was heated at 80° C. for 16 hours. The mixture was concentrated under reduced pressure and the remaining residue was purified by Prep-HPLC using the following conditions: Column, SunFire Prep $C_{18}$ OBD, 19*150 mm, 5 μm; mobile phase, Water (0.1% TFA) and ACN (12% ACN up to 17% in 7 min); Total flow rate, 20 mL/min; Detector, UV 220 nm. This resulted in the TFA salt of 4-(3-(1-aminoethyl)azetidin-1-yl)-N-(bicyclo[1.1.1]pentan-1-yl)-5-(3,5-difluorophenyl)nicotinamide (38.8 mg, 34.0%) as a white solid. MS $(M+H)^+$=399.2.

Example 7. 4-[(3S)-3-amino-3-methylpyrrolidin-1-yl]-N-{bicyclo[1.1.1]pentan-1-yl}-5-(3,5-difluorophenyl)-6-methylpyridine-3-carboxamide (compound 1-74)

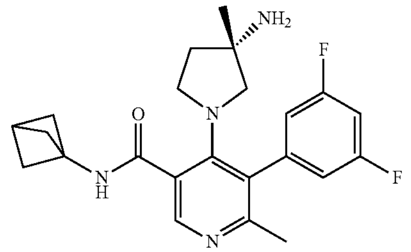 [SMILES: Cc1ncc(C(=O)NC23CC(C2)C3)c(N2CC[C@](C)(N)C2)c1-c1cc(F)cc(F)c1]

Step 7-1, preparation of tert-butyl (S)-(1-(2-chloro-5-formylpyridin-4-yl)-3-methylpyrrolidin-3-yl)carbamate: from 4,6-dichloronicotinaldehyde (5.0 g, 1.0 Eq, 28 mmol) and tert-butyl (S)-(3-methylpyrrolidin-3-yl)carbamate (6.0 g, 1.1 Eq, 30 mmol), the title compound (3.4 g, 35%) was prepared using a similar method to the one described in "Example 4, Step 4-1". MS $(M+H)^+$=340.1, 342.1.

Step 7-2, preparation of tert-butyl (S)-(1-(3-bromo-2-chloro-5-formylpyridin-4-yl)-3-methylpyrrolidin-3-yl)carbamate: from tert-butyl (S)-(1-(2-chloro-5-formylpyridin-4-yl)-3-methylpyrrolidin-3-yl)carbamate (3.4 g, 1.0 Eq, 10 mmol), the title compound (2.3 g, 55%) was prepared using a similar method to the one described in "Example 4, Step 4-2". MS (M+H)+=418.0, 420.0.

Step 7-3, preparation of tert-butyl (S)-(1-(2-chloro-3-(3,5-difluorophenyl)-5-formylpyridin-4-yl)-3-methylpyrrolidin-3-yl)carbamate: from tert-butyl (S)-(1-(3-bromo-2-chloro-5-formylpyridin-4-yl)-3-methylpyrrolidin-3-yl)carbamate (2.3 g, 1.0 Eq, 5.5 mmol) and (3,5-difluorophenyl)boronic acid (0.80 g, 0.92 Eq, 5.07 mmol), the title compound (1.7 g, 68%) was prepared using a similar method to the one described in "Example 4, Step 4-3". MS (M+H)+=452.2, 454.2.

Step 7-4, preparation of (S)-4-(3-((tert-butoxycarbonyl)amino)-3-methylpyrrolidin-1-yl)-6-chloro-5-(3,5-difluorophenyl)nicotinic acid: from tert-butyl (S)-(1-(2-chloro-3-(3,5-difluorophenyl)-5-formylpyridin-4-yl)-3-methylpyrrolidin-3-yl)carbamate (80 mg, 1.0 Eq, 0.18 mmol), the title compound (100 mg, 97%, 80& purity) was prepared using a similar method to the one described in "Example 4, Step 4-5". MS $(M+H)^+$==539.7, 541.7.

Step 7-5, preparation of tert-butyl (S)-(1-(5-(bicyclo[1.1.1]pentan-1-ylcarbamoyl)-2-chloro-3-(3,5-difluorophenyl)pyridin-4-yl)-3-methylpyrrolidin-3-yl)carbamate: from (S)-4-(3-((tert-butoxycarbonyl)amino)-3-methylpyrrolidin-1-yl)-6-chloro-5-(3,5-difluorophenyl)nicotinic acid (100 mg, 1.0 Eq, 0.17 mmol, 80% purity), the title compound (60 mg, 66%) was prepared using a similar method to the one described in "Example 4, Step 4-6". MS $(M+H)^+$ =533.2, 535.2.

Step 7-6, preparation of tert-butyl (S)-(1-(5-(bicyclo[1.1.1]pentan-1-ylcarbamoyl)-3-(3,5-difluorophenyl)-2-methylpyridin-4-yl)-3-methylpyrrolidin-3-yl)carbamate: to a mixture of tert-butyl (S)-(1-(5-(bicyclo[1.1.1]pentan-1-ylcarbamoyl)-2-chloro-3-(3,5-difluorophenyl)pyridin-4-yl)-3-methylpyrrolidin-3-yl)carbamate (35 mg, 1.0 Eq, 0.066 mmol), potassium carbonate (28 mg, 3.1 Eq, 0.20 mmol), 2,4,6-trimethyl-1,3,5,2,4,6-trioxatriborinane (30 mg, 3.6 Eq, 0.24 mmol), and Pd(amphos)$Cl_2$ (15 mg, 0.11 Eq, 0.007 mmol) was added dioxane (1.0 mL) under atmospheric nitrogen. The resulting solution was stirred at 100° C. for 1 hour. The reaction mixture was concentrated under vacuum and the remaining residue was purified by silica gel column eluting with ethyl acetate/petroleum ether (1:1). This resulted in tert-butyl (S)-(1-(5-(bicyclo[1.1.1]pentan-1-ylcarbamoyl)-3-(3,5-difluorophenyl)-2-methylpyridin-4-yl)-3-methylpyrrolidin-3-yl)carbamate (20 mg, 59%) as a yellow solid. MS $(M+H)^+$=513.1.

Step 7-7, preparation of (S)-4-(3-amino-3-methylpyrrolidin-1-yl)-N-(bicyclo[1.1.1]pentan-1-yl)-5-(3,5-difluorophenyl)-6-methylnicotinamide: to a DCM solution (2.0 mL) of tert-butyl (S)-(1-(5-(bicyclo[1.1.1]pentan-1-ylcarbamoyl)-3-(3,5-difluorophenyl)-2-methylpyridin-4-yl)-3-methylpyrrolidin-3-yl)carbamate (20 mg, 1.0 Eq, 0.039 mmol) was added TFA (1.0 mL). The resulting mixture was stirred at ambient temperature for 2 hours. The reaction solution was concentrated under vacuum and the remaining residue was purified by Prep-HPLC using the following conditions: Column, SunFire Prep $C_{18}$ OBD, 19*150 mm 5 μm 10 nm; mobile phase, Water (0.05% TFA) and ACN (16% ACN up to 33% in 7 min); Total flow rate, 20 mL/min; Detector, UV 220 nm. This resulted in the TFA salt of (S)-4-(3-amino-3-methylpyrrolidin-1-yl)-N-(bicyclo[1.1.1]pentan-1-yl)-5-(3,5-difluorophenyl)-6-methylnicotinamide (11.8 mg, 47%) as a white solid. MS $(M+H)^+$=413.2.

Example 8. 4-[(3S)-3-amino-3-methylpyrrolidin-1-yl]-N-{bicyclo[1.1.1]pentan-1-yl}-6-cyanopyridine-3-carboxamide (compound 1-75)

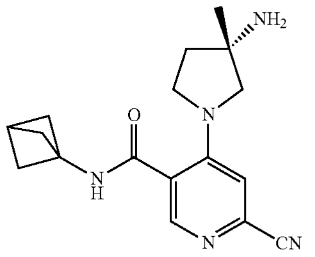 [SMILES: C[C@]1(N)CCN(c2cc(C#N)ncc2C(=O)NC23CC(C2)C3)C1]

Step 8-1, preparation of tert-butyl (S)-(1-(2-cyano-5-formylpyridin-4-yl)-3-methylpyrrolidin-3-yl)carbamate: from tert-butyl (S)-(1-(2-chloro-5-formylpyridin-4-yl)-3-methylpyrrolidin-3-yl)carbamate (50 mg, 1.0 Eq, 0.10 mmol), the title compound (20 mg, 59%) was prepared using a similar method to the one described in "Example 4, Step 4-4". MS (M+H)+=331.3.

Step 8-2, preparation of (S)-4-(3-((tert-butoxycarbonyl)amino)-3-methylpyrrolidin-1-yl)-6-cyanonicotinic acid: from tert-butyl (S)-(1-(2-cyano-5-formylpyridin-4-yl)-3-methylpyrrolidin-3-yl)carbamate (20 mg, 1.0 Eq, 0.061 mmol), the title compound (25 mg, 83%) was prepared using a similar method to the one described in "Example 4, Step 4-5". MS (M+H)+=347.1.

Step 8-3, preparation of tert-butyl (S)-(1-(5-(bicyclo[1.1.1]pentan-1-ylcarbamoyl)-2-cyanopyridin-4-yl)-3-methylpyrrolidin-3-yl)carbamate: form (S)-4-(3-((tert-butoxycarbonyl)amino)-3-methylpyrrolidin-1-yl)-6-cyanonicotinic acid (25 mg, 1.0 Eq, 0.051 mmol), the title compound (10 mg, 48%) was prepared using a similar method to the one described in "Example 4, Step 4-6". MS $(M+H)^+$=412.2.

Step 8-4, preparation of (S)-4-(3-amino-3-methylpyrrolidin-1-yl)-N-(bicyclo[1.1.1]pentan-1-yl)-6-cyanonicotinamide: from tert-butyl (S)-(1-(5-(bicyclo[1.1.1]pentan-1-ylcarbamoyl)-2-cyanopyridin-4-yl)-3-methylpyrrolidin-3-yl)carbamate (10 mg, 1.0 Eq, 0.024 mmol), the TFA salt of the title compound (2.7 mg, 21%) was prepared using a similar method to the one described in "Example 4, Step 4-7". MS $(M+H)^+$=312.2.

Example 9. 4-[(3S)-3-amino-3-methylpyrrolidin-1-yl]-6-cyano-N-[(1S)-1-cyclopropylethyl]-5-[3-(difluoromethoxy)phenyl]pyridine-3-carboxamide (compound 1-120)

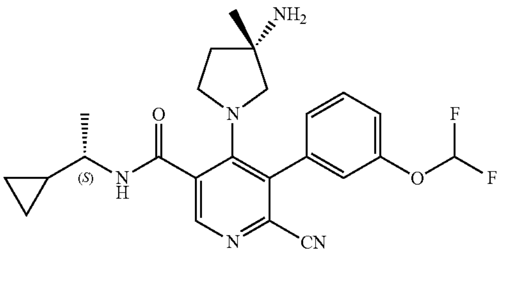

Step 9-1, preparation of ethyl (S)-4-(3-((tert-butoxycarbonyl)amino)-3-methylpyrrolidin-1-yl)-6-chloronicotinate: to a mixture of ethyl 4,6-dichloronicotinate (5.00 g, 1.0 Eq, 22.7 mmol), tert-butyl (S)-(3-methylpyrrolidin-3-yl)carbamate (4.55 g, 1.0 Eq, 22.7 mmol), and N-ethyl-N-isopropylpropan-2-amine (8.81 g, 3.0 Eq, 68.2 mmol) was added MeCN (50 mL). The resulting mixture was stirred at 0° C. for 16 hours. The reaction mixture was concentrated under reduced pressure and the remaining residue was purified by recrystallization. This resulted in 6.0 g of ethyl (S)-4-(3-((tert-butoxycarbonyl)amino)-3-methylpyrrolidin-1-yl)-6-chloronicotinate (68%). MS $(M+H)^+$=384.3.

Step 9-2, preparation of (S)-4-(3-((tert-butoxycarbonyl)amino)-3-methylpyrrolidin-1-yl)-6-chloronicotinic acid: to a MeOH (50 mL) solution of ethyl (S)-4-(3-((tert-butoxycarbonyl)amino)-3-methylpyrrolidin-1-yl)-6-chloronicotinate (6.0 g, 1.0 Eq, 15.6 mmol) was added lithium hydroxide (3.74 g, 9.99 Eq, 156 mmol) and Water (5.0 mL). The resulting mixture was stirred at 50° C. for 1 hour. The organic layer was separated and concentrated under vacuum to afford crude (S)-4-(3-((tert-butoxycarbonyl)amino)-3-methylpyrrolidin-1-yl)-6-chloronicotinic acid (5.60 g, 93%). This material was used for next step without further purification. MS $(M+H)^+$=356.2.

Step 9-3, preparation of tert-butyl ((S)-1-(2-chloro-5-(((S)-1-cyclopropylethyl)carbamoyl)pyridin-4-yl)-3-methylpyrrolidin-3-yl)carbamate: to a DMF (50 mL) solution of (S)-4-(3-((tert-butoxycarbonyl)amino)-3-methylpyrrolidin-1-yl)-6-chloronicotinic acid (1.0 Eq, 15.5 mmol, 5.5 g) was added 2-(3H-[1,2,3]triazolo[4,5-b]pyridin-3-yl)-1,1,3,3-tetramethylisouronium hexafluorophosphate(V) (8.82 g, 1.50 Eq, 23.2 mmol) and N-ethyl-N-isopropylpropan-2-amine (3.0 Eq, 46.3 mmol, 5.99 g). The resulting mixture was stirred at ambient temperature for 10 min followed by the addition of (S)-1-cyclopropylethan-1-amine (2.63 g, 2.00 Eq, 30.9 mmol). The resulting mixture was stirred at ambient temperature for 1 hour. Reaction solution was diluted with water (100 mL) and extracted with ethyl acetate (3×100 mL). Organic layers were combined, washed with brine (2×100 mL), dried over anhydrous sodium sulfate and concentrated under vacuum. The remaining residue was purified by silica gel chromatography eluting with ethyl acetate/petroleum ether (1:2). This resulted in tert-butyl ((S)-1-(2-chloro-5-(((S)-1-cyclopropylethyl)carbamoyl)pyridin-4-yl)-3-methylpyrrolidin-3-yl)carbamate (6.0 g, 87%). MS $(M+H)^+$=423.3.

Step 9-4, preparation of methyl 4-((S)-3-((tert-butoxycarbonyl)amino)-3-methylpyrrolidin-1-yl)-5-(((S)-1-cyclopropylethyl)carbamoyl)picolinate: to a MeOH (20 mL) solution of tert-butyl ((S)-1-(2-chloro-5-(((S)-1-cyclopropylethyl)carbamoyl)pyridin-4-yl)-3-methylpyrrolidin-3-yl)carbamate (1.2 g, 1.0 Eq, 2.8 mmol) was added triethylamine (1.0 g, 3.5 Eq, 9.9 mmol), Pd(dppf)$Cl_2$ (200 mg, 0.096 Eq, 0.273 mmol) under atmospheric nitrogen. The resulting mixture was heated at 130° C. under 20 bar of carbon monoxide for 8 hours. The reaction mixture was concentrated under reduced pressure and the remaining residue was purified by silica gel chromatography eluting with petroleum ether/EtOAc (1:2) to afford methyl 4-((S)-3-((tert-butoxycarbonyl)amino)-3-methylpyrrolidin-1-yl)-5-(((S)-1-cyclopropylethyl)carbamoyl)picolinate (1.0 g, 79%). MS $(M+H)^+$=447.4.

Step 9-5, preparation of tert-butyl ((S)-1-(2-carbamoyl-5-(((S)-1-cyclopropylethyl)carbamoyl)pyridin-4-yl)-3-methylpyrrolidin-3-yl)carbamate: to a sealed tube was added methyl 4-((S)-3-((tert-butoxycarbonyl)amino)-3-methylpyrrolidin-1-yl)-5-(((S)-1-cyclopropylethyl)carbamoyl)picolinate (1.3 g, 1.0 Eq, 2.9 mmol) and ammonia in MeOH (7.0 M) (12 mL, 28 Eq, 82.2 mmol). The resulting mixture was stirred at 80° C. for 2 hours. The reaction solution was concentrated under vacuum to afford crude tert-butyl ((S)-1-(2-carbamoyl-5-(((S)-1-cyclopropylethyl)carbamoyl)pyridin-4-yl)-3-methylpyrrolidin-3-yl)carbamate (1.0 g, 80%). This material was used for next step without further purification. MS $(M+H)^+$=432.2.

Step 9-6, preparation of tert-butyl ((S)-1-(2-cyano-5-(((S)-1-cyclopropylethyl)carbamoyl)pyridin-4-yl)-3-methylpyrrolidin-3-yl)carbamate: to a DCM (30 mL) solution of tert-butyl ((S)-1-(2-carbamoyl-5-(((S)-1-cyclopropylethyl)carbamoyl)pyridin-4-yl)-3-methylpyrrolidin-3-yl)carbamate (1.0 g, 1.0 Eq, 2.3 mmol) was added TEA (1.1 mL, 3.4 Eq, 7.82 mmol) and TFAA (1.3 mL, 4.1 Eq, 9.5 mmol) drop-wise at 0° C. The resulting mixture was stirred at 0° C. for 1 hour. The reaction mixture was quenched with aqueous $K_2CO_3$ and extracted with EtOAc (3×40 mL). The organic layers were combined, washed with brine, dried and concentrated under vacuum. The remaining residue was purified by silica gel chromatography eluting with ethyl acetate/petroleum ether (1/1) to afford tert-butyl ((S)-1-(2-cyano-5-(((S)-1-cyclopropylethyl)carbamoyl)pyridin-4-yl)-3-methylpyrrolidin-3-yl)carbamate (700 mg, 73%) as a yellow solid. MS $(M+H)^+$=414.2.

Step 9-7, preparation of tert-butyl ((S)-1-(3-bromo-2-cyano-5-(((S)-1-cyclopropylethyl)carbamoyl)pyridin-4-yl)-3-methylpyrrolidin-3-yl)carbamate: to a DCM (4.0 mL) solution of tert-butyl ((S)-1-(2-cyano-5-(((S)-1-cyclopropylethyl)carbamoyl)pyridin-4-yl)-3-methylpyrrolidin-3-yl)carbamate (700 mg, 1.0 Eq, 1.69 mmol) was added AcOH (20 mL). 1,3,5-Tribromo-1,3,5-triazinane-2,4,6-trione (620 mg, 1.0 Eq, 1.70 mmol) was added at 0° C. and the resulting mixture was stirred at the same temperature for 20 min. The reaction crude was quenched with saturated $Na_2SO_3$ (10 mL) and extracted with EtOAc (3×40 mL). Organic layers were combined, washed with brine, dried and concentrated under vacuum. The remaining residue was purified by silica gel chromatography eluting with ethyl acetate/petroleum ether (⅓) to afford tert-butyl ((S)-1-(3-bromo-2-cyano-5-(((S)-1-cyclopropylethyl)carbamoyl)pyridin-4-yl)-3-methylpyrrolidin-3-yl)carbamate (410 mg, 49.2%) as a yellow solid. MS $(M+H)^+$=492.1, 494.1.

Step 9-8, preparation of tert-butyl ((S)-1-(2-cyano-5-(((S)-1-cyclopropylethyl)carbamoyl)-3-(3-(difluoromethoxy)phenyl)pyridin-4-yl)-3-methylpyrrolidin-3-yl)carbamate: to a mixture of tert-butyl ((S)-1-(3-bromo-2-cyano-5-(((S)-1-cyclopropylethyl)carbamoyl)pyridin-4-yl)-3-methylpyrrolidin-3-yl)carbamate (50 mg, 1.0 Eq, 0.10 mmol), (3-(difluoromethoxy)phenyl)boronic acid (45 mg, 2.2 Eq, 0.22 mmol), potassium phosphate (66 mg, 3.1 Eq, 0.31 mmol) and Pd(DtBPF)$Cl_2$ (7.0 mg, 0.11 Eq, 0.011 mmol) was added Toluene (2.0 mL) and water (0.2 mL) under atmospheric nitrogen. The resulting mixture was stirred at 80° C. for 1 hour. The reaction mixture was concentrated under reduced pressure and the remaining residue was purified by silica gel chromatography eluting with ethyl acetate/petroleum ether (1:1) to afford crude product. This material was re-purified by Prep-HPLC using the following conditions: Column, SunFire prep OBD 19*150 mm 5 μm C-01; mobile phase, Water (0.05% TFA) and ACN (30% ACN up to 44% in 14 min); Detector, 254 nm. This resulted in tert-butyl ((S)-1-(2-cyano-5-(((S)-1-cyclopropylethyl)carbamoyl)-3-(3-(difluoromethoxy)phenyl)pyridin-4-yl)-3-methylpyrrolidin-3-yl)carbamate (30 mg, 52%) as a white solid. MS $(M+H)^+$=574.4.

Step 9-9, preparation of 4-((S)-3-amino-3-methylpyrrolidin-1-yl)-6-cyano-N—((S)-1-cyclopropylethyl)-5-(3-(difluoromethoxy)phenyl)nicotinamide: to a DCM (3.0 mL) solution of tert-butyl ((S)-1-(2-cyano-5-(((S)-1-cyclopropylethyl)carbamoyl)-3-(3-(difluoromethoxy)phenyl)pyridin-4-yl)-3-methylpyrrolidin-3-yl)carbamate (21 mg, 1.0 Eq, 0.037 mmol) was added TFA (1.0 mL). The resulting mixture was stirred at 25° C. for 1 hour. The reaction solution was concentrated and freeze-dried under vacuum to afford the TFA salt of 4-((S)-3-amino-3-methylpyrrolidin-1-yl)-6-cyano-N—((S)-1-cyclopropylethyl)-5-(3-(difluoromethoxy)phenyl)nicotinamide (12.4 mg, 48%) as a white solid. MS $(M+H)^+$=474.2.

The following compounds were prepared similarly to Example 9 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 1-121 | 394.3 |
| 1-127 | 474.2 |
| 1-128 | 411.2 |
| 1-129 | 459.2 |
| 1-134 | 381.2 |

Example 10. 4-[(3S)-3-amino-3-methylpyrrolidin-1-yl]-N-[(1S)-1-cyclopropylethyl]-5-(3,5-difluorophenyl)-6-methylpyridine-3-carboxamide (compound 1-122)

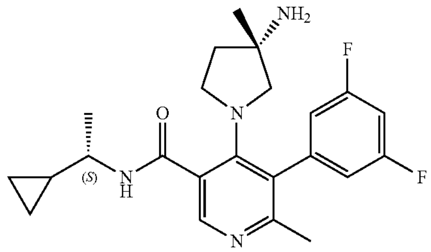

Step 10-1, preparation of tert-butyl ((S)-1-(5-(((S)-1-cyclopropylethyl)carbamoyl)-2-methylpyridin-4-yl)-3-methylpyrrolidin-3-yl)carbamate: to a mixture of tert-butyl ((S)-1-(2-chloro-5-(((S)-1-cyclopropylethyl)carbamoyl)pyridin-4-yl)-3-methylpyrrolidin-3-yl)carbamate (400 mg, 1.0 Eq, 0.946 mmol, "Example 9, step 9-3"), tetrachlorobis{[4-(N,N-dimethylamino)phenyl]-di-t-butylphosphino}dipalladium(II) (67.0 mg, 0.10 Eq, 0.095 mmol), potassium carbonate (392 mg, 3.0 Eq, 2.84 mmol), and 2,4-dimethyl-1,3,5,2,4,6-trioxatriborinane (2.0 Eq, 1.89 mmol, 209 mg) was added 1,4-Dioxane (5.0 mL) under atmospheric nitrogen. The resulting mixture was stirred at 80° C. for 1 hour. The reaction mixture was concentrated, diluted with water (20 mL), and extracted with ethyl acetate (3×20 mL). Organic layers were combined, washed with brine (2×20 mL), dried over anhydrous sodium sulfate and concentrated under vacuum. The remaining residue was purified by silica gel chromatography eluting with ethyl acetate/petroleum ether (2:1) to afford tert-butyl ((S)-1-(5-(((S)-1-cyclopropylethyl)carbamoyl)-2-methylpyridin-4-yl)-3-methylpyrrolidin-3-yl)carbamate (400 mg, 95%). MS $(M+H)^+$=403.4.

Step 10-2, preparation of tert-butyl ((S)-1-(3-bromo-5-(((S)-1-cyclopropylethyl)carbamoyl)-2-methylpyridin-4-yl)-3-methylpyrrolidin-3-yl)carbamate: to a mixture of tert-butyl ((S)-1-(5-(((S)-1-cyclopropylethyl)carbamoyl)-2-methylpyridin-4-yl)-3-methylpyrrolidin-3-yl)carbamate (400 mg, 1.0 Eq, 0.994 mmol), AcOH (5.0 mL) and DCM (1.0 mL) was added 1,3,5-tribromo-1,3,5-triazinane-2,4,6-trione (550 mg, 1.51 Eq, 1.50 mmol) at 0° C. The resulting mixture was stirred at the same temperature for 15 min. The reaction mixture was quenched with aqueous $NaHSO_3$ at ° C. and solids were filtered out. The filtrate was collected and extracted with EtOAc (3×30 mL). Organic layers were combined, washed with water (3×30 mL) and aqueous $NaHCO_3$, dried and concentrated under vacuum. The remaining residue was purified by silica gel chromatography eluting with ethyl acetate/petroleum ether (½) to afford tert-butyl ((S)-1-(3-bromo-5-(((S)-1-cyclopropylethyl)carbamoyl)-2-methylpyridin-4-yl)-3-methylpyrrolidin-3-yl) carbamate (300 mg, 60%). MS $(M+H)^+$=481.2, 483.2.

Step 10-3, preparation of tert-butyl ((S)-1-(5-(((S)-1-cyclopropylethyl)carbamoyl)-3-(3,5-difluorophenyl)-2-methylpyridin-4-yl)-3-methylpyrrolidin-3-yl)carbamate: to a mixture of tert-butyl ((S)-1-(3-bromo-5-(((S)-1-cyclopropylethyl)carbamoyl)-2-methylpyridin-4-yl)-3-methylpyrrolidin-3-yl)carbamate (110 mg, 1.0 Eq, 0.228 mmol), (3,5-difluorophenyl)boronic acid (72 mg, 2.0 Eq, 0.457 mmol), dichloro[1,1'-bis(di-t-butylphosphino)ferrocene]palladium (II) (15 mg, 0.10 Eq, 0.023 mmol) and potassium phosphate (145 mg 3.0 Eq, 0.683 mmol) was added Toluene (3.0 mL) and water (0.3 mL) under atmospheric nitrogen. The resulting mixture was heated at 70° C. for 1 hour. The reaction crude was purified by Prep-HPLC using the following conditions: Column, SunFire Prep $C_{18}$ OBD Column, 19*150 mm 5 μm; mobile phase, Water (0.05% TFA) and ACN (22.0% ACN up to 45.0% in 7 min); Total flow rate, 20 mL/min; Detector, UV 220 nm. This resulted in tert-butyl ((S)-1-(5-(((S)-1-cyclopropylethyl)carbamoyl)-3-(3,5-difluorophenyl)-2-methylpyridin-4-yl)-3-methylpyrrolidin-3-yl)carbamate (40 mg, 33%). MS $(M+H)^+$=515.4.

Step 10-4, preparation of 4-((S)-3-amino-3-methylpyrrolidin-1-yl)-N—((S)-1-cyclopropylethyl)-5-(3,5-difluorophenyl)-6-methylnicotinamide: to a DCM (4.0 mL) of tert-butyl ((S)-1-(5-(((S)-1-cyclopropylethyl)carbamoyl)-3-(3,5-difluorophenyl)-2-methylpyridin-4-yl)-3-methylpyrrolidin-3-yl)carbamate (40 mg, 1.0 Eq, 0.078 mmol) was added TFA (2.0 mL). The resulting mixture was stirred at 25° C. for 1 hour. The reaction solution was concentrated and lyophilized under vacuum to give the TFA salt of 4-((S)-3-amino-3-methylpyrrolidin-1-yl)-N—((S)-1-cyclopropylethyl)-5-(3,5-difluorophenyl)-6-methylnicotinamide as an off-white solid. MS $(M+H)^+$=415.2.

The following compounds were prepared similarly to Example 10 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 1-121 | 394.3 |
| 1-123 | 422.2 |
| 1-124 | 397.2 |

-continued

| Compound no. | MS (M + H)$^+$ |
|---|---|
| 1-125 | 431.2 |
| 1-146 | 437.2 |
| 1-147 | 443.2 |
| 1-148 | 383.3 |
| 1-155 | 451.3 |
| 1-156 | 409.3 |
| 1-157 | 410.3 |
| 1-158 | 414.2 |
| 1-159 | 448.3 |
| 1-160 | 398.3 |

Example 11. 4-[(3S)-3-amino-3-methylpyrrolidin-1-yl]-N-(4,4-difluorocyclohexyl)-5-(3,5-difluorophenyl)-6-methoxypyridine-3-carboxamide (compound 1-144)

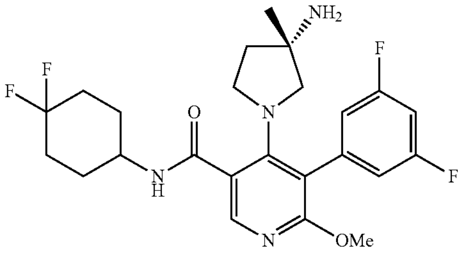 [SMILES: COc1ncc(C(=O)NC2CCC(F)(F)CC2)c(N2CC[C@](C)(N)C2)c1-c1cc(F)cc(F)c1]

Step 11-1, preparation of methyl (S)-4-(3-((tert-butoxycarbonyl)amino)-3-methylpyrrolidin-1-yl)-6-chloronicotinate: to a mixture of methyl 4,6-dichloronicotinate (1.10 g, 1.0 Eq, 5.34 mmol) and tert-butyl (S)-(3-methylpyrrolidin-3-yl)carbamate (1.05 g, 0.982 Eq, 5.24 mmol) was added MeCN (10 mL). At 0° C., DIPEA (2.8 mL, 3.0 Eq, 16.0 mmol) was added and the resulting mixture was stirred at the same temperature for 2 hours. The reaction solution was stirred at ambient temperature for overnight. The reaction crude was concentrated and purified by silica gel chromatography eluting with EtOAc/Hexane (0-60%) to give methyl (S)-4-(3-((tert-butoxycarbonyl)amino)-3-methylpyrrolidin-1-yl)-6-chloronicotinate (1.97 g, 98%). MS (M+H)+=370.3.

Step 11-2, preparation of methyl (S)-4-(3-((tert-butoxycarbonyl)amino)-3-methylpyrrolidin-1-yl)-6-methoxynicotinate: to a MeOH (5 mL) solution of methyl (S)-4-(3-((tert-butoxycarbonyl)amino)-3-methylpyrrolidin-1-yl)-6-chloronicotinate (1.95 g, 1.0 Eq, 5.27 mmol) was added 25% sodium methoxide in MeOH (10.0 mL, 8.3 Eq, 44 mmol). The resulting mixture was heated at 65° C. for overnight. The reaction mixture was concentrated, diluted with ethyl acetate (30 mL), washed with saturated $NH_4Cl$ and brine. The organic layer was concentrated and the remaining residue was purified by C18 reverse phase chromatography eluting with MeCN (0.1% TFA)/water (0.1% TFA) (5-45%). Pure fractions were combined, concentrated, neutralized with saturated $NaHCO_3$ (5.0 mL), added solid NaCl (10 g), and extracted with ethyl acetate (2×20 mL). Organic layers were combined, dried with $MgSO_4$, filtered and concentrated to give methyl (S)-4-(3-((tert-butoxycarbonyl)amino)-3-methylpyrrolidin-1-yl)-6-methoxynicotinate (1.1 g, 57%) as a clear oil. MS (M+H)$^+$=366.2.

Step 11-3, preparation of methyl (S)-5-bromo-4-(3-((tert-butoxycarbonyl)amino)-3-methylpyrrolidin-1-yl)-6-methoxynicotinate: to a DMF (5.0 mL) solution of methyl (S)-4-(3-((tert-butoxycarbonyl)amino)-3-methylpyrrolidin-1-yl)-6-methoxynicotinate (1.06 g, 1.0 Eq, 2.90 mmol) was added NBS (568 mg, 1.1 Eq, 3.19 mmol) portion-wise. The resulting mixture was stirred at ambient temperature for 15 min and LCMS showed complete conversion to desired product. The crude reaction mixture was purified by C18 reverse phase chromatography eluting with MeCN (0.1% TFA)/water (0.1% TFA) (5-85%). Pure fractions were dried under vacuum to remove water and MeCN. The resulting residue was re-dissolved in ethyl acetate, washed with saturated $NaHCO_3$ (5.0 mL) and brine, dried and concentrated to give (S)-5-bromo-4-(3-((tert-butoxycarbonyl)amino)-3-methylpyrrolidin-1-yl)-6-methoxynicotinate (809 mg, 63%) as a clear oil. MS (M+H)$^+$=444.3, 446.1.

Step 11-4, preparation of methyl (S)-4-(3-((tert-butoxycarbonyl)amino)-3-methylpyrrolidin-1-yl)-5-(3,5-difluorophenyl)-6-methoxynicotinate: to a mixture of methyl (S)-5-bromo-4-(3-((tert-butoxycarbonyl)amino)-3-methylpyrrolidin-1-yl)-6-methoxynicotinate (754 mg, 1.0 Eq, 1.70 mmol), (3,5-difluorophenyl)boronic acid (1.07 g, 4.0 Eq, 6.79 mmol), potassium carbonate (1.17 g, 5.0 Eq, 8.48 mmol) and Pd(amphos)$Cl_2$ (120 mg, 0.10 Eq, 0.170 mmol) was added 1,4-Dioxane (7.0 mL) and water (0.7 mL) under atmospheric nitrogen. The resulting mixture was heated at 95° C. for 1 hour. LCMS showed ~50% conversion. Second batch of (3,5-difluorophenyl)boronic acid (1.07 g, 4.0 Eq, 6.79 mmol), potassium carbonate (1.17 g, 5.0 Eq, 8.48 mmol) and Pd(amphos)$Cl_2$ (120 mg, 0.10 Eq, 0.170 mmol) were added under atmospheric nitrogen, and the resulting mixture was heated at 95° C. for another 1 hour. The reaction crude was diluted with ethyl acetate, washed with brine, concentrated and dried. The remaining residue was purified by silica gel chromatography eluting with EtOAc/Hexane (0-35%) to give methyl (S)-4-(3-((tert-butoxycarbonyl)amino)-3-methylpyrrolidin-1-yl)-5-(3,5-difluorophenyl)-6-methoxynicotinate (286 mg, 35%) as a clear oil. MS (M+H)$^+$=478.2.

Step 11-5, preparation of (S)-4-(3-((tert-butoxycarbonyl)amino)-3-methylpyrrolidin-1-yl)-5-(3,5-difluorophenyl)-6-methoxynicotinic acid: to a MeOH (5 mL) solution of methyl (S)-4-(3-((tert-butoxycarbonyl)amino)-3-methylpyrrolidin-1-yl)-5-(3,5-difluorophenyl)-6-methoxynicotinate (286 mg, 1.0 Eq, 0.599 mmol) was added lithium hydroxide hydrate (276 mg, 11.0 Eq, 6.59 mmol) and water (1.0 mL). The resulting mixture was stirred at 50° C. for 24 hours. The reaction crude was concentrated, diluted with ethyl acetate, washed with saturated $NaHSO_4$, dried and concentrated to give crude (S)-4-(3-((tert-butoxycarbonyl)amino)-3-methylpyrrolidin-1-yl)-5-(3,5-difluorophenyl)-6-methoxynicotinic acid (220 mg, 79%) as a white solid. This material was used for next step without further purification. MS (M+H)$^+$=464.4.

Step 11-6, preparation of tert-butyl (S)-(1-(5-((4,4-difluorocyclohexyl)carbamoyl)-3-(3,5-difluorophenyl)-2-methoxypyridin-4-yl)-3-methylpyrrolidin-3-yl)carbamate: to a DMF (0.5 mL) solution of (S)-4-(3-((tert-butoxycarbonyl)amino)-3-methylpyrrolidin-1-yl)-5-(3,5-difluorophenyl)-6-methoxynicotinic acid (30 mg, 1.0 Eq, 0.065 mmol) was added 2-(3H-[1,2,3]triazolo[4,5-b]pyridin-3-yl)-1,1,3,3-tetramethylisouronium hexafluorophosphate(V) (37 mg, 1.5 Eq, 0.097 mmol), 4,4-difluorocyclohexan-1-amine hydrochloride (17 mg, 1.5 Eq, 0.097 mmol) and N-ethyl-Nisopropylpropan-2-amine (0.045 mL, 4.0 Eq, 0.26 mmol). The resulting mixture was stirred at room temperature for 30 minutes. The reaction mixture was diluted with ethyl acetate, washed with water and brine, concentrated and purified by silica gel chromatography eluting with EtOAc/hexane (0-80%). This resulted in 30 mg of tert-butyl (S)-(1-(5-((4,4-difluorocyclohexyl)carbamoyl)-3-(3,5-difluorophenyl)-2-methoxypyridin-4-yl)-3-methylpyrrolidin-3-yl) carbamate as a white solid. MS $(M+H)^+$=581.2.

Step 11-7, preparation of 4-[(3S)-3-amino-3-methylpyrrolidin-1-yl]-N-(4,4-difluorocyclohexyl)-5-(3,5-difluorophenyl)-6-methoxypyridine-3-carboxamide: to a DCM (0.6 mL) solution of tert-butyl (S)-(1-(5-((4,4-difluorocyclohexyl)carbamoyl)-3-(3,5-difluorophenyl)-2-methoxypyridin-4-yl)-3-methylpyrrolidin-3-yl)carbamate (30 mg, 1.0 Eq, 0.051 mmol) was added TFA (0.5 mL). The resulting mixture was stirred at ambient temperature for 0.5 hour. The reaction crude was concentrated and the remaining residue was purified by C18 reverse phase chromatography eluting with MeCN (0.10% TFA)/water (0.1% TFA). Pure fractions were combined, dried under vacuum and treated with 2.0 N HCl in ether (1.0 mL) for 1 hour. The resulting mixture as concentrated and dried under vacuum to the HCl salt of 4-[(3S)-3-amino-3-methylpyrrolidin-1-yl]-N-(4,4-difluorocyclohexyl)-5-(3,5-difluorophenyl)-6-methoxypyridine-3-carboxamide. MS $(M+H)^+$=481.3.

The following compounds were prepared similarly to Example 11 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-137 | 453.2 |
| 1-140 | 459.2 |
| 1-141 | 431.5 |
| 1-145 | 467.4 |
| 1-151 | 445.2 |
| 1-152 | 417.4 |
| 1-193 | 499.1 |
| 1-194 | 471.2 |
| 1-228 | 475.3 |
| 1-229 | 447.2 |
| 1-235 | 417.3 |
| 1-236 | 453.3 |
| 1-237 | 453.2 |
| 1-238 | 460.1 |
| 1-239 | 492.1 |
| 1-240 | 484.1 |
| 1-241 | 516.2 |
| 1-259 | 459.3 |
| 1-260 | 475.3 |
| 1-261 | 475.0 |
| 1-262 | 431.5 |
| 1-263 | 447.3 |
| 1-273 | 447.4 |
| 1-274 | 425.1 |
| 1-282 | 433.2 |
| 1-283 | 461.1 |
| 1-284 | 483.2 |
| 1-285 | 455.1 |
| 1-286 | 449.2 |

Example 12. 4-[(3S)-3-amino-3-methylpyrrolidin-1-yl]-N-{bicyclo[1.1.1]pentan-1-yl}-5-(3,5-difluorophenyl)-6-methoxypyridine-3-carboxamide (compound 1-130)

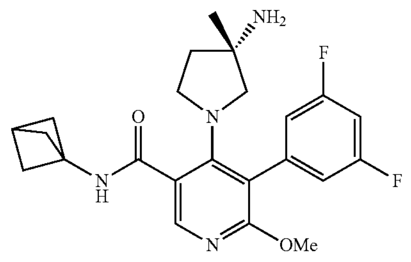 [SMILES: COc1ncc(C(=O)NC23CC(C2)C3)c(N2CC[C@](C)(N)C2)c1-c1cc(F)cc(F)c1]

Step 12-1, preparation of tert-butyl (S)-(1-(5-(bicyclo[1.1.1]pentan-1-ylcarbamoyl)-2-chloro-3-(3,5-difluorophenyl)pyridin-4-yl)-3-methylpyrrolidin-3-yl)carbamate: to a DMF (2.0 mL) solution of (S)-4-(3-((tert-butoxycarbonyl)amino)-3-methylpyrrolidin-1-yl)-6-chloro-5-(3,5-difluorophenyl)nicotinic acid (100 mg, 1.0 Eq, 0.17 mmol, "Step 7-3, Example 7") was added 2-(3H-[1,2,3]triazolo[4,5-b]pyridin-3-yl)-1,1,3,3-tetramethylisouronium hexafluorophosphate(V) (65 mg, 1.0 Eq, 0.17 mmol). The resulting mixture was stirred at 30° C. for 5 min followed by the addition of N-ethyl-N-isopropylpropan-2-amine (90 mg, 4.1 Eq, 0.70 mmol) and bicyclo[1.1.1]pentan-1-amine hydrochloride (25 mg, 1.2 Eq, 0.21 mmol). The reaction mixture was stirred at 30° C. for 2 hours. The resulting solution was diluted with water (20 mL) and extracted with ethyl acetate (3×30 mL). Organic layers were combined, washed with brine (2×20 mL), dried over anhydrous sodium sulfate and concentrated under vacuum. The remaining residue (60 mg, 66%) was used for next step without further purification. MS $(M+H)^+$=533.2, 535.2.

Step 12-2, preparation of (S)-4-(3-amino-3-methylpyrrolidin-1-yl)-N-(bicyclo[1.1.1]pentan-1-yl)-6-chloro-5-(3,5-difluorophenyl)nicotinamide: to a DCM (3.0 mL) of tert-butyl (S)-(1-(5-(bicyclo[1.1.1]pentan-1-ylcarbamoyl)-2-chloro-3-(3,5-difluorophenyl)pyridin-4-yl)-3-methylpyrrolidin-3-yl)carbamate (20 mg, 1.0 Eq, 0.038 mmol) was added TFA (1.0 mL). The resulting mixture was stirred at 25° C. for 2 hours. The reaction solution was concentrated and the remaining residue was purified by Prep-HPLC using the following conditions: Column, SunFire Prep $C_{18}$ OBD Column, 19*150 mm 5 μm 10 nm; mobile phase, Water (0.05% TFA) and ACN (15% ACN up to 27% in 7 min); Total flow rate, 20 mL/min; Detector, UV 220 nm. This resulted in the TFA salt of (S)-4-(3-amino-3-methylpyrrolidin-1-yl)-N-(bicyclo[1.1.1]pentan-1-yl)-6-chloro-5-(3,5-difluorophenyl)nicotinamide (14.1 mg, 57%) as a white solid. MS $(M+H)^+$=433.2, 435.2.

Step 12-3, preparation of 4-[(3S)-3-amino-3-methylpyrrolidin-1-yl]-N-{bicyclo[1.1.1]pentan-1-yl}-5-(3,5-difluorophenyl)-6-methoxypyridine-3-carboxamide: to a MeOH (0.4 mL) solution of (S)-4-(3-amino-3-methylpyrrolidin-1-yl)-N-(bicyclo[1.1.1]pentan-1-yl)-6-chloro-5-(3,5-difluorophenyl)nicotinamide bis(2,2,2-trifluoroacetate) (11 mg, 1.0 Eq, 0.017 mmol) was added 25% sodium methoxide (0.038 mL, 10 Eq, 0.17 mmol). The resulting mixture as stirred at 65° C. for overnight. LCMS showed most starting material was converted to the desired product. The reaction crude was concentrated, 0.5 mL of 25% sodium methoxide was added, and the resulting mixture was heated at 65° C. for another 6 hours. The reaction crude was concentrated, diluted with EtOAc, washed with saturated $NaHSO_4$ and brine, dried and concentrated. The remaining residue was combined with 2 N HCl in ether (1.0 mL) and stirred at ambient temperature for 1 hour. The resulting suspension was filtered and solid was collected and dried under vacuum to afford the HCl salt of 4-[(3S)-3-amino-3-methylpyrrolidin-1-yl]-N—{bicyclo[1.1.1]pentan-1-yl}-5-(3,5-difluorophenyl)-6-methoxypyridine-3-carboxamide as a white solid. MS $(M+H)^+$=429.4.

The following compounds were prepared similarly to Example 12 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-176 | 445.2 |
| 1-177 | 481.2 |
| 1-178 | 471.2 |
| 1-179 | 475.2 |

Example 13. 4-[(3S)-3-amino-3-methylpyrrolidin-1-yl]-5-(4-methyl-1H-1,3-benzodiazol-2-yl)-N-[(2S)-1,1,1-trifluoropropan-2-yl]pyridine-3-carboxamide (compound 2-11)

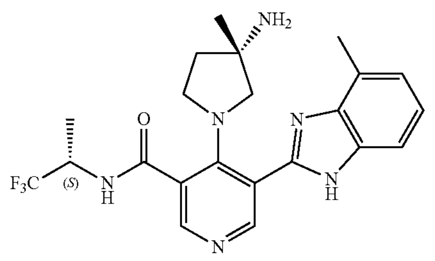

Step 13-1, preparation of methyl (S)-4-(3-((tert-butoxycarbonyl)amino)-3-methylpyrrolidin-1-yl)-6-chloronicotinate: to a mixture of tert-butyl (S)-(1-(3-bromo-5-formylpyridin-4-yl)-3-methylpyrrolidin-3-yl)carbamate (1.50 g, 1.0 Eq, 3.9 mmol "Step 2-1, Example 2"), 3-methylbenzene-1,2-diamine (1.40 g, 2.9 Eq, 11.0 mmol) and sodium metabisulfite (1.50 g, 2.0 Eq, 7.9 mmol) was added DMSO (15 mL). The resulting mixture was stirred at 50° C. for 1 hour. The reaction mixture was concentrated under reduced pressure and the remaining residue was purified by silica gel chromatography eluting with petroleum ether/EtOAc (3:1) to afford tert-butyl (S)-(1-(3-bromo-5-(4-methyl-1H-benzo[d]imidazol-2-yl)pyridin-4-yl)-3-methylpyrrolidin-3-yl)carbamate (960 mg, 49%). MS $(M+H)^+$=486.2, 488.2.

Step 13-2, preparation of ethyl (S)-4-(3-((tert-butoxycarbonyl)amino)-3-methylpyrrolidin-1-yl)-5-(4-methyl-1H-benzo[d]imidazol-2-yl)nicotinate: to a EtOH (10 mL) solution of tert-butyl (S)-(1-(3-bromo-5-(4-methyl-1H-benzo[d]imidazol-2-yl)pyridin-4-yl)-3-methylpyrrolidin-3-yl) carbamate (400 mg, 1.0 Eq, 0.822 mmol) was added dichloro[1,1'-bis(diphenylphosphino)ferrocene]palladium (II) dichloromethane adduct (68 mg, 0.10 Eq, 0.083 mmol) and triethylamine (250 mg, 3.0 Eq, 2.47 mmol). The resulting mixture was saturated with CO and then heated at 120° C. for 12 hours under 20 bar of CO. The reaction mixture was concentrated under vacuum and the remaining residue was purified by purified by silica gel chromatography eluting with petroleum ether/EtOAc (1:1). This resulted in ethyl (S)-4-(3-((tert-butoxycarbonyl)amino)-3-methylpyrrolidin-1-yl)-5-(4-methyl-1H-benzo[d]imidazol-2-yl)nicotinate (120 mg, 30.4%) as a brown solid. MS $(M+H)^+$=480.3.

Step 13-3, preparation of (S)-4-(3-((tert-butoxycarbonyl)amino)-3-methylpyrrolidin-1-yl)-5-(4-methyl-1H-benzo[d]imidazol-2-yl)nicotinic acid: to a EtOH (1.5 mL) solution of ethyl (S)-4-(3-((tert-butoxycarbonyl)amino)-3-methylpyrrolidin-1-yl)-5-(4-methyl-1H-benzo[d]imidazol-2-yl)nicotinate (100 mg, 1.0 Eq, 0.209 mmol) was added sodium hydroxide (125 mg, 15.0 Eq, 3.13 mmol) and water (0.5 mL). The resulting mixture was stirred at 50° C. for 36 hours. The reaction mixture was concentrated under reduced pressure followed by the addition of acetic acid until pH is about 5. The resulting mixture was separated, and the aqueous layer was treated with $NaHCO_3$ until pH is about 7. The aqueous solution was washed with methanol/DCM (1/10) three times to remove remaining starting material. The aqueous phase was spin-dried, and the salts crashed out were removed. The liquid layer was concentrated to afford 100 mg of crude product. This material was used for next step without further purification. MS $(M+H)^+$=452.3.

Step 13-4, preparation of tert-butyl ((S)-3-methyl-1-(3-(4-methyl-1H-benzo[d]imidazol-2-yl)-5-(((S)-1,1,1-trifluoropropan-2-yl)carbamoyl)pyridin-4-yl)pyrrolidin-3-yl)carbamate: to a DMF (2.0 mL) solution of (S)-4-(3-((tert-butoxycarbonyl)amino)-3-methylpyrrolidin-1-yl)-5-(4-methyl-1H-benzo[d]imidazol-2-yl)nicotinic acid (70 mg, 1.0 Eq, 0.16 mmol) was added HATU (60 mg, 1.0 Eq, 0.16 mmol), (S)-1,1,1-trifluoropropan-2-amine hydrochloride (25 mg, 1.1 Eq, 0.17 mmol) and N-ethyl-N-isopropylpropan-2-amine (70 mg, 3.5 Eq, 0.54 mmol). The resulting mixture was stirred at 50° C. for 1.5 hours. The crude product was purified by Prep-HPLC using the following conditions: Column, SunFire Prep $C_{18}$ OBD Column, 19*150 mm 5 μm; mobile phase, Water (0.1% TFA) and ACN (35.0% ACN up to 42.0% in 6 min); Total flow rate, 20 mL/min; Detector, UV 220 nm. This resulted in the TFA salt of tert-butyl ((S)-3-methyl-1-(3-(4-methyl-1H-benzo[d]imidazol-2-yl)-5-(((S)-1,1,1-trifluoropropan-2-yl)carbamoyl)pyridin-4-yl)pyrrolidin-3-yl)carbamate (60 mg, 59%) as a white solid. MS $(M+H)^+$=547.3.

Step 13-5, preparation of 4-[(3S)-3-amino-3-methylpyrrolidin-1-yl]-5-(4-methyl-1H-1,3-benzodiazol-2-yl)-N-[(2S)-1,1,1-trifluoropropan-2-yl]pyridine-3-carboxamide: to a DCM (3.0 mL) solution of tert-butyl ((S)-3-methyl-1-(3-(4-methyl-1H-benzo[d]imidazol-2-yl)-5-(((S)-1,1,1-trifluoropropan-2-yl)carbamoyl)pyridin-4-yl)pyrrolidin-3-yl)carbamate 2,2,2-trifluoroacetate (60 mg, 1.0 Eq, 0.091 mmol) was added TFA (1.0 mL). The resulting mixture was stirred at 25° C. for 2 hours. The reaction solution was concentrated and the remaining residue was purified by Prep-HPLC with the following conditions: Column, SunFire Prep $C_{18}$ OBD Column, 19*150 mm 5 μm 10 nm; mobile phase, Water (0.1% TFA) and ACN (26% ACN up to 38% in 6 min); Total flow rate, 20 mL/min; Detector, UV 220 nm. This resulted in the TFA salt of 4-((S)-3-amino-3-methylpyrrolidin-1-yl)-5-(4-methyl-1H-benzo[d]imidazol-2-yl)-N—((S)-1,1,1-trifluoropropan-2-yl)nicotinamide (54.0 mg, 88%) as a white solid. MS $(M+H)^+$=447.2.

The following compounds were prepared similarly to Example 13 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 2-1 | 379.2 |
| 2-2 | 405.3 |
| 2-3 | 393.2 |
| 2-4 | 419.2 |
| 2-5 | 421.3 |
| 2-6 | 427.2 |
| 2-7 | 433.2 |
| 2-8 | 409.2 |
| 2-9 | 395.2 |
| 2-10 | 447.2 |
| 2-24 | 451.2 |
| 2-25 | 441.5 |
| 2-27 | 461.5 |
| 2-28 | 449.3 |
| 2-31 | 419.2 |
| 2-32 | 461.3 |
| 2-33 | 445.3 |
| 2-34 | 453.3 |
| 2-35 | 445.3 |
| 2-36 | 447.4 |
| 2-37 | 445.5 |
| 2-38 | 433.5 |
| 2-39 | 431.0 |
| 2-40 | 461.3 |
| 2-41 | 473.3 |
| 2-42 | 445.3 |
| 2-43 | 445.3 |
| 2-44 | 473.7 |

Example 14. 4-[(3S)-3-amino-3-methylpyrrolidin-1-yl]-5-(7-fluoro-4-methyl-1H-1,3-benzodiazol-2-yl)-N-[(2S)-1,1,1-trifluoropropan-2-yl]pyridine-3-carboxamide (compound 2-30)

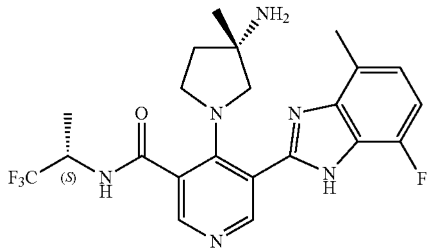

Step 14-1, preparation of methyl (S)-4-(3-((tert-butoxycarbonyl)amino)-3-methylpyrrolidin-1-yl)-5-formylnicotinate: to a MeOH (20 mL) solution of tert-butyl (S)-(1-(3-bromo-5-formylpyridin-4-yl)-3-methylpyrrolidin-3-yl) carbamate (1.9 g, 1.0 Eq, 4.9 mmol, "Step 2-1, Example 2") was added Pd(dppf)$Cl_2$ (0.30 g, 0.08 Eq, 0.4 mmol) and triethylamine (1.5 g, 3.0 Eq, 15 mmol) under atmospheric of CO. The resulting mixture was stirred at 100° C. for 2 hours under 15 bar of CO. The reaction mixture was concentrated under vacuum. The remaining residue was purified by silica gel chromatography eluting with ethyl acetate/petroleum ether (2:1) to afford methyl (S)-4-(3-((tert-butoxycarbonyl)amino)-3-methylpyrrolidin-1-yl)-5-formylnicotinate (1.75 g, 97%) as a yellow solid. MS $(M+H)^+$=364.1.

Step 14-2, preparation of methyl (S)-4-(3-((tert-butoxycarbonyl)amino)-3-methylpyrrolidin-1-yl)-5-(7-fluoro-4-methyl-1H-benzo[d]imidazol-2-yl)nicotinate: to a mixture of methyl (S)-4-(3-((tert-butoxycarbonyl)amino)-3-methylpyrrolidin-1-yl)-5-formylnicotinate (130 mg, 1.0 Eq, 0.358 mmol), $Na_2S_2O_5$ (102 mg, 1.50 Eq, 0.537 mmol) and 3-fluoro-6-methylbenzene-1,2-diamine (100 mg, 1.99 Eq, 0.713 mmol) was added DMSO (2.0 mL). The resulting mixture was stirred at 80° C. for 2 hours. The reaction crude mixtures were purified by Prep-HPLC using the following conditions: Column, C18 120 g; mobile phase, Water (0.1% FA) and ACN (30% ACN up to 80% in 8 min); Total flow rate, 70 mL/min; Detector, UV 220 nm. This resulted in methyl (S)-4-(3-((tert-butoxycarbonyl)amino)-3-methylpyrrolidin-1-yl)-5-(7-fluoro-4-methyl-1H-benzo[d]imidazol-2-yl)nicotinate (160 mg, 74%) as a yellow oil. MS $(M+H)^+$=484.3.

Step 14-3, preparation of (S)-4-(3-((tert-butoxycarbonyl)amino)-3-methylpyrrolidin-1-yl)-5-(7-fluoro-4-methyl-1H-benzo[d]imidazol-2-yl)nicotinic acid: to a mixture of methyl (S)-4-(3-((tert-butoxycarbonyl)amino)-3-methylpyrrolidin-1-yl)-5-(7-fluoro-4-methyl-1H-benzo[d]imidazol-2-yl)nicotinate (160 mg, 1.0 Eq, 0.26 mmol) and NaOH (160 mg, 15 Eq, 4.0 mmol) was added MeOH (5.0 mL) and water (0.5 mL). The resulting mixture was stirred at 60° C. for 16 hours. The reaction mixture was concentrated under reduced pressure, diluted with DCM/MeOH (100 mL), dried over anhydrous $Na_2SO_4$, filtered and concentrated under vacuum. This resulted in the crude (S)-4-(3-((tert-butoxycarbonyl)amino)-3-methylpyrrolidin-1-yl)-5-(7-fluoro-4-methyl-1H-benzo[d]imidazol-2-yl)nicotinic acid (110 mg, 89%) as a yellow oil. This material was used for next step without further purification. MS $(M+H)^+$=470.2.

Step 14-4, preparation of tert-butyl ((S)-1-(3-(7-fluoro-4-methyl-1H-benzo[d]imidazol-2-yl)-5-(((S)-1,1,1-trifluoropropan-2-yl)carbamoyl)pyridin-4-yl)-3-methylpyrrolidin-3-yl)carbamate: to a NMP (3.0 mL) solution of (S)-4-(3-((tert-butoxycarbonyl)amino)-3-methylpyrrolidin-1-yl)-5-(7-fluoro-4-methyl-1H-benzo[d]imidazol-2-yl)nicotinic acid (110 mg, 1.0 Eq, 0.234 mmol) was added HATU (134 mg, 1.50 Eq, 0.352 mmol) and DIEA (106 mg, 3.50 Eq, 0.820 mmol). The resulting mixture was stirred at 20° C. for 15 minutes followed by the addition of (S)-1,1,1-trifluoropropan-2-amine hydrochloride (53 mg, 1.50 Eq, 0.35 mmol). The resulting mixture was stirred at 50° C. for 5 hours. The reaction crude was purified by Prep-HPLC using the following conditions: Column, SunFire Prep $C_{18}$ OBD Column, 19*150 mm, 5 μm; mobile phase, Water (0.1% TFA) and ACN (30% ACN up to 70% in 8 min); Total flow rate, 20 mL/min; Detector, UV 220 nm. This resulted in tert-butyl ((S)-1-(3-(7-fluoro-4-methyl-1H-benzo[d]imidazol-2-yl)-5-(((S)-1,1,1-trifluoropropan-2-yl)carbamoyl)pyridin-4-yl)-3-methylpyrrolidin-3-yl)carbamate (60 mg, 45%) as a white solid. MS $(M+H)^+$=565.4.

Step 14-5, preparation of 4-((S)-3-amino-3-methylpyrrolidin-1-yl)-5-(7-fluoro-4-methyl-1H-benzo[d]imidazol-2-yl)-N—((S)-1,1,1-trifluoropropan-2-yl)nicotinamide: to a DCM (2.0 mL) solution of tert-butyl ((S)-1-(3-(7-fluoro-4-methyl-1H-benzo[d]imidazol-2-yl)-5-(((S)-1,1,1-trifluoropropan-2-yl)carbamoyl)pyridin-4-yl)-3-methylpyrrolidin-3-yl)carbamate (60 mg, 1.0 Eq, 0.11 mmol) was added TFA (2.0 mL). The reaction mixture was stirred at 20° C. for 1 hour. The reaction crude was concentrated under reduced pressure and lyophilized. This resulted in the TFA salt of 4-((S)-3-amino-3-methylpyrrolidin-1-yl)-5-(7-fluoro-4-methyl-1H-benzo[d]imidazol-2-yl)-N—((S)-1,1,1-trifluoropropan-2-yl)nicotinamide (45.3 mg, 62%) as light brown solid. MS $(M+H)^+$=465.2.

The following compounds were prepared similarly to Example 14 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 2-45 | 491.2 |

Example 15. 4-[(3S)-3-amino-3-methylpyrrolidin-1-yl]-N-[(1S)-1-cyclopropylethyl]-N-methyl-5-(4-methyl-1H-1,3-benzodiazol-2-yl)pyridine-3-carboxamide (compound 2-29)

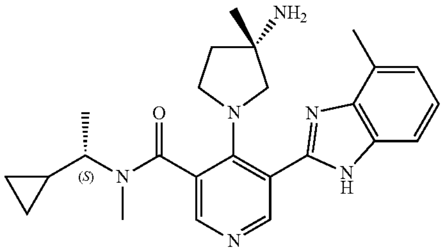

Step 15-1, preparation of 2-(5-bromo-4-chloropyridin-3-yl)-4-methyl-1H-benzo[d]imidazole: to a mixture of 5-bromo-4-chloronicotinaldehyde (250 mg, 1.0 Eq, 1.13 mmol) and 3-methylbenzene-1,2-diamine (208 mg, 1.50 Eq, 1.70 mmol) was added DMSO (5.0 mL). The reaction mixture was stirred at 50° C. for 1 hour. The reaction mixture was poured into water (50 mL) and extracted with EtOAc (3×50 mL). Organic layers were combined, washed with water (2×50 mL) and brine (50 mL), dried over anhydrous $Na_2SO_4$ and concentrated under reduced pressure. This resulted in crude 2-(5-bromo-4-chloropyridin-3-yl)-4-methyl-1H-benzo[d]imidazole (320 mg, 44%) as a brown solid. This material was used for next step without further purification. MS (M+H)$^+$=322.1, 324.1.

Step 15-2, preparation of tert-butyl (S)-(1-(3-bromo-5-(4-methyl-1H-benzo[d]imidazol-2-yl)pyridin-4-yl)-3-methylpyrrolidin-3-yl)carbamate: to a mixture of 2-(5-bromo-4-chloropyridin-3-yl)-4-methyl-1H-benzo[d]imidazole (200 mg, 1.0 Eq, 0.620 mmol) and tert-butyl (S)-(3-methylpyrrolidin-3-yl)carbamate (130 mg, 1.05 Eq, 0.649 mmol) was added MeCN (5.0 mL) and DIEA (0.34 mL, 3.12 Eq, 1.93 mmol). The resulting solution was stirred for at 80° C. for 2 hours. The reaction mixture was cooled to room temperature and concentrated under vacuum. The remaining residue was purified by silica gel chromatography eluting with ethyl acetate/petroleum ether (1:3) to afford tert-butyl (S)-(1-(3-bromo-5-(4-methyl-1H-benzo[d]imidazol-2-yl)pyridin-4-yl)-3-methylpyrrolidin-3-yl)carbamate (210 mg, 69.6%) as a yellow oil. MS (M+H)$^+$=486.0, 488.0.

Step 15-3, preparation of methyl (S)-4-(3-((tert-butoxycarbonyl)amino)-3-methylpyrrolidin-1-yl)-5-(4-methyl-1H-benzo[d]imidazol-2-yl)nicotinate: from tert-butyl (S)-(1-(3-bromo-5-(4-methyl-1H-benzo[d]imidazol-2-yl)pyridin-4-yl)-3-methylpyrrolidin-3-yl)carbamate (210 mg, 1.0 Eq, 0.432 mmol), the title compound (200 mg, 77%) was prepared using a similar method to the one described in as described in "Step 13-2, Example 13". MS (M+H)$^+$=466.2.

Step 15-4, preparation of (S)-4-(3-((tert-butoxycarbonyl)amino)-3-methylpyrrolidin-1-yl)-5-(4-methyl-1H-benzo[d]imidazol-2-yl)nicotinic acid: from methyl (S)-4-(3-((tert-butoxycarbonyl)amino)-3-methylpyrrolidin-1-yl)-5-(4-methyl-1H-benzo[d]imidazol-2-yl)nicotinate (200 mg, 1.0 Eq, 0.33 mmol), the title compound (140 mg, 94%) was prepared using a similar method to the one described in as described in "Step 13-3, Example 13". MS (M+H)$^+$=452.2.

Step 15-5, preparation of tert-butyl ((S)-1-(3-(((S)-1-cyclopropylethyl)(methyl)carbamoyl)-5-(4-methyl-1H-benzo[d]imidazol-2-yl)pyridin-4-yl)-3-methylpyrrolidin-3-yl)carbamate: from (S)-4-(3-((tert-butoxycarbonyl)amino)-3-methylpyrrolidin-1-yl)-5-(4-methyl-1H-benzo[d]imidazol-2-yl)nicotinic acid (65 mg, 1.0 Eq, 0.14 mmol), the title compound (25 mg, 33%) was prepared using a similar method to the one described in as described in "Step 13-4, Example 13". MS (M+H)$^+$=533.3.

Step 15-6, preparation of 4-[(3S)-3-amino-3-methylpyrrolidin-1-yl]-N-[(1S)-1-cyclopropylethyl]-N-methyl-5-(4-methyl-1H-1,3-benzodiazol-2-yl)pyridine-3-carboxamide: from tert-butyl ((S)-1-(3-(((S)-1-cyclopropylethyl)(methyl)carbamoyl)-5-(4-methyl-1H-benzo[d]imidazol-2-yl)pyridin-4-yl)-3-methylpyrrolidin-3-yl)carbamate (25 mg, 1.0 Eq, 0.047 mmol), the title compound (25 mg, 33%) was prepared using a similar method to the one described in as described in "Step 13-5, Example 13". MS (M+H)$^+$=433.3.

The following compounds were prepared similarly to Example 15 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 2-12 | 391.3 |
| 2-13 | 405.3 |
| 2-14 | 419.3 |
| 2-15 | 417.3 |
| 2-16 | 433.4 |
| 2-17 | 469.3 |
| 2-18 | 447.3 |
| 2-19 | 433.3 |
| 2-20 | 433.3 |
| 2-21 | 419.3 |
| 2-22 | 405.3 |
| 2-23 | 419.3 |
| 2-26 | 471.3 |

Example 16. 4-[(3S)-3-amino-3-methylpyrrolidin-1-yl]-N-(4,4-difluorocyclohexyl)-5-[3-(difluoromethoxy)-5-fluorophenyl]-6-methylpyridine-3-carboxamide (compound 1-174)

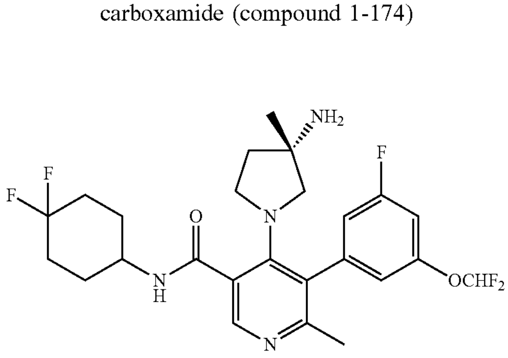

Step 16-1, preparation of ethyl (S)-4-(3-((tert-butoxycarbonyl)amino)-3-methylpyrrolidin-1-yl)-6-methylnicotinate:

to a 1,4-dioxane (30 mL) solution of ethyl (S)-4-(3-((tert-butoxycarbonyl)amino)-3-methylpyrrolidin-1-yl)-6-chloronicotinate (3.00 g, 1 Eq, 7.82 mmol, "Step 9-2, Example 9") was added 2,4,6-trimethyl-1,3,5,2,4,6-trioxatriborinane (20.0 g, 10 Eq, 80 mmol) (50% w/w in THF), Pd(amphos) $Cl_2$ (277 mg, 0.0501 Eq, 391 μmol) and potassium carbonate ((3.24 g, 3.00 Eq, 23.4 mmol) under atmospheric nitrogen. The resulting mixture was stirred at 80° C. for 2 hours. The reaction mixture was quenched with water (100 mL) and extracted with EtOAc (3×100 mL). Organic layers were combined, washed with brine (100 mL), dried over anhydrous $Na_2SO_4$ and concentrated under reduced pressure. The remaining residue was purified by silica gel chromatography eluting with DCM/MeOH (8/1) to afford ethyl (S)-4-(3-((tert-butoxycarbonyl)amino)-3-methylpyrrolidin-1-yl)-6-methylnicotinate (3.02 g, 96%, 90% purity) as a yellow solid. MS $(M+H)^+$=364.2.

Step 16-2, preparation of ethyl (S)-5-bromo-4-(3-((tert-butoxycarbonyl)amino)-3-methylpyrrolidin-1-yl)-6-methylnicotinate: to a mixture of ethyl (S)-4-(3-((tert-butoxycarbonyl)amino)-3-methylpyrrolidin-1-yl)-6-methylnicotinate (900 mg, 1 Eq, 2.48 mmol) and 1,3,5-tribromo-1,3,5-triazinane-2,4,6-trione (1.18 g, 1.30 Eq, 3.23 mmol) was added AcOH (25 mL) and DCM (5.0 mL). The resulting mixture was stirred at 0° C. for 10 min. The reaction mixture was quenched with saturated $NaHSO_3$ solution (100 mL), extracted with EtOAc (2×100 mL), washed with water (2×100 mL), saturated $NaHCO_3$ solution (100 mL), brine (20 mL), dried over anhydrous $Na_2SO_4$ and concentrated. The remaining residue was purified by silica gel chromatography eluting with petroleum ether/EtOAc (2/1) to afford ethyl (S)-5-bromo-4-(3-((tert-butoxycarbonyl)amino)-3-methylpyrrolidin-1-yl)-6-methylnicotinate (400 mg, 36.5%) as a yellow solid. MS $(M+H)^+$=442.1, 444.1.

Step 16-3, preparation of ethyl (S)-4-(3-((tert-butoxycarbonyl)amino)-3-methylpyrrolidin-1-yl)-5-(3-(difluoromethoxy)-5-fluorophenyl)-6-methylnicotinate: to a mixture of ethyl (S)-5-bromo-4-(3-((tert-butoxycarbonyl)amino)-3-methylpyrrolidin-1-yl)-6-methylnicotinate ((400 mg, 1 Eq, 904 μmol), (3-(difluoromethoxy)-5-fluorophenyl)boronic acid (372 mg, 2.00 Eq, 1.81 mmol), Pd(DtBPF)$Cl_2$ (59 mg, 0.10 Eq, 91 μmol) and potassium phosphate (576 mg, 3.00 Eq, 2.71 mmol) was added Toluene (8.0 mL) and water (0.8 mL) under atmospheric nitrogen. The resulting mixture was stirred at 80° C. for 1 hour. The reaction mixture was concentrated and purified by silica gel chromatography eluting with petroleum ether/EtOAc (3/1) to afford ethyl (S)-4-(3-((tert-butoxycarbonyl)amino)-3-methylpyrrolidin-1-yl)-5-(3-(difluoromethoxy)-5-fluorophenyl)-6-methylnicotinate (270 mg, 57.0%) as a yellow solid. MS $(M+H)^+$=524.2.

Step 16-4, preparation of (S)-4-(3-((tert-butoxycarbonyl)amino)-3-methylpyrrolidin-1-yl)-5-(3-(difluoromethoxy)-5-fluorophenyl)-6-methylnicotinic acid: to a MeOH (4.0 mL) solution of ethyl (S)-4-(3-((tert-butoxycarbonyl)amino)-3-methylpyrrolidin-1-yl)-5-(3-(difluoromethoxy)-5-fluorophenyl)-6-methylnicotinate (270 mg, 1 Eq, 516 μmol) was added LiOH (185 mg, 15.0 Eq, 7.72 mmol) and water (2.0 mL). The reaction mixture was stirred at 60° C. for 2 hours. The reaction mixture was concentrated under reduced pressure to remove most of MeOH, and the remaining residue was diluted with water (5 mL). Saturated $NaHSO_4$ solution was added until pH is ~6.0. The resulting mixture was extracted with EtOAc (3×50 mL). Organic layers were combined, washed with brine (50 mL), dried over anhydrous $Na_2SO_4$ and concentrated under vacuum to afford (S)-4-(3-((tert-butoxycarbonyl)amino)-3-methylpyrrolidin-1-yl)-5-(3-(difluoromethoxy)-5-fluorophenyl)-6-methylnicotinic acid (250 mg, 97.8%) as light yellow solid. This material was used for next step without further purification. MS $(M+H)^+$=496.4.

Step 16-5, preparation of tert-butyl (S)-(1-(5-((4,4-difluorocyclohexyl)carbamoyl)-3-(3-(difluoromethoxy)-5-fluorophenyl)-2-methylpyridin-4-yl)-3-methylpyrrolidin-3-yl)carbamate: to a DMF (2.0 mL) solution of (S)-4-(3-((tert-butoxycarbonyl)amino)-3-methylpyrrolidin-1-yl)-5-(3-(difluoromethoxy)-5-fluorophenyl)-6-methylnicotinic acid (80 mg, 1 Eq, 0.16 mmol) was added HATU (92 mg, 1.5 Eq, 0.24 mmol), and DIEA (0.11 mL, 4.0 Eq, 0.64 mmol). The resulting mixture was stirred at 25° C. for 15 min, followed by the addition of 4,4-difluorocyclohexan-1-amine hydrochloride (55 mg, 2.0 Eq, 0.32 mmol). The reaction mixture was stirred at 25° C. for 1 hour. The crude product was purified by Prep-HPLC using the following conditions: Column, SunFire Prep $C_{18}$ OBD Column, 19*150 mm 5 μm; mobile phase, Water (0.05% $NH_3 \cdot H_2O$) and ACN (40.0% ACN up to 65.0% in 7 min); Total flow rate, 20 mL/min; Detector, UV 220 nm. This resulted in tert-butyl (S)-(1-(5-((4,4-difluorocyclohexyl)carbamoyl)-3-(3-(difluoromethoxy)-5-fluorophenyl)-2-methylpyridin-4-yl)-3-methylpyrrolidin-3-yl)carbamate (65 mg, 66%) as a white solid. MS $(M+H)^+$=613.4.

Step 16-5, preparation of (S)-4-(3-amino-3-methylpyrrolidin-1-yl)-N-(4,4-difluorocyclohexyl)-5-(3-(difluoromethoxy)-5-fluorophenyl)-6-methylnicotinamide: to a DCM (3.0 mL) of tert-butyl (S)-(1-(5-((4,4-difluorocyclohexyl)carbamoyl)-3-(3-(difluoromethoxy)-5-fluorophenyl)-2-methylpyridin-4-yl)-3-methylpyrrolidin-3-yl)carbamate (65 mg, 1 Eq, 0.11 mmol) was added TFA (2.0 mL). The resulting mixture was stirred at 25° C. for 1 hour. The reaction mixture was concentrated and lyophilized under vacuum to afford the TFA salt of (S)-4-(3-amino-3-methylpyrrolidin-1-yl)-N-(4,4-difluorocyclohexyl)-5-(3-(difluoromethoxy)-5-fluorophenyl)-6-methylnicotinamide (62.2 mg, 79%) as a white solid. MS $(M+H)^+$=513.2.

The following compounds were prepared similarly to Example 16 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-171 | 491.1 |
| 1-172 | 485.2 |
| 1-173 | 463.2 |
| 1-181 | 465.2 |
| 1-223 | 445.2 |
| 1-224 | 431.2 |
| 1-230 | 429.1 |
| 1-231 | 477.1 |
| 1-232 | 459.1 |
| 1-233 | 451.2 |
| 1-242 | 444.1 |
| 1-243 | 468.2 |
| 1-255 | 424.2 |
| 1-256 | 410.2 |
| 1-257 | 462.2 |
| 1-258 | 448.2 |
| 1-268 | 484.3 |
| 1-269 | 456.2 |
| 1-272 | 417.2 |
| 1-275 | 462.1 |
| 1-276 | 445.1 |
| 1-277 | 467.2 |
| 1-278 | 433.2 |

-continued

| Compound no. | MS (M + H)$^+$ |
|---|---|
| 1-279 | 443.1 |
| 1-280 | 435.3 |
| 1-287 | 459.2 |
| 1-288 | 415.2 |
| 1-289 | 431.2 |

Example 17. 4-[(3S)-3-amino-3-methylpyrrolidin-1-yl]-N-[(1S)-1-cyclopropylethyl]-2-methoxy-2'-(trifluoromethyl)-[3,4'-bipyridine]-5-carboxamide (compound 1-166)

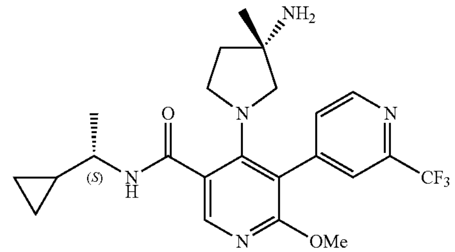

Step 17-1, preparation of methyl (S)-4-(3-((tert-butoxycarbonyl)amino)-3-methylpyrrolidin-1-yl)-6-methoxynicotinate: to a MeOH (10 mL) solution of ethyl (S)-4-(3-((tert-butoxycarbonyl)amino)-3-methylpyrrolidin-1-yl)-6-chloronicotinate (2.0 g, 1 Eq, 5.2 mmol, "Step 9-1, Example 9") was added sodium methanolate (2.4 g, 8.5 Eq, 44 mmol). The resulting mixture was stirred at 65° C. for 16 hours. The reaction mixture was quenched with water (100 mL), extracted with AcOEt (3×40 mL). Organic layers were combined, washed with brine, dried and concentrated under vacuum. The remaining residue was purified by silica gel chromatography eluting with ethyl acetate/petroleum ether (⅓) to afford methyl (S)-4-(3-((tert-butoxycarbonyl)amino)-3-methylpyrrolidin-1-yl)-6-methoxynicotinate (930 mg, 49%) as a yellow solid. MS (M+H)$^+$=366.3.

Step 17-2, preparation of (S)-4-(3-((tert-butoxycarbonyl)amino)-3-methylpyrrolidin-1-yl)-6-methoxynicotinic acid: from methyl (S)-4-(3-((tert-butoxycarbonyl)amino)-3-methylpyrrolidin-1-yl)-6-methoxynicotinate (900 mg, 1.0 Eq, 2.46 mmol), the title compound (865 mg) was prepared using a similar method to the one described in "Step 11-5, Example 11". MS (M+H)$^+$=352.2.

Step 17-3, preparation of tert-butyl ((S)-1-(5-(((S)-1-cyclopropylethyl)carbamoyl)-2-methoxypyridin-4-yl)-3-methylpyrrolidin-3-yl)carbamate: to a DMF (10 mL) solution of (S)-4-(3-((tert-butoxycarbonyl)amino)-3-methylpyrrolidin-1-yl)-6-methoxynicotinic acid (900 mg, 1 Eq, 2.56 mmol) was added DIEA (1.0 g, 1.4 mL, 3.0 Eq, 7.7 mmol) and HATU (1.2 g, 1.2 Eq, 3.2 mmol). The resulting mixture was stirred at room temperature for 10 min followed by the addition of (S)-1-cyclopropylethan-1-amine hydrochloride (600 mg, 1.93 Eq, 4.93 mmol). The reaction mixture was stirred at ambient temperature for 16 hours. The reaction crude was purified by Prep-HPLC using the following conditions: Column, SunFire prep OBD 19*150 mm 5 μm C-01; mobile phase, Water (0.05% FA) and ACN (40% ACN up to 80% in 7 min); Detector 254 nm & 220 nm; flow rate 20 mL/min. This resulted in tert-butyl ((S)-1-(5-(((S)-1-cyclopropylethyl)carbamoyl)-2-methoxypyridin-4-yl)-3-methylpyrrolidin-3-yl)carbamate (700 mg, 65.3%) as a white solid. MS (M+H)$^+$=420.2.

Step 17-4, preparation of tert-butyl ((S)-1-(3-bromo-5-(((S)-1-cyclopropylethyl)carbamoyl)-2-methoxypyridin-4-yl)-3-methylpyrrolidin-3-yl)carbamate: to a DCM (4.0 mL) of tert-butyl ((S)-1-(5-(((S)-1-cyclopropylethyl)carbamoyl)-2-methoxypyridin-4-yl)-3-methylpyrrolidin-3-yl)carbamate (700 mg, 1 Eq, 1.67 mmol) was added AcOH (20 mL) and 1,3,5-tribromo-1,3,5-triazinane-2,4,6-trione (600 mg, 0.981 Eq, 1.64 mmol) at 0° C. The resulting mixture was stirred at 0° C. for 20 min. The reaction crude was quenched with $NaHSO_3$ (10 mL) and extracted with AcOEt (3×40 mL). Organic layers were combined, washed with brine, dried and concentrated under vacuum. The remaining residue was purified by silica gel chromatography eluting with ethyl acetate/petroleum ether (⅓) to afford tert-butyl ((S)-1-(3-bromo-5-(((S)-1-cyclopropylethyl)carbamoyl)-2-methoxypyridin-4-yl)-3-methylpyrrolidin-3-yl)carbamate (500 mg, 60.1%) as a yellow solid. MS (M+H)$^+$=500.2, 502.2.

Step 17-5, preparation of tert-butyl ((S)-1-(5-(((S)-1-cyclopropylethyl)carbamoyl)-2-methoxy-2'-(trifluoromethyl)-[3,4'-bipyridin]-4-yl)-3-methylpyrrolidin-3-yl)carbamate: to a mixture of tert-butyl ((S)-1-(3-bromo-5-(((S)-1-cyclopropylethyl)carbamoyl)-2-methoxypyridin-4-yl)-3-methylpyrrolidin-3-yl)carbamate (70 mg, 1 Eq, 0.14 mmol), (2-(trifluoromethyl)pyridin-4-yl)boronic acid (60 mg, 2.2 Eq, 0.31 mmol), $Pd(dppf)Cl_2$ (10 mg, 0.097 Eq, 14 μmol) and potassium phosphate (90 mg, 3.0 Eq, 0.42 mmol) was added 1,4-Dioxane (2.0 mL) and water (0.2 mL) under atmospheric nitrogen. The resulting mixture was stirred at 80° C. for 1 hour. The reaction mixture was concentrated under reduced pressure. The remaining residue was purified by silica gel column chromatography eluting with DCM/MeOH (5:1) to afford crude product. This material was re-purified by Prep-HPLC using the following conditions: Column, SunFire prep OBD 19*150 mm 5 μm C-01; mobile phase, Water (0.05% FA) and MeCN (27% MeCN up to 47% in 7 min); Detector, 254 nm; flow rate 20 mL/min. This resulted in tert-butyl ((S)-1-(5-(((S)-1-cyclopropylethyl)carbamoyl)-2-methoxy-2'-(trifluoromethyl)-[3,4'-bipyridin]-4-yl)-3-methylpyrrolidin-3-yl)carbamate (45 mg, 59%) as a white solid. MS (M+H)$^+$=564.5.

Step 17-6, preparation of 4-[(3S)-3-amino-3-methylpyrrolidin-1-yl]-N-[(1S)-1-cyclopropylethyl]-2-methoxy-2'-(trifluoromethyl)-[3,4'-bipyridine]-5-carboxamide: to a DCM (3.0 mL) solution of tert-butyl ((S)-1-(5-(((S)-1-cyclopropylethyl)carbamoyl)-2-methoxy-2'-(trifluoromethyl)-[3,4'-bipyridin]-4-yl)-3-methylpyrrolidin-3-yl)carbamate (45 mg, 1 Eq, 80 μmol) was added TFA (1.0 mL). The resulting mixture was stirred at ambient temperature for 1 hour. The reaction solution was concentrated and freeze-dried under vacuum to afford the TFA salt of 4-((S)-3-amino-3-methylpyrrolidin-1-yl)-N—((S)-1-cyclopropylethyl)-2-methoxy-2'-(trifluoromethyl)-[3,4'-bipyridine]-5-carboxamide as a light yellow solid. MS (M+H)$^+$=464.2.

The following compounds were prepared similarly to Example 17 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)+ |
|---|---|
| 1-153 | 438.3 |
| 1-154 | 479.2 |
| 1-164 | 481.2 |
| 1-165 | 461.2 |
| 1-167 | 430.2 |
| 1-182 | 477.3 |
| 1-183 | 477.1 |
| 1-184 | 503.3 |
| 1-185 | 439.3 |
| 1-186 | 465.3 |
| 1-187 | 442.4 |
| 1-188 | 507.1 |

Example 18. 4-[(3S)-3-amino-3-methylpyrrolidin-1-yl]-N-[(1S)-1-cyclopropylethyl]-5-(3,5-difluorophenyl)-6-(2,2,2-trifluoroethoxy)pyridine-3-carboxamide (compound 1-190)

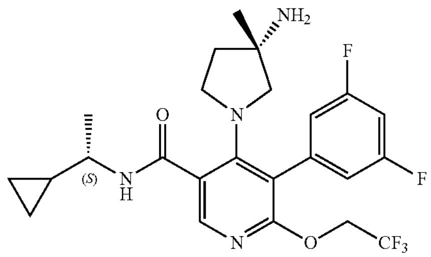

Step 18-1, preparation of 1 tert-butyl ((S)-1-(3-bromo-2-chloro-5-(((S)-1-cyclopropylethyl)carbamoyl)pyridin-4-yl)-3-methylpyrrolidin-3-yl)carbamate: from tert-butyl ((S)-1-(2-chloro-5-(((S)-1-cyclopropylethyl)carbamoyl)pyridin-4-yl)-3-methylpyrrolidin-3-yl)carbamate (1.6 g, 1 Eq, 4.5 mmol, "Step 9-3, Example 9"), the title compound (1.30 g) was prepared using a similar method to the one described in "Step 5-3, Example 5". MS $(M+H)^+$=503.2.

Step 18-2, preparation of tert-butyl ((S)-1-(2-chloro-5-(((S)-1-cyclopropylethyl)carbamoyl)-3-(3,5-difluorophenyl)pyridin-4-yl)-3-methylpyrrolidin-3-yl)carbamate: to a mixture of tert-butyl ((S)-1-(3-bromo-2-chloro-5-(((S)-1-cyclopropylethyl)carbamoyl)pyridin-4-yl)-3-methylpyrrolidin-3-yl)carbamate (1.3 g, 1 Eq, 2.6 mmol), (3,5-difluorophenyl)boronic acid (420 mg, 1.0 Eq, 2.66 mmol), $K_3PO_4$ (1.6 g, 2.9 Eq, 7.5 mmol) and Pd(DtBPF)$Cl_2$ (180 mg, 0.11 Eq, 276 μmol) was added Toluene (20 mL) and water (2.0 mL). The resulting mixture was stirred at 60° C. for 30 min. The reaction mixture was concentrated and the remaining residue was purified by silica gel chromatography eluting with DCM/MeOH (5:1) to afford tert-butyl ((S)-1-(2-chloro-5-(((S)-1-cyclopropylethyl)carbamoyl)-3-(3,5-difluorophenyl)pyridin-4-yl)-3-methylpyrrolidin-3-yl)carbamate (1.0 g, 72%) as a yellow solid. MS $(M+H)^+$=535.2.

Step 18-3, preparation of tert-butyl ((S)-1-(5-(((S)-1-cyclopropylethyl)carbamoyl)-3-(3,5-difluorophenyl)-2-(2,2,2-trifluoroethoxy)pyridin-4-yl)-3-methylpyrrolidin-3-yl)carbamate: to a mixture of tert-butyl ((S)-1-(2-chloro-5-(((S)-1-cyclopropylethyl)carbamoyl)-3-(3,5-difluorophenyl) pyridin-4-yl)-3-methylpyrrolidin-3-yl)carbamate (40 mg, 1 Eq, 75 μmol), cesium carbonate (70 mg, 2.9 Eq, 0.21 mmol), 2,2,2-trifluoroethan-1-ol (80 mg, 11 Eq, 0.80 mmol) and $Pd_2(dba)_3 \cdot CHCl_3$ (8 mg, 0.1 Eq, 9 μmol) and BINAP (15 mg, 0.32 Eq, 24 μmol) was added Toluene (2.0 mL) under atmospheric nitrogen. The resulting mixture was stirred at 100° C. for 16 hours. The reaction mixture was concentrated and the remaining residue was purified by silica gel chromatography eluting with DCM/MeOH (20:1) to afford tert-butyl ((S)-1-(5-(((S)-1-cyclopropylethyl)carbamoyl)-3-(3,5-difluorophenyl)-2-(2,2,2-trifluoroethoxy)pyridin-4-yl)-3-methylpyrrolidin-3-yl)carbamate (20 mg, 45%) as a light yellow solid. MS $(M+H)^+$=599.4.

Step 18-4, preparation of 4-[(3S)-3-amino-3-methylpyrrolidin-1-yl]-N-[(1S)-1-cyclopropylethyl]-5-(3,5-difluorophenyl)-6-(2,2,2-trifluoroethoxy)pyridine-3-carboxamide: to a DCM (3.0 mL) solution of tert-butyl ((S)-1-(5-(((S)-1-cyclopropylethyl)carbamoyl)-3-(3,5-difluorophenyl)-2-(2,2,2-trifluoroethoxy)pyridin-4-yl)-3-methylpyrrolidin-3-yl) carbamate (30 mg, 1 Eq, 50 μmol) was added TFA (1.0 mL). The resulting mixture was stirred at 25° C. for 1 hour. The reaction solution was concentrated and the remaining residue was purified by Prep-HPLC using the following conditions: Column, SunFire prep OBD 19*150 mm 5 μm C-01; mobile phase, Water (0.05% FA) and ACN (15% ACN up to 38% in 7 min); Detector, 254 nm. This resulted in the formic acid salt of 4-((S)-3-amino-3-methylpyrrolidin-1-yl)-N—((S)-1-cyclopropylethyl)-5-(3,5-difluorophenyl)-6-(2,2,2-trifluoroethoxy)nicotinamide (21.6 mg, 79%) as a white solid. MS $(M+H)^+$=499.2.

The following compounds were prepared similarly to Example 18 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)+ |
|---|---|
| 1-191 | 457.2 |
| 1-200 | 539.2 |
| 1-201 | 553.3 |
| 1-202 | 567.4 |
| 1-203 | 511.3 |
| 1-204 | 525.3 |
| 1-205 | 539.3 |
| 1-246 | 461.2 |
| 1-247 | 475.1 |
| 1-264 | 489.2 |
| 1-265 | 503.3 |
| 1-266 | 487.2 |
| 1-267 | 507.2 |

Example 19. 4-[(3S)-3-amino-3-methylpyrrolidin-1-yl]-N-[(1S)-1-cyclopropylethyl]-5-(3,5-difluorophenyl)-6-(trifluoromethyl)pyridine-3-carboxamide (compound 1-189)

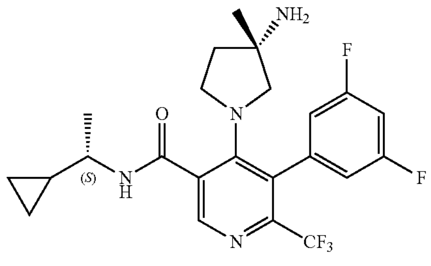

Step 19-1, preparation of tert-butyl (S)-(1-(5-formyl-2-(trifluoromethyl)pyridin-4-yl)-3-methylpyrrolidin-3-yl)carbamate: to a mixture of 4-chloro-6-(trifluoromethyl)nicotinaldehyde (100 mg, 1 Eq, 477 µmol), tert-butyl (S)-(3-methylpyrrolidin-3-yl)carbamate (110 mg, 1.15 Eq, 549 µmol), and N-ethyl-N-isopropylpropan-2-amine (200 mg, 3.24 Eq, 1.55 mmol) was added MeCN (2.0 mL). The resulting mixture was stirred at 80° C. for 1 hour. The reaction mixture was concentrated and the remaining residue was purified by silica gel chromatography eluting with petroleum/EtOAc (3/1) to afford tert-butyl (S)-(1-(5-formyl-2-(trifluoromethyl)pyridin-4-yl)-3-methylpyrrolidin-3-yl) carbamate (100 mg, 56.1%) as a yellow solid. MS $(M+H)^+$=374.1.

Step 19-2, preparation of (S)-4-(3-((tert-butoxycarbonyl) amino)-3-methylpyrrolidin-1-yl)-6-(trifluoromethyl)nicotinic acid: to a mixture of tert-butyl (S)-(1-(5-formyl-2-(trifluoromethyl)pyridin-4-yl)-3-methylpyrrolidin-3-yl) carbamate (90 mg, 1 Eq, 0.24 mmol), 2-methylbut-2-ene (500 mg, 30 Eq, 7.13 mmol), $NaH_2PO_4 \cdot 2H_2O$ (100 mg, 2.7 Eq, 641 µmol), and sodium chlorite (36 mg, 1.7 Eq, 0.40 mmol) was added 2-methylpropan-2-ol (2.0 mL) and water (0.4 mL). The resulting mixture was stirred at 30° C. for 1 hour. The resulting solution was diluted with saturated $NaHSO_4$ (20 mL) and extracted with ethyl acetate (3×20 mL). Organic layers were combined, washed with brine (2×20 mL), dried over anhydrous sodium sulfate and concentrated under vacuum. This resulted in crude (S)-4-(3-((tert-butoxycarbonyl)amino)-3-methylpyrrolidin-1-yl)-6-(trifluoromethyl)nicotinic acid (95 mg, 81%) as a yellow solid. This material was used for next step without further purification. MS $(M+H)^+$=390.1.

Step 19-3, preparation of tert-butyl ((S)-1-(5-(((S)-1-cyclopropylethyl)carbamoyl)-2-(trifluoromethyl)pyridin-4-yl)-3-methylpyrrolidin-3-yl)carbamate: to a DMF (2.0 mL) solution of (S)-4-(3-((tert-butoxycarbonyl)amino)-3-methylpyrrolidin-1-yl)-6-(trifluoromethyl)nicotinic acid (95 mg, 1 Eq, 0.24 mmol) was added HATU (100 mg, 1.1 Eq, 263 µmol) and DIEA (100 mg, 0.14 mL, 3.2 Eq, 774 µmol). The resulting mixture was stirred at ambient temperature for 15 min followed by the addition of (S)-1-cyclopropylethan-1-amine hydrochloride (40 mg, 1.3 Eq, 0.33 mmol). The reaction mixture was stirred at ambient temperature for 1 hour. The resulting solution was diluted with saturated $NaHCO_3$ (20 mL) and extracted with ethyl acetate (3×20 mL). Organic layers were combined, washed with brine (2×20 mL), dried over anhydrous sodium sulfate and concentrated under vacuum. The remaining residue was purified by silica gel chromatography eluting with petroleum/EtOAc (2/1). This resulted in tert-butyl ((S)-1-(5-(((S)-1-cyclopropylethyl)carbamoyl)-2-(trifluoromethyl)pyridin-4-yl)-3-methylpyrrolidin-3-yl)carbamate (80 mg, 72%) as a yellow solid. MS $(M+H)^+$=457.2.

Step 19-4, preparation of tert-butyl ((S)-1-(3-bromo-5-(((S)-1-cyclopropylethyl)carbamoyl)-2-(trifluoromethyl) pyridin-4-yl)-3-methylpyrrolidin-3-yl)carbamate: to a DCM (0.5 mL) solution of tert-butyl ((S)-1-(5-(((S)-1-cyclopropylethyl)carbamoyl)-2-(trifluoromethyl)pyridin-4-yl)-3-methylpyrrolidin-3-yl)carbamate (75 mg, 1 Eq, 0.16 mmol) was added AcOH (2.5 mL) 1,3,5-tribromo-1,3,5-triazinane-2,4,6-trione (75 mg, 1.2 Eq, 0.21 mmol) at 0° C. The resulting mixture was stirred at 0° C. for 15 min. The reaction solution was quenched with saturated $Na_2CO_3$ (20 mL) followed by the addition of saturated $NaHSO_4$ until pH was adjusted to 6-7. The resulting solution was extracted with ethyl acetate (3×20 mL) and organic layers were combined. The organic was washed with brine (2×20 mL), dried over anhydrous sodium sulfate and concentrated under vacuum. The remaining residue was purified by silica gel chromatography eluting with ethyl acetate/petroleum ether (1:3) to afford tert-butyl ((S)-1-(3-bromo-5-(((S)-1-cyclopropylethyl)carbamoyl)-2-(trifluoromethyl)pyridin-4-yl)-3-methylpyrrolidin-3-yl)carbamate (75 mg, 85%). MS $(M+H)^+$=535.2, 537.2.

Step 19-5, preparation of tert-butyl ((S)-1-(5-(((S)-1-cyclopropylethyl)carbamoyl)-3-(3,5-difluorophenyl)-2-(trifluoromethyl)pyridin-4-yl)-3-methylpyrrolidin-3-yl)carbamate: to a mixture of tert-butyl ((S)-1-(3-bromo-5-(((S)-1-cyclopropylethyl)carbamoyl)-2-(trifluoromethyl)pyridin-4-yl)-3-methylpyrrolidin-3-yl)carbamate (30 mg, 1 Eq, 56 µmol), (3,5-difluorophenyl)boronic acid (20 mg, 2.3 Eq, 0.13 mmol), $Pd(DtBPF)Cl_2$ (5.0 mg, 0.14 Eq, 7.7 µmol) and $K_3PO_4$ (40 mg, 3.4 Eq, 0.19 mmol) was added Toluene (1.0 mL) and water (0.1 mL) under atmospheric nitrogen. The resulting mixture was stirred at ambient temperature for 0.5 hour. The reaction mixture was concentrated and the remaining residue was purified by silica gel chromatography eluting with petroleum ether/EtOAc (2/1). The crude product was purified again by Prep-HPLC using the following conditions: Column, SunFire Prep $C_{18}$ OBD Column, 19*150 mm 5 µm; mobile phase, Water (0.1% FA) and ACN (18.0% ACN up to 30.0% in 7 min); Total flow rate, 20 mL/min; Detector, UV 220 nm. This resulted in tert-butyl ((S)-1-(5-(((S)-1-cyclopropylethyl)carbamoyl)-3-(3,5-difluorophenyl)-2-(trifluoromethyl)pyridin-4-yl)-3-methylpyrrolidin-3-yl)carbamate (6.0 mg, 19%) as a white solid. MS $(M+H)^+$=498.4.

Step 19-6, preparation of 4-[(3S)-3-amino-3-methylpyrrolidin-1-yl]-N-[(1S)-1-cyclopropylethyl]-5-(3,5-difluorophenyl)-6-(trifluoromethyl)pyridine-3-carboxamide: to a DCM (2.0 mL) of tert-butyl ((S)-1-(5-(((S)-1-cyclopropylethyl)carbamoyl)-3-(3,5-difluorophenyl)-2-(trifluoromethyl)pyridin-4-yl)-3-methylpyrrolidin-3-yl)carbamate (6.0 mg, 1 Eq, 11 µmol) was added TFA (1.0 mL). The reaction mixture was stirred at ambient temperature for 1 hour. The resulting solution was concentrated and freeze-dried under vacuum. This resulted in the TFA salt of 4-((S)-3-amino-3-methylpyrrolidin-1-yl)-N—((S)-1-cyclopropylethyl)-5-(3,5-difluorophenyl)-6-(trifluoromethyl)nicotinamide (4.5 mg, 61%) as a white solid. MS $(M+H)^+$=469.2.

The following compounds were prepared similarly to Example 19 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-189 | 469.2 |
| 1-195 | 485.2 |
| 1-197 | 488.3 |
| 1-198 | 471.1 |
| 1-199 | 455.2 |
| 1-206 | 478.3 |
| 1-208 | 464.2 |
| 1-209 | 469.2 |
| 1-210 | 483.2 |
| 1-211 | 519.2 |
| 1-212 | 483.2 |
| 1-213 | 469.2 |

-continued

| Compound no. | MS (M + H)$^+$ |
|---|---|
| 1-214 | 505.2 |
| 1-215 | 487.2 |
| 1-216 | 471.2 |
| 1-217 | 485.2 |

Example 20. 3-[(3S)-3-amino-3-methylpyrrolidin-1-yl]-N-(dicyclopropylmethyl)-2-(3,5-difluorophenyl)pyridine-4-carboxamide (compound 3-4)

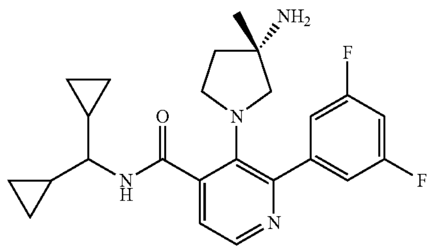 [SMILES: C[C@]1(N)CCN(c2c(C(=O)NC(C3CC3)C3CC3)ccnc2-c2cc(F)cc(F)c2)C1]

Step 20-1, preparation of methyl (S)-3-(3-((tert-butoxycarbonyl)amino)-3-methylpyrrolidin-1-yl)-2-chloroisonicotinate: to a 1,4-Dioxane (10 mL) solution of methyl 2-chloro-3-fluoroisonicotinate (431.5 mg, 1 Eq, 2.276 mmol) was added tert-butyl (S)-(3-methylpyrrolidin-3-yl)carbamate (21.13 mg, 1 Eq, 105.5 μmol) and potassium carbonate (786.4 mg, 2.5 Eq, 5.691 mmol). The resulting mixture was stirred at 70° C. for 24 hours. The reaction mixture was quenched with water, extracted with EtOAc, washed with brine and concentrated. The remaining residue was purified by silica gel chromatography eluting with EtOAc/Hexane (0-70%) to give methyl (S)-3-(3-((tert-butoxycarbonyl)amino)-3-methylpyrrolidin-1-yl)-2-chloroisonicotinate (501 mg, 59.5%) as an off-white solid. MS (M+H)$^+$=370.3.

Step 20-2, preparation of methyl (S)-3-(3-((tert-butoxycarbonyl)amino)-3-methylpyrrolidin-1-yl)-2-(3,5-difluorophenyl)isonicotinate: to a mixture of methyl (S)-3-(3-((tert-butoxycarbonyl)amino)-3-methylpyrrolidin-1-yl)-2-chloroisonicotinate (497 mg, 1 Eq, 1.34 mmol), (3,5-difluorophenyl)boronic acid (424 mg, 2 Eq, 2.69 mmol), potassium carbonate (557 mg, 3 Eq, 4.03 mmol) and Pd(amphos)$Cl_2$ (47.6 mg, 0.05 Eq, 67.2 μmol) was added 1,4-Dioxane (6.0 mL) and Water (0.7 mL) under atmospheric nitrogen. The resulting mixture was heated at 100° C. for 1 hour. The reaction mixture was quenched with water, extracted with ethyl acetate, washed with brine and concentrated. The remaining residue was purified by silica gel chromatography eluting with EtOAc/hexane (0-30%) to methyl (S)-3-(3-((tert-butoxycarbonyl)amino)-3-methylpyrrolidin-1-yl)-2-(3,5-difluorophenyl)isonicotinate (550 mg, 91.5%) as an off-white solid. MS (M+H)$^+$=448.0.

Step 20-3, preparation of (S)-3-(3-((tert-butoxycarbonyl)amino)-3-methylpyrrolidin-1-yl)-2-(3,5-difluorophenyl)isonicotinic acid: to a solution of methyl (S)-3-(3-((tert-butoxycarbonyl)amino)-3-methylpyrrolidin-1-yl)-2-(3,5-difluorophenyl)isonicotinate (580 mg, 1 Eq, 1.30 mmol) in THF/$H_2O$ (4:1) was added lithium hydroxide (310 mg, 10 Eq, 13.0 mmol). The resulting mixture was stirred at 60° C. for overnight. The reaction crude was acidified by saturated $NaHSO_4$, extracted with ethyl acetate, washed with brine, dried over $MgSO_4$ and concentrated to give the crude (S)-3-(3-((tert-butoxycarbonyl)amino)-3-methylpyrrolidin-1-yl)-2-(3,5-difluorophenyl)isonicotinic acid (510 mg, 90.8%) as a light yellow solid. This material was used for next step without further purification. MS (M+H)$^+$=434.4.

Step 20-4, preparation of tert-butyl (S)-(1-(4-((dicyclopropylmethyl)carbamoyl)-2-(3,5-difluorophenyl)pyridin-3-yl)-3-methylpyrrolidin-3-yl)carbamate: to a DMF (0.5 mL) solution of (S)-3-(3-((tert-butoxycarbonyl)amino)-3-methylpyrrolidin-1-yl)-2-(3,5-difluorophenyl)isonicotinic acid (30 mg, 1 Eq, 69 μmol) was added 2-(3H-[1,2,3]triazolo[4,5-b]pyridin-3-yl)-1,1,3,3-tetramethylisouronium hexafluorophosphate(V) (39 mg, 1.5 Eq, 0.10 mmol), dicyclopropylmethanamine hydrochloride (15 mg, 1.5 Eq, 0.10 mmol) and N-ethyl-Nisopropylpropan-2-amine (36 mg, 48 μL, 4 Eq, 0.28 mmol). The resulting mixture was stirred at 40° C. for 2 hours. The reaction mixture was diluted with ethyl acetate, washed with water and brine, dried and concentrated to give crude tert-butyl (S)-(1-(4-((dicyclopropylmethyl)carbamoyl)-2-(3,5-difluorophenyl)pyridin-3-yl)-3-methylpyrrolidin-3-yl)carbamate. This material was used for next step without purification.

Step 20-5, preparation of (S)-3-(3-amino-3-methylpyrrolidin-1-yl)-N-(dicyclopropylmethyl)-2-(3,5-difluorophenyl)isonicotinamide: to a DCM (0.6 mL) solution of crude tert-butyl (S)-(1-(4-((dicyclopropylmethyl)carbamoyl)-2-(3,5-difluorophenyl)pyridin-3-yl)-3-methylpyrrolidin-3-yl)carbamate was added TFA (0.5 mL). The resulting mixture was stirred at ambient temperature for 0.5 hour. The reaction crude was concentrated and the remaining residue was purified by C18 reverse phase chromatography eluting with MeCN (0.1% TFA)/water (0.10% TFA). Pure fractions were combined and concentrated under vacuum. The remaining residue was stirred in 2.0 N HCl in ether (1.0 mL) for 1 hour. The resulting mixture was concentrated and dried under vacuum to give the HCl salt of (S)-3-(3-amino-3-methylpyrrolidin-1-yl)-N-(dicyclopropylmethyl)-2-(3,5-difluorophenyl)isonicotinamide. MS (M+H)$^+$=427.4.

The following compounds were prepared similarly to Example 20 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 3-1 | 401.5 |
| 3-2 | 415.6 |
| 3-3 | 437.3 |
| 3-5 | 427.4 |
| 3-6 | 428.8 |
| 3-7 | 468.2 |
| 3-8 | 401.3 |

Example 21. 3-[(3S)-3-amino-3-methylpyrrolidin-1-yl]-5-chloro-N-[(1S)-1-cyclopropylethyl]-4-(3,5-difluorophenyl)pyridine-2-carboxamide (compound 4-1)

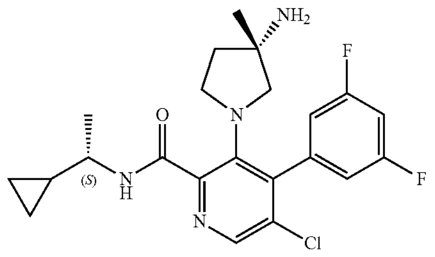

Step 21-1, preparation of 5-chloro-3-fluoropicolinonitrile: to a mixture of 2-bromo-5-chloro-3-fluoropyridine (5.00 g, 1 Eq, 23.8 mmol), zinc(II) cyanide (1.67 g, 0.599 Eq, 14.2 mmol), $Pd_2(dba)_3 \cdot CHCl_3$ (246 mg, 0.0100 Eq, 238 μmol) and (9,9-dimethyl-9H-xanthene-4,5-diyl)bis(diphenylphosphane) (275 mg, 0.0200 Eq, 475 μmol) was added DMF (60 mL). The reaction mixture was stirred at 120° C. for 2 hours. The reaction mixture was quenched with water (200 mL) and extracted with EtOAc (3×100 mL). Organic layers were combined, washed with water (2×100 mL) and brine (200 mL), dried over anhydrous $Na_2SO_4$ and concentrated. The remaining residue was purified by silica gel chromatography eluting with petroleum/EtOAc (5/1) to afford 5-chloro-3-fluoropicolinonitrile (2.80 g, 75.3%) as a white solid. $^1H$ NMR (300 MHz, Chloroform-d) δ 8.54 (dd, J=1.9, 0.8 Hz, 1H), 7.70 (dd, J=8.0, 1.9 Hz, 1H).

Step 21-2, preparation of 5-chloro-3-fluoro-4-iodopicolinonitrile: to a mixture of di-isopropylamine (1.86 g, 1.20 Eq, 18.4 mmol) in THF (80 mL) was added n-butyl lithium (1.18 g, 7.4 mL, 1.20 Eq, 18.4 mmol) (2.5 M in n-hexane) at −78° C. under atmospheric nitrogen. The resulting mixture was stirred at −30° C. for 25 min, followed by the addition of 5-chloro-3-fluoropicolinonitrile (2.40 g, 1 Eq, 15.3 mmol) in THF (40 mL) drop-wise at −78° C. The reaction mixture was stirred at −78° C. for 20 min. At −78° C., an iodine solution (5.84 g, 1.50 Eq, 23.0 mmol) in THF (20 mL) was added rapidly and the reaction mixture was stirred at the same temperature for 20 min. The reaction mixture was quenched with 200 mL of $Na_2S_2O_3$ solution and extracted with EtOAc (3×100 mL). Organic layers were combined, washed with brine (100 mL), dried over anhydrous $Na_2SO_4$ and concentrated under vacuum. This resulted in crude 5-chloro-3-fluoro-4-iodopicolinonitrile (4.10 g, 73%, LCMS 77% purity) as a yellow solid. This material was used for next step without further purification.

Step 21-3, preparation of 5-chloro-4-(3,5-difluorophenyl)-3-fluoropicolinonitrile: to a mixture of crude 5-chloro-3-fluoro-4-iodopicolinonitrile (1.00 g, 1 Eq, 2.7 mmol, 77% purity), (3,5-difluorophenyl)boronic acid (860 mg, 2.0 Eq, 5.45 mmol), potassium phosphate (2.00 g, 3.5 Eq, 9.42 mmol), and $Pd(DtBPF)Cl_2$ (270 mg, 0.15 Eq, 414 μmol) was added Toluene (15 mL) and water (1.5 mL) under atmospheric nitrogen. The reaction mixture was stirred at 45° C. for 5 hours. The resulting mixture was purified by silica gel chromatography eluting with petroleum ether/EtOAc (4/1). This resulted in 5-chloro-4-(3,5-difluorophenyl)-3-fluoropicolinonitrile (546 mg, 52%) (70% purity) as a yellow oil.

Step 21-4, preparation of tert-butyl (S)-(1-(5-chloro-2-cyano-4-(3,5-difluorophenyl)pyridin-3-yl)-3-methylpyrrolidin-3-yl)carbamate: to a mixture of 5-chloro-4-(3,5-difluorophenyl)-3-fluoropicolinonitrile (546 mg, 1 Eq, 1.4 mmol), tert-butyl (S)-(3-methylpyrrolidin-3-yl)carbamate (400 mg, 1.4 Eq, 2.00 mmol), and N-ethyl-N-isopropylpropan-2-amine (740 mg, 4.0 Eq, 5.73 mmol) was added MeCN (10 mL). The reaction mixture was stirred at 80° C. for 1 hour. The resulting mixture was concentrated under reduced pressure and the remaining residue was purified by silica gel chromatography eluting with petroleum ether/EtOAc (5/1) to afford tert-butyl (S)-(1-(5-chloro-2-cyano-4-(3,5-difluorophenyl)pyridin-3-yl)-3-methylpyrrolidin-3-yl)carbamate (440 mg, 69%) as a yellow solid. MS $(M+H)^+$=449.2, 451.2.

Step 21-5, preparation of (S)-3-(3-((tert-butoxycarbonyl)amino)-3-methylpyrrolidin-1-yl)-5-chloro-4-(3,5-difluorophenyl)picolinic acid: to a EtOH (2.5 mL) solution of tert-butyl (S)-(1-(5-chloro-2-cyano-4-(3,5-difluorophenyl)pyridin-3-yl)-3-methylpyrrolidin-3-yl)carbamate (200 mg, 1 Eq, 446 μmol) was added potassium hydroxide (250 mg, 10.0 Eq, 4.46 mmol) and water (1.25 mL). The resulting mixture was stirred at 100° C. for 16 hours. The reaction mixture was poured into water (30 mL), the pH was adjusted to 5-6 by adding saturated $NaHSO_4$, and extracted with EtOAc (3×30 mL). Organic layers were combined, washed with brine (30 mL), dried over anhydrous $Na_2SO_4$ and concentrated under reduced pressure. This resulted in (S)-3-(3-((tert-butoxycarbonyl)amino)-3-methylpyrrolidin-1-yl)-5-chloro-4-(3,5-difluorophenyl)picolinic acid (102 mg, 37%, 75% purity) as a yellow oil. MS $(M+H)^+$=468.3.

Step 21-6, preparation of tert-butyl ((S)-1-(5-chloro-2-(((S)-1-cyclopropylethyl)carbamoyl)-4-(3,5-difluorophenyl)pyridin-3-yl)-3-methylpyrrolidin-3-yl)carbamate: to a DMF (2.0 mL) solution of (S)-3-(3-((tert-butoxycarbonyl)amino)-3-methylpyrrolidin-1-yl)-5-chloro-4-(3,5-difluorophenyl)picolinic acid (102 mg, 1 Eq, 0.16 mmol) was added DIEA (85 mg, 4.0 Eq, 0.66 mmol), HATU (93 mg, 1.5 Eq, 0.24 mmol) and (S)-1-cyclopropylethan-1-amine hydrochloride (40 mg, 2.0 Eq, 0.33 mmol). The resulting mixture was stirred at ambient temperature for 1 hour. The reaction crude was purified by Prep-HPLC using the following conditions: Column, SunFire Prep $C_{18}$ OBD Column, 19*150 mm, 5 μm; mobile phase, Water (0.1% TFA) and ACN (70% ACN up to 90% in 7 min); Total flow rate, 20 mL/min; Detector, UV 220 nm. This resulted in tert-butyl ((S)-1-(5-chloro-2-(((S)-1-cyclopropylethyl)carbamoyl)-4-(3,5-difluorophenyl)pyridin-3-yl)-3-methylpyrrolidin-3-yl)carbamate (32 mg, 37%) as a light yellow solid. MS $(M+H)^+$=535.3.

Step 21-7, preparation of 3-((S)-3-amino-3-methylpyrrolidin-1-yl)-5-chloro-N—((S)-1-cyclopropylethyl)-4-(3,5-difluorophenyl)picolinamide: to a DCM (1.0 mL) solution of tert-butyl ((S)-1-(5-chloro-2-(((S)-1-cyclopropylethyl)carbamoyl)-4-(3,5-difluorophenyl)pyridin-3-yl)-3-methylpyrrolidin-3-yl)carbamate (15 mg, 1 Eq, 28 μmol) was added TFA (1.0 mL). The reaction mixture was stirred at ambient temperature for 1 hour. The reaction mixture was concentrated under reduced pressure and lyophilized under vacuum. This resulted in the TFA salt of 3-((S)-3-amino-3-methylpyrrolidin-1-yl)-5-chloro-N—((S)-1-cyclopropylethyl)-4-(3,5-difluorophenyl)picolinamide (15.9 mg, 86%) as a light yellow solid. MS $(M+H)^+$=435.1.

Example 22. 3-[(3S)-3-amino-3-methylpyrrolidin-1-yl]-N-[(1S)-1-cyclopropylethyl]-4-(3,5-difluorophenyl)-5-methylpyridine-2-carboxamide (compound 4-2)

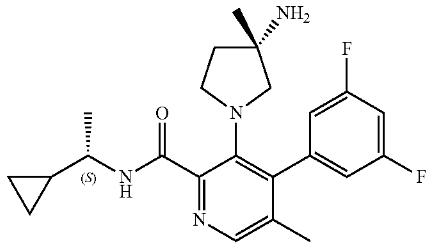

Step 22-1, preparation of tert-butyl ((S)-1-(2-(((S)-1-cyclopropylethyl)carbamoyl)-4-(3,5-difluorophenyl)-5-methylpyridin-3-yl)-3-methylpyrrolidin-3-yl)carbamate: to a mixture of tert-butyl ((S)-1-(5-chloro-2-(((S)-1-cyclopropylethyl)carbamoyl)-4-(3,5-difluorophenyl)pyridin-3-yl)-3-methylpyrrolidin-3-yl)carbamate (15 mg, 1 Eq, 28 μmol, "Step 21-6, Example 21"), 2,4,6-trimethyl-1,3,5,2,4,6-trioxatriborinane (35 mg, 9.9 Eq, 0.28 mmol) (50% w/w in THF), Pd(Amphos)$Cl_2$ (2.0 mg, 0.10 Eq, 2.8 μmol) and potassium carbonate (12 mg, 3.1 Eq, 87 μmol) was added 1,4-Dioxane (0.5 mL) under atmospheric nitrogen. The reaction mixture was stirred at 80° C. for 2 hours. The reaction mixture was purified by silica gel chromatography eluting with petroleum ether/EtOAc (3/1). The resulting material was further re-purified by Prep-HPLC using the following conditions: Column, SunFire Prep $C_{18}$ OBD Column, 19*150 mm, 5 μm; mobile phase, Water (0.05% $NH_3 \cdot H_2O$) and ACN (50% ACN up to 85% in 7 min); Total flow rate, 20 mL/min; Detector, UV 220 nm. This resulted in tert-butyl ((S)-1-(2-(((S)-1-cyclopropylethyl)carbamoyl)-4-(3,5-difluorophenyl)-5-methylpyridin-3-yl)-3-methylpyrrolidin-3-yl)carbamate (10 mg, 69%) as white solid. MS $(M+H)^+$=515.4.

Step 22-2, preparation of 3-((S)-3-amino-3-methylpyrrolidin-1-yl)-N—((S)-1-cyclopropylethyl)-4-(3,5-difluorophenyl)-5-methylpicolinamide: to a DCM (2.0 mL) of tert-butyl ((S)-1-(2-(((S)-1-cyclopropylethyl)carbamoyl)-4-(3,5-difluorophenyl)-5-methylpyridin-3-yl)-3-methylpyrrolidin-3-yl)carbamate (10 mg, 1 Eq, 19 μmol) was added TFA (2.0 mL). The resulting mixture was stirred at 25° C. for 1 hour. The reaction mixture was concentrated under reduced pressure and lyophilized under vacuum. This resulted in the TFA salt of 3-((S)-3-amino-3-methylpyrrolidin-1-yl)-N—((S)-1-cyclopropylethyl)-4-(3,5-difluorophenyl)-5-methylpicolinamide (9.0 mg, 72%) as an off-white solid. MS $(M+H)^+$=414.2.

Example 23. 4-[(3S)-3-amino-3-methylpyrrolidin-1-yl]-6-cyano-N-[(1S)-1-cyclopropylethyl]-5-(3,5-difluorophenyl)pyridine-3-carboxamide (compound 1-77)

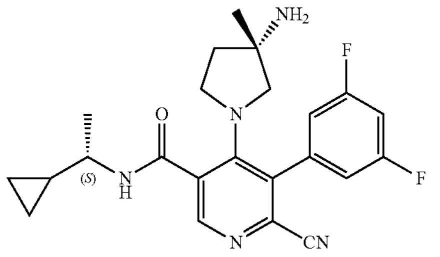

Step 23-1, preparation of tert-butyl (S)-(1-(2-chloro-5-formylpyridin-4-yl)-3-methylpyrrolidin-3-yl)carbamate: to a mixture of 4,6-dichloronicotinaldehyde (5.0 g, 1 Eq, 28 mmol), tert-butyl (S)-(3-methylpyrrolidin-3-yl)carbamate (6.0 g, 1.1 Eq, 30 mmol) and TEA (9.0 g, 12 mL, 3.1 Eq, 89 mmol) was added DMF (60 mL). The resulting mixture was stirred at 50° C. for 4 hours. The reaction mixture was quenched with water (100 mL) and extracted EtOAc (3×40 mL). Organic layers were combined, washed with brine, dried and concentrated under vacuum. The remaining residue was purified by silica gel chromatography eluting with EtOAc/petroleum ether (⅓) to afford tert-butyl (S)-(1-(2-chloro-5-formylpyridin-4-yl)-3-methylpyrrolidin-3-yl)carbamate (3.4 g, 35%) as a yellow solid. MS $(M+H)^+$=340.1, 342.1.

Step 23-2, preparation of tert-butyl (S)-(1-(3-bromo-2-chloro-5-formylpyridin-4-yl)-3-methylpyrrolidin-3-yl)carbamate: to an acetic acid (40 mL) solution of tert-butyl (S)-(1-(2-chloro-5-formylpyridin-4-yl)-3-methylpyrrolidin-3-yl)carbamate (3.4 g, 1 Eq, 10 mmol) was added NBS (2.0 g, 1.1 Eq, 11 mmol) at 10° C. portion-wise. The resulting mixture was stirred at the same temperature for 2 hours. The reaction solution was quenched with saturated $NaHCO_3$ and extracted with EtOAc (3×40 mL). Organic layers were combined, washed with brine, dried and concentrated under vacuum. The remaining residue was purified by silica gel chromatography eluting with EtOAc/petroleum ether (¼) to afford tert-butyl (S)-(1-(3-bromo-2-chloro-5-formylpyridin-4-yl)-3-methylpyrrolidin-3-yl)carbamate (2.3 g, 55%) as a yellow solid. MS $(M+H)^+$=418.0, 420.0.

Step 23-3, preparation of tert-butyl (S)-(1-(2-chloro-3-(3,5-difluorophenyl)-5-formylpyridin-4-yl)-3-methylpyrrolidin-3-yl)carbamate: to a mixture of tert-butyl (S)-(1-(3-bromo-2-chloro-5-formylpyridin-4-yl)-3-methylpyrrolidin-3-yl)carbamate (2.3 g, 1 Eq, 5.5 mmol), (3,5-difluorophenyl) boronic acid (800 mg, 0.92 Eq, 5.07 mmol), potassium phosphate (3.7 g, 3.2 Eq, 17 mmol) and Pd(DtBPF)$Cl_2$ (370 mg, 0.10 Eq, 568 μmol) was added Toluene (92 mL) and water (9.2 mL) under atmospheric nitrogen. The resulting mixture was stirred at 40° C. for 1.5 hours. The resulting mixture was concentrated under reduced pressure. The remaining residue was purified by silica gel chromatography eluting with EtOAc/petroleum ether (1:2) to afford tert-butyl (S)-(1-(2-chloro-3-(3,5-difluorophenyl)-5-formylpyridin-4-yl)-3-methylpyrrolidin-3-yl)carbamate (1.7 g, 68%) as a yellow solid. MS $(M+H)^+$=452.2, 454.2.

Step 23-4, preparation of tert-butyl (S)-(1-(2-cyano-3-(3,5-difluorophenyl)-5-formylpyridin-4-yl)-3-methylpyrrolidin-3-yl)carbamate: to a mixture of tert-butyl (S)-(1-(2- chloro-3-(3,5-difluorophenyl)-5-formylpyridin-4-yl)-3-methylpyrrolidin-3-yl)carbamate (1.7 g, 1 Eq, 3.8 mmol), zinc(II) cyanide (900 mg, 2.0 Eq, 7.66 mmol), $Pd_2(dba)_3 \cdot CHCl_3$ (400 mg, 0.10 Eq, 386 μmol) and (9,9-dimethyl-9H-xanthene-4,5-diyl)bis(diphenylphosphane) (440 mg, 0.20 Eq, 760 μmol) was added DMF (20 mL) under atmospheric nitrogen. The resulting mixture was heated under microwave radiation at 135° C. for 1 hour. The reaction mixture was quenched with water (100 mL) and extracted with EtOAc (3×40 mL). Organic layers were combined, washed with brine, dried and concentrated under vacuum. The remaining residue was purified by silica gel chromatography eluting with EtOAc/petroleum ether (1/1) to afford tert-butyl (S)-(1-(2-cyano-3-(3,5-difluorophenyl)-5-formylpyridin-4-yl)-3-methylpyrrolidin-3-yl)carbamate (720 mg, 43%) as a yellow solid. MS $(M+H)^+$=443.1.

Step 23-5, preparation of (S)-4-(3-((tert-butoxycarbonyl)amino)-3-methylpyrrolidin-1-yl)-6-cyano-5-(3,5-difluorophenyl)nicotinic acid: to a 2-methylpropan-2-ol (10 mL) solution of tert-butyl (S)-(1-(2-cyano-3-(3,5-difluorophenyl)-5-formylpyridin-4-yl)-3-methylpyrrolidin-3-yl)carbamate (720 mg, 1 Eq, 1.63 mmol) was added sodium dihydrogen phosphate dihydrate (800 mg, 3.15 Eq, 5.13 mmol), 2-methylbut-2-ene (3.4 g, 30 Eq, 48 mmol), sodium chlorite (300 mg, 2.04 Eq, 3.32 mmol) and water (3.3 mL). The resulting mixture was stirred at ambient temperature for 1 hour. The reaction mixture was quenched with saturated $NaHSO_4$ (50 mL) and extracted with EtOAc (3×40 mL). Organic layers were combined, washed with brine, dried and concentrated under vacuum to afford crude (S)-4-(3-((tert-butoxycarbonyl)amino)-3-methylpyrrolidin-1-yl)-6-cyano-5-(3,5-difluorophenyl)nicotinic acid (670 mg, 89.8%) as a yellow solid. This material was used for next step without further purification. MS $(M+H)^+$=459.2.

Step 23-6, preparation of tert-butyl ((S)-1-(2-cyano-5-(((S)-1-cyclopropylethyl)carbamoyl)-3-(3,5-difluorophenyl)pyridin-4-yl)-3-methylpyrrolidin-3-yl)carbamate: from (S)-4-(3-((tert-butoxycarbonyl)amino)-3-methylpyrrolidin-1-yl)-6-cyano-5-(3,5-difluorophenyl)nicotinic acid (70 mg, 1.0 Eq, 0.15 mmol), the title compound (54 mg, 67%) was prepared using a similar method to the one described in "Example 5, Step 5-6". MS (M+H)+=526.3.

Step 23-7, preparation of 4-[(3S)-3-amino-3-methylpyrrolidin-1-yl]-6-cyano-N-[(1S)-1-cyclopropylethyl]-5-(3,5-difluorophenyl)pyridine-3-carboxamide: from tert-butyl ((S)-1-(2-cyano-5-(((S)-1-cyclopropylethyl)carbamoyl)-3-(3,5-difluorophenyl)pyridin-4-yl)-3-methylpyrrolidin-3-yl)carbamate (54 mg, 1.0 Eq, 0.10 mmol), the HCl salt of the title compound (28 mg, 67%) was prepared using a similar method to the one described in "Example 5, Step 5-7". MS $(M+H)^+$=426.3.

Example 24. 4-[(3S)-3-aminopyrrolidin-1-yl]-N-(4,4-difluorocyclohexyl)-5-(3,5-difluorophenyl)-6-methoxypyridine-3-carboxamide (compound 1-150)

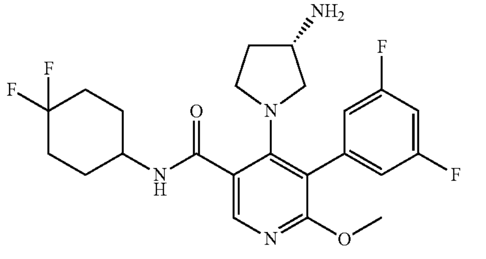 [SMILES: COc1ncc(C(=O)NC2CCC(F)(F)CC2)c(N2CC[C@H](N)C2)c1-c1cc(F)cc(F)c1]

Step 24-1, preparation of methyl (S)-4-(3-((tert-butoxycarbonyl)amino)pyrrolidin-1-yl)-6-chloronicotinate: to a mixture of methyl 4, 6-dichloronicotinate (1.20 g, 1 Eq, 5.82 mmol) and MeCN (7.0 mL) was added tert-butyl(S)-pyrrolidin-3-ylcarbamate (1.19 g, 1.1 Eq, 6.41 mmol) and DIPEA (2.26 g, 3.1 mL, 3 Eq, 17.5 mmol). The resulting mixture was stirred at ambient temperature for 24 hours. The reaction crude was concentrated and the remaining residue was purified by silica gel chromatography eluting with EtOAc/hexane (0-50%) to give methyl (S)-4-(3-((tert-butoxycarbonyl)amino)pyrrolidin-1-yl)-6-chloronicotinate (2.07 g, 97%) as a white solid. MS $(M+H)^+$=356.2.

Step 24-2, preparation of methyl (S)-4-(3-((tert-butoxycarbonyl)amino)pyrrolidin-1-yl)-6-methoxynicotinate: to a mixture of MeOH (3.0 mL) and methyl (S)-4-(3-((tert-butoxycarbonyl)amino)pyrrolidin-1-yl)-6-chloronicotinate (2.0 g, 1 Eq, 5.6 mmol) was added sodium methoxide solution in MeOH (25% Wt, 13 mL, 10 Eq, 56 mmol). The resulting mixture was heated at 65° C. for 6 hours. The reaction crude was concentrated, diluted with saturated $NH_4Cl$ (20 mL), and extracted with ethyl acetate (3×20 mL). Organic layers were combined and concentrated. The remaining residue was purified by silica gel chromatography eluting with EtOAc/hexane (0-50%) to give methyl (S)-4-(3-((tert-butoxycarbonyl)amino)pyrrolidin-1-yl)-6-methoxynicotinate (1.15 g, 58%) as a clear oil. $(M+H)^+$=352.3.

Step 24-3, preparation of methyl (S)-5-bromo-4-(3-((tert-butoxycarbonyl)amino)pyrrolidin-1-yl)-6-methoxynicotinate: to a DMF (5 mL) solution of methyl (S)-4-(3-((tert-butoxycarbonyl)amino)pyrrolidin-1-yl)-6-methoxynicotinate (1.15 g, 1 Eq, 3.27 mmol) was added NBS (699 mg, 1.2 Eq, 3.93 mmol) portion-wise at ambient temperature. The resulting mixture was stirred at the same temperature for 0.5 hour. The reaction crude was purified by C18 reverse phase chromatography eluting with MeCN (0.1% TFA)/water (0.1% TFA) (5-75%). Pure fractions were combined, neutralized with saturated $NaHCO_3$ (5 mL), added solid NaCl (15 g), and extracted with ethyl acetate (2×20 mL). Organic layer was dried with $MgSO_4$, filtered and concentrated. The resulting residue was re-purified by silica gel chromatography eluting with EtOAc/hexane (0-50%) to give methyl (S)-5-bromo-4-(3-((tert-butoxycarbonyl)amino)pyrrolidin-1-yl)-6-methoxynicotinate (801 mg, 57%) as a clear oil. $(M+H)^+$=430.3, 432.3.

Step 24-4, preparation of methyl (S)-4-(3-((tert-butoxycarbonyl)amino)pyrrolidin-1-yl)-5-(3,5-difluorophenyl)-6-methoxynicotinate: to a 1,4-Dioxane (7.0 mL) solution of methyl (S)-5-bromo-4-(3-((tert-butoxycarbonyl)amino)pyrrolidin-1-yl)-6-methoxynicotinate (760 mg, 1 Eq, 1.77 mmol) was added (3,5-difluorophenyl)boronic acid (837 mg, 3 Eq, 5.30 mmol), potassium carbonate (976 mg, 4 Eq, 7.06 mmol), $Pd(amphos)Cl_2$ (62.5 mg, 0.05 Eq, 88.3 μmol) and Water (0.7 mL) under atmospheric nitrogen. The resulting mixture was heated at 100° C. for 1 hour. The reaction crude was concentrated and the remaining residue was purified by silica gel chromatography to give methyl (S)-4-(3-((tert-butoxycarbonyl)amino)pyrrolidin-1-yl)-5-(3,5-difluorophenyl)-6-methoxynicotinate (631 mg, 77.1%) as a gummy oil. MS $(M+H)^+$=464.4.

Step 24-5, preparation of (S)-4-(3-((tert-butoxycarbonyl)amino)pyrrolidin-1-yl)-5-(3,5-difluorophenyl)-6-methoxynicotinic acid: to a MeOH (5.0 mL) solution of methyl (S)-4-(3-((tert-butoxycarbonyl)amino)pyrrolidin-1-yl)-5-(3,5-difluorophenyl)-6-methoxynicotinate (631 mg, 1 Eq, 1.36 mmol) was added lithium hydroxide hydrate (628 mg, 11 Eq, 15.0 mmol) and Water (0.5 mL). The resulting mixture was heated at 50° C. for 24 hours. The resulting mixture was concentrated, diluted with ethyl acetate, washed with saturated $NaHSO_4$, dried and concentrated to give (S)-4-(3-((tert-butoxycarbonyl)amino)pyrrolidin-1-yl)-5-(3,5-difluorophenyl)-6-methoxynicotinic acid (580 mg, 94.8%) as a yellow solid. This material was used for next step without further purification. MS $(M+H)^+$=450.2.

Step 24-6, preparation of tert-butyl (S)-(1-(5-((4,4-difluorocyclohexyl)carbamoyl)-3-(3,5-difluorophenyl)-2-methoxypyridin-4-yl)pyrrolidin-3-yl)carbamate: to a solution of (S)-4-(3-((tert-butoxycarbonyl)amino)pyrrolidin-1-yl)-5-(3,5-difluorophenyl)-6-methoxynicotinic acid (30 mg, 1 Eq, 67 μmol) and 2-(3H-[1,2,3]triazolo[4,5-b]pyridin-3-yl)-1,1,3,3-tetramethylisouronium hexafluorophosphate (V) (38 mg, 1.5 Eq, 0.10 mmol) in DMF was added 4,4-difluorocyclohexan-1-amine hydrochloride (17 mg, 1.5 Eq, 0.10 mmol) and DIPEA (35 mg, 47 μL, 4 Eq, 0.27 mmol). The reaction mixture was stirred at 40° C. for overnight. The reaction mixture was diluted with ethyl acetate, washed with water and brine, dried and concentrated to give 38 mg of the crude product. This material was used for next step without further purification. MS $(M+H)^+$=567.1.

Step 24-7, preparation of (S)-4-(3-aminopyrrolidin-1-yl)-N-(4,4-difluorocyclohexyl)-5-(3,5-difluorophenyl)-6-methoxynicotinamide: to a DCM (0.6 mL) solution of tert-butyl (S)-(1-(5-((4,4-difluorocyclohexyl)carbamoyl)-3-(3,5-difluorophenyl)-2-methoxypyridin-4-yl)pyrrolidin-3-yl)carbamate (38 mg, 1 Eq, 67 μmol) was added TFA (0.7 g, 0.5 mL, 102 Eq, 6 mmol). The resulting mixture was stirred at ambient temperature for 0.5 hour. The reaction crude was concentrated and the remaining residue was purified by C18 reverse phase chromatography eluting with MeCN (0.1% TFA)/water (0.1% TFA). Pure fractions were combined and dried under vacuum. The remaining residue was treated with 2.0 N HCl in ether (1.0 mL) for 1 hour and concentrated to give the HCl salt of (S)-4-(3-aminopyrrolidin-1-yl)-N-(4,4-difluorocyclohexyl)-5-(3,5-difluorophenyl)-6-methoxynicotinamide as a white solid (32 mg, 88%). MS $(M+H)^+$=467.1. The following compounds were prepared similarly to Example 24 with appropriate substituting reagents and substrates at different steps and they may require additional functional group modifications via well-known chemistry with appropriate reagents. Different salts, such as HCl or formic acid or TFA salt, may be obtained.

| Compound no. | MS (M + H)$^+$ |
|---|---|
| 1-196 | 433.3 |

Example 25. 4-[(3S)-3-amino-3-methylpyrrolidin-1-yl]-2-cyano-2'-methoxy-N-[(2S)-1,1,1-trifluoropropan-2-yl]-[3,4'-bipyridine]-5-carboxamide (compound 1-170)

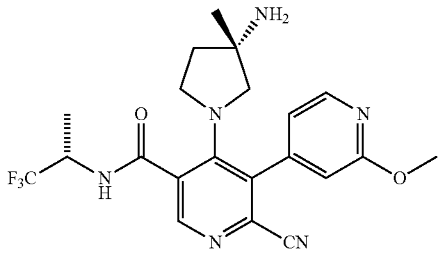 [SMILES: COc1cc(-c2c(C#N)ncc(C(=O)N[C@@H](C)C(F)(F)F)c2N2CC[C@](C)(N)C2)ccn1]

Step 25-1, preparation of ethyl (S)-4-(3-((tert-butoxycarbonyl)amino)-3-methylpyrrolidin-1-yl)-2-cyano-2'-methoxy-[3,4'-bipyridine]-5-carboxylate: to a mixture of ethyl (S)-5-bromo-4-(3-((tert-butoxycarbonyl)amino)-3-methylpyrrolidin-1-yl)-6-cyanonicotinate (100 mg, 1 Eq, 221 μmol, "Step 5-3, Example 5"), (2-methoxypyridin-4-yl) boronic acid (50 mg, 1.5 Eq, 0.33 mmol), potassium phosphate (150 mg, 3.20 Eq, 707 μmol) and Pd(DTBPF)$Cl_2$ (20 mg, 0.14 Eq, 31 μmol) was added toluene (2.0 mL) and water (0.2 mL) under atmospheric nitrogen. The resulting mixture was stirred at 80° C. for 1 hour. The reaction mixture was concentrated under vacuum and the remaining residue was purified by silica gel chromatography eluting with ethyl acetate/petroleum ether (½). This resulted in ethyl (S)-4-(3-((tert-butoxycarbonyl)amino)-3-methylpyrrolidin-1-yl)-2-cyano-2'-methoxy-[3,4'-bipyridine]-5-carboxylate (70 mg, 66%) as a yellow oil. MS $(M+H)^+$=482.2.

Step 25-2, preparation of (S)-4-(3-((tert-butoxycarbonyl)amino)-3-methylpyrrolidin-1-yl)-2-cyano-2'-methoxy-[3,4'-bipyridine]-5-carboxylic acid: to a MeOH (2.0 mL) solution of ethyl (S)-4-(3-((tert-butoxycarbonyl)amino)-3-methylpyrrolidin-1-yl)-2-cyano-2'-methoxy-[3,4'-bipyridine]-5-carboxylate (70 mg, 1 Eq, 0.15 mmol) was added LiOH (40 mg, 11 Eq, 1.7 mmol) and water (0.2 mL). The resulting solution was stirred at 50° C. for 1 hour. The reaction mixture was cooled to room temperature and concentrated under vacuum. The remaining residue was diluted with water (30 ml) and the pH was adjusted to 6-7 using saturated $NaHCO_3$ solution. The resulting mixture was extracted with ethyl acetate (3×30 mL). Organic layers were combined, dried over anhydrous sodium sulfate and concentrated under vacuum. This resulted in crude (S)-4-(3-((tert-butoxycarbonyl)amino)-3-methylpyrrolidin-1-yl)-2-cyano-2'-methoxy-[3,4'-bipyridine]-5-carboxylic acid (50 mg, 76%) as a yellow oil. MS $(M+H)^+$=454.2.

Step 25-3, preparation of tert-butyl ((S)-1-(2-cyano-2'-methoxy-5-(((S)-1,1,1-trifluoropropan-2-yl)carbamoyl)-[3,4'-bipyridin]-4-yl)-3-methylpyrrolidin-3-yl)carbamate: to a DMF (2.0 mL) solution was added (S)-4-(3-((tert-butoxycarbonyl)amino)-3-methylpyrrolidin-1-yl)-2-cyano-2'-methoxy-[3,4'-bipyridine]-5-carboxylic acid (50 mg, 1 Eq, 0.11 mmol), 2-(3H-[1,2,3]triazolo[4,5-b]pyridin-3-yl)-1,1,3,3-tetramethylisouronium hexafluorophosphate (V) (45 mg, 1.1 Eq, 0.12 mmol) and N-ethyl-N-isopropylpropan-2-amine (50 mg, 3.5 Eq, 0.39 mmol). The resulting mixture was stirred at 25° C. for 5 min followed by the addition of (S)-1,1,1-trifluoropropan-2-amine hydrochloride (25 mg, 1.5 Eq, 0.17 mmol). The reaction mixture was stirred at 25° C. for 1 hour. The reaction crude was purified by Prep-HPLC using the following conditions: Column, SunFire Prep $C_{18}$ OBD Column, 19*150 mm 5 um; mobile phase, Water (0.1% $NH_3 \cdot H_2O$) and ACN (22.0% ACN up to 35.0% in 6 min); Total flow rate, 20 mL/min; Detector, UV 220 nm. This resulted in tert-butyl ((S)-1-(2-cyano-2'-methoxy-5-(((S)-1,1,1-trifluoropropan-2-yl)carbamoyl)-[3,4'-bipyridin]-4-yl)-3-methylpyrrolidin-3-yl)carbamate (20 mg, 33%) as a white solid. MS $(M+H)^+$=549.3.

Step 25-4, preparation of 4-((S)-3-amino-3-methylpyrrolidin-1-yl)-2-cyano-2'-methoxy-N—((S)-1,1,1-trifluoropropan-2-yl)-[3,4'-bipyridine]-5-carboxamide: to a DCM (2 mL) solution of tert-butyl ((S)-1-(2-cyano-2'-methoxy-5-(((S)-1,1,1-trifluoropropan-2-yl)carbamoyl)-[3,4'-bipyridin]-4-yl)-3-methylpyrrolidin-3-yl)carbamate (20 mg, 1 Eq, 36 μmol) was added TFA (1.0 mL). The resulting mixture was stirred at ambient temperature for 1 hour. The reaction solution was concentrated and dried under lyophilization. This resulted in the TFA salt of 4-((S)-3-amino-3-methylpyrrolidin-1-yl)-2-cyano-2'-methoxy-N—((S)-1,1,1-trifluoropropan-2-yl)-[3,4'-bipyridine]-5-carboxamide (18.1 mg, 73%) as a white solid. MS $(M+H)^+$=449.1.

Example 26. 4-[(3S)-3-amino-3-methylpyrrolidin-1-yl]-6-cyano-5-(3,5-difluorophenyl)-N-[(2S)-1,1,1-trifluoropropan-2-yl]pyridine-3-carboxamide (compound 1-192)

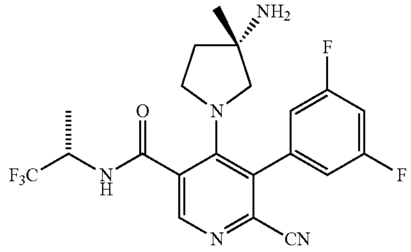 [SMILES: C[C@H](NC(=O)c1cnc(C#N)c(-c2cc(F)cc(F)c2)c1N1CC[C@](C)(N)C1)C(F)(F)F]

Step 26-1, preparation of ethyl 4-chloro-6-cyanonicotinate: to a mixture of ethyl 4,6-dichloronicotinate (100 g, 1 Eq, 454 mmol), zinc(II) cyanide (32.0 g, 0.60 Eq, 273 mmol), Tris(dibenzylideneacetone)dipalladium(0) chloroform adduct (4.71 g, 0.010 Eq, 4.55 mmol) and (9,9-dimethyl-9H-xanthene-4,5-diyl)bis(diphenylphosphane) (5.26 g, 0.020 Eq, 9.09 mmol) was added DMF (800 mL) under atmospheric nitrogen. The reaction mixture was stirred at 130° C. for 2 hours. The reaction mixture was poured into water (3000 mL) and extracted with EtOAc (3×1000 mL). Organic layers were combined, washed with water (3×1500 mL) and brine (1000 mL), dried over anhydrous $Na_2SO_4$, and concentrated under reduced pressure. The remaining residue was purified by silica gel chromatography eluting with petroleum ether/EtOAc/DCM=10/1/1. This resulted in ethyl 4-chloro-6-cyanonicotinate (68.0 g, 0.23 mol, 50%, 70% Purity) as a yellow solid. MS $(M+H)^+$=211.1, 212.1.

Step 26-2, preparation of ethyl (S)-4-(3-((tert-butoxycarbonyl)amino)-3-methylpyrrolidin-1-yl)-6-cyanonicotinate: to an MeCN (200 mL) solution of ethyl 4-chloro-6-cyanonicotinate (15 g, 1 Eq, 71 mmol) was added 2,3,4,6,7,8,9,10-octahydropyrimido[1,2-a]azepine (10 g, 0.92 Eq, 66 mmol) and tert-butyl (S)-(3-methylpyrrolidin-3-yl)carbamate (30 g, 2.1 Eq, 0.15 mol). The resulting mixture was stirred at 50° C. for 1 hour. The reaction crude was quenched with water (100 mL) and extracted with EtOAc (3×40 mL). The organic layers were combined, washed with brine, dried and concentrated under vacuum. The remaining residue was purified by silica gel chromatography eluting with ethyl acetate/petroleum ether (⅓) to afford ethyl (S)-4-(3-((tert-butoxycarbonyl)amino)-3-methylpyrrolidin-1-yl)-6-cyanonicotinate (16.0 g, 42.7 mmol, 60%) as a yellow solid. MS $(M+H)^+$=375.1.

Step 26-3, preparation of ethyl (S)-4-(3-((tert-butoxycarbonyl)amino)-3-methylpyrrolidin-1-yl)-5-chloro-6-cyanonicotinate: to an AcOH (130 mL) solution of (S)-4-(3-((tert-butoxycarbonyl)amino)-3-methylpyrrolidin-1-yl)-6-cyanonicotinate (13.0 g, 1 Eq, 34.7 mmol) was added 1-chloropyrrolidine-2,5-dione (14 g, 3.0 Eq, 0.10 mol). The resulting mixture was stirred at 35° C. for 3 hours. The reaction crude was quenched with aqueous $NaHCO_3$ and extracted with DCM (3×200 mL). The organic layers were combined, washed with brine, dried and concentrated under vacuum. The remaining residue was purified by silica gel chromatography eluting with ethyl acetate/petroleum ether (¼) to afford ethyl (S)-4-(3-((tert-butoxycarbonyl)amino)-3-methylpyrrolidin-1-yl)-5-chloro-6-cyanonicotinate (8.2 g, 20 mmol, 58%) as a yellow solid. MS $(M+H)^+$=409.2.

Step 26-4, preparation of ethyl (S)-4-(3-((tert-butoxycarbonyl)amino)-3-methylpyrrolidin-1-yl)-6-cyano-5-(3,5-difluorophenyl)nicotinate: to a mixture of ethyl (S)-4-(3-((tert-butoxycarbonyl)amino)-3-methylpyrrolidin-1-yl)-5-chloro-6-cyanonicotinate (7.5 g, 1 Eq, 18 mmol), (3,5-difluorophenyl)boronic acid (8.5 g, 2.9 Eq, 54 mmol), potassium carbonate (7.6 g, 3.0 Eq, 55 mmol) and Pd(amphos)$Cl_2$ (800 mg, 0.062 Eq, 1.13 mmol) was added 1,4-Dioxane (80 mL) and Water (8 mL) under atmospheric nitrogen. The resulting mixture was stirred at 120° C. for 1 hour. The reaction crude was concentrated under reduced pressure. The remaining residue was purified by silica gel chromatography eluting with EtOAc/petroleum ether (1:5) to afford ethyl (S)-4-(3-((tert-butoxycarbonyl)amino)-3-methylpyrrolidin-1-yl)-6-cyano-5-(3,5-difluorophenyl) nicotinate (5.2 g, 11 mmol, 58%) as a yellow solid. MS $(M+H)^+$=487.3.

Step 26-5, preparation of (S)-4-(3-((tert-butoxycarbonyl) amino)-3-methylpyrrolidin-1-yl)-6-cyano-5-(3,5-difluorophenyl)nicotinic acid: to a MeOH (60 mL) solution of ethyl (S)-4-(3-((tert-butoxycarbonyl)amino)-3-methylpyrrolidin-1-yl)-6-cyano-5-(3,5-difluorophenyl)nicotinate (5.2 g, 1 Eq, 11 mmol) was added LiOH (2.6 g, 10 Eq, 0.11 mol) and Water (6 mL). The resulting mixture was stirred at 50° C. for 3 hours. The reaction crude was quenched with aqueous $NaHSO_4$ and extracted with EtOAc (3×40 mL). The organic layers were combined, washed with brine, dried and concentrated under vacuum to afford crude (S)-4-(3-((tert-butoxycarbonyl)amino)-3-methylpyrrolidin-1-yl)-6-cyano-5-(3,5-difluorophenyl)nicotinic acid (3.7 g, 8.1 mmol, 76%) as a yellow solid. This material was used for next step without further purification. MS $(M+H)^+$=459.3.

Step 26-6, preparation of tert-butyl ((S)-1-(2-cyano-3-(3,5-difluorophenyl)-5-(((S)-1,1,1-trifluoropropan-2-yl)carbamoyl)pyridin-4-yl)-3-methylpyrrolidin-3-yl)carbamate: to a NMP (7.0 mL) solution of (S)-4-(3-((tert-butoxycarbonyl)amino)-3-methylpyrrolidin-1-yl)-6-cyano-5-(3,5-difluorophenyl)nicotinic acid (500 mg, 1 Eq, 1.09 mmol) was added 2-(3H-[1,2,3]triazolo[4,5-b]pyridin-3-yl)-1,1,3,3-tetramethylisouronium hexafluorophosphate (V) (430 mg, 1.04 Eq, 1.13 mmol), N-ethyl-N-isopropylpropan-2-amine (550 mg, 3.90 Eq, 4.26 mmol) and (S)-1,1,1-trifluoropropan-2-amine hydrochloride (200 mg, 1.23 Eq, 1.34 mmol). The resulting mixture was stirred at 50° C. for 2 hours. The reaction solution was diluted with saturated $Na_2CO_3$ (50 mL) and extracted with ethyl acetate (3×50 mL). Organic layers were combined, washed with brine (2×50 mL), dried over anhydrous sodium sulfate and concentrated under vacuum. The remaining residue was purified by silica gel chromatography eluting with ethyl acetate/petroleum ether (⅓) to give crude product. This material was re-purified by Prep-HPLC using the following conditions: Column, $C_{18}$ silica gel; mobile phase, Water (0.1% FA) and ACN (45.0% up to 85.0% in 8 min); Total flow rate, 70 mL/min; Detector, UV 220 nm. This resulted in tert-butyl ((S)-1-(2-cyano-3-(3,5-difluorophenyl)-5-(((S)-1,1,1-trifluoropropan-2-yl)carbamoyl)pyridin-4-yl)-3-methylpyrrolidin-3-yl)carbamate (360 mg, 59.6%) as a yellow solid. MS $(M+H)^+$=554.2.

Step 26-7, preparation of 4-((S)-3-amino-3-methylpyrrolidin-1-yl)-6-cyano-5-(3,5-difluorophenyl)-N—((S)-1,1,1-trifluoropropan-2-yl)nicotinamide: 4.0 M HCl in dioxane (10 mL) was added into tert-butyl ((S)-1-(2-cyano-3-(3,5-difluorophenyl)-5-(((S)-1,1,1-trifluoropropan-2-yl)carbamoyl)pyridin-4-yl)-3-methylpyrrolidin-3-yl)carbamate with stirring. The resulting mixture was stirred at 30° C. for 1.5 hour. The reaction mixture was concentrated and dried under lyophilization (twice). This resulted in the HCl salt of 4-((S)-3-amino-3-methylpyrrolidin-1-yl)-6-cyano-5-(3,5-difluorophenyl)-N—((S)-1,1,1-trifluoropropan-2-yl)nicotinamide (317.4 mg, 86.7%) as a light yellow solid. MS $(M+H)^+$=454.2.

Example 27. 4-[(3S)-3-amino-3-methylpyrrolidin-1-yl]-5-(3,5-difluorophenyl)-N-[(2S)-1,1,1-trifluoropropan-2-yl]pyridine-3-carboxamide (compound 1-54)

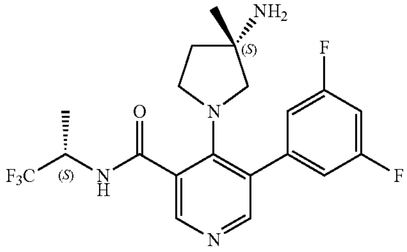

Step 27-1, preparation of tert-butyl ((S)-1-(3-(3,5-difluorophenyl)-5-(((S)-1,1,1-trifluoropropan-2-yl)carbamoyl)pyridin-4-yl)-3-methylpyrrolidin-3-yl)carbamate: to a DMF (1.3 mL) solution of (S)-4-(3-((tert-butoxycarbonyl)amino)-3-methylpyrrolidin-1-yl)-5-(3,5-difluorophenyl)nicotinic acid (57 mg, 1 Eq, 0.132 mmol, "Step 3-2, Example 3") was added 2-(3H-[1,2,3]triazolo[4,5-b]pyridin-3-yl)-1,1,3,3-tetramethylisouronium hexafluorophosphate (V) (60 mg, 1.20 Eq, 0.159 mmol), N-ethyl-N-isopropylpropan-2-amine (0.222 mL, 10.1 Eq, 1.33 mmol) and (S)-1,1,1-trifluoropropan-2-amine hydrochloride (120 mg, 6.0 Eq, 0.793 mmol) under atmospheric nitrogen. The resulting mixture was stirred at 60° C. for 2 hours. The reaction mixture was diluted with ethyl acetate (30 mL), washed with saturated $NH_4Cl$, $NaHCO_3$ and brine, dried over anhydrous sodium sulfate and concentrated. The remaining residue was purified by silica gel chromatography eluting with EtOAc/hexane (0-100%) to give tert-butyl ((S)-1-(3-(3,5-difluorophenyl)-5-(((S)-1,1,1-trifluoropropan-2-yl)carbamoyl)pyridin-4-yl)-3-methylpyrrolidin-3-yl)carbamate (62 mg, 89.0%) as a white powder. (MS $(M+H)^+$=529.3.

Step 27-2, preparation of 4-[(3S)-3-amino-3-methylpyrrolidin-1-yl]-5-(3,5-difluorophenyl)-N-[(2S)-1,1,1-trifluoropropan-2-yl]pyridine-3-carboxamide: to a DCM (1.0 mL) solution of tert-butyl ((S)-1-(3-(3,5-difluorophenyl)-5-(((S)-1,1,1-trifluoropropan-2-yl)carbamoyl)pyridin-4-yl)-3-methylpyrrolidin-3-yl)carbamate (62 mg, 1.0 Eq, 0.12 mmol) was added TFA (0.40 mL, 44 Eq, 5.19 mmol). The resulting mixture was stirred at ambient temperature for 1 hour. The reaction crude was concentrated, and the remaining residue was purified by C18 reverse phase chromatography eluting with MeCN (0.1% TFA)/water (0.1% TFA) (5-35%). Pure fractions were combined, concentrated, neutralized with saturated $NaHCO_3$ (3 mL), added solid NaCl (5 g), and extracted with DCM (2×20 mL). Organic layer were combined, dried with $Na_2SO_4$, filtered and concentrated with 1.0 M HCl in ethyl acetate (0.2 mL) to give the HCl salt of 4-[(3S)-3-amino-3-methylpyrrolidin-1-yl]-5-(3,5-difluorophenyl)-N-[(2S)-1,1,1-trifluoropropan-2-yl]pyridine-3-carboxamide (28 mg, 48%) as a white solid. MS (M+H)=429.3.

Example 28. 4-[(3S)-3-amino-3-methylpyrrolidin-1-yl]-6-cyclopropyl-N-(4,4-difluoro cyclohexyl)-5-(3,5-difluorophenyl)pyridine-3-carboxamide (compound 1-281)

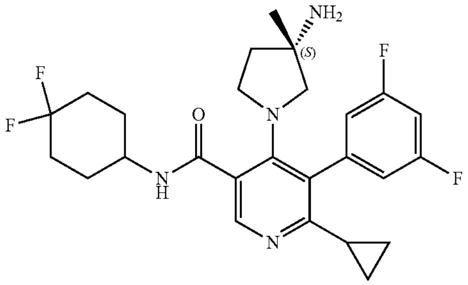

Step 28-1, preparation of ethyl (S)-4-(3-((tert-butoxycarbonyl)amino)-3-methylpyrrolidin-1-yl)-6-chloronicotinate: to an ACN (10 mL) solution of ethyl 4,6-dichloronicotinate (1.0 g, 1 Eq, 4.5 mmol) and tert-butyl (S)-(3-methylpyrrolidin-3-yl)carbamate (920 mg, 1.0 Eq, 4.59 mmol) was added DIEA (2.0 g, 2.7 mL, 3.4 Eq, 15 mmol) drop-wise at 0° C. The resulting mixture was stirred at 25° C. for 16 hours. The reaction crude was filtered and the filtrate was concentrated under vacuum to afford the crude title compound (1.5 g, 3.9 mmol, 86%) as a white solid. This material was used for next step without further purification. MS $(M+H)^+$=384.2.

Step 28-2, preparation of ethyl (S)-4-(3-((tert-butoxycarbonyl)amino)-3-methylpyrrolidin-1-yl)-6-cyclopropylnicotinate: to a THF (5 mL) solution of ethyl (S)-4-(3-((tert-butoxycarbonyl)amino)-3-methylpyrrolidin-1-yl)-6-chloronicotinate (500 mg, 1 Eq, 1.30 mmol) was added zinc(II) bromide (150 mg, 0.511 Eq, 666 μmol), tri-tert-butylphosphane (60 mg, 0.23 Eq, 0.30 mmol) and $Pd(OAc)_2$ (30 mg, 0.10 Eq, 0.13 mmol) under atmospheric nitrogen. Cyclopropylmagnesium bromide (1.0 M, 6 mL, 5 Eq, 6 mmol) was added at ambient temperature drop-wise. The resulting mixture was stirred at the same temperature for 3 hours. The reaction crude was quenched with saturated $NH_4Cl$ and extracted with ethyl acetate (3×40 mL). The organic layers were combined, washed with brine, dried and concentrated under vacuum. The remaining residue was purified by silica gel chromatography eluting with ethyl acetate/petroleum ether (⅓) to afford ethyl (S)-4-(3-((tert-butoxycarbonyl)amino)-3-methylpyrrolidin-1-yl)-6-cyclopropylnicotinate (230 mg, 591 μmol, 45.3%) as a yellow solid. MS $(M+H)^+$=390.1.

Step 28-3, preparation of ethyl (S)-5-bromo-4-(3-((tert-butoxycarbonyl)amino)-3-methylpyrrolidin-1-yl)-6-cyclopropylnicotinate: ethyl (S)-4-(3-((tert-butoxycarbonyl)amino)-3-methylpyrrolidin-1-yl)-6-cyclopropylnicotinate (230 mg, 1 Eq, 591 μmol) was combined with AcOH (6 mL) and DCM (1.2 mL) followed by the addition of 1,3,5-tribromo-1,3,5-triazinane-2,4,6-trione (320 mg, 1.48 Eq, 875 μmol) 0° C. portion-wise. The resulting mixture was stirred at the same temperature for 20 min. The reaction crude was quenched with saturated $NaHSO_3$ (10 mL) and extracted with ethyl acetate (3×40 mL). The organic layers were combined, washed with saturated $NaHCO_3$ and brine, dried and concentrated under vacuum. The remaining residue was purified by silica gel chromatography eluting with ethyl acetate/petroleum ether (1/3) to afford ethyl (S)-5-bromo-4-(3-((tert-butoxycarbonyl)amino)-3-methylpyrrolidin-1-yl)-6-cyclopropylnicotinate (130 mg, 278 μmol, 47.0%) as a yellow solid. MS $(M+H)^+$=468.1, 470.1.

Step 28-4, preparation of ethyl (S)-4-(3-((tert-butoxycarbonyl)amino)-3-methylpyrrolidin-1-yl)-6-cyclopropyl-5-(3,5-difluorophenyl)nicotinate: to a Toluene (2 mL) solution of ethyl (S)-5-bromo-4-(3-((tert-butoxycarbonyl)amino)-3-methylpyrrolidin-1-yl)-6-cyclopropylnicotinate (120 mg, 1 Eq, 256 μmol) was added (3,5-difluorophenyl) boronic acid (80 mg, 2.0 Eq, 0.51 mmol), $K_3PO_4$ (160 mg, 2.94 Eq, 754 μmol), Pd(DTBPF)$Cl_2$ (18 mg, 0.11 Eq, 28 μmol) and water (0.2 mL) under atmospheric nitrogen. The resulting mixture was stirred at 80° C. for 1 hour. The reaction mixture was concentrated and the remaining residue was purified by silica gel chromatography eluting with ethyl acetate/petroleum ether (1:3) to afford ethyl (S)-4-(3-((tert-butoxycarbonyl)amino)-3-methylpyrrolidin-1-yl)-6-cyclopropyl-5-(3,5-difluorophenyl)nicotinate (103 mg, 205 μmol, 80.2%) as a light yellow solid. MS $(M+H)^+$=502.2.

Step 28-5, preparation of (S)-4-(3-((tert-butoxycarbonyl)amino)-3-methylpyrrolidin-1-yl)-6-cyclopropyl-5-(3,5-difluorophenyl)nicotinic acid: to a MeOH (5 mL) solution of ethyl (S)-4-(3-((tert-butoxycarbonyl)amino)-3-methylpyrrolidin-1-yl)-6-cyclopropyl-5-(3,5-difluorophenyl) nicotinate (103 mg, 1 Eq, 205 μmol) was added NaOH (80 mg, 9.7 Eq, 2.0 mmol) and water (1 mL). The resulting mixture was stirred at 70° C. for 4 hours. The reaction solution was concentrated under vacuum and diluted with water. Saturated $NaHSO_4$ was added until pH=4-5. The resulting mixture was extracted with DCM (3×40 mL). Organic layers were combined, washed with brine, dried and concentrated under vacuum to afford crude (S)-4-(3-((tert-butoxycarbonyl)amino)-3-methylpyrrolidin-1-yl)-6-cyclopropyl-5-(3,5-difluorophenyl)nicotinic acid (80 mg, 0.17 mmol, 82.0%) as a yellow solid. This material was used in next step without further purification. MS $(M+H)^+$=474.2.

Step 28-6, preparation of tert-butyl (S)-(1-(2-cyclopropyl-5-((4,4-difluorocyclohexyl) carbamoyl)-3-(3,5-difluorophenyl)pyridin-4-yl)-3-methylpyrrolidin-3-yl)carbamate: to DMF (2 mL) solution of crude (S)-4-(3-((tert-butoxycarbonyl)amino)-3-methylpyrrolidin-1-yl)-6-cyclopropyl-5-(3,5-difluorophenyl) nicotinic acid (20 mg, 1 Eq, 42 μmol) was added DIEA (2.0 g, 2.7 mL, 3.4 Eq, 15 mmol) and HATU (20 mg, 1.2 Eq, 53 μmol). The resulting mixture was stirred at ambient temperature for 10 min followed by the addition of 4,4-difluorocyclohexan-1-amine (20 mg, 3.5 Eq, 0.15 mmol). The reaction mixture was stirred at the same temperature for 1 hour. The reaction crude (5 mL) was purified by Prep-HPLC using the following conditions: Column, SunFine prep OBD 19*150 mm 5 μm C-01; mobile phase, water (0.05% FA) and ACN (27% ACN up to 47% in 7 min); Detector 254 & 220 nm; flow rate, 20 mL/min. This resulted in tert-butyl (S)-(1-(2-cyclopropyl-5-((4,4-difluorocyclohexyl)carbamoyl)-3-(3,5-difluorophenyl)pyridin-4-yl)-3-methylpyrrolidin-3-yl)carbamate (11 mg, 19 μmol, 44%) as a white solid. MS $(M+H)^+$=591.1.

Step 28-7, preparation of 4-[(3S)-3-amino-3-methylpyrrolidin-1-yl]-6-cyclopropyl-N-(4,4-difluoro cyclohexyl)-5-(3,5-difluorophenyl)pyridine-3-carboxamide: to a DCM (3 mL) solution of tert-butyl (S)-(1-(2-cyclopropyl-5-((4,4-difluorocyclohexyl)carbamoyl)-3-(3,5-difluorophenyl)pyridin-4-yl)-3-methylpyrrolidin-3-yl)carbamate (12 mg, 1 Eq, 20 μmol) was added TFA (1 mL). The resulting mixture was stirred at ambient temperature for 1 hour. The reaction solution was concentrated and the remaining residue was freeze-dried with water and ACN to afford the TFA salt of 4-[(3S)-3-amino-3-methylpyrrolidin-1-yl]-6-cyclopropyl-N-(4,4-difluoro cyclohexyl)-5-(3,5-difluorophenyl)pyridine-3-carboxamide (10.1 mg, 14.1 μmol, 69%) as a light yellow solid. MS $(M+H)^+$=491.2.

The following compounds were prepared similarly to Example 28 with appropriate substituting reagents and substrates at different steps and they may require additional functional group modifications via well-known chemistry with appropriate reagents. Different salts, such as HCl or formic acid or TFA salt, may be obtained.

| Compound no. | MS $(M + H)^+$ |
|---|---|
| 1-290 | 469.2 |

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example B-1: SSTR Assays

Membrane Preparation:

Crude membrane fractions are prepared from Chinese hamster ovary (CHO) cells stably expressing one of the five human or rodent somatostatin receptor subtypes. The cells are grown to 85-100% confluence on standard tissue culture dishes in DM-MEM growth media (Gibco) with following additives: 10% fetal bovine serum (Gibco), 100 U/mL penicillin (Gibco), 100 μg/mL streptomycin (Gibco), 10 mM HEPES (Gibco), 0.5 mg/mL G-418 (Gibco). To prepare membranes, cells are washed once with 1× Dulbecco's phosphate buffered saline (Gibco) containing 10 mM HEPES (Gibco) then once with sodium free binding buffer (50 mM Tris Base, 5 mM $MgCl_2$-$6H_20$ and 1 mM EGTA adjusted to pH 7.8). The cells are then scraped into binding buffer containing a protease inhibitor cocktail (100 μg/mL pepstatin A (Sigma), 50 μg/mL leupeptin (Sigma), 25 μg/mL aprotinin (Sigma) and 10 mg/mL Bacitracin (USB Corporation)). The cells are centrifuged at 43,500×g, homogenized, and the resulting membranes are collected by centrifugation at 67,000×g. The membranes are then resuspended in binding buffer containing the protease inhibitor cocktail using a glass dounce homogenizer.

Functional Assays

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology,* 2005, 2.2.1-2.2). One example of an intracellular cAMP assay is described below.

cAMP Assay Protocol for SST2R:

Four days prior to the assay, 5,000 Chinese hamster ovary cells (CHO-$K_1$, ATCC #CCL-61) stably expressing the human somatostatin receptor subtype 2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 μg/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. On the day of the assay, the media is aspirated and the cells are treated with 50 μL of 1.6 μM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 μL of lysis buffer (HRTF cAMP kit, Cisbio). The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

cAMP Assay Protocol for SST5R:

Four days prior to the assay, 2,000 Chinese hamster ovary cells (CHO-$K_1$, ATCC #CCL-61) stably expressing the human somatostatin receptor subtype 5 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 g/mL streptomycin; 2 mM L-glutamine (Gemini Bio-Products #400-110) and 0.25 mg/mL G418 Sulfate (GoldBio #108321-42-2). The cells are cultured at 37° C., 5% CO2 and 95% humidity. On the day of the assay, the media is aspirated and the cells are treated with 50 μL of 1.6 μM NKH477 (Sigma #N3290) plus various dilutions of compounds of the invention in assay buffer [1× Hank's Balanced Salt Solution (ThermoFisher #SH3058802), 0.5 mM HEPES pH 7.4, 0.1% bovine serum albumin, 0.2 mM 3-Isobutyl-1-methylxanthine (IBMX, VWR #200002-790)]. The cells are incubated for 20 minutes at 37° C. (the final concentration of the compounds of the invention are typically 0-10,000 nM). The cells are treated with 50 μL of lysis buffer (HRTF cAMP kit, Cisbio) for 30 minutes and then the lysate is diluted to 250 μL with assay buffer. The lysate is transferred to 384-well plates and cAMP detection and visualization antibodies are added and incubated for 1-24 hours at room temperature. The time-resolved fluorescent signal is read with a Tecan M1000Pro multiplate reader. The intracellular cAMP concentrations are calculated by regression to a standard curve and are plotted vs. the concentration of the compounds of the invention and the $EC_{50}$ of the compounds are calculated using standard methods. All data manipulations are in GraphPad Prism v6 or v7.

Illustrative biological activity of compounds is demonstrated in the following Tables, by evaluating the inhibition of cAMP activities via human SST receptors.

Table A demonstrates illustrative biological activity of compounds by evaluating the inhibition of cAMP activities via human SST5 receptor, where a means $EC_{50}$ is <10 nM; b means $EC_{50}$ is between 10 to 100 nM; c means $EC_{50}$ is between 100 to 1000 nM; d means $EC_{50}$ is >1000 nM.

TABLE A

Representative SST5 Activity

| Compd No. | SST5 potency |
|---|---|
| 1-1 | a |
| 1-2 | b |
| 1-3 | a |
| 1-4 | a |
| 1-5 | a |
| 1-6 | a |
| 1-7 | c |
| 1-8 | c |
| 1-9 | c |
| 1-10 | b |
| 1-11 | a |
| 1-12 | a |
| 1-13 | a |
| 1-14 | a |
| 1-15 | a |
| 1-16 | a |
| 1-17 | a |
| 1-18 | b |
| 1-19 | a |
| 1-20 | a |
| 1-21 | a |
| 1-22 | a |
| 1-23 | b |
| 1-24 | a |
| 1-25 | a |
| 1-26 | a |
| 1-27 | a |
| 1-28 | b |
| 1-29 | b |
| 1-30 | a |

TABLE A-continued

| Representative SST5 Activity | |
|---|---|
| Compd No. | SST5 potency |
| 1-31 | a |
| 1-32 | a |
| 1-33 | a |
| 1-34 | a |
| 1-35 | a |
| 1-36 | b |
| 1-37 | b |
| 1-38 | a |
| 1-39 | c |
| 1-40 | b |
| 1-41 | a |
| 1-42 | a |
| 1-43 | a |
| 1-44 | a |
| 1-45 | a |
| 1-46 | a |
| 1-47 | a |
| 1-48 | a |
| 1-49 | a |
| 1-50 | a |
| 1-51 | a |
| 1-52 | a |
| 1-53 | a |
| 1-54 | a |
| 1-55 | a |
| 1-56 | a |
| 1-57 | a |
| 1-58 | a |
| 1-59 | a |
| 1-60 | a |
| 1-61 | a |
| 1-62 | a |
| 1-63 | b |
| 1-64 | a |
| 1-65 | a |
| 1-66 | a |
| 1-67 | a |
| 1-68 | a |
| 1-69 | a |
| 1-70 | a |
| 1-71 | a |
| 1-72 | a |
| 1-73 | a |
| 1-74 | a |
| 1-75 | c |
| 1-76 | a |
| 1-77 | a |
| 1-78 | a |
| 1-79 | a |
| 1-80 | c |
| 1-81 | a |
| 1-82 | a |
| 1-83 | a |
| 1-84 | a |
| 1-85 | a |
| 1-86 | a |
| 1-87 | a |
| 1-88 | a |
| 1-89 | a |
| 1-90 | a |
| 1-91 | a |
| 1-92 | a |
| 1-93 | a |
| 1-94 | a |
| 1-95 | a |
| 1-96 | a |
| 1-97 | a |
| 1-98 | a |
| 1-99 | d |
| 1-100 | a |
| 1-101 | a |
| 1-102 | b |
| 1-103 | a |
| 1-104 | a |
| 1-105 | b |
| 1-106 | b |

TABLE A-continued

| Representative SST5 Activity | |
|---|---|
| Compd No. | SST5 potency |
| 1-107 | b |
| 1-108 | a |
| 1-109 | c |
| 1-110 | a |
| 1-111 | c |
| 1-112 | a |
| 1-113 | a |
| 1-114 | a |
| 1-115 | a |
| 1-116 | a |
| 1-117 | c |
| 1-118 | a |
| 1-119 | c |
| 1-120 | a |
| 1-121 | a |
| 1-122 | a |
| 1-123 | a |
| 1-124 | a |
| 1-125 | a |
| 1-126 | a |
| 1-127 | a |
| 1-128 | a |
| 1-129 | a |
| 1-130 | a |
| 1-131 | a |
| 1-132 | a |
| 1-133 | c |
| 1-134 | a |
| 1-135 | a |
| 1-136 | b |
| 1-137 | a |
| 1-138 | a |
| 1-139 | a |
| 1-140 | a |
| 1-141 | a |
| 1-142 | a |
| 1-143 | a |
| 1-144 | a |
| 1-145 | a |
| 1-146 | a |
| 1-147 | a |
| 1-148 | a |
| 1-149 | a |
| 1-150 | a |
| 1-151 | a |
| 1-152 | a |
| 1-153 | a |
| 1-154 | a |
| 1-155 | d |
| 1-156 | b |
| 1-157 | a |
| 1-158 | a |
| 1-159 | a |
| 1-160 | a |
| 1-161 | a |
| 1-162 | a |
| 1-163 | a |
| 1-164 | a |
| 1-165 | a |
| 1-166 | a |
| 1-167 | a |
| 1-168 | a |
| 1-169 | a |
| 1-170 | a |
| 1-171 | a |
| 1-172 | a |
| 1-173 | a |
| 1-174 | a |
| 1-175 | b |
| 1-176 | a |
| 1-177 | a |
| 1-178 | a |
| 1-179 | a |
| 1-180 | a |
| 1-181 | a |
| 1-182 | a |

TABLE A-continued

| Representative SST5 Activity | |
|---|---|
| Compd No. | SST5 potency |
| 1-183 | a |
| 1-184 | a |
| 1-185 | b |
| 1-186 | a |
| 1-187 | a |
| 1-188 | a |
| 1-189 | a |
| 1-190 | a |
| 1-191 | a |
| 1-192 | a |
| 1-193 | c |
| 1-194 | a |
| 1-195 | a |
| 1-196 | a |
| 1-197 | a |
| 1-198 | a |
| 1-199 | a |
| 1-200 | a |
| 1-201 | a |
| 1-202 | a |
| 1-203 | a |
| 1-204 | d |
| 1-205 | a |
| 1-209 | a |
| 1-210 | a |
| 1-211 | a |
| 1-212 | a |
| 1-213 | a |
| 1-214 | a |
| 1-215 | a |
| 1-216 | a |
| 1-217 | a |
| 1-218 | c |
| 1-219 | a |
| 1-222 | a |
| 1-223 | b |
| 1-224 | b |
| 1-225 | a |
| 1-226 | a |
| 1-227 | c |
| 1-228 | a |
| 1-229 | a |
| 1-230 | a |
| 1-231 | a |
| 1-232 | a |
| 1-233 | a |
| 1-234 | a |
| 1-235 | d |
| 1-236 | d |
| 1-237 | d |
| 1-238 | a |
| 1-239 | a |
| 1-240 | a |
| 1-241 | b |
| 1-242 | a |
| 1-243 | a |
| 1-244 | a |
| 1-245 | a |
| 1-246 | a |
| 1-247 | a |
| 1-259 | a |
| 1-260 | a |
| 1-261 | a |
| 1-262 | a |
| 1-263 | a |
| 1-264 | a |
| 1-265 | a |
| 1-266 | a |
| 1-267 | a |
| 1-268 | a |
| 1-269 | a |
| 1-272 | a |
| 1-273 | a |
| 1-274 | d |
| 1-275 | a |
| 1-276 | a |

TABLE A-continued

| Representative SST5 Activity | |
|---|---|
| Compd No. | SST5 potency |
| 1-277 | a |
| 1-278 | a |
| 1-279 | a |
| 1-280 | a |
| 1-281 | a |
| 1-282 | a |
| 1-283 | a |
| 1-284 | a |
| 1-285 | a |
| 1-286 | a |
| 1-287 | a |
| 1-288 | a |
| 1-289 | a |
| 1-290 | a |
| 1-206 | a |
| 1-208 | a |
| 1-248 | a |
| 1-249 | a |
| 1-250 | a |
| 1-251 | a |
| 1-252 | a |
| 1-253 | a |
| 1-254 | a |
| 1-255 | a |
| 1-256 | a |
| 1-257 | a |
| 1-258 | a |
| 1-270 | a |
| 1-271 | a |
| 1-220 | a |
| 1-221 | b |
| 2-1 | b |
| 2-2 | b |
| 2-3 | b |
| 2-4 | a |
| 2-5 | c |
| 2-6 | a |
| 2-7 | a |
| 2-8 | b |
| 2-9 | c |
| 2-10 | a |
| 2-11 | a |
| 2-12 | b |
| 2-13 | a |
| 2-14 | a |
| 2-15 | a |
| 2-16 | a |
| 2-17 | b |
| 2-18 | a |
| 2-19 | a |
| 2-20 | a |
| 2-21 | b |
| 2-22 | b |
| 2-23 | b |
| 2-24 | a |
| 2-25 | b |
| 2-26 | a |
| 2-27 | a |
| 2-28 | b |
| 2-29 | a |
| 2-30 | a |
| 2-31 | a |
| 2-32 | a |
| 2-33 | a |
| 2-34 | b |
| 2-35 | a |
| 2-36 | a |
| 2-37 | a |
| 2-38 | a |
| 2-39 | b |
| 2-40 | a |
| 2-41 | a |
| 2-42 | a |
| 2-43 | a |
| 2-44 | b |
| 2-45 | a |

TABLE A-continued

| Representative SST5 Activity | |
|---|---|
| Compd No. | SST5 potency |
| 3-1 | b |
| 3-2 | a |
| 3-3 | c |
| 3-4 | a |
| 3-5 | b |
| 3-6 | a |
| 3-7 | b |
| 3-8 | b |
| 4-1 | a |
| 4-2 | b |
| 4-3 | a |
| 4-4 | b |
| 4-5 | d |

Table B demonstrates illustrative biological selectivity of exemplary compounds for the SST5 receptor over SST2 receptor, by evaluating the inhibition of cAMP activities via human SST5 receptor and human SST2 receptor, where a means $FC_{50}$ is <10 nM; b means $FC_{50}$ is between 10 to 100 nM; c means $FC_{50}$ is between 100 to 1000 nM; d means $FC_{50}$ is >1000 nM; +=10 to 99; ++=100 to 499; +++=>500.

TABLE B

| Illustrative Selectivity Data Demonstrating Preference forSST5 vs SST2 | | | |
|---|---|---|---|
| Compd No. | SST5 potency | SST2 potency | Fold selectivity for SST5 vs SST2 |
| 1-1 | a | b | ++ |
| 1-2 | b | a | − |
| 1-3 | a | c | + |
| 1-4 | a | c | ++ |
| 1-5 | a | c | +++ |
| 1-6 | a | b | ++ |
| 1-10 | b | d | ++ |
| 1-11 | a | d | +++ |
| 1-12 | a | c | +++ |
| 1-13 | a | c | +++ |
| 1-16 | a | c | +++ |
| 1-17 | a | c | ++ |
| 1-19 | a | c | ++ |
| 1-20 | a | c | +++ |
| 1-21 | a | b | ++ |
| 1-22 | a | c | ++ |
| 1-24 | a | b | +++ |
| 1-25 | a | c | +++ |
| 1-30 | a | c | ++ |
| 1-31 | a | c | ++ |
| 1-34 | a | c | ++ |
| 1-35 | a | c | ++ |
| 1-41 | a | b | ++ |
| 1-44 | a | c | ++ |
| 1-47 | a | c | +++ |
| 1-48 | a | c | +++ |
| 1-49 | a | c | +++ |
| 1-51 | a | c | +++ |
| 1-54 | a | c | ++ |
| 1-57 | a | c | ++ |
| 1-58 | a | c | +++ |
| 1-61 | a | d | +++ |
| 1-64 | a | d | +++ |
| 1-66 | a | d | +++ |
| 1-67 | a | d | +++ |
| 1-68 | a | d | +++ |
| 1-69 | a | c | +++ |
| 1-70 | a | d | +++ |
| 1-71 | a | c | +++ |
| 1-72 | a | c | +++ |
| 1-73 | a | d | +++ |

TABLE B-continued

| Illustrative Selectivity Data Demonstrating Preference forSST5 vs SST2 | | | |
|---|---|---|---|
| Compd No. | SST5 potency | SST2 potency | Fold selectivity for SST5 vs SST2 |
| 1-74 | a | d | +++ |
| 1-76 | a | d | +++ |
| 1-77 | a | b | +++ |
| 1-78 | a | b | +++ |
| 1-79 | a | c | +++ |
| 1-81 | a | c | +++ |
| 1-85 | a | c | +++ |
| 1-86 | a | c | +++ |
| 1-87 | a | c | +++ |
| 1-90 | a | c | +++ |
| 1-91 | a | c | +++ |
| 1-92 | a | c | +++ |
| 1-93 | a | b | +++ |
| 1-94 | a | c | ++ |
| 1-96 | a | c | ++ |
| 1-98 | a | c | ++ |
| 1-100 | a | d | +++ |
| 1-101 | a | d | +++ |
| 1-103 | a | d | +++ |
| 1-104 | a | d | +++ |
| 1-108 | a | d | +++ |
| 1-110 | a | d | +++ |
| 1-112 | a | c | +++ |
| 1-113 | a | d | +++ |
| 1-114 | a | d | +++ |
| 1-115 | a | d | +++ |
| 1-116 | a | d | +++ |
| 1-118 | a | d | +++ |
| 1-120 | a | b | +++ |
| 1-121 | a | d | +++ |
| 1-122 | a | c | +++ |
| 1-123 | a | c | +++ |
| 1-124 | a | c | +++ |
| 1-125 | a | b | +++ |
| 1-126 | a | d | +++ |
| 1-127 | a | c | +++ |
| 1-128 | a | c | +++ |
| 1-129 | a | c | +++ |
| 1-130 | a | c | +++ |
| 1-132 | a | d | +++ |
| 1-135 | a | c | +++ |
| 1-137 | a | c | +++ |
| 1-153 | a | c | +++ |
| 1-154 | a | d | +++ |
| 1-155 | d | | +++ |
| 1-157 | a | d | +++ |
| 1-158 | a | d | +++ |
| 1-159 | a | d | +++ |
| 1-160 | a | c | +++ |
| 1-161 | a | d | ++ |
| 1-162 | a | d | +++ |
| 1-163 | a | c | ++ |
| 1-164 | a | c | +++ |
| 1-165 | a | c | +++ |
| 1-166 | a | d | +++ |
| 1-167 | a | d | +++ |
| 1-168 | a | c | +++ |
| 1-169 | a | c | +++ |
| 1-170 | a | c | +++ |
| 1-171 | a | b | +++ |
| 1-172 | a | c | +++ |
| 1-173 | a | c | ++ |
| 1-174 | a | c | +++ |
| 1-176 | a | c | +++ |
| 1-177 | a | b | +++ |
| 1-178 | a | b | +++ |
| 1-179 | a | c | +++ |
| 1-180 | a | b | +++ |
| 1-181 | a | c | +++ |
| 1-182 | a | d | +++ |
| 1-183 | a | d | +++ |
| 1-184 | a | c | +++ |

TABLE B-continued

Illustrative Selectivity Data Demonstrating Preference forSST5 vs SST2

| Compd No. | SST5 potency | SST2 potency | Fold selectivity for SST5 vs SST2 |
|---|---|---|---|
| 1-186 | a | c | +++ |
| 1-187 | a | d | +++ |
| 1-188 | a | c | +++ |
| 1-192 | a | b | ++ |
| 1-195 | a | b | ++ |
| 1-196 | a | d | +++ |
| 1-197 | a | c | +++ |
| 1-198 | a | b | ++ |
| 1-199 | a | c | +++ |
| 1-200 | a | c | +++ |
| 1-201 | a | d | +++ |
| 1-202 | a | d | +++ |
| 1-209 | a | | +++ |
| 1-210 | a | b | +++ |
| 1-212 | a | c | +++ |
| 1-213 | a | c | +++ |
| 1-214 | a | d | +++ |
| 1-215 | a | c | +++ |
| 1-216 | a | d | +++ |
| 1-217 | a | c | +++ |
| 1-226 | a | c | ++ |
| 1-228 | a | b | +++ |
| 1-229 | a | b | +++ |
| 1-230 | a | c | ++ |
| 1-231 | a | c | +++ |
| 1-232 | a | d | +++ |
| 1-233 | a | d | +++ |
| 1-234 | a | c | +++ |
| 1-238 | a | c | +++ |
| 1-239 | a | d | +++ |
| 1-240 | a | c | +++ |
| 1-241 | b | | |
| 1-242 | a | d | +++ |
| 1-244 | a | c | +++ |
| 1-245 | a | d | +++ |
| 1-246 | a | c | +++ |
| 1-247 | a | d | +++ |
| 1-259 | a | b | +++ |
| 1-260 | a | c | +++ |
| 1-261 | a | c | +++ |
| 1-262 | a | c | +++ |
| 1-263 | a | d | +++ |
| 1-264 | a | d | +++ |
| 1-265 | a | d | +++ |
| 1-266 | a | d | +++ |
| 1-267 | a | c | +++ |
| 1-268 | a | d | +++ |
| 1-269 | a | c | +++ |
| 1-272 | a | c | +++ |
| 1-273 | a | c | +++ |
| 1-275 | a | c | +++ |
| 1-276 | a | c | ++ |
| 1-277 | a | d | +++ |
| 1-278 | a | d | +++ |
| 1-279 | a | c | +++ |
| 1-280 | a | c | +++ |
| 1-282 | a | c | +++ |
| 1-283 | a | c | +++ |
| 1-284 | a | c | +++ |
| 1-285 | a | c | +++ |
| 1-286 | a | c | +++ |
| 1-287 | a | b | +++ |
| 1-288 | a | c | +++ |
| 1-289 | a | c | +++ |
| 1-206 | a | d | +++ |
| 1-208 | a | c | +++ |
| 1-248 | a | d | +++ |
| 1-249 | a | c | +++ |
| 1-250 | a | d | +++ |
| 1-251 | a | d | +++ |
| 1-252 | a | c | +++ |
| 1-253 | a | c | +++ |

TABLE B-continued

Illustrative Selectivity Data Demonstrating Preference forSST5 vs SST2

| Compd No. | SST5 potency | SST2 potency | Fold selectivity for SST5 vs SST2 |
|---|---|---|---|
| 1-254 | a | d | +++ |
| 1-255 | a | d | +++ |
| 1-256 | a | d | +++ |
| 1-257 | a | d | +++ |
| 1-258 | a | d | +++ |
| 1-270 | a | d | +++ |
| 1-271 | a | d | +++ |
| 2-7 | a | c | ++ |
| 2-11 | a | b | + |
| 2-15 | a | c | ++ |
| 2-26 | a | c | +++ |
| 2-29 | a | b | + |
| 2-30 | a | b | + |
| 2-35 | a | c | ++ |
| 2-36 | a | c | +++ |
| 2-37 | a | c | ++ |
| 2-38 | a | c | + |
| 2-41 | a | c | + |
| 2-42 | a | c | ++ |
| 2-43 | a | b | + |
| 2-45 | a | c | ++ |
| 3-2 | a | d | +++ |
| 3-6 | a | d | +++ |
| 4-1 | a | d | +++ |
| 4-(3-(aminomethyl) pyrrolidin-1-yl)-N,5-bis(3,5-dimethylphenyl) nicotinamide | a | a | 0.084 |
| 4-(4-aminopiperidin-1-yl)-N,5-bis(3,5-dimethylphenyl) nicotinamide | d | a | 0.000096 |
| N-(4-(3-(aminomethyl) pyrrolidin-1-yl)-5-(3,5-dimethylphenyl) pyridin-3-yl)-3-chloro-4-fluorobenzamide | d | a | 0.0055 |

Example B-2: Liver Microsomal Stability Assay Protocol

The in vitro stabilities of compounds of interest were determined for various species using pooled male and female human, pooled male Sprague-Dawley rat, pooled male Cynomolgus monkey, and pooled male Beagle dog liver microsomes at microsomal protein concentrations of 0.5 mg/mL. Incubations were carried out in a potassium phosphate buffer (50 mM). The NADPH-generating system was composed of NADP+ (1 mM), magnesium chloride (3 mM), EDTA (1 mM), glucose-6-phosphate (5 mM) and glucose-6-phosphate dehydrogenase (1 Unit/mL) for all experiments. Compounds of interest in DMSO/acetonitrile were added to achieve a final incubation concentration of 1 μM (final DMSO content was 0.1% v/v and final acetonitrile content was 0.9%). The final incubation volume was 400 μL. Incubations were conducted at 37° C. for 0, 5, 10, 20, 40 and 60 minutes in a shaking water bath and terminated by removing 50 μL of incubation mixture and adding to 100 μL of ice cold acetonitrile containing internal standard. Following precipitation by centrifugation at 3500 rpm and 4° C. for 30 minutes, compounds of interest and internal standard were analyzed in the resultant supernatant using a multiple reaction monitoring (MRM) LC-MS/MS method. MS conditions were optimized for each analyte. Depletion rates of compounds of interest were measured and half-life, scaled intrinsic clearance, and predicted scaled systemic clearance calculations were made using this data.

Example B-3: Genetic Models of Hyperinsulinism in Rodents

Representative assays evaluating the effect of a selective somatostatin subtype (sst5) agonist described herein in genetic models of hyperinsulinism in rodents, specifically the SUR1$^{-/-}$ mouse model, are described. The SURP$^{-/-}$ mouse reproduces the key pathophysiological features of KATP congential hyperinsulinism (HI), the most common and severe genetic form of hyperinsulinism. SURP$^{-/-}$ mice are both significantly more hypoglycemic when fasted and significantly more hyperglycemic when glucose-loaded compared with control wild-type. Evaluation of the effect of oral administration of a somatostatin subtype (sst5) agonist described herein on plasma glucose levels after a fast is described below.

In Vivo Experiments:

SURP$^{-/-}$ mice and wild type mice are administered a somatostatin subtype (sst5) agonist described herein at a dose of 30 mg/Kg/day for 1 week. Fasting plasma glucose, insulin, and betahydroxybutyrate concentrations are measured after a 16 hr fast at baseline and after 1 week of treatment. Glucose and an insulin tolerance tests are performed during the treatment period.

Sample size: Average fasting plasma glucose levels in SURP$^{-/-}$ mice are 59.4+/−5.0 mg/dL. With 5 mice per group there is greater than 90% power to detect a difference of 20% (equivalent to bringing the levels to normal range) on fasting plasma glucose levels in treated versus control-treated SUR1$^{-/-}$ mice (using alpha 0.05).

Treatment groups: (1) a compound described herein; (2) selective somatostatin 2 agonist; and (3) Placebo.

Genotype groups: (1) SURP$^{-/-}$ mice; and (2) Wild type mice

Experimental Procedures

Fasting Evaluation: Fasting plasma glucose are measured after a 16 hour fast. Plasma glucose and betahydroxybutyrate levels are checked by a hand held glucose meter (Nova Stat Strip glucose meters) in blood obtained from a tail nick (only one nick will be necessary) and 15 microliters of blood are collected to measure insulin levels.

Intraperitoneal glucose tolerance test: After an overnight fast, mice are given an i.p. dose of glucose (2 g/kg). Plasma glucose and insulin concentrations are measured at baseline and every 30 min for 2 hrs. Fifteen microliters of blood/time point is obtained and measured for insulin levels.

Insulin tolerance test: After a 6 hr fast, mice are given an i.p. injection of insulin (1 unit/kg). Glucose concentration is measured at baseline and every 10 min for 30 minutes or until the mice reach a hypoglycemic state, then every 30 min for 2 hrs.

In Vitro Experiments:

The direct effects of a somatostatin subtype (sst5) agonist described herein or selective somatostatin 2 agonist on insulin secretion are tested in isolated pancreatic islets from wild type and SUR1$^{-/-}$ mice. The direct effects of the compounds are also tested in islets isolated from patients with $K_{ATP}$HI who undergo pancreatectomy and those from healthy human volunteers.

Batch incubation: 5 islets for each well with 4 replicates of each condition in 96-well plate format are used for the study. Islets are exposed to 4 concentrations of glucose (0, 5, 10 and 25 mM) or mixture of amino acids (0, 2, 4 and 10 mM) in the absence or presents of 4 concentrations of 2 compounds (a somatostatin subtype (sst5) agonist described herein, somatostatin 2 agonist). The effects of compounds and the effective doses on insulin secretion are obtained after those experiments.

Cytosolic calcium measurements: Cytosolic calcium ($[Ca^{2+}]$) dynamics are assessed using Fura-2 as calcium indicator; islets isolated from wild type or SUR1$^{-/-}$ mice are exposed to glucose and amino acids. The effects of the compounds on $[Ca^{2+}]$, dynamics are directly evaluated.

Islets perifusion: After batch incubations and calcium measurements, the effective concentration of compounds are determined. The effects of those compounds with effective dose on insulin secretion dynamics are evaluated in perifused islets.

$K_{ATP}$HI human islets: Compounds are also tested with $K_{ATP}$HI human islets. Islets are isolated from surgical specimens from patients with $K_{ATP}$HI who underwent pancreatectomy. $K_{ATP}$HI are perifused in response to amino acid and glucose stimulation in the absence or presence of the compounds. $[Ca^{2+}]$, dynamics are also tested.

The examples and embodiments described herein are for illustrative purposes only and various modifications or changes suggested to persons skilled in the art are to be included within the spirit and purview of this application and scope of the appended claims.

What is claimed is:

1. A method of treating hyperinsulinism in a mammal, the method comprising administering a compound to the mammal in need thereof, wherein the compound is 4-[(3S)-3-amino-3-methylpyrrolidin-1-yl]-6-cyano-5-(3,5-difluorophenyl)-N-[(2S)-1,1, 1-trifluoropropan-2-yl] pyridine-3-carboxamide, or a pharmaceutically acceptable salt thereof.

2. The method of claim 1, wherein the compound is 4-[(3S)-3-amino-3-methylpyrrolidin-1-yl]-6-cyano-5-(3,5-difluorophenyl)-N-[(2S)-1,1,1-trifluoropropan-2-yl] pyridine-3-carboxamide.

3. The method of claim 1, wherein the compound is a pharmaceutically acceptable salt of 4-[(3S)-3-amino-3-methylpyrrolidin-1-yl]-6-cyano-5-(3,5-difluorophenyl)-N-[(2S)-1,1,1-trifluoropropan-2-yl] pyridine-3-carboxamide.

4. The method of claim 1, wherein the hyperinsulinism is congenital hyperinsulinism or drug induced hyperinsulinism.

* * * * *